United States Patent
Bossard et al.

(10) Patent No.: US 9,493,544 B2
(45) Date of Patent: *Nov. 15, 2016

(54) VON WILLEBRAND FACTOR- AND FACTOR VIII-POLYMER CONJUGATES HAVING A RELEASABLE LINKAGE

(75) Inventors: Mary J. Bossard, Madison, AL (US); Gayle Stephenson, Decatur, AL (US); Zhihao Fang, Madison, AL (US); Harold Zappe, Harvest, AL (US); Stacy Mitchell, Madison, AL (US); Ping Zhang, Madison, AL (US); Friedrich Scheiflinger, Vienna (AT); Peter Turecek, Klosterneuburg (AT); Juergen Siekmann, Vienna (AT); Katalin Varadi, Vienna (AT); Herbert Gritsch, Vienna (AT)

(73) Assignees: Nektar Therapeutics, San Francisco, CA (US); Baxalta Incorporated, Bannockburn, IL (US); Baxalta GmbH, Glattpark (Opfikon) (CH)

( * ) Notice: Subject to any disclaimer, the term of this patent is extended or adjusted under 35 U.S.C. 154(b) by 659 days.

This patent is subject to a terminal disclaimer.

(21) Appl. No.: 13/620,285

(22) Filed: Sep. 14, 2012

(65) Prior Publication Data

US 2013/0012442 A1    Jan. 10, 2013

Related U.S. Application Data

(63) Continuation of application No. 13/371,275, filed on Feb. 10, 2012, now Pat. No. 8,349,800, which is a continuation of application No. 12/006,059, filed on Dec. 27, 2007, now Pat. No. 8,133,865.

(60) Provisional application No. 60/877,531, filed on Dec. 27, 2006.

(51) Int. Cl.
| | |
|---|---|
| C07K 14/755 | (2006.01) |
| C07K 14/745 | (2006.01) |
| C07K 17/08 | (2006.01) |
| A61K 47/48 | (2006.01) |

(52) U.S. Cl.
CPC ....... *C07K 14/755* (2013.01); *A61K 47/48215* (2013.01)

(58) Field of Classification Search
None
See application file for complete search history.

(56) References Cited

U.S. PATENT DOCUMENTS

| | | | |
|---|---|---|---|
| 4,179,337 A | 12/1979 | Davis et al. | |
| 4,510,233 A | 4/1985 | Yokoyama et al. | |
| 5,122,614 A | 6/1992 | Zalipsky | |
| 5,298,643 A | 3/1994 | Greenwald | |
| 5,612,039 A | 3/1997 | Policappelli et al. | |
| 5,621,039 A | 4/1997 | Hallahan et al. | |
| 5,629,384 A | 5/1997 | Veronese et al. | |
| 5,637,749 A | 6/1997 | Greenwald | |
| 5,932,462 A | 8/1999 | Harris et al. | |
| 5,969,040 A | 10/1999 | Hallahan et al. | |
| 6,037,452 A | 3/2000 | Minamino et al. | |
| 6,048,720 A | 4/2000 | Dalborg et al. | |
| 6,362,254 B2 | 3/2002 | Harris et al. | |
| 6,514,491 B1 | 2/2003 | Bentley et al. | |
| 6,566,506 B2 | 5/2003 | Greenwald et al. | |
| 7,060,259 B2 | 6/2006 | Bentley et al. | |
| 7,125,843 B2 | 10/2006 | DeFrees et al. | |
| 7,199,223 B2 | 4/2007 | Bossard et al. | |
| 7,884,075 B2 | 2/2011 | Scheiflinger et al. | |
| 2005/0079155 A1 | 4/2005 | Marshall | |
| 2006/0171920 A1 | 8/2006 | Schechter et al. | |
| 2006/0293499 A1 | 12/2006 | Bentley et al. | |
| 2007/0027073 A1 | 2/2007 | Rubinstein et al. | |
| 2008/0058504 A1 | 3/2008 | Bossard et al. | |

FOREIGN PATENT DOCUMENTS

| | | |
|---|---|---|
| EP | 1249846 A2 | 10/2002 |
| WO | WO 94/15625 A1 | 7/1994 |
| WO | WO 2004/075923 A2 | 9/2004 |
| WO | WO 2004/089280 A2 | 10/2004 |
| WO | WO 2005/014049 A2 | 2/2005 |
| WO | WO 2006/071801 A2 | 7/2006 |
| WO | WO 2006/138752 A2 | 12/2006 |
| WO | WO 2007/019331 A2 | 2/2007 |
| WO | WO 2007/075534 A2 | 7/2007 |

OTHER PUBLICATIONS

Enzon Pharmaceuticals, "Macromolecular Engineering Technologies", pp. 1-14 (2004).
Nektar, "Transforming Therapeutics, Nektar Molecule Engineering: Polyethylene Glycol and Derivatives for Advanced PEGylation", Catalog, pp. 1-20 (2003).
Nekt AR, "Transfonning Therapeutics, Nektar Advanced PEGylation: Polyethylene Glycol and Derivatives for Advanced PEGylation", Catalog, pp. 1-24 (2004).
NOF Corporation, "PEG Derivatives, Phospholipid and Drug Delivery Materials for Pharmaceuticals", Catalog—1$^{st}$, pp. 1-46 (2003).
NOF Corporation, "PEG Derivatives, Phospholipid and Drug Delivery Materials for Pharmaceuticals", Catalog—2nd, pp. 1-50 (2003).
NOF Corporation, "PEG Derivatives, Phospholipids and Drug Delivery Materials for Pharmaceutical Products and Fonnulations", Catalog—Ver.8, pp. 1-59 (Apr. 2006).

(Continued)

*Primary Examiner* — Lisa J Hobbs
(74) *Attorney, Agent, or Firm* — Susan T. Evans; Mark A. Wilson; McDermott Will & Emery LLP

(57) ABSTRACT

The present invention provides von Willebrand Factor-polymer conjugates and Factor VIII-polymer conjugates, each having a releasable linkage. Methods of making conjugates, methods for administering conjugates, are also provided.

20 Claims, 55 Drawing Sheets

(56) References Cited

OTHER PUBLICATIONS

Polypure, "Products; PEG amines; PEG acids and amino acids; PEG thiols and disulfides", Biotins (Apr. 2004).

Polypure, "Products; PEG amines; PEG acids and amino acids; PEG thiols and disulfides", Biotins (Apr. 2005).

Quanta Biodesign, "Labeling, Derivatization and Crosslinking Reagents for Biological and Related Materials with dPEG", p. 1-38, Mar. 12, 2004.

Quanta Biodesign, "Labeling, Modification and Crosslinking Reagents incorporating our unique monodispersed dPEG Technology", pp. 1-31, Nov. 5, 2004.

Quanta Biodesign, Ltd., "Leading innovator, producer and provider of monodisperse PEG (dPEG) derivatives", Product Catalog, pp. 1-51, Updated: Jul. 18, 2005.

Quanta Biodesign, Ltd., "Leading innovator, producer and provider of mono disperse discrete PEG (dPEG) derivatives", Product Catalog, pp. 1-51, Updated: Nov. 17, 2005.

Shearwater Polymers, Inc., Catalog, pp. 2-49 (Mar. 1995).

Shearwater Polymers, Inc., "Polyethylene Glycol and Derivatives", Catalog, pp. 1-53 (Jul. 1997).

Shearwater Polymers, Inc., "Polyethylene Glycol and Derivatives: Functionalized Biocompatible Polymers for Research and Pharmaceuticals", Catalog, pp. 1-50 (2000).

Shearwater Corporation, "Polyethylene Glycol and Derivatives for Biomedical Applications", Catalog, pp. 1-17(2001).

Bodansky et al., "Derivatives of S-9 fluorenylmethyl-L-cysteine", Int. J. Peptide Protein Res., vol. 20, pp. 434-437 (1982).

Bordwell et al., "Steric inhibition of synergistic radical stabilizing effects", J. Org. chem.., pp. 58-93 (1990).

Eisenbeis et al., "A practical large scale synthesis of 9-(hydroxymethyl)-fluorene-4-carboxylic acid (HOFmCO2H)", Synthetic comm.., vol. 31, No. 22, pp. 3533-3536 (2001).

Gershonov et al., "New concept for long-acting insulin: spontaneous conversion of inactive modified insulin to the active hormone in circulation: 9-fluorenylmethoxycarbonyl derivative of insulin", Diabetes, vol. 48, pp. 1437-1442 (1999).

Gershonov et al., "A novel approach for a water-soluble long-acting insulin prodrug: design, preparation, and analysis of [(2-sulfo)-9 fluorenylmethoxycarbonyl]3-inulin", J. Med. Chem., vol. 43, pp. 2530-2537 (2000).

Greenwald, "Drug delivery systems: anticancer Prodrugs and their polymeric conjugates", Exp. Opin. Ther. Patents, vol. 7, No. 6, pp. 601-609 (1997).

Harris et al., "Effect of pegylation on pharmaceuticals", Nature Reviews, vol. 2, pp. 214-221 (2003).

International Search Report and Written Opinion from related PCT Patent Application No. PCT/US2007/026522 mailed on Mar. 4, 2009. Application mow published as PCT Patent Publication No. WO 2008/082669 on Jul. 10, 2008.

Liu et al., "A novel Fmoc-based anchorage for the synthesis of protected peptides on solid phase", Int. J. Peptide Protein Res., vol. 35, pp. 95-98 (1990).

Lottner et al., "Hematoporphyrin-derived soluble porphyrin-platinum conjugates with combined cytotoxic and phototoxic antitumor activity", J. Med. Chem., vol. 45, pp. 2064-2078 (2002).

Ouchi et al., "Design of antitumor agent-terminated poly(ethylene glycol) conjugate as macromolecular prodrugs", Polymer Preprints, vol. 38, No. 1, pp. 582-583 (1997).

Ouchi et al., "Synthesis and antitumor activity of poly(ethylene glycols)s linked to 5-fluorouracil via a urethane or urea bond", Drug Design and Discovery, vol. 9, pp. 93-105 (1992).

Peleg-Shulman et al., "Reversible PEGylation: a novel technology to release native interferon alpha2 over a prolonged time period", J. Med. Chem., vol. 47, pp. 4897-4904 (2004).

Pitzer et al., "New compounds: fluorine derivatives as potential carcinogens", J. Pharm. Sci., vol. 57, No. 2, pp. 348-349 (1968).

Rostin et al., "B-domain deleted recombinant coagulation factor VIII modified with monomethoxy polyethylene glycol", Bioconjugate Chem., vol. 11, pp. 387-396 (2000).

Shechter et al., "Prolonging the half-life of human interferon-alpha2 in circulation: design, preparation, and analysis of (2-sulfo-9-fluorenylmethoxycarbonyl)7-interferon-alpha2", PNAS, vol. 98, No. 3, pp. 1212-1217 (2001).

Shechter et al., "Reversible PEGylation of peptide YY3-36 prolongs its inhibition of food intake in mice", FEBS Letters, vol. 579, pp. 2439-2444 (2005).

Shechter et al., "New twchnologies to prolong life-time of peptide and protein drugs in vivo", Int. J. Peptide Res. Ther., vol. 13, No. 1-2, pp. 105-117 (2006).

Shechter et al., "Prolonging the actions of protein and peptide drugs by a novel approach of reversible pegylation", Proc. Third Int. Twenty-Eighth Eur. Peptide Symp., Prague, Czech Republic, pp. 48-51, Sep. 5-10, 2004.

Sims et al., "A method for the estimation of polyethylene glycol in plasma protein fractions", Analytical Biochemistry, vol. 107, pp. 60-63 (1980).

Tsubery et al., "Prolonging the action of protein and peptide drugs by a novel approach of reversible polyethylene glycol modification", J. Biological Chemistry, vol. 279, No. 37, pp. 38118-38124 (2004).

Zalipsky, "Synthesis of an end-group functionalized polyethykene glycol-lipid conjugate for preparation of polymer-grafted liposomes", Bioconjugate Chem., vol. 4, pp. 296-299 (1993).

Zier et al., "Polyethylene glycol bound benzyl-and fluorenyl derivatives as solubilizing side-chain protecting groups in peptide synthesis", Tetrahedron Letters, vol. 35, No. 7, pp. 1039-1042 (1994).

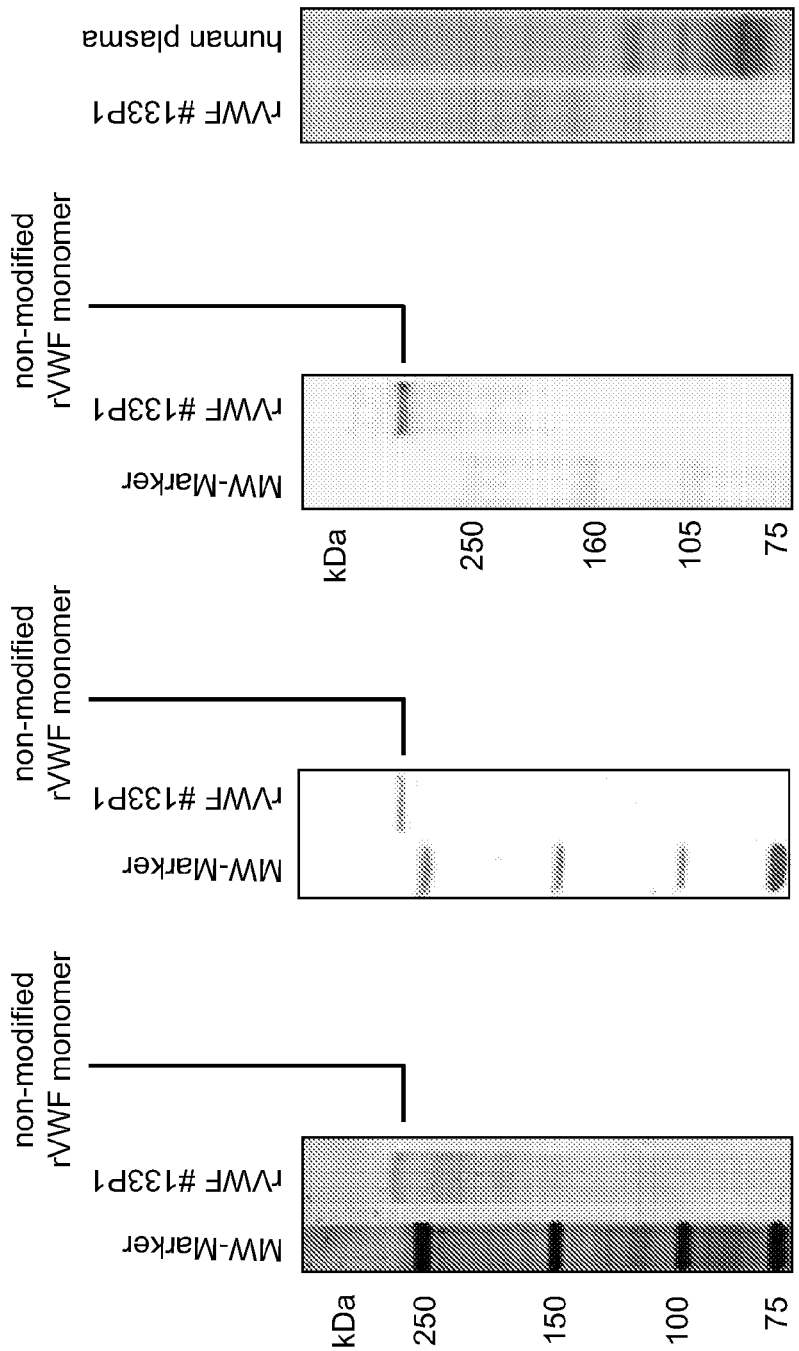

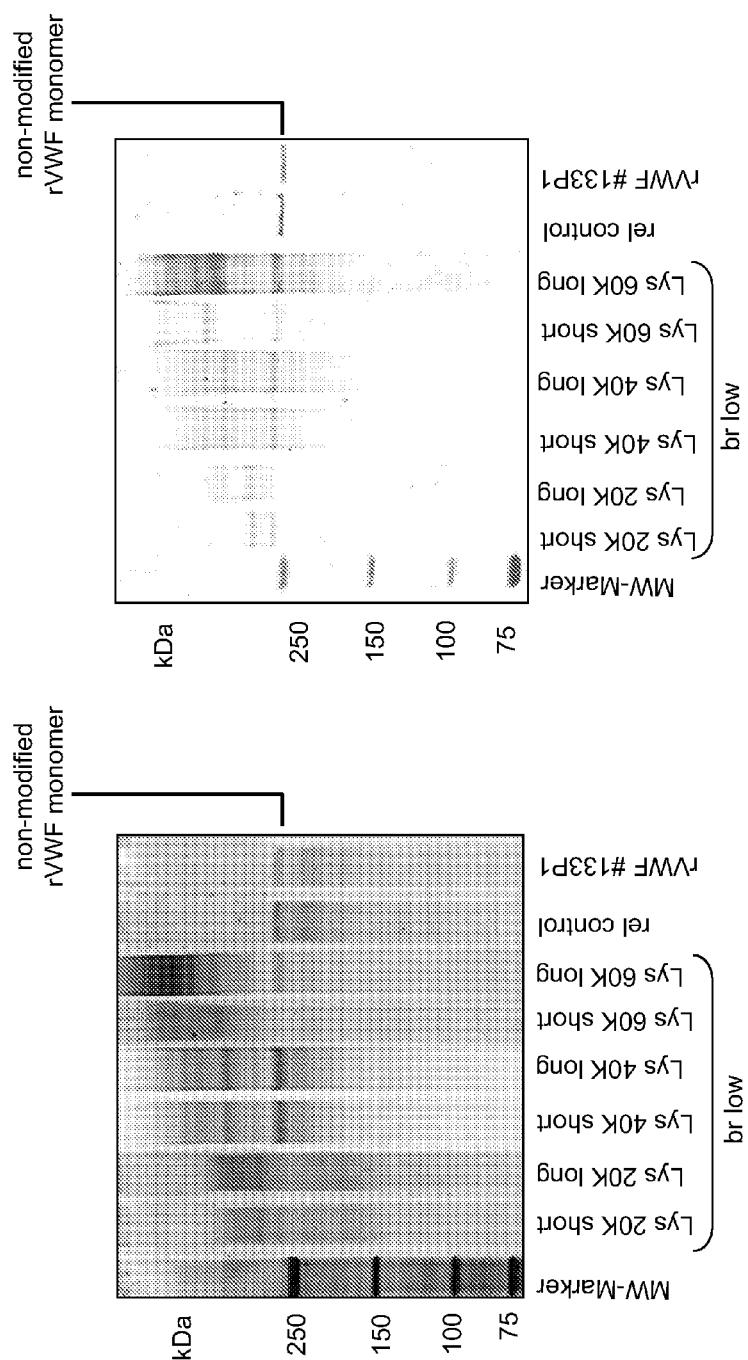

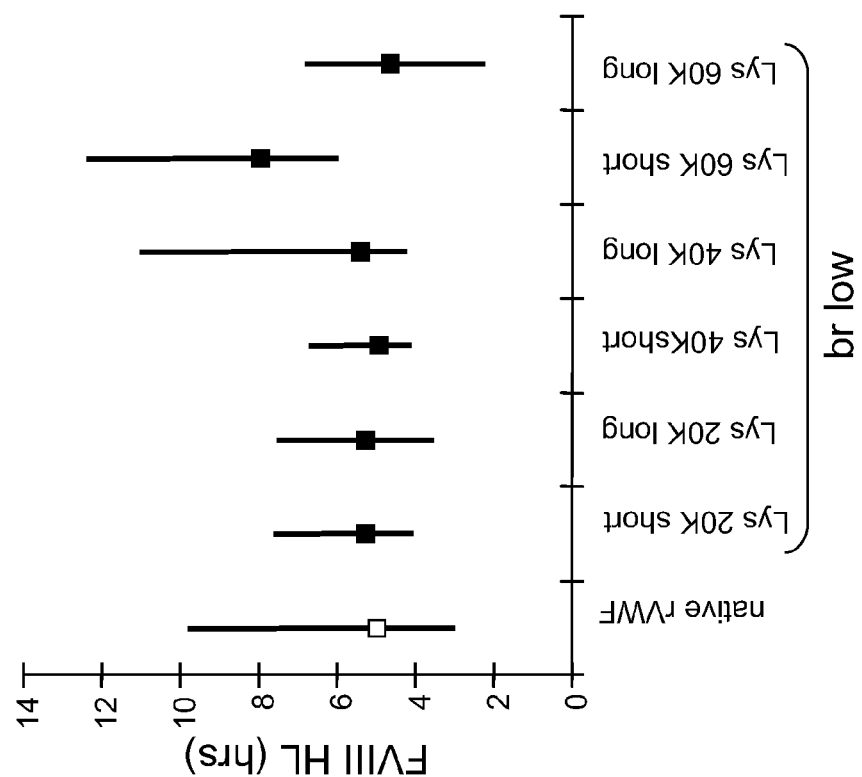
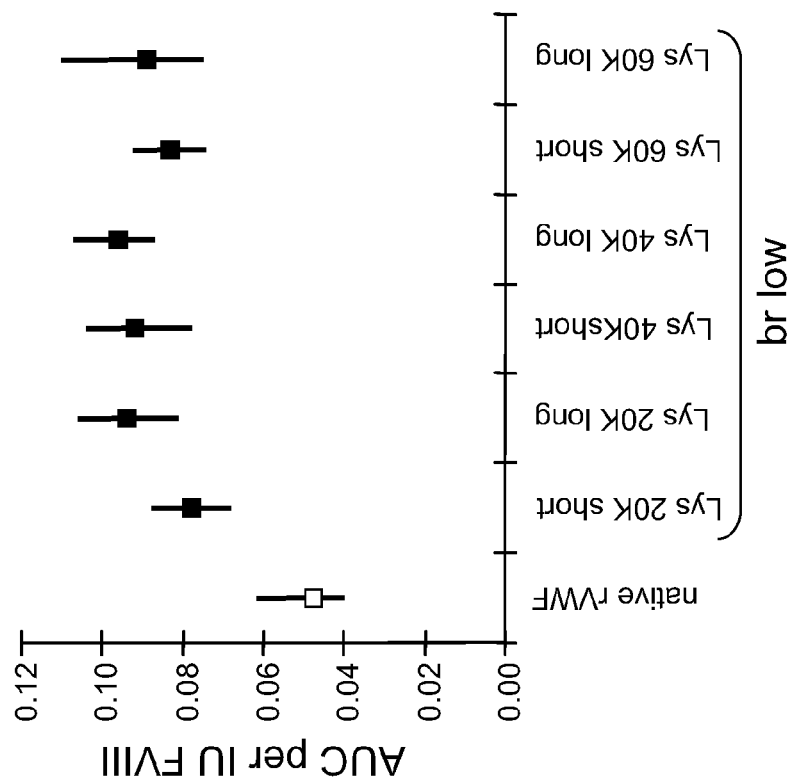
Figure 24A
Figure 24B

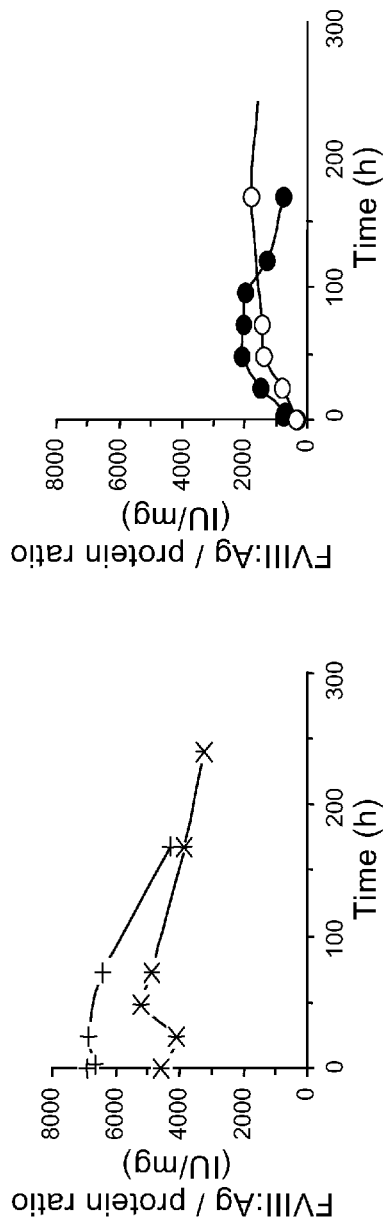
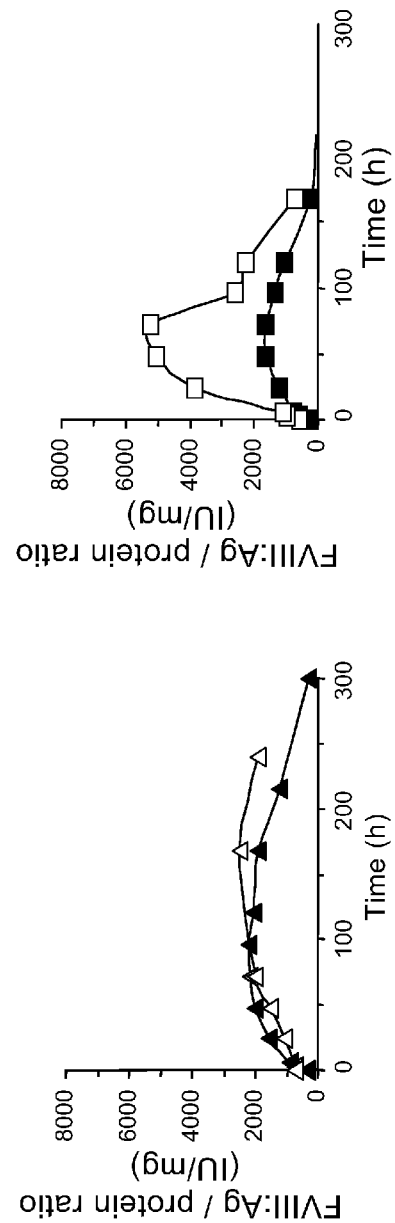

VON WILLEBRAND FACTOR- AND FACTOR VIII-POLYMER CONJUGATES HAVING A RELEASABLE LINKAGE

CROSS-REFERENCE TO RELATED APPLICATION

This application is a continuation of U.S. application Ser. No. 13/371,275, filed Feb. 10, 2012, now U.S. Pat. No. 8,349,800, which is a continuation of U.S. application Ser. No. 12/006,059, filed Dec. 27, 2007, now U.S. Pat. No. 8,133,865, which claims the benefit of priority to U.S. Provisional Application No. 60/877,531, filed Dec. 27, 2006, the contents each of which is expressly incorporated herein by reference in its entirety.

BACKGROUND OF THE INVENTION

The present invention relates generally to polymer-active agent conjugates having a releasable linkage to thereby release the active agent in vivo. In addition, the invention relates to, among other things, methods for synthesizing the conjugates, methods for purifying the conjugates, and so on.

BACKGROUND OF THE INVENTION

Scientists and clinicians face a number of challenges in their attempts to develop active agents into forms suited for delivery to a patient. Active agents that are polypeptides, for example, are often delivered via injection rather than orally. In this way, the polypeptide is introduced into the systemic circulation without exposure to the proteolytic environment of the stomach. Injection of polypeptides, however, has several drawbacks. For example, many polypeptides have a relatively short half-life, thereby necessitating repeated injections, which are often inconvenient and painful. Moreover, some polypeptides can elicit one or more immune responses with the consequence that the patient's immune system attempts to destroy or otherwise neutralize the immunogenic polypeptide. Of course, once the polypeptide has been destroyed or otherwise neutralized, the polypeptide cannot exert its intended pharmacodynamic activity. Thus, delivery of active agents such as polypeptides is often problematic even when these agents are administered by injection.

Some success has been achieved in addressing the problems of delivering active agents via injection. For example, conjugating the active agent to a water-soluble polymer has resulted in a polymer-active agent conjugate having reduced immunogenicity and antigenicity. In addition, these polymer-active agent conjugates often have greatly increased half-lives compared to their unconjugated counterparts as a result of decreased clearance through the kidney and/or decreased enzymatic degradation in the systemic circulation. As a result of having a greater half-life, the polymer-active agent conjugate requires less frequent dosing, which in turn reduces the overall number of painful injections and inconvenient visits with a health care professional. Moreover, active agents that were only marginally soluble demonstrate a significant increase in water solubility when conjugated to a water-soluble polymer.

Due to its documented safety as well as its approval by the FDA for both topical and internal use, polyethylene glycol has been conjugated to active agents. When an active agent is conjugated to a polymer of polyethylene glycol or "PEG," the conjugated active agent is conventionally referred to as "PEGylated." The commercial success of PEGylated active agents such as PEGASYS® PEGylated interferon alpha-2a (Hoffmann-La Roche, Nutley, N.J.), PEG-INTRON® PEGylated interferon alpha-2b (Schering Corp., Kennilworth, N.J.), and NEULASTA™ PEG-filgrastim (Amgen Inc., Thousand Oaks, Calif.) demonstrates that administration of a conjugated form of an active agent can have significant advantages over the unconjugated counterpart. Small molecules such as distearoylphosphatidylethanolamine (Zalipsky (1993) *Bioconjug. Chem.* 4(4):296-299) and fluorouracil (Ouchi et al. (1992) *Drug Des. Discov.* 9(1):93-105) have also been PEGylated. Harris et al. have provided a review of the effects of PEGylation on pharmaceuticals. Harris et al. (2003) *Nat. Rev. Drug Discov.* 2(3): 214-221.

Despite these successes, conjugation of a polymer to an active agent to result in a commercially relevant drug is often challenging. For example, conjugation can result in the polymer being attached at or near a site on the active agent that is necessary for pharmacologic activity (e.g., at or near a binding site). Such conjugates may therefore have unacceptably low activity due to, for example, the steric effects introduced by the polymer. Attempts to remedy conjugates having unacceptably low activity can be frustrated when the active agent has few or no other sites suited for attachment to a polymer. Thus, additional PEGylation alternatives have been desired.

One suggested approach for solving this and other problems is "reversible PEGylation" wherein the native active agent (or a moiety having increased activity compared to the PEGylated active agent) is released. For example, reversible PEGylation has been disclosed in the field of cancer chemotherapies. See Greenwald (1997) *Exp. Opin. Ther. Patents* 7(6):601-609. U.S. Patent Application Publication No. 2005/0079155 describes conjugates using reversible linkages. As described in this publication, reversible linkages can be effected through the use of an enzyme substrate moiety. It has been pointed out, however, that approaches relying on enzymatic activity are dependent on the availability of enzymes. See Peleg-Schulman (2004) *J. Med. Chem.* 47:4897-4904. Patient variability around the amount and activity of these enzymes can introduce inconsistent performance of the conjugate among different populations. Thus, additional approaches that do not rely on enzymatic processes for polymer release have been described as being desirable.

Another approach for reversible PEGylation is described in U.S. Pat. No. 7,060,259, which described (among other things) water-soluble prodrugs in which a biologically active agent is linked to a water-soluble non-immunogenic polymer by a hydrolyzable carbamate bond. As described therein, the biologically active agent can be readily released by the hydrolysis of the carbmate bond in vivo without the need for adding enzymes or catalytic materials.

Another approach for reversible PEGylation is described in Peleg-Schulman (2004) *J. Med. Chem.* 47:4897-4904, WO 2004/089280 and U.S. Patent Application Publication No. 2006/0171920. Although this approach has been applied to a limited number of active agents, these references ignore other active agents for which reversible PEGylation would be particularly suited. Yet another releasable approach is described in U.S. Patent Application Publication No. 2006/0293499.

In the area of bleeding disorders, proteins (such as, for example, von Willebrand Factor and Factor VIII) can sometimes be administered to a patient to address or otherwise ameliorate the bleeding disorder. Due to the relatively short half-life of such proteins, it would be advantageous to increase the in vivo half-life of these proteins by, for example, reversible PEGylation. Thus, the present invention seeks to solve this and other needs in the art.

SUMMARY OF THE INVENTION

In one or more embodiments of the invention, a conjugate of the following formula is provided:

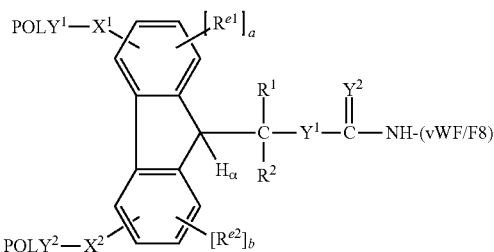

wherein:
POLY$^1$ is a first water-soluble polymer;
POLY$^2$ is a second water-soluble polymer;
X$^1$ is a first spacer moiety;
X$^2$ is a second spacer moiety;
H$_\alpha$ is an ionizable hydrogen atom;
R$^1$ is H or an organic radical;
R$^2$ is H or an organic radical;
(a) is either zero or one;
(b) is either zero or one;
R$^{e1}$, when present, is a first electron altering group;
R$^{e2}$, when present, is a second electron altering group; and
Y$^1$ is O or S;
Y$^2$ is O or S; and
(vWF/F8) is a residue of an amine-containing biologically active agent selected from the group consisting of a von Willebrand Factor moiety and a Factor VIII moiety.

In one or more embodiments of the invention, methods for preparing conjugates are provided.

In one or more embodiments of the invention, pharmaceutical preparations comprising the conjugates are provided.

In one or more embodiments of the invention, methods for administering the conjugates are provided.

In one or more embodiments of the invention, a construct is provided, the construct comprising a conjugate as provided herein bound to at least one Factor VIII moiety.

In one or more embodiments of the invention, a von Willebrand Factor-water soluble polymer conjugate is provided, the conjugate having an in vivo half-life increased by a factor of at least 1.5 as compared to the in vivo half-life of a von Willebrand Factor moiety not conjugated to the water-soluble polymer.

In one or more embodiments of the invention, a von Willebrand Factor-water soluble polymer conjugate is provided, the conjugate having an in vivo half-life increased by a factor of at least 2 as compared to the in vivo half-life of a von Willebrand Factor moiety not conjugated to the water-soluble polymer.

In one or more embodiments of the invention, a Factor VIII moiety-water soluble polymer conjugate is provided, the conjugate having an in vivo half-life increased by a factor of at least 1.5 as compared to the in vivo half-life of a Factor VIII moiety not conjugated to the water-soluble polymer.

BRIEF DESCRIPTION OF THE FIGURES

FIGS. 7A-7D show the structural characterization of native rVWF 133P1 by electrophoresis. FIG. 7A: Reduced SDS-PAGE followed by silver-staining. FIG. 7B: Reduced SDS-PAGE followed by Coomassie staining. FIG. 7C: Immunoblot with a polyclonal anti-human VWF antibody of the gels of the reduced SDS-PAGE. FIG. 7D: VWF multimer distribution visualized by 2.5% agarose gel electrophoresis detected with anti VWF antibody. Further information concerning this figure is provided in Example 5.

FIGS. 8A and 8B show the domain structure of releasable PEGylated rVWF conjugates visualized by reducing SDS-PAGE with protein staining. FIG. 8A: Reduced SDS-PAGE followed by silver-staining. FIG. 8B: Reduced SDS-PAGE followed by Coomassie staining. Further information concerning this figure is provided in Example 5.

FIG. 9A: Immunoblot with a polyclonal anti-human VWF antibody of the gels of the reduced SDS-PAGE. FIG. 9B: Immunoblot with a polyclonal anti-PEG antibody of the gels of the reduced SDS-PAGE. Further information concerning this figure is provided in Example 5.

FIG. 10A: Multimer distribution detected with anti VWF antibody in the gel. FIG. 10B: PEGylated VWF multimers detected with anti PEG antibody after immunolotting. Further information concerning this figure is provided in Example 5.

FIG. 11A: VWF multimer structure visualized by anti VWF antibody in the gel. FIG. 11B: PEGylated VWF multimers detected with anti PEG antibody after immunolotting. Further information concerning this figure is provided in Example 5.

FIG. 16A: Time-dependent changes in VWF:Ag. FIG. 16B: Time-dependent changes in FVIII:activity. Data are displayed as IU VWF:Ag/ml or IU FVIII/ml mouse plasma. Circles: PEGylated rVWF (1.6 mg/kg) and rFVIII.(200 IU/kg); triangles: native rVWF (1.6 mg/kg) and rFVIII (200 IU/kg). The symbols show the mean values±SD of the 6 plasma samples obtained at each time point. Further information concerning this figure is provided in Example 5.

FIG. 17A: Time-dependent changes in VWF:Ag. FIG. 17B: Time-dependent changes in FVIII:activity. Data are displayed as IU VWF:Ag/ml or IU FVIII/ml mouse plasma. Circles: PEGylated rVWF (1.6 mg/kg) and rFVIII (200 IU/kg); triangles: native rVWF (1.6 mg/kg) and rFVIII (200 IU/kg). The symbols show the mean values±SD of the 6 plasma samples obtained at each time point. Further information concerning this figure is provided in Example 5.

FIG. 18A: Time-dependent changes in VWF:Ag. FIG. 18B: Time-dependent changes in FVIII:activity. Data are displayed as IU VWF:Ag/ml or IU FVIII/ml mouse plasma. Circles: PEGylated rVWF (1.6 mg/kg) and rFVIII (180 IU/kg); triangles: native rVWF (1.6 mg/kg) and rFVIII (190 IU/kg). The symbols show the mean values±SD of the 6 plasma samples obtained at each time point. Further information concerning this figure is provided in Example 5.

FIG. 19A: Time-dependent changes in VWF:Ag. FIG. 19B: Time-dependent changes in FVIII:activity. Data are displayed as IU VWF:Ag/ml or IU FVIII/ml mouse plasma. Circles: PEGylated rVWF (1.6 mg/kg) and rFVIII (190 IU/kg); triangles: native rVWF (1.6 mg/kg) and rFVIII (190 IU/kg). The symbols show the mean values÷SD of the 6 plasma samples obtained at each time point. Further information concerning this figure is provided in Example 5.

FIG. 20A: Time-dependent changes in VWF:Ag. FIG. 20B: Time-dependent changes in FVIII:activity. Data are displayed as IU VWF:Ag/ml or IU FVIII/ml mouse plasma. Circles: PEGylated rVWF (1.6 mg/kg) and rFVIII (200 IU/kg); triangles: native rVWF (1.6 mg/kg) and rFVIII (200 IU/kg). The symbols show the mean values±SD of the 6 plasma samples obtained at each time point. Further information concerning this figure is provided in Example 5.

FIG. 21A: Time-dependent changes in VWF:Ag. FIG. 21B: Time-dependent changes in FVIII:activity. Data are displayed as IU VWF:Ag/ml or IU FVIII/ml mouse plasma. Circles: PEGylated rVWF (1.6 mg/kg) and rFVIII (200 IU/kg); triangles: native rVWF (1.6 mg/kg) and rFVIII (200 IU/kg). The symbols show the mean values±SD of the 6 plasma samples obtained at each time point. Further information concerning this figure is provided in Example 5.

FIG. 22A: Time-dependent changes in VWF:Ag. FIG. 22B: Time-dependent changes in FVIII: activity. Open squares: PEGylated rVWF Lys 20K br short low and rFVIII; squares: PEGylated rVWF Lys 20K br long low and rFVIII; open triangels: PEGylated rVWF Lys 40K br short low and rFVIII; triangles: PEGylated rVWF Lys 40K br long low and rFVIII; circles: PEGylated rVWF Lys 60K br short low and rFVIII; circles: PEGylated rVWF Lys 60K br long low and rFVIII; and stars: native rVWF (133 pool 1) and rFVIII. Further information concerning this figure is provided in Example 5.

FIGS. 24A and 24B show the AUC and half life for FVIII, co-injected with PEGylated rVWF candidates, respectively. Further information concerning this figure is provided in Example 5.

FIG. 28A: Immunoblot with a polyclonal anti-human FVIII antibody. FIG. 28B: Immunoblot with a polyclonal antibody directed against PEG. Further information concerning this figure is provided in Example 6.

FIG. 29A: Immunoblot with a monoclonal anti-human FVIII HC-A2 domain antibody. FIG. 29B: Immunoblot with a monoclonal anti-human FVIII LC-A3 domain antibody. Further information concerning this figure is provided in Example 6.

FIG. 35A: Thrombin generation curves obtained with rFVIII MOQ HEPES01-E spiked into FVIII deficient plasma; line a: without rFVIII; line b: 0.0025 µg rFVIII/ml; line c: 0.01 µg rFVIII/ml; line d: 0.025 µg rFVIII/ml; line e: 0.1 µg rFVIII/ml. FIG. 35B: Linear dose response curves of native rFVIII MOQ HEPES01-E. Further information concerning this figure is provided in Example 6.

FIG. 37A: native rFVIII MOQ HEPES01-E (stars) and FVIII control (cross). FIG. 37B: PEG-rFVIII Lys 20K br short (closed circles) and long (open circles). FIG. 37C: PEG-rFVIII Lys 40K br short (closed triangles) and long (open triangles). FIG. 37D: PEG-rFVIII Lys 60K br short (closed squares) and long (open squares). Further information concerning this figure is provided in Example 6.

FIGS. 38A-38D show the recovery of FVIII:Ag upon incubation in buffer at pH 8.1. FIG. 38A: native rFVIII MOQ HEPES01-E (stars) and FVIII control (cross). FIG. 38B: PEG-rFVIII Lys 20K br short (closed circles) and long (open circles). FIG. 38C: PEG-rFVIII Lys 40K br short (closed triangles) and long (open triangles). FIG. 38D: PEG-rFVIII Lys 60K br short (closed squares) and long (open squares). Further information concerning this figure is provided in Example 6.

FIG. 42A: Changes in FVIII activity upon incubation expressed as IU FVIII:Chrom activity/mg protein. FIG. 42B: Changes of the FVIII specific activities relative to the initial value expressed as % of the initial values measured immediately after the addition to the plasma. Symbols: black stars, native rFVIII MOQ HEPES 01-E; closed circles, PEG-rFVIII Lys 20K br short; open circles, PEG-rFVIII Lys 20K br long; closed triangles, PEG-rFVIII Lys 40K br short; open triangles, PEG-rFVIII Lys 40K br long. Further information concerning this figure is provided in Example 6.

FIG. 43A: Changes in ratio of FVIII antigen/protein upon incubation expressed as IU FVIII:Ag/mg protein. FIG. 43B: Changes of the ratio FVIII antigen/protein relative to the initial value expressed as % of the initial values measured immediately after the addition to the plasma. Symbols: black stars, native rFVIII MOQ HEPES01-E; closed circles, PEG-rFVIII Lys 20K br short; open circles, PEG-rFVIII Lys 20K br long; closed triangles, PEG-rFVIII Lys 40K br short; open triangles: PEG-rFVIII Lys 40K br long. Further information concerning this figure is provided in Example 6.

FIG. 44A: absolute FVIII activity levels in plasma; closed circles, PEG-rFVIII (320 IU/kg, 168 µg/kg); closed triangles, native rFVIII (170 IU/kg, 25 µg/kg). The symbols show the mean values +/−SD of the 6 plasma samples obtained at each point of time. Further information concerning this figure is provided in Example 6.

FIG. 45A: absolute FVIII activity levels in plasma; closed circles, PEG-rFVIII (210 IU/kg, 164 µg/kg); closed triangles, native rFVIII (200 IU/kg, 35 µg/kg). The symbols show the mean values +/−SD of the 6 plasma samples obtained at each point of time. Further information concerning this figure is provided in Example 6.

FIG. 46A: absolute FVIII activity levels in plasma; closed circles, PEG-rFVIII (230 IU/kg, 94 µg/kg); closed triangles: native rFVIII (230 IU/kg, 32 µg/kg). The symbols show the mean values +/−SD of the 6 plasma samples obtained at each point of time. Further information concerning this figure is provided in Example 6.

FIG. 47A: absolute FVIII activity levels in plasma; closed circles: PEG-rFVIII (230 IU/kg, 94 µg/kg); closed triangles: native rFVIII (230 IU/kg, 32 µg/kg). The symbols show the mean values +/−SD of the 6 plasma samples obtained at each point of time. Further information concerning this figure is provided in Example 6.

FIG. 48A: absolute FVIII activity levels in plasma; closed circles, PEG-rFVIII (200 IU/kg, 133 µg/kg); closed triangles: native rFVIII (190 IU/kg, 32 µg/kg). The symbols show the mean values +/−SD of the 6 plasma samples obtained at each point of time. Further information concerning this figure is provided in Example 6.

FIG. 49A: absolute FVIII activity levels in plasma; closed circles: PEG-rFVIII (170 IU/kg, 62 µg/kg); closed triangles: native rFVIII (190 IU/kg, 32 µg/kg). The symbols show the mean values +/−SD of the 6 plasma samples obtained at each point of time. Further information concerning this figure is provided in Example 6.

FIG. 51A: Area under the curve (dose adjusted). The symbols show the mean values +/−95% confidence intervals for the respective PEG-rFVIII conjugate; data for rFVIII native are the mean+/−95% confidence intervals of all control groups performed, equivalent to 24 animals per time point; open squares: native rFVIII; closed squares: PEG-rFVIII. Further information concerning this figure is provided in Example 6.

DETAILED DESCRIPTION OF THE INVENTION

Figure 1:
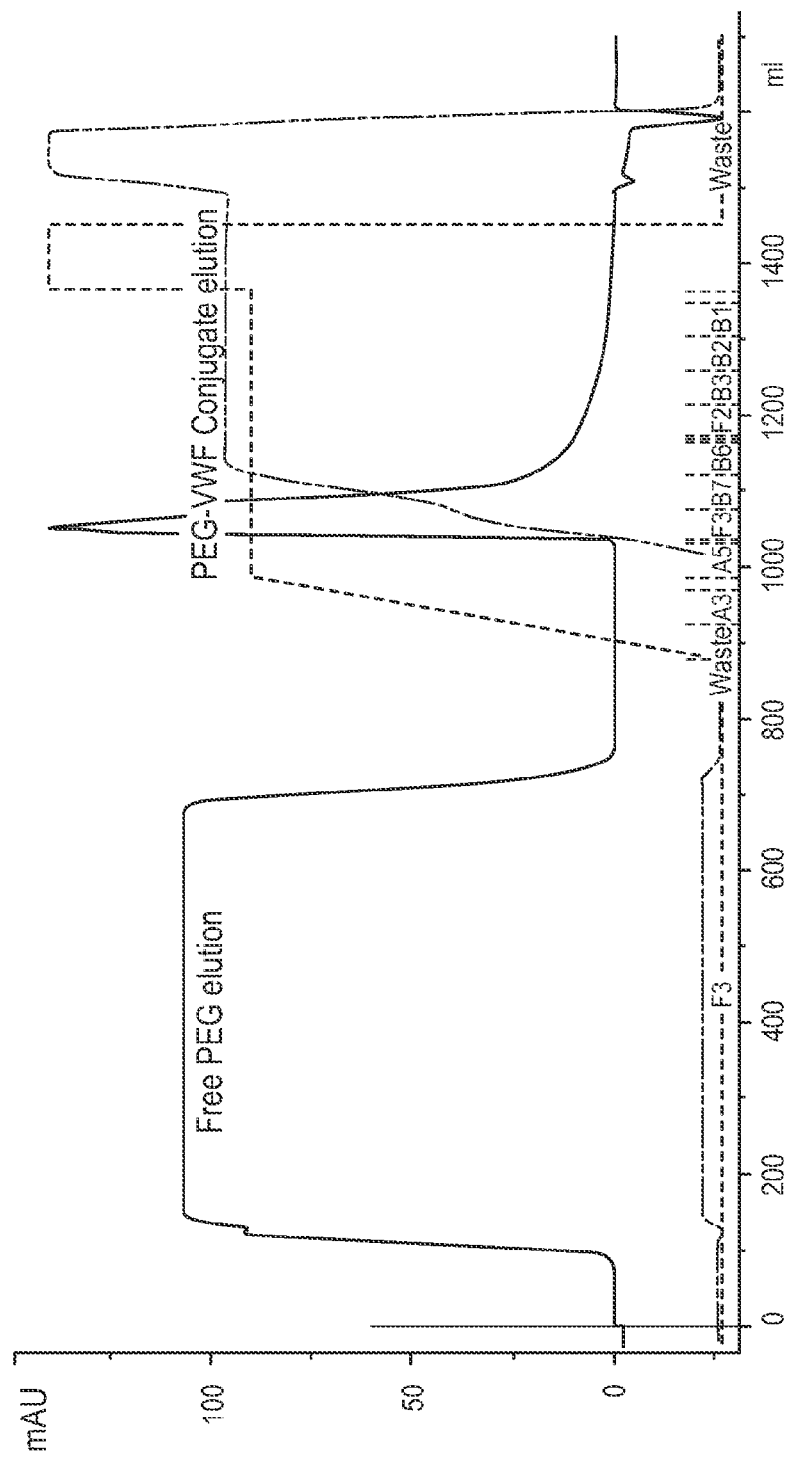
FIG. 1 shows a typical chromatogram of a conjugate composition prepared in accordance with the procedure set forth in Example 1A.

Before describing the present invention in detail, it is to be understood that this invention is not limited to particular polymers, synthetic techniques, active agents, and the like, as such may vary.

It must be noted that, as used in this specification and the claims, the singular forms "a," "an," and "the" include plural referents unless the context clearly dictates otherwise. Thus, for example, reference to a "polymer" includes a single polymer as well as two or more of the same or different polymers, reference to a "conjugate" refers to a single conjugate as well as two or more of the same or different conjugates, reference to an "excipient" includes a single excipient as well as two or more of the same or different excipients, and the like.

In describing and claiming the present invention, the following terminology will be used in accordance with the definitions described below.

"PEG," "polyethylene glycol" and "poly(ethylene glycol)" as used herein, are meant to encompass any water-soluble poly(ethylene oxide). Typically, PEGs for use in accordance with the invention comprise the following structure "—O(CH$_2$CH$_2$O)$_n$—" where (m) is 2 to 4000. As used herein, PEG also includes "—CH$_2$CH$_2$—O(CH$_2$CH$_2$O)$_m$—CH$_2$CH$_2$—" and "—(CH$_2$CH$_2$O)$_m$—," depending upon whether or not the terminal oxygens have been displaced. When the PEG further comprises a spacer moiety (to be described in greater detail below), the atoms comprising the spacer moiety, when covalently attached to a water-soluble polymer segment, do not result in the formation of an oxygen-oxygen bond (i.e., an "—O—O—" or peroxide linkage). Throughout the specification and claims, it should be remembered that the term "PEG" includes structures having various terminal or "end capping" groups and so forth. The term "PEG" also means a polymer that contains a majority, that is to say, greater than 50%, of —CH$_2$CH$_2$O— monomeric subunits. With respect to specific forms, the PEG can take any number of a variety of molecular weights, as well as structures or geometries such as "branched," "linear," "forked," "multifunctional," and the like, to be described in greater detail below.

The terms "end-capped" or "terminally capped" are interchangeably used herein to refer to a terminal or endpoint of a polymer having an end-capping moiety. Typically, although not necessarily, the end-capping moiety comprises a hydroxy or C$_{1-20}$ alkoxy group. Thus, examples of end-capping moieties include alkoxy (e.g., methoxy, ethoxy and benzyloxy), as well as aryl, heteroaryl, cyclo, heterocyclo, and the like. In addition, saturated, unsaturated, substituted and unsubstituted forms of each of the foregoing are envisioned. Moreover, the end-capping group can also be a silane. The end-capping group can also advantageously comprise a detectable label. When the polymer has an end-capping group comprising a detectable label, the amount or location of the polymer and/or the moiety (e.g., active agent) of interest to which the polymer is coupled can be determined by using a suitable detector. Such labels include, without limitation, fluorescers, chemiluminescers, moieties used in enzyme labeling, colorimetric (e.g., dyes), metal ions, radioactive moieties, and the like. Suitable detectors include photometers, films, spectrometers, and the like.

"Non-naturally occurring" with respect to a polymer or water-soluble polymer means a polymer that in its entirety is not found in nature. A non-naturally occurring polymer or water-soluble polymer may, however, contain one or more subunits or portions of a subunit that are naturally occurring, so long as the overall polymer structure is not found in nature.

The term "water-soluble polymer" is any polymer that is soluble in water at room temperature. Typically, a water-soluble polymer will transmit at least about 75%, more preferably at least about 95% of light, transmitted by the same solution after filtering. On a weight basis, a water-soluble polymer will preferably be at least about 35% (by weight) soluble in water, more preferably at least about 50% (by weight) soluble in water, still more preferably about 70% (by weight) soluble in water, and still more preferably about 85% (by weight) soluble in water. It is still more preferred, however, that the water-soluble polymer is about 95% (by weight) soluble in water and most preferred that the water-soluble polymer is completely soluble in water.

Molecular weight in the context of a water-soluble polymer of the invention, such as PEG, can be expressed as either a number average molecular weight or a weight average molecular weight. Unless otherwise indicated, all references to molecular weight herein refer to the weight average molecular weight. Both molecular weight determinations, number average and weight average, can be measured using gel permeation chromatography or other liquid chromatography techniques. Other methods for measuring molecular weight values can also be used, such as the use of end-group analysis or the measurement of colligative properties (e.g., freezing-point depression, boiling-point elevation, or osmotic pressure) to determine number average molecular weight or the use of light scattering techniques, ultracentrifugation or viscometry to determine weight average molecular weight. The polymers of the invention are typically polydisperse (i.e., number average molecular weight and weight average molecular weight of the polymers are not equal), possessing low polydispersity values of preferably less than about 1.2, more preferably less than about 1.15, still more preferably less than about 1.10, yet still more preferably less than about 1.05, and most preferably less than about 1.03.

As used herein, the term "carboxylic acid" is a moiety having a

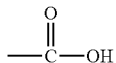

functional group [also represented as a "—COOH" or —C(O)OH], as well as moieties that are derivatives of a carboxylic acid, such derivatives including, for example, protected carboxylic acids. Thus, unless the context clearly dictates otherwise, the term carboxylic acid includes not only the acid form, but corresponding esters and protected forms as well. With regard to protecting groups suited for a carboxylic acid and any other functional group described herein, reference is made to Greene et al., "PROTECTIVE GROUPS IN ORGANIC SYNTHESIS" 3$^{rd}$ Edition, John Wiley and Sons, Inc., New York, 1999.

The terms "reactive" and "activated" when used in conjunction with a particular functional group, refer to a reactive functional group that reacts readily with an electrophile or a nucleophile on another molecule. This is in contrast to those groups that require strong catalysts or highly impractical reaction conditions in order to react (i.e., a "nonreactive" or "inert" group).

The terms "protected," "protecting group," and "protective group" refer to the presence of a moiety (i.e., the protecting group) that prevents or blocks reaction of a particular chemically reactive functional group in a molecule under certain reaction conditions. The protecting group will vary depending upon the type of chemically reactive functional group being protected as well as the reaction conditions to be employed and the presence of additional reactive or protecting groups in the molecule, if any. Protecting groups known in the art can be found in Greene et al., supra.

As used herein, the term "functional group" or any synonym thereof is meant to encompass protected forms thereof.

The terms "spacer" or "spacer moiety" are used herein to refer to an atom or a collection of atoms optionally appearing between one moiety and another. The spacer moieties may be hydrolytically stable or may include one or more physiologically hydrolyzable or enzymatically releasable linkages.

An "organic radical" as used herein includes, for example, alkyl, substituted alkyl, alkenyl, substituted alkenyl, alkynyl, substituted alkynyl, aryl and substituted aryl.

"Alkyl" refers to a hydrocarbon chain, typically ranging from about 1 to 20 atoms in length. Such hydrocarbon chains are preferably but not necessarily saturated and may be branched or straight chain, although typically straight chain is preferred. Exemplary alkyl groups include methyl, ethyl, propyl, butyl, pentyl, 1-methylbutyl, 1-ethylpropyl, 3-methylpentyl, and the like. As used herein, "alkyl" includes cycloalkyl when three or more carbon atoms are referenced and lower alkyl.

"Lower alkyl" refers to an alkyl group containing from 1 to 6 carbon atoms, and may be straight chain or branched, as exemplified by methyl, ethyl, n-butyl, iso-butyl, and tert-butyl.

"Cycloalkyl" refers to a saturated or unsaturated cyclic hydrocarbon chain, including bridged, fused, or spiro cyclic compounds, preferably made up of 3 to about 12 carbon atoms, more preferably 3 to about 8 carbon atoms.

"Non-interfering substituents" are those groups that, when present in a molecule, are typically non-reactive with other functional groups contained within the molecule.

The term "substituted" as in, for example, "substituted alkyl," refers to a moiety (e.g., an alkyl group) substituted with one or more non-interfering substituents, such as, but not limited to: $C_3$-$C_8$ cycloalkyl, e.g., cyclopropyl, cyclobutyl, and the like; halo, e.g., fluoro, chloro, bromo, and iodo; cyano; alkoxy, lower phenyl; substituted phenyl; and the like, for one or more hydrogen atoms. "Substituted aryl" is aryl having one or more non-interfering groups as a substituent. For substitutions on a phenyl ring, the substituents may be in any orientation (i.e., ortho, meta, or para). "Substituted ammonium" is ammonium having one or more non-interfering groups (e.g., an organic radical) as a substituent.

"Alkoxy" refers to an —O—R group, wherein R is alkyl or substituted alkyl, preferably $C_1$-$C_{20}$ alkyl (e.g., methoxy, ethoxy, propyloxy, benzyl, etc.), more preferably $C_1$-$C_7$ alkyl.

As used herein, "alkenyl" refers to a branched or unbranched hydrocarbon group of 2 to 15 atoms in length, containing at least one double bond. Exemplary alkenyl include (without limitation) ethenyl, n-propenyl, isopropenyl, n-butenyl, iso-butenyl, octenyl, decenyl, tetradecenyl, and the like.

The term "alkynyl" as used herein refers to a branched or unbranched hydrocarbon group of 2 to 15 atoms in length, containing at least one triple bond. Exemplary alkynyl include (without limitation) ethynyl, n-butynyl, iso-pentynyl, octynyl, decynyl, and so forth.

"Aryl" means one or more aromatic rings, each of 5 or 6 core carbon atoms. Aryl includes multiple aryl rings that may be fused, as in naphthyl, or unfused, as in biphenyl. Aryl rings may also be fused or unfused with one or more cyclic hydrocarbon, heteroaryl, or heterocyclic rings. As used herein, "aryl" includes heteroaryl. An aromatic-containing moiety (e.g., $Ar^1$, $Ar^2$, and so forth), means a structure containing aryl.

"Heteroaryl" is an aryl group containing from one to four heteroatoms, preferably N, O, or S, or a combination thereof. Heteroaryl rings may also be fused with one or more cyclic hydrocarbon, heterocyclic, aryl, or heteroaryl rings.

"Heterocycle" or "heterocyclic" means one or more rings of 5-12 atoms, preferably 5-7 atoms, with or without unsaturation or aromatic character and having at least one ring atom which is not a carbon. Preferred heteroatoms include sulfur, oxygen, and nitrogen.

"Substituted heteroaryl" is heteroaryl having one or more non-interfering groups as substituents.

"Substituted heterocycle" is a heterocycle having one or more side chains formed from non-interfering substituents.

"Electrophile" refers to an ion or atom or collection of atoms, that may be ionic, having an electrophilic center, i.e., a center that is electron seeking, capable of reacting with a nucleophile.

"Nucleophile" refers to an ion or atom or collection of atoms that may be ionic having a nucleophilic center, i.e., a center that is seeking an electrophilic center or with an electrophile.

A "physiologically cleavable" as well as a "hydrolyzable" bond is a relatively weak bond that reacts with water (i.e., is hydrolyzed) under physiological conditions. The tendency of a bond to hydrolyze in water will depend not only on the general type of linkage connecting two central atoms but also on the substituents attached to these central atoms. Exemplary hydrolyzable bonds include, but are not limited to, carboxylate ester, phosphate ester, anhydride, acetal, ketal, acyloxyalkyl ether, imine, and ortho esters.

A "releasable linkage" includes, but is not limited to, a physiologically cleavable bond, a hydrolyzable bond, and an enzymatically degradable linkage. Thus, a "releasable linkage" is a linkage that may undergo either hydrolysis or cleavage by some other mechanism (e.g., enzyme-catalyzed, acid-catalyzed, base-catalyzed, and so forth) under physiological conditions. For example, a "releasable linkage" can involve an elimination reaction that has a base abstraction of a proton, (e.g., an ionizable hydrogen atom, $H_\alpha$), as the driving force. For purposes herein, a "releasable linkage" is synonymous with a "degradable linkage,"

An "enzymatically releasable linkage" means a linkage that is subject to degradation by one or more enzymes.

A "hydrolytically stable" linkage or bond refers to a chemical bond, typically a covalent bond, that is substantially stable in water, that is to say, does not undergo hydrolysis under physiological conditions to any appreciable extent over an extended period of time. Examples of hydrolytically stable linkages include but are not limited to the following: carbon-carbon bonds (e.g., in aliphatic chains), ethers, amides, and the like. Generally, a hydrolytically stable linkage is one that exhibits a rate of hydrolysis of less than about 1-2% per day under physiological conditions. Hydrolysis rates of representative chemical bonds can be found in most standard chemistry textbooks. It must be pointed out that some linkages can be hydrolytically stable or hydrolyzable, depending upon (for example) adjacent and neighboring atoms and ambient conditions. One of ordinary skill in the art can determine whether a given linkage or bond is hydrolytically stable or hydrolyzable in a given context by, for example, placing a linkage-containing molecule of interest under conditions of interest and testing for evidence of hydrolysis (e.g., the presence and amount of two molecules resulting from the cleavage of a single molecule). Other approaches known to those of ordinary skill in the art for determining whether a given linkage or bond is hydrolytically stable or hydrolyzable can also be used.

The terms "active agent," "biologically active agent" and "pharmacologically active agent" are used interchangeably herein and are defined to include any agent, drug, compound, composition of matter or mixture that provides some pharmacologic, often beneficial, effect that can be demonstrated in vivo or in vitro. This includes food supplements, nutrients, nutriceuticals, drugs, proteins, vaccines, antibodies, vitamins, and other beneficial agents. As used herein, these terms further include any physiologically or pharmacologically active substance that produces a localized or systemic effect in a patient.

"Pharmaceutically acceptable excipient" or "pharmaceutically acceptable carrier" refers to an excipient that can be included in the compositions of the invention and that causes no significant adverse toxicological effects to the patient.

"Pharmacologically effective amount," "physiologically effective amount," and "therapeutically effective amount" are used interchangeably herein to mean the amount of a polymer-active agent conjugate—typically present in a pharmaceutical preparation—that is needed to provide a desired level of active agent and/or conjugate in the bloodstream or in a target tissue. The exact amount will depend upon numerous factors, e.g., the particular active agent, the components and physical characteristics of the pharmaceutical preparation, intended patient population, patient considerations, and the like, and can readily be determined by one of ordinary skill in the art, based upon the information provided herein and available in the relevant literature.

"Multifunctional" in the context of a polymer means a polymer having 3 or more functional groups contained therein, where the functional groups may be the same or different. Multifunctional polymers will typically contain from about 3-100 functional groups, or from 3-50 functional groups, or from 3-25 functional groups, or from 3-15 functional groups, or from 3 to 10 functional groups, or will contain 3, 4, 5, 6, 7, 8, 9 or 10 functional groups within the polymer. A "difunctional" polymer means a polymer having two functional groups contained therein, either the same (i.e., homodifunctional) or different (i.e., heterodifunctional).

"Branched," in reference to the geometry or overall structure of a polymer, refers to polymer having 2 or more polymer "arms." A branched polymer may possess 2 polymer arms, 3 polymer arms, 4 polymer arms, 6 polymer arms, 8 polymer arms or more. One particular type of highly branched polymer is a dendritic polymer or dendrimer, which, for the purposes of the invention, is considered to possess a structure distinct from that of a branched polymer.

A "dendrimer" or dendritic polymer is a globular, size monodisperse polymer in which all bonds emerge radially from a central focal point or core with a regular branching pattern and with repeat units that each contribute a branch point. Dendrimers exhibit certain dendritic state properties such as core encapsulation, making them unique from other types of polymers.

A basic or acidic reactant described herein includes neutral, charged, and any corresponding salt forms thereof.

The term "patient," refers to a living organism suffering from or prone to a condition that can be prevented or treated by administration of a conjugate as provided herein, and includes both humans and animals.

As used herein, "drug release rate" means a rate (stated as a half-life) in which half of the total amount of polymer-active agent conjugates in a system will cleave into the active agent and a polymeric residue.

"Optional" and "optionally" mean that the subsequently described circumstance may or may not occur, so that the description includes instances where the circumstance occurs and instances where it does not.

As used herein, the "halo" designator (e.g., fluoro, chloro, iodo, bromo, and so forth) is generally used when the halogen is attached to a molecule, while the suffix "ide" (e.g., fluoride, chloride, iodide, bromide, and so forth) is used when the halogen exists in its independent ionic form (e.g., such as when a leaving group leaves a molecule).

In the context of the present discussion, it should be recognized that the definition of a variable provided with respect to one structure or formula is applicable to the same variable repeated in a different structure, unless the context dictates otherwise.

As previously stated, the present invention comprises (among other things) conjugates having a releasable linkage.

Before describing exemplary conjugates of the invention, embodiments of a water-soluble polymer and a functional group capable of reacting with an amino group of an active agent to form a releasable linkage, such as a carbamate linkage, will be discussed.

With respect to a given water-soluble polymer, each water-soluble polymer (e.g., POLY, POLY$^1$ and POLY$^2$) can comprise any polymer so long as the polymer is water-soluble and non-peptidic. Although preferably a poly(ethylene glycol), a water-soluble polymer for use herein can be, for example, other water-soluble polymers such as other poly(alkylene glycols) [also referred to as "poly(alkyleneoxides)"], such as poly(propylene glycol) ("PPG"), copolymers of ethylene glycol and propylene glycol and the like, poly(olefinic alcohol), poly(vinylpyrrolidone), poly(hydroxyalkylmethacrylamide), poly(hydroxyalkylmethacrylate), poly(saccharides), poly(α-hydroxy acid), poly(vinyl alcohol), polyphosphazene, polyoxazoline, poly(N-acryloylmorpholine), such as described in U.S. Pat. No. 5,629,384. The water soluble polymer can be a homopolymer, copolymer, terpolymer, nonrandom block polymer, and random block polymer of any of the foregoing. In addition, a water-soluble polymer can be linear, but can also be in other forms (e.g., branched, forked, and the like) as will be described in further detail below. In the context of being present within an overall structure, a water-soluble polymer has from 1 to about 300 termini.

In instances where the polymeric reagent comprises two or more water-soluble polymers, each water-soluble polymer in the overall structure can be the same or different. It is preferred, however, that all water-soluble polymers in the overall structure are of the same type. For example, it is preferred that all water-soluble polymers within a given structure are poly(ethylene glycol)polymers.

Although the weight-average molecular weight of any individual water-soluble polymer can vary, the weight average molecular weight of any given water-soluble polymer will typically be in the following range: 100 Daltons to about 150,000 Daltons. Exemplary ranges, however, include weight-average molecular weights in the following ranges: in the range of from about 880 Daltons to about 5,000 Daltons; in the range of greater than 5,000 Daltons to about 100,000 Daltons; in the range of from about 6,000 Daltons to about 90,000 Daltons; in the range of from about 10,000 Daltons to about 85,000 Daltons; in the range of greater than 10,000 Daltons to about 85,000 Daltons; in the range of from about 20,000 Daltons to about 85,000 Daltons; in the range of from about 53,000 Daltons to about 85,000 Daltons; in the range of from about 25,000 Daltons to about 120,000 Daltons; in the range of from about 29,000 Daltons to about 120,000 Daltons; in the range of from about 35,000 Daltons to about 120,000 Daltons; in the range of about 880 Daltons to about 60,000 Daltons; in the range of about 440 Daltons to about 40,000 Daltons; in the range of about 440 Daltons to about 30,000 Daltons; and in the range of from about 40,000 Daltons to about 120,000 Daltons. For any given water-soluble polymer, PEGs having a molecular weight in one or more of these ranges are preferred.

Exemplary weight-average molecular weights for the water-soluble polymer include about 100 Daltons, about 200 Daltons, about 300 Daltons, about 400 Daltons, about 440 Daltons, about 500 Daltons, about 600 Daltons, about 700 Daltons, about 750 Daltons, about 800 Daltons, about 900 Daltons, about 1,000 Daltons, about 1,500 Daltons, about 2,000 Daltons, about 2,200 Daltons, about 2,500 Daltons, about 3,000 Daltons, about 4,000 Daltons, about 4,400 Daltons, about 4,500 Daltons, about 5,000 Daltons, about 5,500 Daltons, about 6,000 Daltons, about 7,000 Daltons, about 7,500 Daltons, about 8,000 Daltons, about 9,000 Daltons, about 10,000 Daltons, about 11,000 Daltons, about 12,000 Daltons, about 13,000 Daltons, about 14,000 Daltons, about 15,000 Daltons, about 16,000 Daltons, about 17,000 Daltons, about 18,000 Daltons, about 19,000 Daltons, about 20,000 Daltons, about 22,500 Daltons, about 25,000 Daltons, about 30,000 Daltons, about 35,000 Daltons, about 40,000 Daltons, about 45,000 Daltons, about 50,000 Daltons, about 55,000 Daltons, about 60,000 Daltons, about 65,000 Daltons, about 70,000 Daltons, and about 75,000 Daltons. Branched versions of the water-soluble polymer (e.g., a branched 40,000 Dalton water-soluble polymer comprised of two 20,000 Dalton polymers) having a total weight average molecular weight of any of the foregoing can also be used.

The polymeric reagent used to prepare the conjugate will comprise at least one water-soluble polymer having a total size in the range suited for the desired rate of release of the conjugate formed therefrom. For example, a conjugate having a relatively long release rate can be prepared from a polymeric reagent having a size suited for (a) extended circulation prior to release of the active agent from the conjugate, and (b) moderately rapid in vivo clearance of the species liberated from the conjugate upon release from the conjugate. Likewise, when the conjugate has a relatively fast release rate, then the polymeric reagent would typically have a lower molecular weight.

When a PEG is used as the water-soluble polymer(s) in the polymeric reagent, the PEG typically comprises a number of ($OCH_2CH_2$) monomers [or ($CH_2CH_2O$) monomers, depending on how the PEG is defined]. As used throughout the description, the number of repeating units is identified by the subscript "n" in "($OCH_2CH_2$)$_n$." Thus, the value of (n) typically falls within one or more of the following ranges: from 2 to about 3400, from about 4 to about 1500, from about 100 to about 2300, from about 100 to about 2270, from about 136 to about 2050, from about 225 to about 1930, from about 450 to about 1930, from about 1200 to about 1930, from about 568 to about 2727, from about 660 to about 2730, from about 795 to about 2730, from about 795 to about 2730, from about 909 to about 2730, and from about 1,200 to about 1,900. For any given polymer in which the molecular weight is known, it is possible to determine the number of repeating units (i.e., "n") by dividing the total weight-average molecular weight of the polymer by the molecular weight of the repeating monomer.

Each water-soluble polymer is typically biocompatible and non-immunogenic. With respect to biocompatibility, a substance is considered biocompatible if the beneficial effects associated with use of the substance alone or with another substance (e.g., an active agent) in connection with living tissues (e.g., administration to a patient) outweighs any deleterious effects as evaluated by a clinician, e.g., a physician. With respect to non-immunogenicity, a substance is considered non-immunogenic if use of the substance alone or with another substance in connection with living tissues does not produce an immune response (e.g., the formation of antibodies) or, if an immune response is produced, that such a response is not deemed clinically significant or important as evaluated by a clinician. It is particularly preferred that the water-soluble polymers described herein as well as conjugates of active agents and the polymers are biocompatible and non-immunogenic.

In one form useful, free or nonbound PEG is a linear polymer terminated at each end with hydroxyl groups:

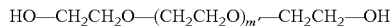

wherein (m') typically ranges from zero to about 4,000, preferably from about 20 to about 1,000.

The above polymer, alpha-, omega-dihydroxylpoly(ethylene glycol), can be represented in brief form as HO-PEG-OH where it is understood that the -PEG-symbol can represent the following structural unit:

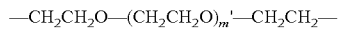

where (m') is as defined as above.

Another type of free or nonbound PEG useful in the present invention is methoxy-PEG-OH, or mPEG in brief, in which one terminus is the relatively inert methoxy group, while the other terminus is a hydroxyl group. The structure of mPEG is given below.

where (m') is as described above.

Multi-armed or branched PEG molecules, such as those described in U.S. Pat. No. 5,932,462, can also be used as the PEG polymer. For example, PEG can have the structure:

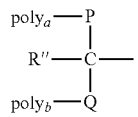

wherein:

$poly_a$ and $poly_b$ are PEG backbones (either the same or different), such as methoxy poly(ethylene glycol);

R" is a nonreactive moiety, such as H, methyl or a PEG backbone; and

P and Q are nonreactive linkages. In a preferred embodiment, the branched PEG polymer is methoxy poly(ethylene glycol) disubstituted lysine.

In addition, the PEG can comprise a forked PEG. An example of a free or nonbound forked PEG is represented by the following formula:

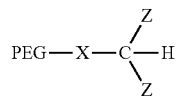

wherein: X is a spacer moiety and each Z is an activated terminal group linked to CH by a chain of atoms of defined length. The chain of atoms linking the Z functional groups to the branching carbon atom serve as a tethering group and may comprise, for example, alkyl chains, ether chains, ester chains, amide chains and combinations thereof. U.S. Pat. No. 6,362,254, discloses various forked PEG structures capable of use in the present invention.

The PEG polymer may comprise a pendant PEG molecule having reactive groups, such as carboxyl, covalently attached along the length of the PEG rather than at the end of the PEG chain. The pendant reactive groups can be attached to the PEG directly or through a spacer moiety, such as an alkylene group.

In addition to the above-described forms of PEG, each water-soluble polymer in the polymeric reagent can also be prepared with one or more weak or releasable linkages in the polymer, including any of the above described polymers. For example, PEG can be prepared with ester linkages in the polymer that are subject to hydrolysis. As shown below, this hydrolysis results in cleavage of the polymer into fragments of lower molecular weight:

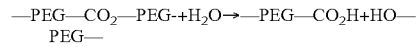

Other hydrolytically releasable linkages, useful as a releasable linkage within a polymer backbone, include carbonate linkages; imine linkages resulting, for example, from reaction of an amine and an aldehyde (see, e.g., Ouchi et al. (1997) *Polymer Preprints* 38(1):582-3); phosphate ester linkages formed, for example, by reacting an alcohol with a phosphate group; hydrazone linkages which are typically formed by reaction of a hydrazide and an aldehyde; acetal linkages that are typically formed by reaction between an aldehyde and an alcohol; ortho ester linkages that are, for example, formed by reaction between a formate and an alcohol; amide linkages formed by an amine group, e.g., at an end of a polymer such as PEG, and a carboxyl group of another PEG chain; urethane linkages formed from reaction of, e.g., a PEG with a terminal isocyanate group and a PEG alcohol; peptide linkages formed by an amine group, e.g., at an end of a polymer such as PEG, and a carboxyl group of a peptide; and oligonucleotide linkages formed by, for example, a phosphoramidite group, e.g., at the end of a polymer, and a 5' hydroxyl group of an oligonucleotide.

It is understood by those of ordinary skill in the art that the term poly(ethylene glycol) or PEG represents or includes all the above forms of PEG.

Those of ordinary skill in the art will recognize that the foregoing discussion concerning substantially water-soluble polymers is by no means exhaustive and is merely illustrative, and that all polymeric materials having the qualities described above are contemplated. As used herein, the term "water-soluble polymer" refers both to a molecule as well as the residue of water-soluble polymer that has been attached to another moiety. The following description of a water-soluble polymer are applicable not only to the polymeric reagent, but to the corresponding conjugates formed using the described polymeric reagents.

The functional group of the polymeric reagents used to form the conjugates described herein is a functional group capable of reacting with an amino group of an active agent to form a releasable linkage, such as a carbamate linkage. The invention is not limited with respect to the specific functional group so long as the functional group is capable of reacting with an amino group of an active agent to form a releasable linkage, such as a carbamate linkage. Exemplary functional groups capable of reacting with an amino group of an active agent include those functional groups selected from the group consisting of active carbonates such as N-succinimidyl, 1-benzotriazolyl, imidazole, carbonate halides (such as carbonate chloride and carbonate bromide), phenolates (such as p-nitrophenolate) and so forth. Also, as a special case, if the active agent is available with the active amine group converted into an isocyanate or isothiocyanate group, then the functional group of the polymeric reagent can be hydroxyl as the reaction of these components provides a releasable carbamate linkage.

$R^1$ is H or an organic radical;
$R^2$ is H or an organic radical;
(a) is either zero or one;
(b) is either zero or one;
$R^{e1}$, when present, is a first electron altering group;
$R^{e2}$, when present, is a second electron altering group; and
(FG) is a functional group capable of reacting with an amino group of an active agent to form a releasable linkage, such as a carbamate linkage.

Exemplary polymeric reagents fall within the following formulae:

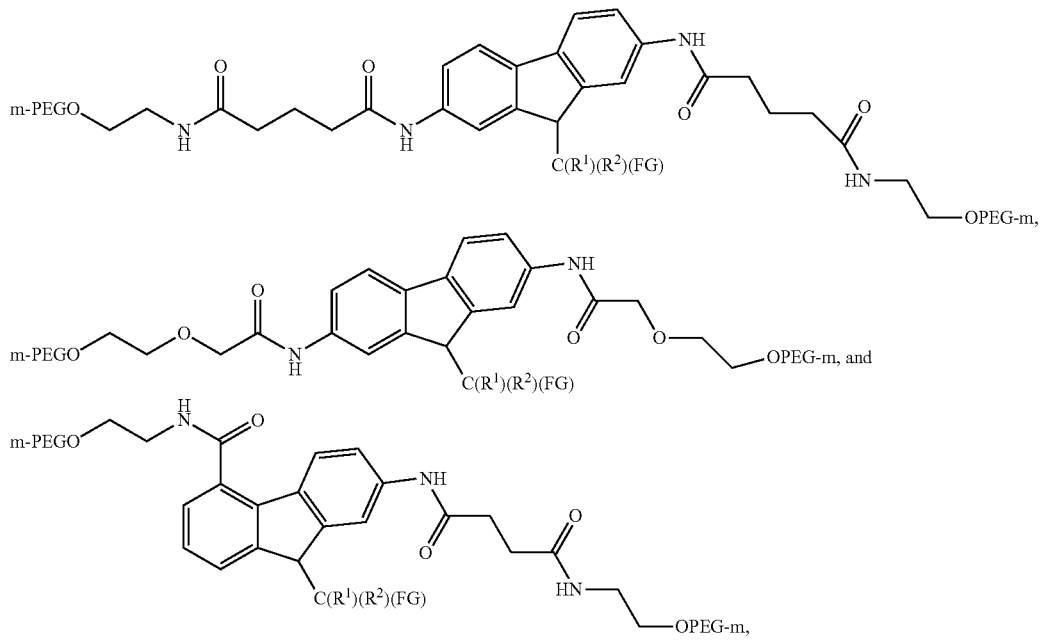

Exemplary polymeric reagents will now be discussed in further detail. It must be remembered that while stereochemistry is not specifically shown in any formulae or structures (whether for a polymeric reagent, conjugate, or any other formula or structure), the provided formulae and structures contemplate both enantiomers, as well as compositions comprising mixtures of each enantiomer in equal amounts (i.e., a racemic mixture) and unequal amounts.

An exemplary polymeric reagent has the following structure:

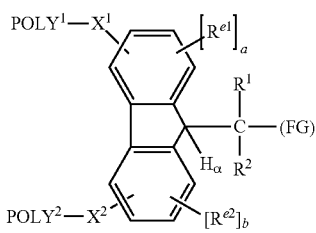

wherein:
POLY$^1$ is a first water-soluble polymer;
POLY$^2$ is a second water-soluble polymer;
X$^1$ is a first spacer moiety;
X$^2$ is a second spacer moiety;
H$_\alpha$ is an ionizable hydrogen atom;

wherein, in each instance: (FG) is a functional group capable of reacting with an amino group of an active agent to form a releasable linkage, such as a carbamate linkage; $R^1$ is H or an organic radical; and $R^2$ is H or an organic radical.

Still other exemplary polymeric reagents have the structure:

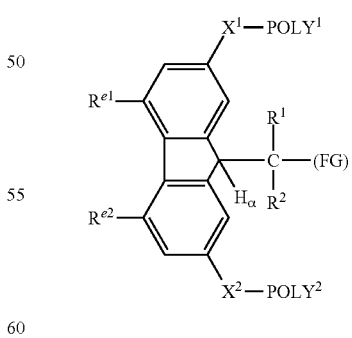

wherein each of POLY$^1$, POLY$^2$, X$^1$, X$^2$, $R^1$, $R^2$, H$_\alpha$ and (FG) is as previously defined, and $R^{e1}$ is a first electron altering group; and $R^{e2}$ is a second electron altering group.

Still other exemplary polymeric reagents fall within the following structures

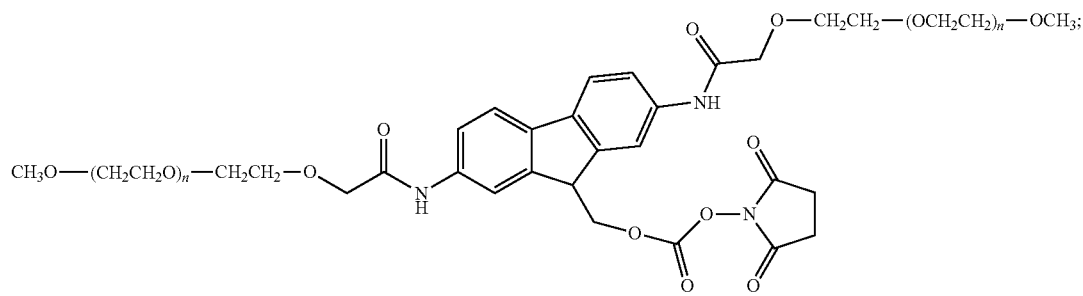
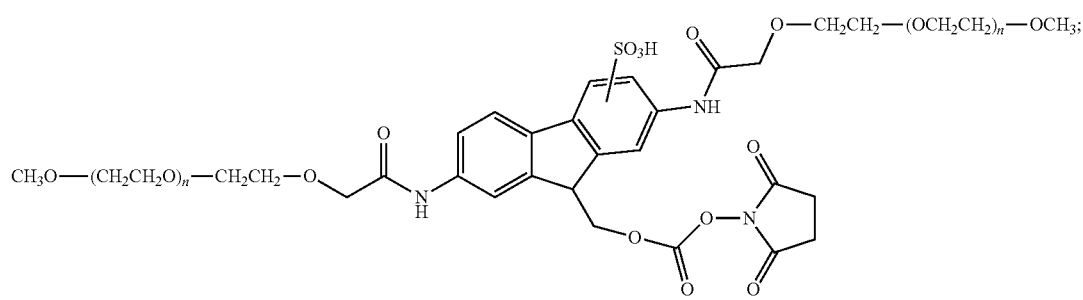
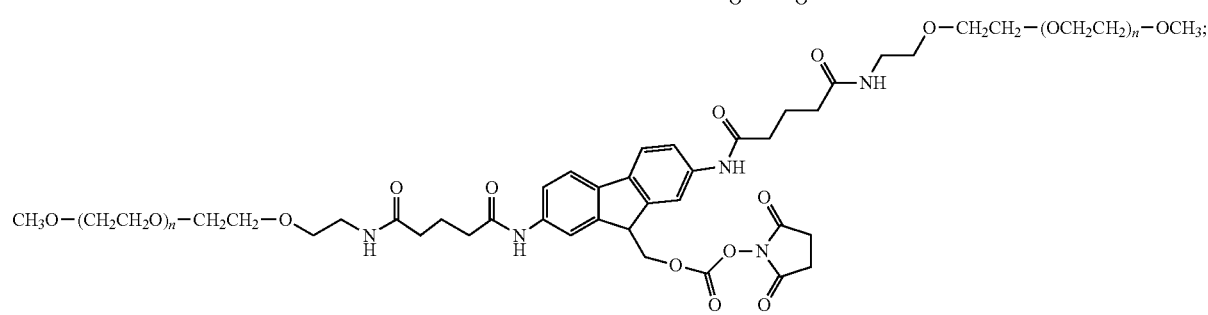
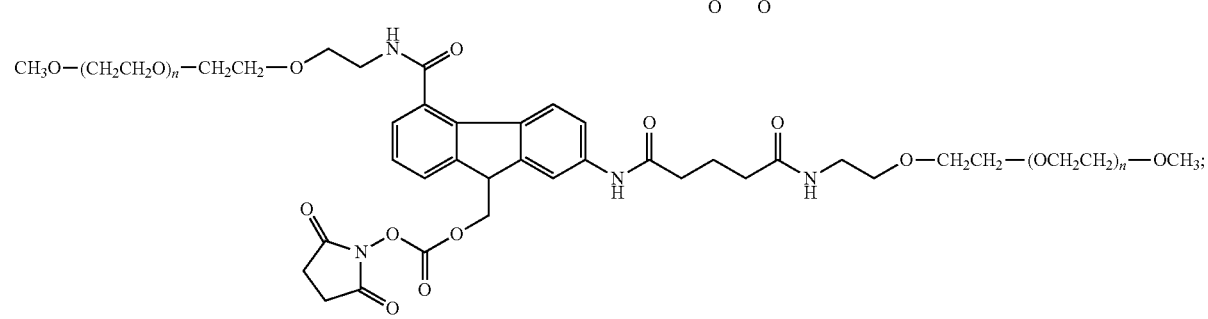
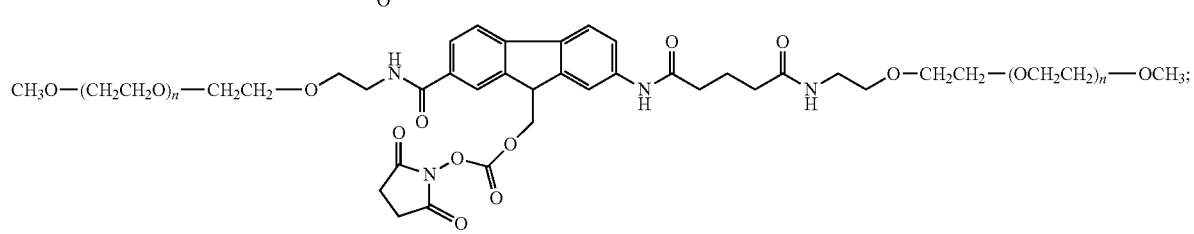
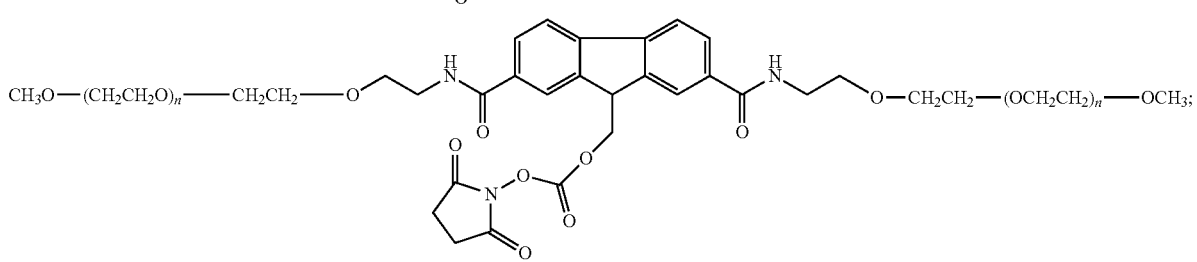

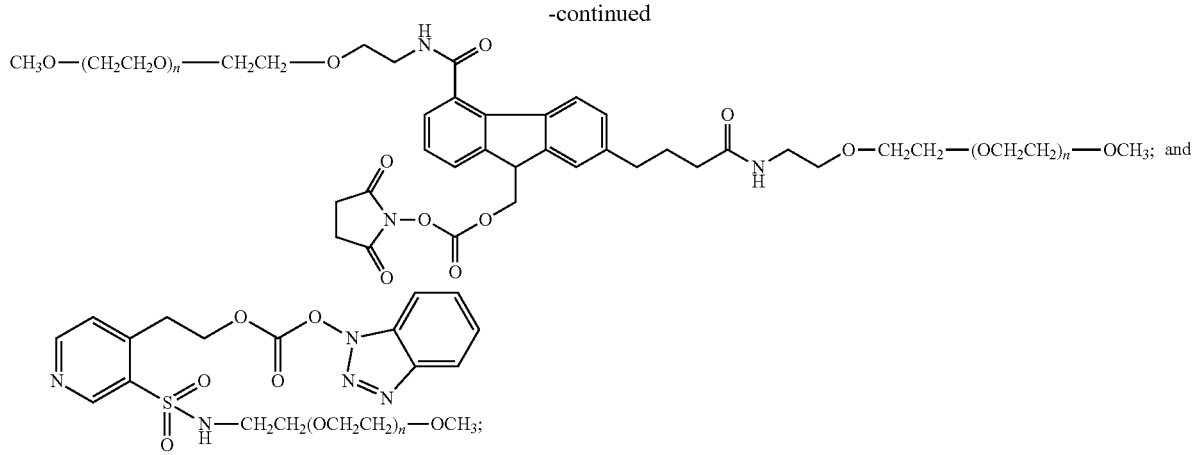

wherein, for each structure and in each instance, (n) is independently an integer from 4 to 1500.

The polymeric reagents can be prepared in any number of ways. Consequently, synthesis of the polymeric reagents is not limited to the specific technique or approach used in their preparation.

In one method for preparing a polymeric reagent useful in preparing the conjugates described herein, the method comprises: (a) providing an aromatic-containing moiety bearing a first attachment site, a second attachment site and an optional third attachment site; (b) reacting a functional group reagent with the first attachment site to result in the first attachment site bearing a functional group capable of reacting with an amino group of an active agent and result in a releasable linkage, such as a carbamate; and (c) reacting a water-soluble polymer bearing a reactive group with the second attachment site and, when present, the optional third attachment site to result in (i) the second attachment site bearing a water-soluble polymer through a spacer moiety and (ii) the optional third attachment site, when present, bearing a second water-soluble polymer through a spacer moiety. In some instances, (b) is performed before step (c) while in other instances, (c) is performed before step (b).

Thus, in this method for preparing a polymeric reagent, a required step is (a) providing an aromatic-containing moiety bearing a first attachment site, a second attachment site and an optional third attachment site. In the context of a synthetic preparation, it is understood that "providing" a material means to obtain the material (by, for example, synthesizing it or obtaining it commercially). An exemplary aromatic-containing moiety, for illustrative purposes, is 9-hydroxymethyl-2,7-diaminofluorene, as shown below.

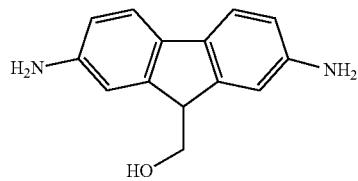

This aromatic-containing moiety, 9-hydroxymethyl-2,7-diaminofluorene, is an example of an aromatic-containing moiety having three attachment sites: a hydroxyl group at the 9 position and amino groups at each of the 2 and 7 positions. The aromatic-containing moiety can be provided in a base or salt form. With respect to 9-hydroxymethyl-2,7-diaminofluorene, it is possible to use the dihydrochloride form. Other aromatic-containing moieties can be provided via synthetic preparation and/or purchase from a commercial supplier.

Having provided the aromatic-containing moiety, another step in the method broadly includes the step of reacting a water-soluble polymer bearing a reactive group with the attachment site(s) on the aromatic-containing moiety. Here, any art-known approach for attaching a water-soluble polymer to one or more attachment sites on the aromatic-containing moiety can be used and the method is not limited to the specific approach. For example, an amine-reactive PEG (such as an N-succinimidyl ester-terminated mPEG, formed, for example, from the reaction of N-hydroxysuccinimide and $CH_3O$—$CH_2CH_2$—$(OCH_2CH_2)$—$OCH_2CH_2$—$OCH_2COOH$ with dicyclohexyl carbodiimide (DCC) or diisopropyl carbodiimide (DIC) as a condensing agent and optionally in the presence of a base) can be reacted with an amine bearing aromatic-containing moiety such as 9-hydroxymethyl-2,7-diaminofluorene.

In some instances, reaction of the water-soluble polymer bearing a reactive group with the aromatic-containing moiety will result in all possible attachment sites having water-soluble polymer attached thereto. In such circumstances it is necessary to remove at least one water-soluble polymer so that an attachment site is made available for reaction with a functional group reagent. Thus, for example, reaction of the N-succinimidyl ester-terminated mPEG discussed in the previous paragraph with 9-hydroxymethyl-2,7-diaminofluorene results in a mixture comprising (a) a species bearing two water-soluble polymers, one at each of the two amine sites, and (b) a species bearing three water-soluble polymers, one at each of the two amine sites, and one at the hydroxyl site. Here, it is possible to remove and collect higher molecular weight species by using size-exclusion chromatography. In addition it is possible to treat the mixture to high pH [treating, for example, the mixture to lithium hydroxide (LiOH), sodium hydroxide (NaOH), potassium hydroxide (KOH)], followed by ion-exchange chromatography (IEC). In either case, the result is a composition containing mostly 9-hydroxymethyl-2,7-diaminofluorene bearing two water-soluble polymers, one at each of the two amine sites. A third hydroxyl site is thereby available for reaction with a functional group reagent.

The final step is reacting a reactive site of the aromatic-containing moiety with a functional group reagent. A preferred approach is to react the hydroxyl-containing 9-hydroxymethyl-2,7-diaminofluorene bearing two water-soluble polymers, one at each of the two amine sites with triphosgene followed by treatment with N-hydroxysuccinimide. In this way, a functional group capable of reacting with an amino group of an active agent to form a releasable linkage, such as a carbamate linkage (in this case, an "activated carbonate") is formed on the hydroxyl-containing reactive site.

No matter which approach is used, the steps of the synthetic method take place in an appropriate solvent. One of ordinary skill in the art can determine whether any specific solvent is appropriate for any given reaction. Typically, however, the solvent is preferably a nonpolar solvent or a polar aprotic solvent. Nonlimiting examples of nonpolar solvents include benzene, xylene, dioxane, tetrahydrofuran (THF), t-butyl alcohol and toluene. Particularly preferred nonpolar solvents include toluene, xylene, dioxane, tetrahydrofuran, and t-butyl alcohol. Exemplary polar aprotic solvents include, but are not limited to, DMSO (dimethyl sulfoxide), HMPA (hexamethylphosphoramide), DMF (dimethylformamide), DMA (dimethylacetamide), NMP(N-methylpyrrolidinone).

Once prepared, the polymeric reagents can be isolated. Known methods can be used to isolate the polymeric reagent, but it is particularly preferred to use chromatography, e.g., size exclusion chromatography. Alternately or in addition, the method includes the step of purifying the polymeric reagent once it is formed. Again, standard art-known purification methods can be used to purify the polymeric reagent.

The polymeric reagents are sensitive to moisture and oxygen and are ideally stored under an inert atmosphere, such as under argon or under nitrogen, and at low temperature. In this way, potentially degradative processes associated with, for example, atmospheric oxygen, are reduced or avoided entirely. In some cases, to avoid oxidative degradation, antioxidants, such as butylated hydroxyl toluene (BHT), can be added to the polymeric reagent prior to storage. In addition, it is preferred to minimize the amount of moisture associated with the storage conditions to reduce potentially damaging reactions associated with water, e.g., hydrolysis of the active ester. Moreover, it is preferred to keep the storage conditions dark in order to prevent certain degradative processes that involve light. Thus, preferred storage conditions include one or more of the following: storage under dry argon or another dry inert gas; storage at temperatures below about −15° C.; storage in the absence of light; and storage with a suitable amount (e.g., about 50 to about 500 parts per million) of an antioxidant such as BHT.

The above-described polymeric reagents are useful for conjugation to biologically active agents. For example, an amino group (e.g., primary amine) on an active agent will react with the functional group capable of reacting with an amino group of an active agent to form a releasable linkage, such as a carbamate linkage.

Exemplary conjugates include those of the following formulae:

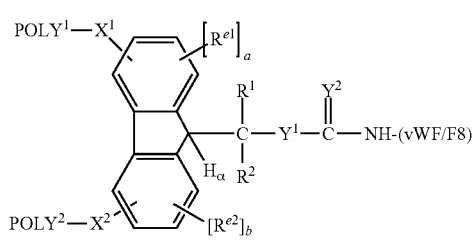

wherein:
POLY$^1$ is a first water-soluble polymer;
POLY$^2$ is a second water-soluble polymer;
X$^1$ is a first spacer moiety;
X$^2$ is a second spacer moiety;
H$_\alpha$ is an ionizable hydrogen atom;
R$^1$ is H or an organic radical;
R$^2$ is H or an organic radical;
(a) is either zero or one;
(b) is either zero or one;
R$^{e1}$, when present, is a first electron altering group;
R$^{e2}$, when present, is a second electron altering group;
Y$^1$ is O or S;
Y$^2$ is O or S; and
(vWF/F8) is a residue of a amine-containing biologically active agent selected from the group consisting of a von Willebrand Factor moiety and a Factor VIII moiety.

Exemplary conjugates have the following structure:

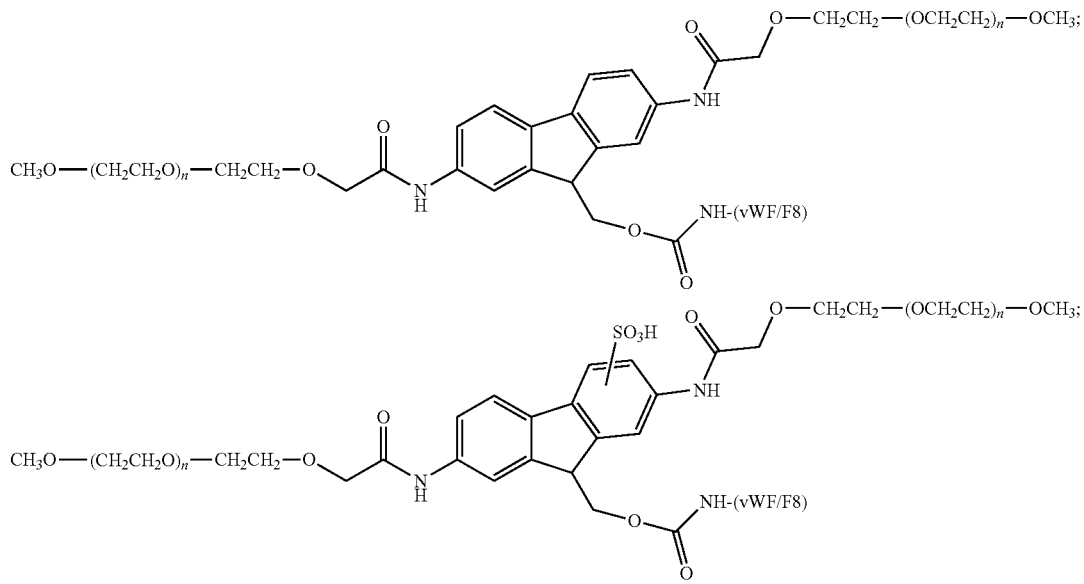

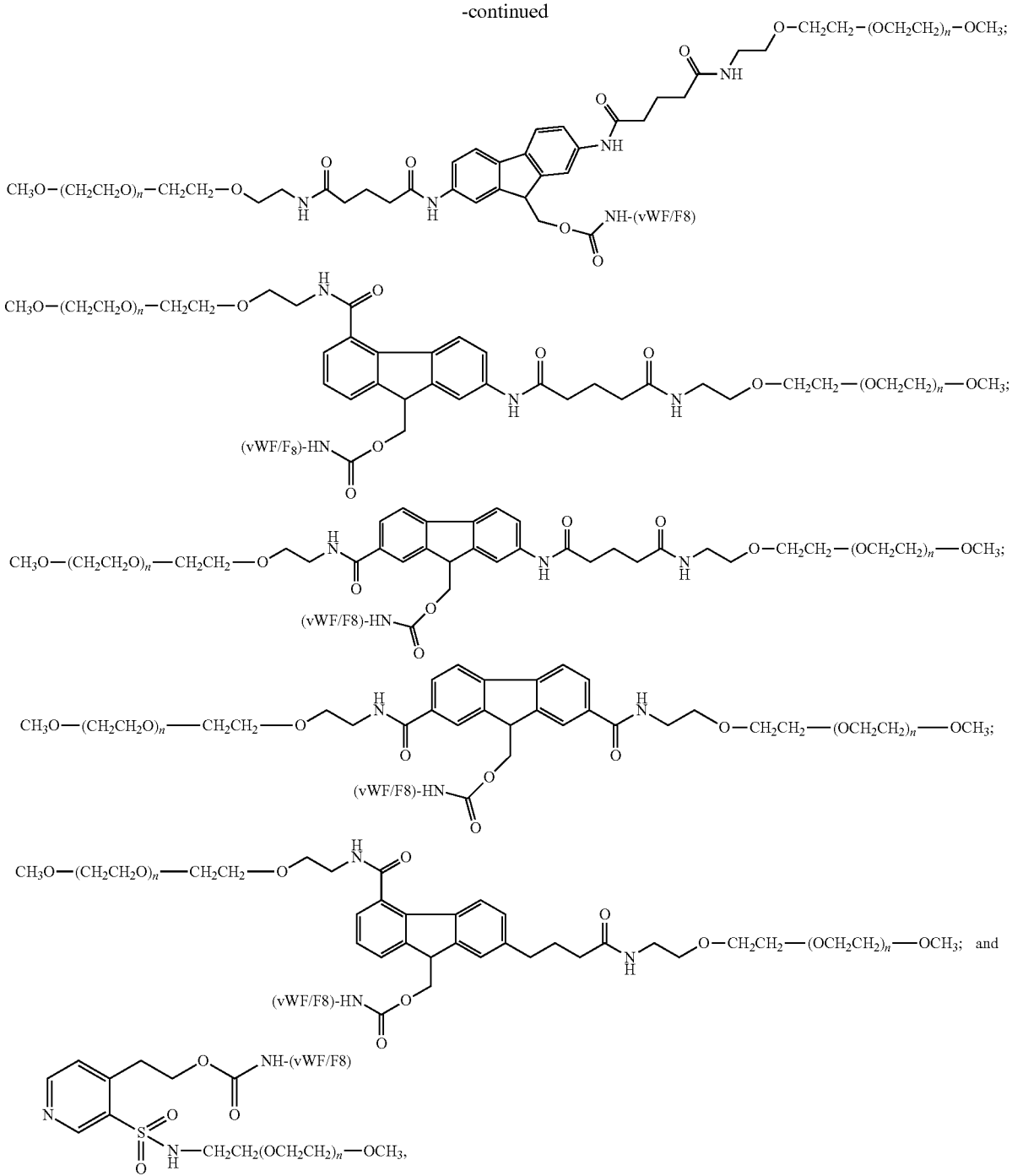

wherein, for each structure and in each instance, (n) is independently an integer from 4 to 1500, and (vWF/F8) is a residue of a biologically active agent selected from the group consisting of a von Willebrand Factor moiety and a Factor VIII moiety.

The biologically active agent to which a polymeric reagent as described herein can be conjugated, is an amine-containing biologically active agent. Typically, the biologically active agent will be a macromolecule, such as a polypeptide, having a molecular weight greater than about 3,500 Daltons. Pharmacologically active polypeptides represent a preferred type of biologically active agent. It should be understood that for purposes of the present discussion, the term "polypeptide" will be generic for oligopeptides and proteins. With regard to polypeptides, the amine to which the polymeric reagent couples to can be on the N-terminus or an amine-containing side chain of an amino acid (such as lysine) within the polypeptide.

The invention also provides for a method of preparing a conjugate comprising the step of contacting a polymeric reagent with a biologically active agent under conditions suitable to form a covalent attachment between the polymer and the biologically active agent. Typically, the polymer is added to the active agent or surface at an equimolar amount (with respect to the desired number of groups suitable for reaction with the reactive group) or at a molar excess. For example, the polymeric reagent can be added to the target active agent at a molar ratio of about 1:1 (polymeric reagent: active agent), 1.5:1, 2:1, 3:1, 4:1, 5:1, 6:1, 8:1, or 10:1. The conjugation reaction is allowed to proceed until substantially no further conjugation occurs, which can generally be determined by monitoring the progress of the reaction over time. Progress of the reaction can be monitored by withdrawing aliquots from the reaction mixture at various time points and analyzing the reaction mixture by SDS-PAGE or MALDI-TOF mass spectrometry or any other suitable analytical method. Once a plateau is reached with respect to the amount of conjugate formed or the amount of unconjugated polymer remaining, the reaction is assumed to be complete. Typically, the conjugation reaction takes anywhere from minutes to several hours (e.g., from 5 minutes to 24 hours or more). The resulting product mixture is preferably, but not necessarily, purified to separate out excess reagents, unconjugated reactants (e.g., active agent) undesired multi-conjugated species, and free or unreacted polymer. The resulting conjugates can then be further characterized using analytical methods such as MALDI, capillary electrophoresis, gel electrophoresis, and/or chromatography.

It is possible to characterize the degree of attachment (that is, the number—often expressed in terms of an average number in the context of a composition of conjugates—of polymeric reagents that became attached to the protein) of a conjugate. To determine the average number of water-soluble polymer molecules on protein conjugates, analytical techniques such as SDS-PAGE, SEC, IEC, MALDI-TOF, and so forth can be used. Spectrophotometric detection of the residual primary amine on a protein using TNBSA following water-soluble polymer attachment has led to the qualitative and quantitative estimation of degree of attachment. With respect to von Willebrand Factor-water-soluble polymer conjugates, the degree of attachment was qualitatively described as low, medium, and high based on SDS-PAGE. When analyzing the degree of attachment of releasable von Willebrand Factor-water-soluble polymer conjugates by SDS-PAGE under reducing conditions, release of the water-soluble polymer during sample treatment and electrophoresis can lead to an overall underestimate of the true degree of PEGylation.

One approach for the determination of the degree of PEG-based polymers attachment is a modification of the work of Nag and Barker. See Nag et al. (1996) *Anal. Biochem.* 237:224-231 and Barker et al. (2001) *Anal. Biochem.* 290:382-385. The method is based on principle of partitioning of a chromophore, ammonium ferrothiocyanate, from the aqueous phase into the chloroform phase in the presence of PEG (as the chromophore itself can not be extracted into the chloroform phase without the PEG presence). Digestion of von Willebrand Factor by pronase frees the PEG from the conjugate, and the quantity of the PEG is determined subsequently by the ammonium ferrothiocyanate method. Using this principle, a reverse phase HPLC method that circumvents the need for chloroform extraction was developed to determine the degree of attachment for the conjugates described herein.

With respect to polymer-active agent conjugates, the conjugates can be purified to obtain/isolate different conjugated species. Alternatively, and more preferably for lower molecular weight (e.g., less than about 20 kiloDaltons, more preferably less than about 10 kiloDaltons) polymers, the product mixture can be purified to obtain the distribution of water-soluble polymer segments per active agent. For example, the product mixture can be purified to obtain an average of anywhere from one to five PEGs per active agent (e.g., polypeptide). The strategy for purification of the final conjugate reaction mixture will depend upon a number of factors, including, for example, the molecular weight of the polymer employed, the particular active agent, the desired dosing regimen, and the residual activity and in vivo properties of the individual conjugate(s).

If desired, conjugates having different molecular weights can be isolated using gel filtration chromatography. That is to say, gel filtration chromatography is used to fractionate differently numbered polymer-to-active agent ratios (e.g., 1-mer, 2-mer, 3-mer, and so forth, wherein "1-mer" indicates 1 polymer to active agent, "2-mer" indicates two polymers to active agent, and so on) on the basis of their differing molecular weights (where the difference corresponds essentially to the average molecular weight of the water-soluble polymer segments). For example, in an exemplary reaction where a 100 kDa protein is randomly conjugated to a polymeric reagent having a molecular weight of about 20 kDa, the resulting reaction mixture will likely contain unmodified protein (MW 100 kDa), mono-PEGylated protein (MW 120 kDa), di-PEGylated protein (MW 140 kDa), and so forth. While this approach can be used to separate PEG and other polymer conjugates having different molecular weights, this approach is generally ineffective for separating positional isomers having different polymer attachment sites within the protein. For example, gel filtration chromatography can be used to separate from each other mixtures of PEG 1-mers, 2-mers, 3-mers, and so forth, although each of the recovered PEG-mer compositions may contain PEGs attached to different reactive amino groups (e.g., lysine residues) within the active agent.

Gel filtration columns suitable for carrying out this type of separation include Superdex™ and Sephadex™ columns available from Amersham Biosciences (Piscataway, N.J.). Selection of a particular column will depend upon the desired fractionation range desired. Elution is generally carried out using a suitable buffer, such as phosphate, acetate, or the like. The collected fractions may be analyzed by a number of different methods, for example, (i) optical density (OD) at 280 nm for protein content, (ii) bovine serum albumin (BSA) protein analysis, (iii) iodine testing for PEG content [Sims et al. (1980) *Anal. Biochem,* 107: 60-63], and (iv) sodium dodecyl sulfate polyacrylamide gel electrophoresis (SDS PAGE), followed by staining with barium iodide.

Separation of positional isomers is carried out by reverse phase chromatography using a reverse phase-high performance liquid chromatography (RP-HPLC) C18 column (Amersham Biosciences or Vydac) or by ion exchange chromatography using an ion exchange column, e.g., a Sepharose™ ion exchange column available from Amersham Biosciences. Either approach can be used to separate polymer-active agent isomers having the same molecular weight (positional isomers).

An amine-containing biologically active agent for use in coupling to a polymer as presented herein may be a von Willebrand Factor moiety or a Factor VIII moiety.

With respect to a von Willebrand Factor moiety ("vWF"), the von Willebrand Factor moiety useful for the present invention includes any protein that has the same activity (although not necessarily the same degree of activity) as native, human von Willebrand Factor and includes all forms of native, human von Willebrand Factor, including the monomeric and multimeric forms. Useful forms include homomultimers of at least two von Willebrand Factors. The von Willebrand Factor moiety may be either a biologically active derivative, or when to be used solely as a stabilizer for Factor VIII, the von Willebrand Factor moiety may be of a form that is not biologically active. It should also be understood that the present invention encompasses different forms of von Willebrand Factor moieties to be used in combination. For example, a composition useful for the present invention may include different multimers, different derivatives and both biologically active derivatives and derivatives not biologically active.

The biologically activity of a von Willebrand Factor moiety can be measured in two different in vitro assays (Turecek et al., (2002) *Semin. Thromb. Hemost.* 28:149-160). The ristocetin cofactor assay is based on the agglutination of fresh formalin-fixed platelets induced by the antibiotic ristocetin in the presence of a protein having von Willebrand Factor activity. The degree of platelet agglutination depends on the protein concentration and can be measured by the turbidimetic method, e.g., by use of an aggregometer (Weiss et al. (1973) *J. Clin. Invest.* 52:2708-2716; Macfarlane et al. (1975) *Thromb. Diath. Haemorrh.* 34:306-308). The second method is the collagen binding assay, which is based on ELISA technology (Brown et al. (1986) *Thromb. Res.* 43:303-311; Favaloro (2000) *Thromb. Haemost.* 83:127-135). A microtiter plate is coated with type I or III collagen. The proposed von Willebrand Factor moiety is bound to the collagen surface and subsequently detected with an enzyme-labeled polyclonal antibody. The last step is the substrate reaction, which can be photometrically monitored with an ELISA reader. Such methods are useful for determining the von Willebrand Factor activity of both the moiety itself (and therefore can be used as a "von Willebrand Factor moiety") as well as the corresponding polymer-moiety conjugate.

Von Willebrand Factor- and Factor VIII-water-soluble polymer conjugates are biologically active and exhibit increased in vivo half-lives as compared to their corresponding non-conjugated versions. The increase in the in vivo half-life can be assessed by measuring the pharmacokinetics of the conjugate, von Willebrand Factor, and Factor VIII in Factor VIII deficient mice as described in Examples 5 and 6 below. Briefly, Factor VIII deficient mice are treated with a bolus injection of von Willebrand Factor, or a von Willebrand Factor- or Factor VIII-water-soluble polymer conjugate, premixed with Factor VIII via the tail vein, and von Willebrand Factor antigen levels are measured in plasma samples at various time points. In addition, Factor VIII deficient mice can be treated with a bolus injection of Factor VIII, or a von Willebrand Factor- or Factor VIII-water-soluble polymer conjugate, and Factor VIII antigen levels are measured in plasma samples at various time points. Von Willebrand Factor antigen and Factor VIII antigen can be measured via ELISA assay.

The von Willebrand Factor moiety includes plasma-derived von Willebrand Factor and recombinant von Willebrand Factor. The von Willebrand Factor moiety may be produced by any method known in the art. One specific example is disclosed in WO 86/06096.

With respect to a Factor VIII moiety, the Factor VIII moiety useful for the present invention includes any protein that has the same activity (although not necessarily the same degree of activity) as native, human Factor VIII. Included as a possible Factor VIII moiety is native, human Factor VIII, which is a 2,351 amino acid, single chain glycoprotein that is structurally organized as A1-A2-B-A3-C1-C2. When the expressed polypeptide is translocated into the lumen of the endoplasmic reticulum, however, a 19-amino acid signal sequence is cleaved, resulting in a second sequence. This second sequence, herein provided lacks the leading 19 amino acids. It will be appreciated that a Factor VIII moiety is not limited to merely "active" forms of Factor VIII (e.g., Factor VIIIa) and that the term "Factor VIII moiety" encompasses "precursor" forms as well as other substances that having a similar procoagulant effect.

For any given moiety, it is possible to determine whether that moiety has Factor VIII activity. For example, several animal lines have been intentionally bred with the genetic mutation for hemophilia such that an animal produced from such a line has very low and insufficient levels of Factor VIII. Such lines are available from a variety of sources such as, without limitation, the Division of Laboratories and Research, New York Department of Public Health, Albany, N.Y. and the Department of Pathology, University of North Carolina, Chapel Hill, N.C. Both of these sources, for example, provide canines suffering from canine hemophilia A. In order to test the Factor VIII activity of any given moiety in question, the moiety is injected into the diseased animal, a small cut made and bleeding time compared to a untreated diseased animal as a control. Another method useful for determining Factor VIII activity is to determine cofactor and procoagulant activity. See, for example, Mertens et al. (1993) *Brit. J. Haernatol.* 85:133-42. Other methods known to those of ordinary skill in the art can also be used to determine whether a given moiety has Factor VIII activity. Such methods are useful for determining the Factor VIII activity of both the moiety itself (and therefore can be used as a "Factor VIII moiety") as well as the corresponding polymer-moiety conjugate.

Nonlimiting examples of Factor VIII moieties include the following: Factor VIII; Factor VIIIa; Factor VIII:C; Factor VIII:vWF; B-domain deleted Factor VIII (and other truncated versions of Factor VIII); hybrid proteins, such as those described in U.S. Pat. No. 6,158,888; glycosylated proteins having Factor VIII activity, such as those described in U.S. Patent Application Publication No. US2003/0077752; and peptide mimetics having Factor VIII activity. Preferred truncated Factor VIII versions (encompassed by the term "B-domain deleted Factor VIII) corresponds to a protein having the amino acid sequence of human Factor VIII having a deletion corresponding to at least 581 amino acids within the region between $Arg^{759}$ and $Ser^{1709}$, more preferably wherein the deletion corresponds to one of the region between $Pro^{1000}$ and $Asp^{1582}$, the region between $Thr^{778}$ and $Pro^{1659}$, and the region between $Thr^{778}$ and $Glu^{1694}$.

With respect to both the von Willebrand Factor and Factor VIII moieties, biologically active fragments, deletion variants, substitution variants or addition variants of any of the foregoing that maintain at least some degree of the desired von Willebrand or Factor VIII activity can also be used.

The active agent can advantageously be modified to include one or more amino acid residues such as, for example, lysine, cysteine and/or arginine, in order to provide facile attachment of the polymer to an atom within the side chain of the amino acid. Techniques for adding amino acid residues are well known to those of ordinary skill in the art. Reference is made to J. March, Advanced Organic Chemistry: Reactions Mechanisms and Structure, 4th Ed. (New York: Wiley-Interscience, 1992).

The active agent can be obtained from blood-derived sources. For example, Factor VIII can be fractionated from human plasma using precipitation and centrifugation techniques known to those of ordinary skill in the art. See, for example, Wickerhauser (1976) *Transfusion* 16(4):345-350 and Slichter et al. (1976) *Transfusion* 16(6):616-626. Factor VIII can also be isolated from human granulocytes. See Szmitkoski et al. (1977) *Haematoiogia (Budap.)* 11(1-2): 177-187.

In addition, the active agent can also be obtained from recombinant methods. Briefly, recombinant methods involve constructing the nucleic acid encoding the desired polypeptide or fragment, cloning the nucleic acid into an expression vector, transforming a host cell (e.g., bacteria, yeast, or mammalian cell such as Chinese hamster ovary cell or baby hamster kidney cell), and expressing the nucleic acid to produce the desired polypeptide or fragment. Methods for producing and expressing recombinant polypeptides in vitro and in prokaryotic and eukaryotic host cells are known to those of ordinary skill in the art. See, for example, U.S. Pat. No. 4,868,122.

The above exemplary biologically active agents are meant to encompass, where applicable, analogues, agonists, antagonists, inhibitors, isomers, and pharmaceutically acceptable salt forms thereof. In reference to peptides and proteins, the invention is intended to encompass synthetic, recombinant, native, glycosylated, and non-glycosylated forms, as well as biologically active fragments thereof. In addition, the term "active agent" is intended to encompass the active agent prior to conjugation as well as the active agent "residue" following conjugation.

The present invention also includes pharmaceutical preparations comprising a conjugate as provided herein in combination with a pharmaceutical excipient. Generally, the conjugate itself will be in a solid form (e.g., a precipitate), which can be combined with a suitable pharmaceutical excipient that can be in either solid or liquid form.

Exemplary excipients include, without limitation, those selected from the group consisting of carbohydrates, inorganic salts, antimicrobial agents, antioxidants, surfactants, buffers, acids, bases, and combinations thereof.

A carbohydrate such as a sugar, a derivatized sugar such as an alditol, aldonic acid, an esterified sugar, and/or a sugar polymer may be present as an excipient. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myo-inositol, and the like.

The excipient can also include an inorganic salt or buffer such as citric acid, sodium chloride, potassium chloride, sodium sulfate, potassium nitrate, sodium phosphate monobasic, sodium phosphate dibasic, and combinations thereof.

The preparation may also include an antimicrobial agent for preventing or deterring microbial growth. Nonlimiting examples of antimicrobial agents suitable for the present invention include benzalkonium chloride, benzethonium chloride, benzyl alcohol, cetylpyridinium chloride, chlorobutanol, phenol, phenylethyl alcohol, phenylmercuric nitrate, thimersol, and combinations thereof.

An antioxidant can be present in the preparation as well. Antioxidants are used to prevent oxidation, thereby preventing the deterioration of the conjugate or other components of the preparation. Suitable antioxidants for use in the present invention include, for example, ascorbyl palmitate, butylated hydroxyanisole, butylated hydroxytoluene, hypophosphorous acid, monothioglycerol, propyl gallate, sodium bisulfate, sodium formaldehyde sulfoxylate, sodium metabisulfite, and combinations thereof.

A surfactant may be present as an excipient. Exemplary surfactants include: polysorbates, such as "Tween 20" and "Tween 80," and pluronics such as F68 and F88 (both of which are available from BASF, Mount Olive, N.J.); sorbitan esters; lipids, such as phospholipids such as lecithin and other phosphatidylcholines, phosphatidylethanolamines (although preferably not in liposomal form), fatty acids and fatty esters; steroids, such as cholesterol; and chelating agents, such as EDTA, zinc and other such suitable cations.

Acids or bases may be present as an excipient in the preparation. Nonlimiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The pharmaceutical preparations encompass all types of formulations and in particular those that are suited for injection, e.g., powders that can be reconstituted as well as suspensions and solutions. The amount of the conjugate (i.e., the conjugate formed between the active agent and the polymer described herein) in the composition will vary depending on a number of factors, but will optimally be a therapeutically effective dose when the composition is stored in a unit dose container (e.g., a vial). In addition, the pharmaceutical preparation can be housed in a syringe. A therapeutically effective dose can be determined experimentally by repeated administration of increasing amounts of the conjugate in order to determine which amount produces a clinically desired endpoint.

The amount of any individual excipient in the composition will vary depending on the activity of the excipient and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects.

Generally, however, the excipient will be present in the composition in an amount of about 1% to about 99% by weight, preferably from about 5%-98% by weight, more preferably from about 15-95% by weight of the excipient, with concentrations less than 30% by weight most preferred.

These foregoing pharmaceutical excipients along with other excipients are described in "Remington: The Science & Practice of Pharmacy", 19$^{th}$ ed., Williams & Williams, (1995), the "Physician's Desk Reference", 52$^{nd}$ ed., Medical Economics, Montvale, N.J. (1998), and Kibbe, A. H., Handbook of Pharmaceutical Excipients, 3$^{rd}$ Edition, American Pharmaceutical Association, Washington, D.C., 2000.

The pharmaceutical preparations of the present invention are typically, although not necessarily, administered via injection and are therefore generally liquid solutions or suspensions immediately prior to administration. The pharmaceutical preparation can also take other forms such as syrups, creams, ointments, tablets, powders, and the like. Other modes of administration are also included, such as pulmonary, rectal, transdermal, transmucosal, oral, intrathecal, subcutaneous, intra-arterial, and so forth.

As previously described, the conjugates can be administered parenterally by intravenous injection, or less preferably by intramuscular or by subcutaneous injection. Suitable formulation types for parenteral administration include ready-for-injection solutions, dry powders for combination with a solvent prior to use, suspensions ready for injection, dry insoluble compositions for combination with a vehicle prior to use, and emulsions and liquid concentrates for dilution prior to administration, among others.

The invention also provides a method for administering a conjugate as provided herein to a patient suffering from a condition that is responsive to treatment with conjugate. The method comprises administering, generally via injection, a therapeutically effective amount of the conjugate (preferably provided as part of a pharmaceutical preparation). The method of administering may be used to treat any condition that can be remedied or prevented by administration of the particular conjugate. Those of ordinary skill in the art appreciate which conditions a specific conjugate can effectively treat. The actual dose to be administered will vary depend upon the age, weight, and general condition of the subject as well as the severity of the condition being treated, the judgment of the health care professional, and conjugate being administered. Therapeutically effective amounts are known to those skilled in the art and/or are described in the pertinent reference texts and literature. Generally, a therapeutically effective amount will range from about 0.001 mg to 100 mg, preferably in doses from 0.01 mg/day to 75 mg/day, and more preferably in doses from 0.10 mg/day to 50 mg/day.

The unit dosage of any given conjugate (again, preferably provided as part of a pharmaceutical preparation) can be administered in a variety of dosing schedules depending on the judgment of the clinician, needs of the patient, and so forth. The specific dosing schedule will be known by those of ordinary skill in the art or can be determined experimentally using routine methods. Exemplary dosing schedules include, without limitation, administration five times a day, four times a day, three times a day, twice daily, once daily, three times weekly, twice weekly, once weekly, twice monthly, once monthly, and any combination thereof. Once the clinical endpoint has been achieved, dosing of the composition is halted.

It is to be understood that while the invention has been described in conjunction with the preferred specific embodiments thereof, that the foregoing description as well as the experimental that follow are intended to illustrate and not limit the scope of the invention. Other aspects, advantages and modifications within the scope of the invention will be apparent to those skilled in the art to which the invention pertains.

All articles, books, patents, patent publications and other publications referenced herein are hereby incorporated by reference in their entireties.

Experimental

The practice of the invention will employ, unless otherwise indicated, conventional techniques of organic synthesis and the like, which are understood by one of ordinary skill in the art and are explained in the literature. In the following examples, efforts have been made to ensure accuracy with respect to numbers used (e.g., amounts, temperatures, and so forth), but some experimental error and deviation should be accounted for. Unless otherwise indicated, temperature is in degrees Celsius and pressure is at or near atmospheric pressure at sea level. All reagents were obtained commercially unless otherwise indicated. All generated NMR was obtained from a 300 or 400 MHz NMR spectrometer manufactured by Bruker (Billerica, Mass.). All processing is carried out in glass or glass-lined vessels and contact with metal-containing vessels or equipment is avoided.

The following abbreviations will be used.
FVIII; rFVIII factor VIII; recombinant FVIII
HPLC high pressure liquid chromatography
hydr hydrolyzable
PEG-rVWF PEGylated rVWF
PEGrFVIII PEGylated rFVIII
rVWF recombinant von Willebrand factor
rFVIII recombinant FVIII
SDS-PAGE sodium dodecylsulfate polyacrylamide gel electrophoresis The rVWF product used for PEGylation was a purified rVWF preparation derived from a Chinese hamster ovary (CHO) cell line and was purified using conventional purification techniques.

Polymeric reagents were made in accordance with the basic approaches described in U.S. Patent Application Publication No. 2006/0293499 and had the following structures:

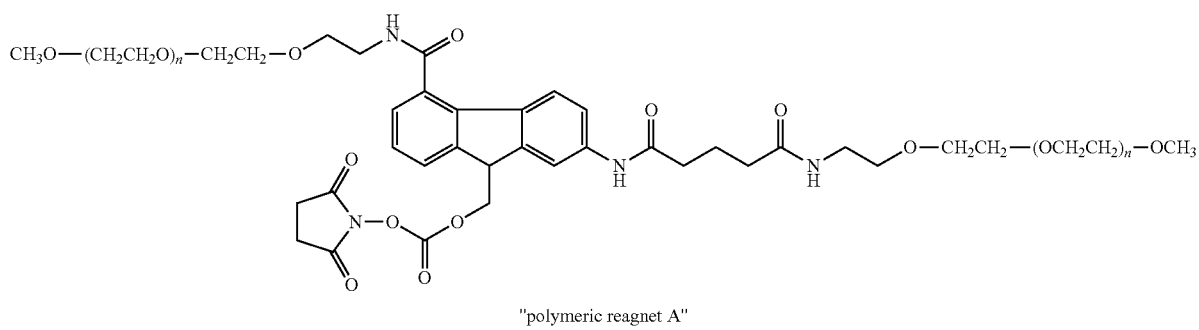

"polymeric reagnet A"

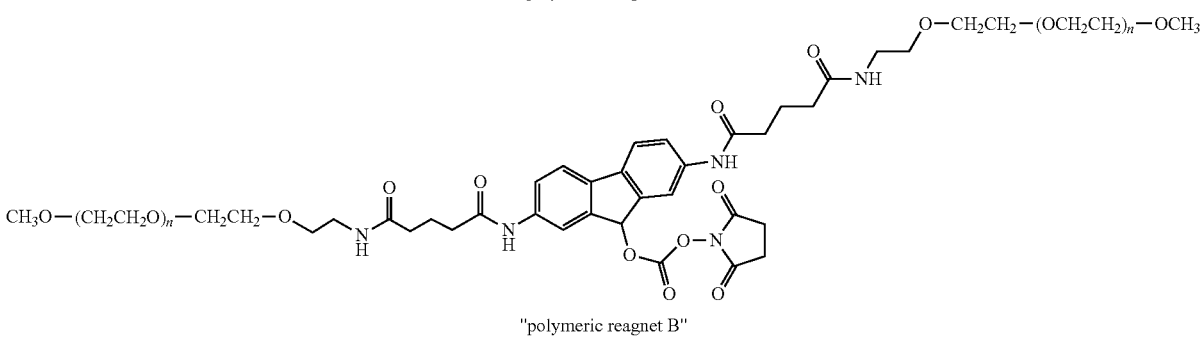

"polymeric reagnet B"

Example 1A

Preparation of vWF Conjugate

20,000 Da Total Polymer Weight Average Molecular Weight

Lys 20K br long

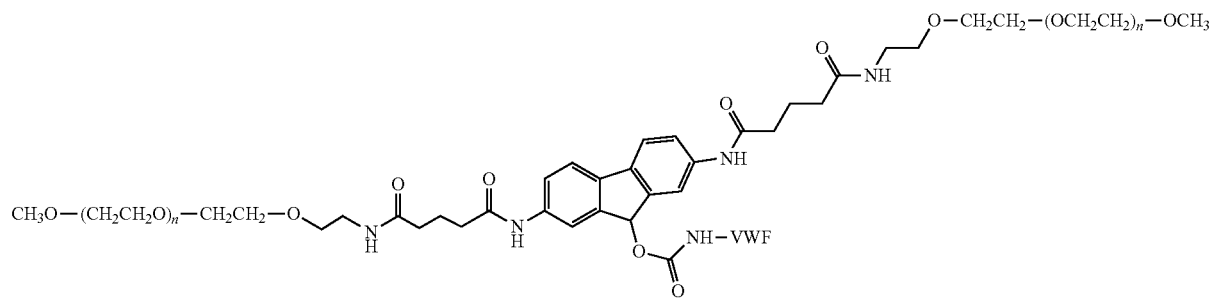

(wherein VWF is a residue of von Willebrand Factor)

An appropriate quantity of VWF protein solution was thawed (using warm water of ±30° C.) so as to result in a protein solution having 60 mg of protein content. The protein solution was poured into a new sterilized 400 mL disposable polypropylene beaker. If necessary, the temperature of the protein solution was adjusted to 22° C. (±1° C.). If necessary, the protein solution was diluted with a solution [20 mM HEPES (pH 7.4), 150 mM NaCl, 0.5% w/v sucrose] or concentrated to ensure a concentration of 0.45 mg/mL±0.05 mg/mL. A sample of 0.2 mL was retained and stored at 4° C. for later concentration verification. The protein solution beaker was placed under an overhead stirrer, wherein the impeller was lowered into the protein solution approximately ¾ down (i.e., ¼ from the bottom) and the impeller set to stirring at 60 rpm (±2 rpm). In order to prevent contamination as much as possible, the beaker was covered.

A seventy-five molar excess (relative to von Willebrand Factor monomer mass of 278 kDa) of polymeric reagent B having a total polymer weight average molecular weight (i.e., the sum of the weight average molecular weight of each polymer "arm") of about 20,000 Da was weighed and placed into a 50 mL polypropylene Falcon tube and dissolved by adding 2 mM HCl in an amount sufficient to provide a 5% w/v PEG or 50 mg/mL PEG solution). Optionally, the PEG solution can be centrifuged (using a Beckman bench top centrifuge equipped with holders for 50 mL Falcon tubes, at 1000 rpm) which will result in a clear solution collected at the bottom of the tube. As soon as the PEG solution was formed, it was pumped via a syringe pump into the protein solution at a rate of 1.5 mL/min (90 mL/h). The tube transporting the PEG solution was placed in the beaker such that the PEG solution was fed into the protein solution at the level of the impeller. Hereafter, the protein solution combined with the PEG solution is referred to as the "PEGylation reaction mixture". Stirring of the PEGylation reaction mixture was continued for five hours, with temperature (22° C.±1° C.) and pH monitored at intervals as required.

Following five hours of stirring (the pH of the PEGylation reaction solution should be 7.3±0.1), 14.5 mL of a 0.1M glycine solution was added (at 1.5 mL/min in the same way the PEG solution was added to the PEGylation reaction solution) to thereby form a glycine-containing PEGylation reaction mixture. The final concentration of glycine in the glycine-containing PEGylation reaction mixture should be 10 mM (±1 mM). The glycine-containing PEGylation reaction mixture was stirred at 60 rpm for another two hours.

Following two hours of stirring, a 0.2 mL sample was removed and stored at 4° C. for protein determination.

To purify the conjugate within the glycine-containing PEGylation reaction mixture, the glycine-containing PEGylation reaction mixture was diluted with 3 glycine-containing PEGylation reaction volumes of solution A [20 mM sodium citrate (pH 6.1), 0.5% w/v sucrose] to reduce the NaCl concentration below 100 mM and to dilute the unbound free polymeric reagent B. Following dilution, the glycine-containing PEGylation reaction solution was mixed with gentle rotation (swirling) or mixing with an overhead stirrer. The conjugate was purified by cation exchange chromatography on an AKTA Basic System. A Millipore Vantage 44 mm ID column packed with GE-Healthcare SP—HP media. The packed bed height was 100-105 mm resulting in a column volume of 150-160 mL, thereby resulting in a column loading of <0.4 mg/mL. The flow rate in the column was set to 15 mL/min (linear flow rate of 1 cm/min). The mobile phase used for the purification included solution A [20 mM sodium citrate (pH 6.1), 0.5% w/v sucrose] and solution B [20 mM sodium citrate (pH 6.1), 0.5% w/v sucrose, 1.0 M NaCl], or a mixture of both, wherein the mobile phase was run using a gradient. The following gradient was used: Step 1: 0% of the starting mobile phase contained solution B; Step 2: for the first retention volume equaling 0.7 of the column volume, the mobile phase contained 0 to 70% of solution B; Step 3: for the next retention volume equaling 2.5 of the column volume, 70% of the mobile phase contained solution B. The UV absorbance of the eluent was monitored at 280 nm. The unbound free polymeric reagent B eluted during Step 1. The conjugate, which eluted during Steps 2 and 3, was collected as soon as the absorbance began to rise from the baseline and was stopped when the peak diminished back to 7% of maximum peak height. A typical chromatogram prepared in accordance with this procedure is provided as FIG. 1.

Example 1B

Preparation of vWF Conjugate 40,000 Da Total Polymer Weight Average
Molecular Weight Lys 40K br long The basic procedure of Example 1A was repeated except that polymeric reagent B having a total polymer weight average molecular weight of about 40,000 Da was used instead of about 20,000 Da.

Example 1C

Preparation of vWF Conjugate 60,000 Da Total Polymer Weight Average
Molecular Weight Lys 60K br long The basic procedure of Example 1A was repeated except that polymeric reagent B having a total polymer weight average molecular weight of about 60,000 Da was used instead of about 20,000 Da.

Example 2A

Preparation of FVIII Conjugate 20,000 Da Total Polymer Weight Average
Molecular Weight Lys 20K br long FVIII protein solution (3.23 mg/mL protein concentration) was quickly thawed (using a warm water bath at room temperature for five minutes) and, using a 1000 µL pipettor, approximately 3.1 mL of the warmed FVIII protein solution was placed in a 50 mL conical tube.

A 42.8 molar ratio (relative to Factor VIII) of polymeric reagent B (38 mg) having a total polymer weight average molecular weight (i.e., the sum of the weight average molecular weight of each polymer "arm") of about 20,000 Da was placed into a 2 mL microcentrifuge tube. The weighed polymeric reagent B was suspended in 500 µL of 2 mM HCl. Polymeric reagent B was solubilized by alternating and centrifuging the microcentrifuge tube over a twenty second period.

Using a pipettor, the solution of polymeric reagent B so formed was added to the warmed FVIII protein solution dropwise over 10-20 seconds. The resulting mixture was maintained at room temperature (approximately 22° C.) for one hour. At the end of one hour, 36 µL of a 0.1M glycine solution was added to thereby form a glycine-containing PEGylation reaction mixture. A 100 µL sample was placed in a 500 µL microcentrifuge tube and then placed in a −80° C. freezer.

To remove salt within the glycine-containing PEGylation reaction mixture, a 5 mL HiTrap DeSalt column was pre-equilibrated with 20 mM histidine, 10 mM $CaCl_2$, 0.1% Tween 80, pH 6.5]. Once equilibrated, the entire volume of the glycine-containing PEGylation reaction mixture was loaded onto the column and fractions were collected and pooled. Protein-containing fractions were collected, placed in a container and immediately placed in a standard ice bath.

Figure 2A:
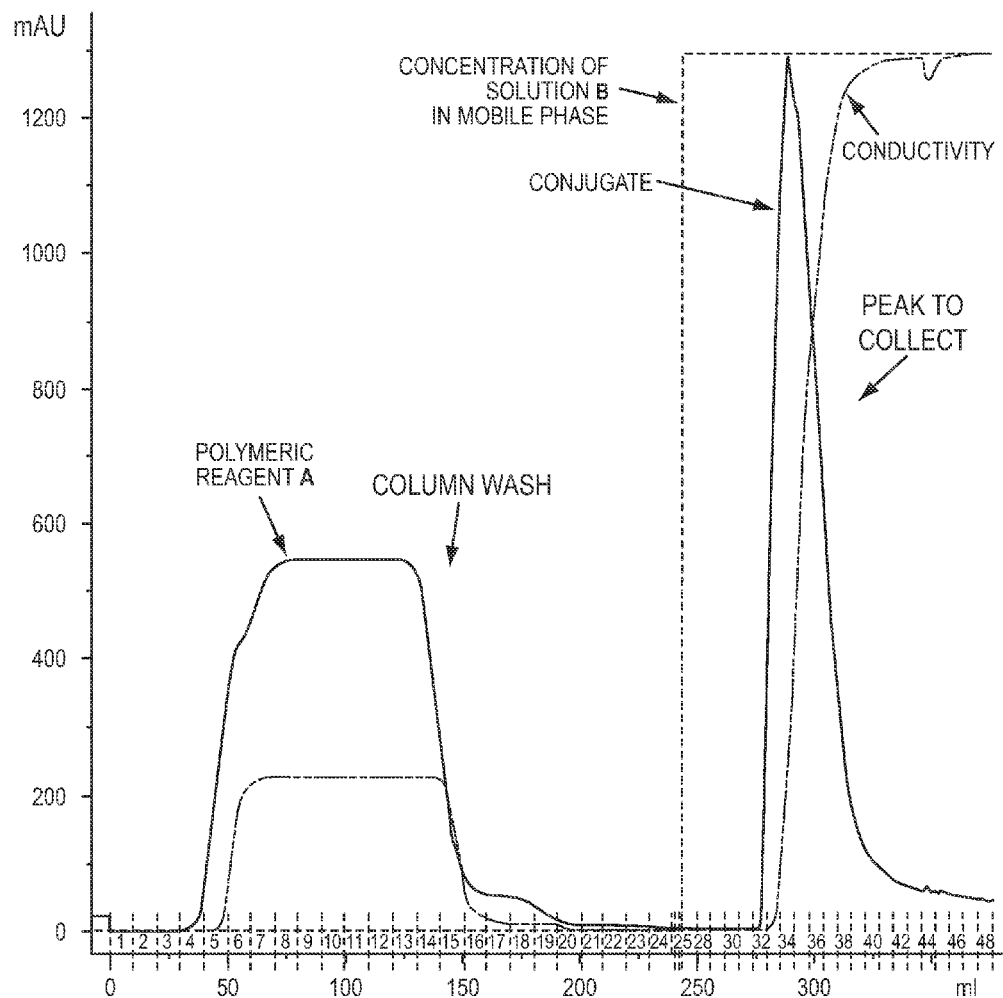
FIG. 2A shows a typical separation profile of a conjugate composition prepared in accordance with the procedure set forth in Example 2A.

To purify the conjugate within the glycine-containing PEGylation reaction mixture, the glycine-containing PEGylation reaction mixture was diluted 1:10 solution A [20 mM histidine, 10 mM $CaCl_2$, 0.1% Tween 80, pH 6.5]. The conjugate was purified by cation exchange chromatography on an AKTA Basic System. The column used was a 5 mL HiTrap Q HP column (system and column washed with 0.1M NaOH and complete removal of NaOH was verified by testing for neutral or near neutral pH following washing with Milli-Q water or purification buffer). The column was washed with 10 mL of solution A at 2.0 mL/min and the flow through was collected in 5 mL fractions. The mobile phase used for the purification included solution A, solution B [20 mM histidine, 10 mM $CaCl_2$, 0.1% Tween 80, pH 6.5, 1M NaCl], or a mixture of both, wherein the mobile phase was run using a gradient. A column wash of 2 column volumes (10 mL) of solution A was run. The following gradient was used: 0% of the starting mobile phase contained solution B; a step to 50% of solution B in the mobile was used and held for 15 mL (the peak was collected in approximately 2 mL fractions and were stored on ice); a step to 100% of solution B in the mobile phase was used and held for 5 mL; and finally, a step back to 0% of solution B in the mobile phase was used and held for 15 mL. A typical separation profile is provided as FIG. 2A.

Protein determination was carried out by thawing 1×0.2 mL aliquot of purified conjugated sample and 100 µL/mL of Factor VIII. A standard curve with points at 0.2, 0.5, 0.75 and 1.5 mg/mL of Factor VIII was prepared. For each run (sample, standard, or purification buffer), 30 µL of the appropriate substance was placed in a clean 5 mL tube and 1.5 mL of Pierce Protein Assay Reagent (Pierce Biotechnology, Inc., Rockford Ill.) was added to the tube and was

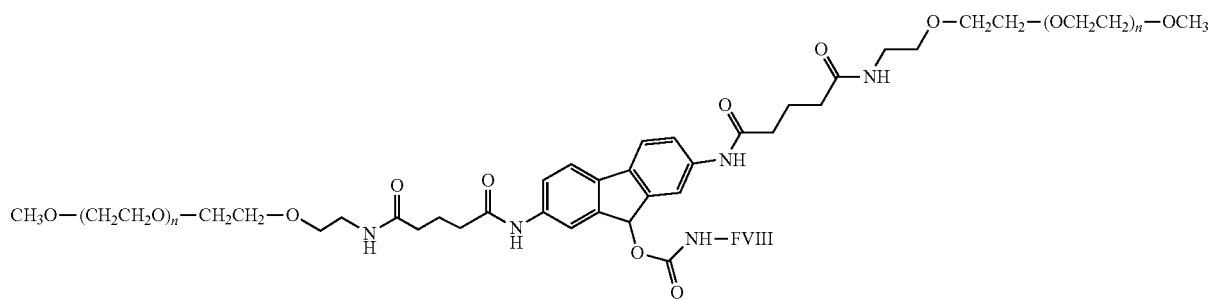

(wherein FVIII is a residue of Factor VIII)

followed by mixing of the contents of the tube. After incubation for ten minutes at room temperature (22° C.), the contents of each tube were read using a spectrophotometer at 595 nm.

Figure 2B:
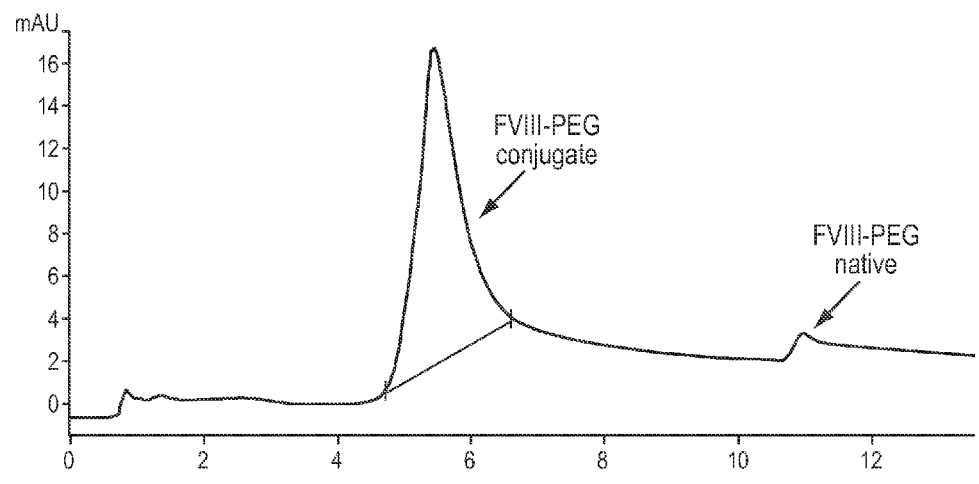
FIG. 2B shows a typical chromatogram of a conjugate composition prepared in accordance with the procedure set forth in Example 2A.

Analysis via ion-exchange chromatography was carried out by placing a 4.6×50 Mini Q column (GE Healthcare Bio-Sciences Corp, Piscataway N.J.) on an Agilent 1100 chromatography system (Agilent Technologies, Inc., Santa Clara Calif.), wherein buffers were the same as those used for purification and the maximum flow rate used was 0.5 mL/minute. Thirty microliter purified conjugate sample (or Factor VIII as control) were diluted with 30 μL of 2 mM HCl and placed in an HPLC vial with 200 μL. The following gradient was used: for time zero, 0% of the mobile phase contained solution B; for time zero to two minutes, 0% of the mobile phase contained solution B; for time two minutes to 2.5 minutes, 27% of the mobile phase contained solution B; for time 2.5 minutes to 8 minutes, 27% of the mobile phase contained solution B; for time 8 minutes to 8.5 minutes, 70% of the mobile phase contained solution B; for time 8.5 minutes to 14 minutes, 70% of the mobile phase contained solution B. For each injection, 30 μL of sample or control were used. In the chromatogram at 280 nm, peaks will correspond to the following: native Factor VIII at about 11 minutes and conjugated Factor VIII was earlier. A typical chromatogram prepared in accordance with this procedure is provided as FIG. 2B.

The purified conjugate sample was analyzed by SDS-PAGE by allowing a 3-8% TRIS-acetate gel (Invitrogen Corporation, Carlsbad Calif.) warming to room temperature, wherein a standard curve of polymeric reagent B in 2 mM HCL at concentrations of 0.001%, 0.01% and 0.1% of polymeric reagent B (w/v). The standard was prepared by placing 10 μL of HiMark molecular weight marker (Invitrogen Corporation, Carlsbad Calif.) into lane 1. Purified conjugate sample or control (Factor VIII) (10 μL volumn) were each individually diluted with 30 μL of 2 mM HCl, wherein 30 microliters of each HCl diluted sample or control was combined with 104 of 4×LDS Sample Buffer (Invitrogen Corporation, Carlsbad Calif.), wherein 25 μL of the solution was then transferred to the designated well. Immediately, the gel was placed in the gel apparatus and was run for 60 minutes at 150 volts. Following completion of the run, the gel was removed from the gel apparatus and rinsed in deionized water. The gel was then stained with a barium iodine stain (performed by: adding 15 mL 0.1M perchloric acid to the gel followed by a five minute incubation period; followed by addition to the gel of 5 mL of 5% barium chloride then 2 mL of iodine followed by a five minute incubation period) followed by rinsing with deionized water. Five minutes after the gel was rinsed with deionized water, the gel was analyzed with a Kodak Gel Logic Scanner system (Eastman Kodak Company, New Haven Conn.), wherein unreacted polymeric reagent B was identified. After scanning, any remaining water was poured off the gel and 50 mL of Pierce Imperial Stain (Pierce Biotechnology, Inc., Rockford Ill.) was added to the gel. Following incubation at room temperature for thirty minutes, the gel was rinsed with deionized water and allowed to stand for one hour in 200 mL of deionized water. During the hour period, several changes of water were completed. After the hour, the gel was analyzed with a Kodak Gel Logic Scanner system (Eastman Kodak Company, New Haven, Conn.).

Example 2A1

Preparation of FVIII Conjugate 20,000 Da Total Polymer Weight Average Molecular Weight Lys 20K br long-resynthesized The synthetic procedure of Example 2A was repeated. Upon carrying out the procedure again, it was noted that some differences in the polymer to Factor VIII ratio was observed between the resynthesized conjugates and those of Example 2A, which might be explained by the use of different analytical methods. As investigated by barium-iodine staining, however, no free polymeric reagent B remained in any sample solution.

Example 2B

Preparation of FVIII Conjugate 40,000 Da Total Polymer Weight Average Molecular Weight Lys 40K br long The basic procedure of Example 1A was repeated except that polymeric reagent B having a total polymer weight average molecular weight of about 40,000 Da was used instead of about 20,000 Da.

Example 2B1

Preparation of FVIII Conjugate 40,000 Da Total Polymer Weight Average Molecular Weight Lys 40K br long-resynthesized The synthetic procedure of Example 2B was repeated. Upon carrying out the procedure again, it was noted that some differences in the polymer to Factor VIII ratio was observed between the resynthesized conjugates and those of Example 2A, which might be explained by the use of different analytical methods. As investigated by barium-iodine staining, however, no free polymeric reagent B remained in any sample solution.

Example 2C

Preparation of FVIII Conjugate 60,000 Da Total Polymer Weight Average Molecular Weight Lys 60K br long The basic procedure of Example 2A was repeated except that polymeric reagent B having a total polymer weight average molecular weight of about 60,000 Da was used instead of about 20,000 Da.

Example 3A

Preparation of vWF Conjugate 20,000 Da Total Polymer Weight Average Molecular Weight Lys 20K br short

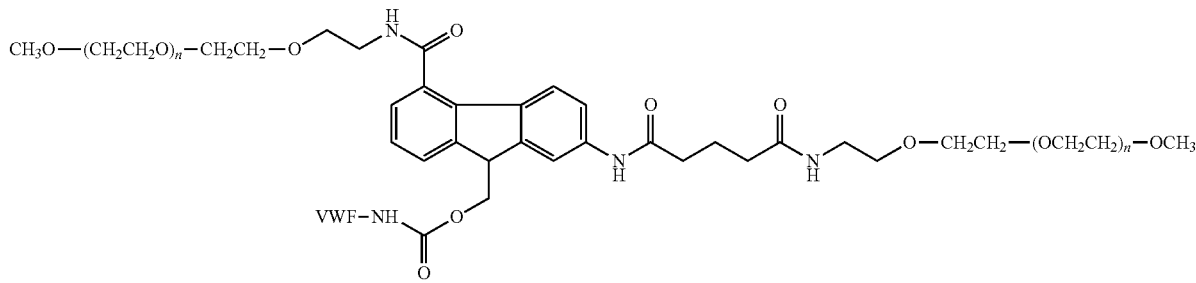

(wherein VWF is a residue of von Willebrand Factor)

Figure 3A:
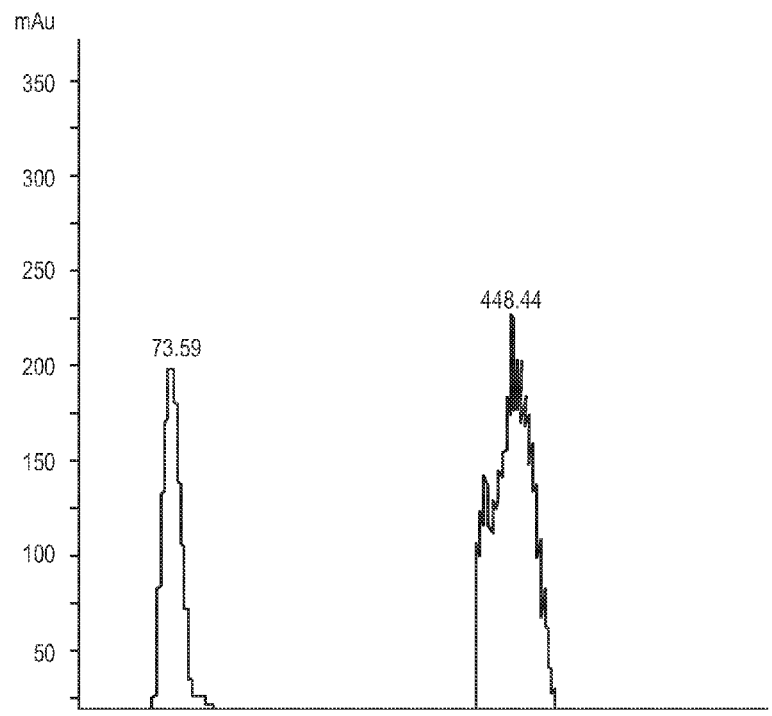
FIG. 3A shows a chromatogram following anion exchange chromatography of a conjugate composition prepared in accordance with the procedure set forth in Example 3A.
Figure 3B:
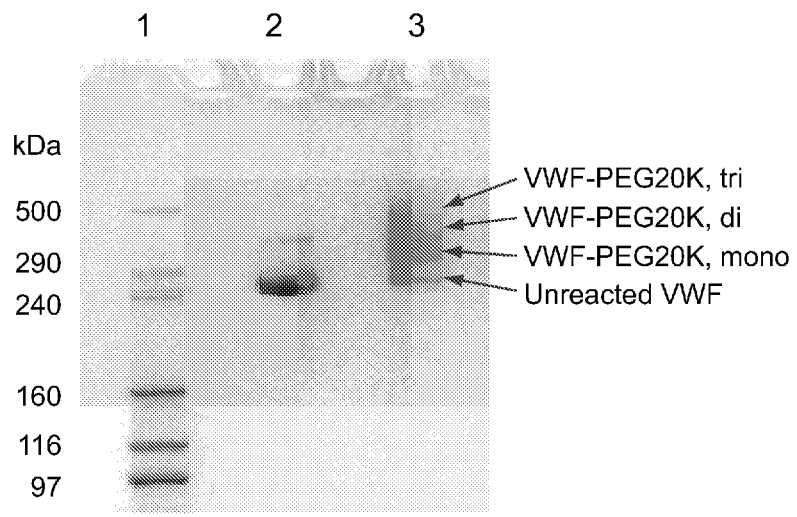
FIG. 3B shows a gel following SDS-PAGE analysis under reduced conditions of a conjugate composition prepared in accordance with the procedure set forth in Example 3A. NuPAGE Novex Tris-Acetate Gel (3-8%) with Tris-Acetate SDS Running Buffer. The gel was stained by Pierce GelCode Blue stain. Lane 1: Invitrogen HiMark Unstained High Molecular Weight Protein Standard. Lane 2: rVWF standard. Lane 3: conjugate.
Figure 3C:
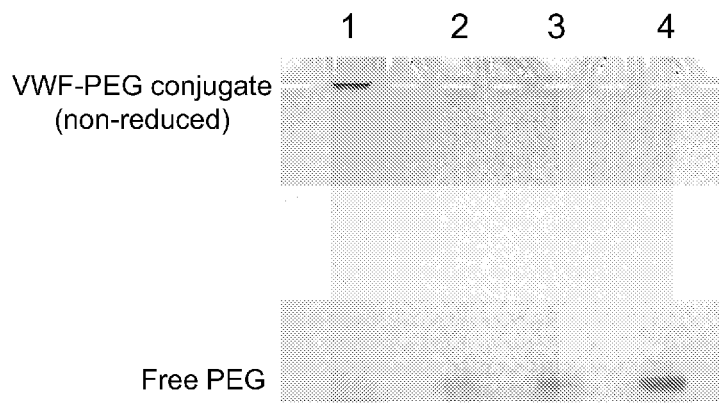
FIG. 3C shows a gel following SDS-PAGE analysis under non-reduced conditions of a conjugate composition prepared in accordance with the procedure set forth in Example 3A. NuPAGE Novex Tris-Acetate Gel (3-8%) with Tris-Acetate SDS Running Buffer. The PEG was detected by Barium chloride/iodine stain. Lane 1: conjugate. Lane 2: 0.002 wt/v % of PEG20K control. Lane 3: 0.005 wt/v % of PEG20K control. Lane 4: 0.01 wt/v % of PEG20K control.

(175 mL) of von Willebrand Factor ("VWF") solution (0.344 mg/mL in 20 mM HEPES, 150 mM NaCl, 0.5% Sucrose, pH 7.4) was allowed to thaw to room temperature. A 175 molar ratio (relative to VWF) of polymeric reagent A (766.3 mg) having a total polymer weight average molecular weight (i.e., the sum of the weight average molecular weight of each polymer "arm") of about 20,000 Da, which was freshly dissolved in 7.7 mL of 2 mM HCl, was slowly pipetted into the VWF solution. The mixture was allowed to shake gently on a shaker for two hours at room temperature. The reaction was quenched by addition of 1.8 mL of 1M glycine in water, which was allowed to shake gently on a shaker at room temperature for another three hours. The solution was diluted by slow addition of 175 mL of 20 mM MES Buffer at pH 6.10 with 0.5 wt % sucrose. The solution was mixed well by gentle swirling, and then was stored at 4° C. overnight. The unbound polymeric reagent A in the solution was then removed by ion exchange chromatography. See the chromatogram below. The resulting conjugate was characterized by SDS-PAGEs. The chromatogram following anion exchange chromatography is provided in FIG. 3A. FIGS. 3B and 3C shows the gels following SDS-PAGE analysis under reduced and non-reduced conditions, respectively.

Example 3B

Figure 4A:
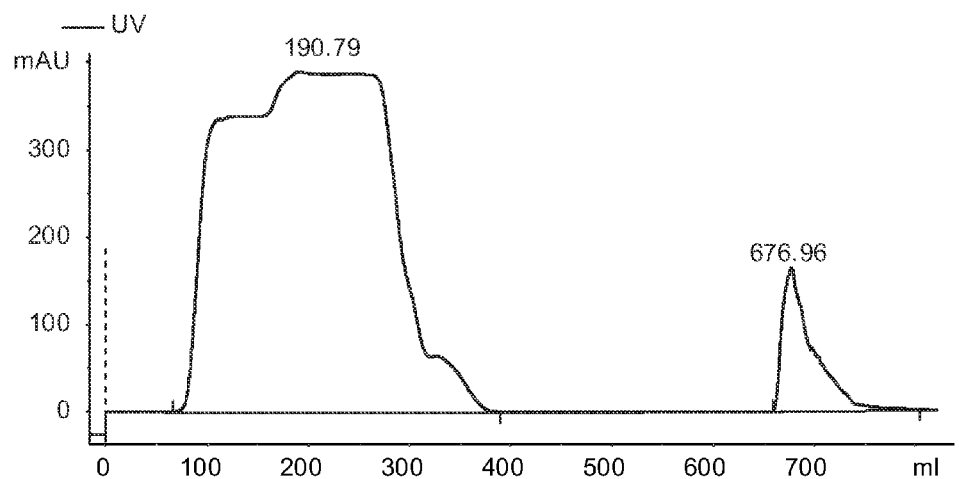
FIGS. 4A and 4B show chromatograms following ion exchange chromatography of conjugate compositions prepared in accordance with the procedures set forth in Examples 3B and 3C, respectively.

Preparation of vWF Conjugate 40,000 Da Total Polymer Weight Average Molecular Weight Lys 40K br short An aliquot (175 mL) of von Willebrand Factor ("VWF") solution (60.2 mg protein content) was allowed to thaw to room temperature. A 135 molar ratio (relative to VWF) of polymeric reagent A (1.374 g) having a total polymer weight average molecular weight (i.e., the sum of the weight average molecular weight of each polymer "arm") of about 40,000 Da, which was freshly dissolved in 13.7 mL of 2 mM HCl, was slowly pipetted into the VWF solution. The mixture was allowed to shake gently on a shaker for three hours at room temperature. The reaction was quenched by addition of 945 µL of 2 M glycine in water, which was allowed to shake gently on a shaker at room temperature for another three hours. The solution was diluted by slow addition of 175 mL of 20 mM MES Buffer at pH 6.10 with 0.5 wt % sucrose. The solution was mixed well by gentle swirling, and then was stored at 4° C. overnight. The unbound polymeric reagent A in the solution was then removed by ion exchange chromatography. See FIG. 4A for the corresponding chromatogram.

Example 3C

Figure 4B:
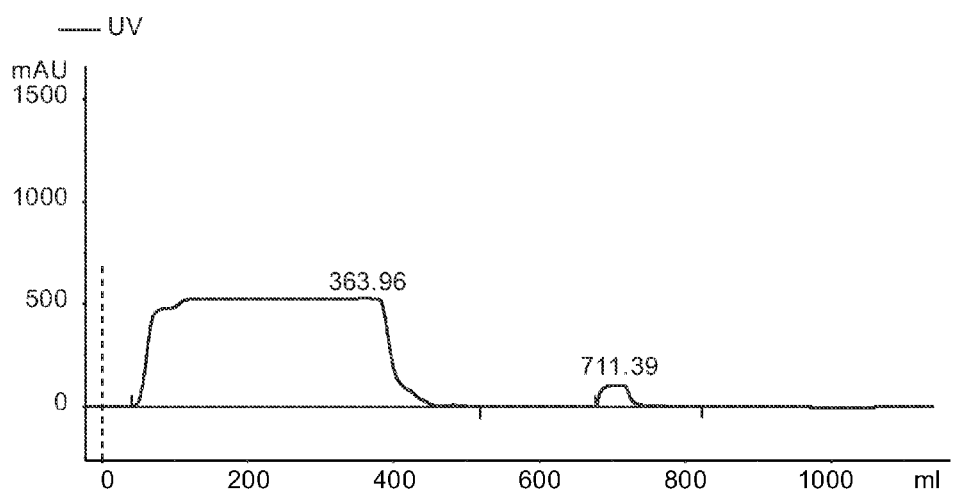

Preparation of vWF Conjugate 60,000 Da Total Polymer Weight Average Molecular Weight Lys 60K br short An aliquot (175 mL) of von Willebrand Factor ("VWF") solution (60.2 mg protein content) was allowed to thaw to room temperature. A 150 molar ratio (relative to VWF) of polymeric reagent A (2.406 g) having a total polymer weight average molecular weight (i.e., the sum of the weight average molecular weight of each polymer "arm") of about 60,000 Da, which was freshly dissolved in 13.7 mL of 2 mM HCl, was slowly pipetted into the VWF solution. The mixture was allowed to shake gently on a shaker for three hours at room temperature (22° C.). The reaction was quenched by addition of 875 µL of 2 M glycine in water, which was allowed to shake gently on a shaker at room temperature for another three hours. The solution was diluted by slow addition of 175 mL of 20 mM MES Buffer at pH 6.10 with 0.5 wt % sucrose. The solution was mixed well by gentle swirling, and then was stored at 4° C. overnight. The free PEG in the solution was then removed by ion exchange chromatography. See FIG. 4B for the corresponding chromatogram.

Example 4A

Preparation of Factor VIII Conjugate

20,000 Da Total Polymer Weight Average Molecular Weight

Lys 20K br short

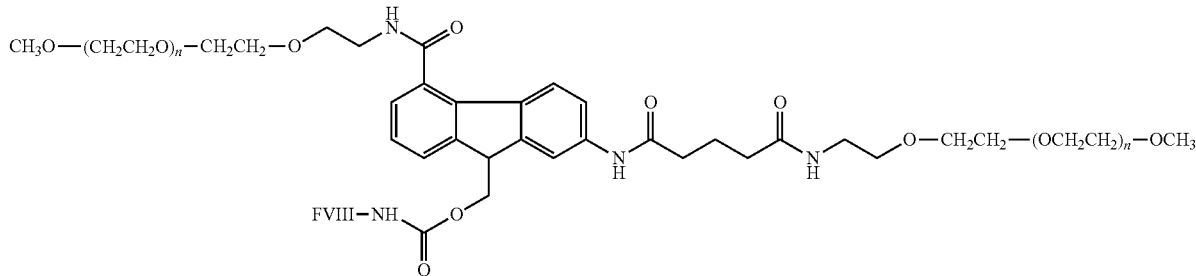

(wherein FVIII is a residue of Factor VIII)

Factor VIII protein solution (3.23 mg/mL protein concentration) was quickly thawed (using a warm water bath at room temperature for five minutes) and, using 165 µL of the warmed FVIII protein solution was placed intpa 1 mL microcentrifuge tube. The microcentrifuge tube was placed in standard ice bath (not dry ice as solution should not freeze), thereby forming a chilled Factor VIII protein solution.

A 70 molar ratio (relative to Factor VIII) of polymeric reagent A having a total polymer weight average molecular weight (i.e., the sum of the weight average molecular weight of each polymer "arm") of about 20,000 Da was placed into a 1 mL microcentrifuge tube. The weighed polymeric reagent A was suspended 2 mM HCl to form a polymeric reagent A solution. After ensuring that the polymeric reagent A was dissolved (achieved by vortexing the solution for five seconds followed by centrifuging for ten seconds), all of the polymeric reagent A solution was added to the chilled Factor VIII protein solution, the resulting mixture was placed on a rocker plate at room temperature for one hour. At the end of one hour, 18.8 µL of a 50 mM glycine solution was added to thereby form a glycine-containing PEGylation reaction mixture. The glycine-containing PEGylation reaction mixture was rocked for twenty minutes at room temperature on a rocker plate.

To remove salt within the glycine-containing PEGylation reaction mixture, a mL HiTrap DeSalt column was pre-equilibrated with 20 mM MOPS, 10 mM CaCl$_2$, 0.1% Tween 80, pH 6.5. Once equilibrated, the reaction was diluted with Milli-Q water (Millipore Corporation, Billerica, Mass.) to a final volume of 1 mL. The entire volume was then loaded onto the column and fractions were collected and pooled. Protein-containing fractions were immediately placed in standard ice bath. A typical chromatogram prepared in accordance with this procedure is provided below.

Figure 5:
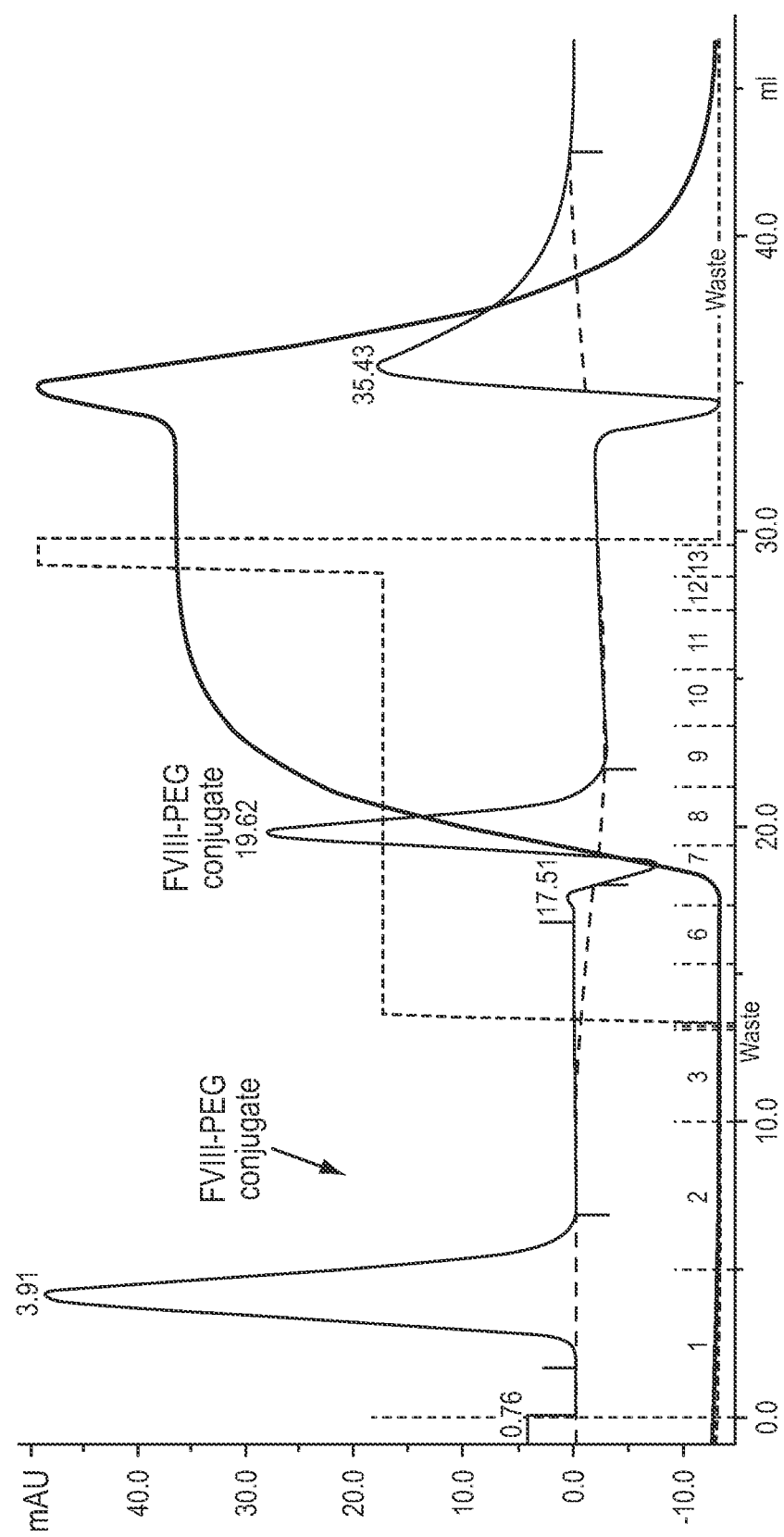
FIG. 5 shows a chromatogram of a conjugate composition prepared in accordance with the procedure set forth in Example 4A.

To purify the conjugate within the desalted glycine-containing PEGylation reaction mixture (to remove unconjugate PEG species), the conjugate was purified by cation exchange chromatography on an ÄKTA Basic System. The column used was a 5 mL HiTrap Q HP column (regenerated with 20 mM MOPS, 10 mM CaCl$_2$, 0.1% Tween 80, pH 6.5+1M NaCl and pre-equilibrated with 20 mM MOPS, 10 mM CaCL$_2$, 0.1% Tween 80, pH 6.5. The desalted glycine-containing PEGylation reaction mixture was loaded onto the column and purification was carried out with a step gradient from 0-50% mM MOPS, 10 mM CaCl$_2$, 0.1% Tween 80, pH6.5+1M NaCl. The fractions were collected, pooled and stored in a container that was placed immediated in standard ice bath. See the chromatogram provided as FIG. 5.

Figure 6A:
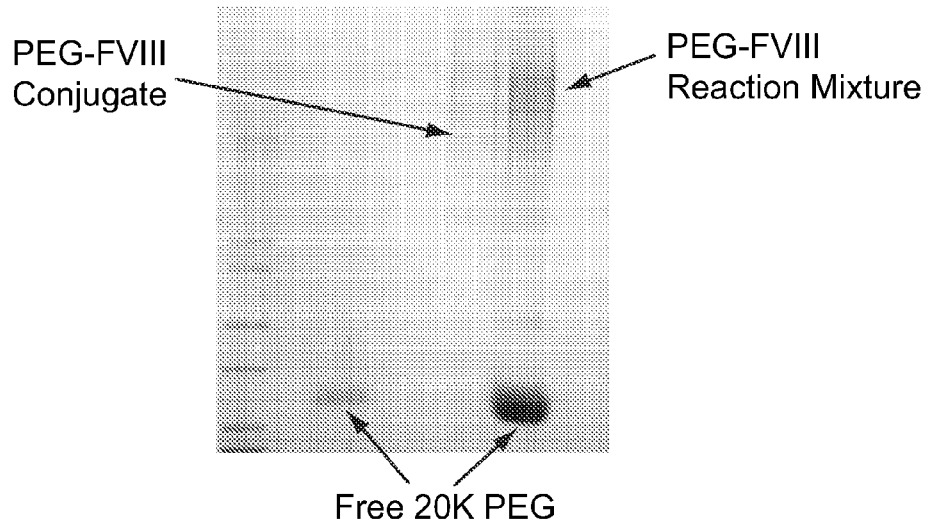
FIGS. 6A and 6B show gels following SDS-PAGE analysis using Barium Iodide staining and Coomassie staining, respectively, of a conjugate composition prepared in accordance with the procedures set forth in Example 4A.

The purified conjugate was analyzed by SDS-PAGE by allowing a 3-8% TRIS-acetate gel (Invitrogen Corporation, Carlsbad Calif.) warming to room temperature, wherein a standard curve of polymeric reagent B in 2 mM HCL at concentrations of 0.001%, 0.01% and 0.1% of polymeric reagent B (w/v). The standard was prepared by placing 10 µl, of HiMark molecular weight marker (Invitrogen Corporation, Carlsbad Calif.) into lane 1. Purified conjugate sample or control were each individually diluted with 30 µL of 2 mM HCl, wherein 30 microliteres of each HCl diluted sample or control was combined with 10 µL of 4×LDS Sample Buffer (Invitrogen Corporation, Carlsbad Calif.), wherein 25 µL of the solution was then transferred to the designated well. Immediately, the gel was placed in the gel apparatus and was run for 60 minutes at 150 volts. Following completion of the run, the gel was removed from the gel apparatus and rinsed in deionized water. The gel was then stained with a barium iodine stain (performed by: adding 15 mL 0.1M perchloric acid to the gel followed by a five minute incubation period; followed by addition to the gel of 5 mL of 5% barium chloride then 2 mL of iodine followed by a five minute incubation period) followed by rinsing with deionized water. Five minutes after the gel was rinsed with deionized water, the gel was analyzed with a Kodak Gel Scanner (Eastman Kodak Company, New Haven Conn.). See FIG. 6A.

Figure 6B:
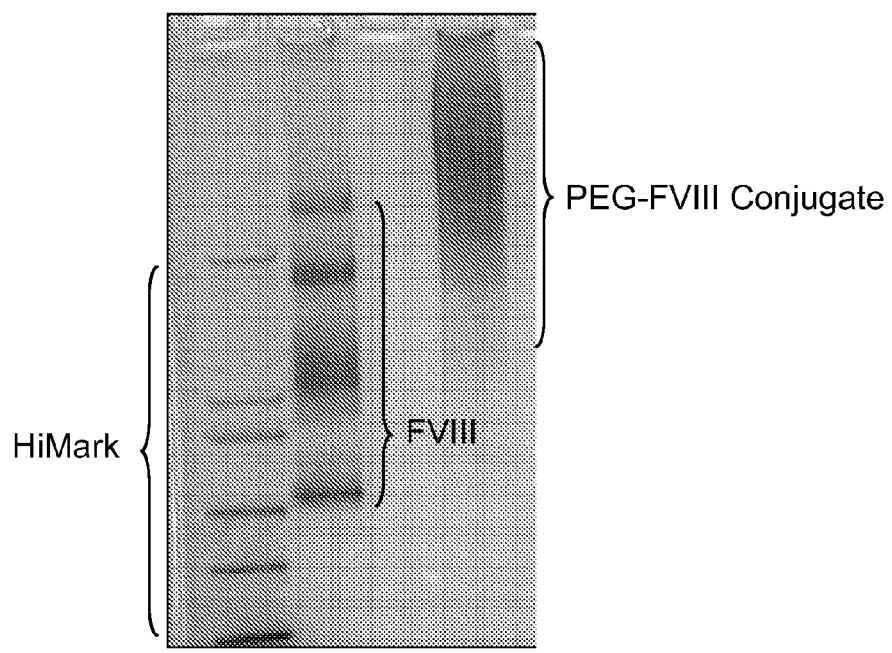

After scanning, any remaining water was poured off the gel and 50 mL of Gel Code Blue (Invitrogen Corporation, Carlsbad Calif.) was added to the gel. Following incubation at room temperature for thirty minutes, the gel was rinsed with deionized water and allowed to stand for one hour in 200 mL of deionized water. During the hour period, several changes of water were completed. After the hour, the gel was analyzed with a Kodak Gel Scanner (Eastman Kodak Company, New Haven Conn.), wherein uncongated Factor VIII was identified. See FIG. 6B.

Example 4B

Preparation of Factor VIII Conjugate

40,000 Da Total Polymer Weight Average Molecular Weight

Lys 40K br short

The basic procedure of Example 4A was repeated except that polymeric reagent A having a total polymer weight average molecular weight of about 40,000 Da was used instead of about 20,000 Da.

Example 4B1

Preparation of Factor VIII Conjugate

40,000 Da Total Polymer Weight Average Molecular Weight

Lys 40K br short-resynthesized

The basic procedure of Example 4A was repeated except that: (a) polymeric reagent A having a total polymer weight average molecular weight of about 40,000 Da was used instead of about 20,000 Da; and (b) a molar excess of 150 of polymeric reagent A relative to Factor VIII was used for the conjugation step, wherein 5 mg of polymeric reagent A was placed into a clean 1 mL microcentrifuge tube and was dissolved in 504 of 2 mM HCl. Vortex the solution for 5 seconds, then centrifuge for 10 seconds to completely dissolve the PEG. Add all 50 μL of PEG solution to the chilled FVIII and place on rocker plate at room temperature for 1 hour. Quench with 21.5 μL of 50 mM Glycine. Continue rocking for 20 minutes at room temperature.

Example 4C

Preparation of Factor VIII Conjugate

60,000 Da Total Polymer Weight Average Molecular Weight

Lys 60K br short

The basic procedure of Example 4A was repeated except that polymeric reagent A having a total polymer weight average molecular weight of about 60,000 Da was used instead of about 20,000 Da.

Example 5

In Vitro and In Vivo Experiments of PEGylated rVWF

Sodium dodecylsulfate polyacrylamide gel electrophoresis (SDS-PAGE) was performed under reducing conditions as described in this Example 5 followed by silver staining (FIG. 7A) and Coomassie staining (FIG. 7B). Under reducing conditions mature rVWF appeared as a prominent single band (monomer) with a MW of ~260 kDa with some minor bands down to 150 kDa. When the gels were immunoblotted with a polyclonal anti-human VWF antibody, as demonstrated in FIG. 7C, rVWF monomers show MWs apparently higher than 280 kD due to the use of different MW standards. Native rVWF 133P1 appeared as a single VWF monomer in the anti-VWF immunoblot with some minor, non-relevant degradation bands. Multimer composition was investigated by non-reducing agarose gel electrophoresis using a high resolution gel to demonstrate the integrity of the multimeric structure and to confirm that no satellite or other degradation bands had occurred (FIG. 7D). Analytical data of Native rVWF 133P1 is provided in Table 1.

TABLE 1

| Analytical Data of Native rVWF 133P1 Starting material rVWF 133P1 | |
|---|---|
| Protein Bradford (mg/ml) | 0.344 |
| VWF:Ag (IU/ml) | 54.6 |
| VWF:Ag/total protein (IU/mg) | 158.7 |
| VWF:RCo (IU/ml) | 24.3 |
| VWF:RCo (IU/IU Ag) | 0.45 |
| VWF:CB (U/ml) | 63.5 |
| VWF:FVIIIB capacity (%) | 84 |
| VWF:FVIIIB (U/ml) | 46 |
| VWF:FVIIIB affinity; KD (M) | 5.49E−10 |

Releasable rVWF Conjugates:

PEG-rVWF conjugates with releasable bonds via the amino groups of the lysine residues of rVWF were prepared in accordance with Examples 1A, 1B, 1C, 3A, 3B and 3C. The PEG-rVWF conjugates had total PEG molecular weights of about 20K, 40K or 60K. Table 2 summarizes the PEGylation degree of the conjugates.

TABLE 2

PEGylation degree of the releasable PEG-rVWF preparations

| Material Name | Protein (ng/ml) | PEG/monomer | | | |
|---|---|---|---|---|---|
| | | SDS-PAGE* | Ferrothiocyanate** | HPLC | Free PEG |
| Lys 20K br short low | 0.304 | 1-2 | — | 3.7 | <0.002% |
| Lys 20K br long low | 0.450 | <2 | 5.2 | 4.0 | <0.002% |
| Lys 40K br short low | 0.228 | <2 | 2.18 | 3.2 | <0.002% |
| Lys 40K br long low | 0.315 | 1 | — | 1.9 | <0.001% |
| Lys 60K br short low | 0.216 | <2 | 1.6 | 4.2 | <0.005% |
| Lys 60K br long low | 0.410 | 1 | — | 3.2 | <0.00625% |

The protein content of the PEGylated rVWF was determined using the Bradford assay with unmodified rVWF 133P1 as standard.
The remaining free PEG was determined by barium iodide staining of the non-reducing SDS-PAGE.
*The number of PEGs per molecule was counted by analyzing the Coomassie stained reducing SDS-PAGE followed by gel-scanning analysis.
**The number of PEGs per molecule was determined with the pronase/ammonium ferrothiocyanate method.

Some differences in the PEG to VWF monomer ratio determined were shown with the different methods applied. The HPLC method, which does not require a PEG extraction step, gave an average higher number of PEG/monomer than that given by the SDS-PAGE method. Thus, the original target of a low PEGylation degree of 1-2 PEG/VWF monomer ("monoPEGylation") was exceeded in all preparations except in the Lys 40K br long low conjugate. As investigated by barium iodide staining, no free PEG remained in the sample solution.

The protein content of the samples was measured according to the principle described by Bradford using the Protein Assay Dye Reagent Concentrate from Bio-Rad Laboratories (Hercules, Calif., USA). Bradford (1976) *Anal. Biochem.*

72:248-254. The microassay procedure was performed according to the manufacturer's instructions and calibrated using a certified human serum preparation (Qualitrol HS-N, DiaSys Diagnostics, Holzheim, Germany; distributed by VWR, Darmstadt, Germany), obtaining a calibration range of 20 to 1.8 µg protein/ml. Pre-dilution of concentrated samples as well as sample dilutions were prepared with 0.9% NaCl solution.

Determination of VWF:Ag:

Two different VWF:Ag assays were used during the experiments: SIMIT and sandwich ELISA.

A single incubation multilayer immune technique (SIMIT) for the in vitro characterization of the conjugates was one analytic technique used. The double sandwich VWF:Ag ELISA was set up with a commercially available antibody combination of a polyclonal rabbit anti-human VWF:antibody (A-082) and a peroxidase-labeled polyclonal rabbit anti-human VWF antibody (P-0226; both obtained from Dakopatts, Glostrup, Denmark) using the single incubation multilayer immune technique SIMIT. Wells of microtiter plates (NUNC Maxisorb F96; obtained from VWR) were coated with 1 µg antihuman VWF:antibody diluted in coat buffer (100 mM sodium carbonate, 100 mM sodium hydrogen carbonate, adjusted to pH 9.5 with HCl). Phosphate-buffered saline containing Tween-20 (PBST) used as washing buffer was composed of 137 mM NaCl, 2.7 mM KCl, 1.5 mM potassium dihydrogen phosphate, 7 mM disodium hydrogenphosphate dihydrate and 0.5 ml Tween-20 (Bio-Rad, EIA grade). For the dilution of samples and the antibody conjugate, 0.1% non-fat dry milk and 2 mM benzamidine was added to the washing buffer. All incubations were done at room temperature. Peroxidase activity was detected by using tetramethyl-benzidine (TMB) as substrate. The developed color intensity was measured with an ELISA reader at 450 nm. A normal reference plasma calibrated against the actual WHO standard was used for the construction of a calibration curve. A dilution series consisting of the six geometric 1+1 dilutions 1/100-1/3200 was prepared and analyzed in duplicates on each single plate obtaining a VWF:Ag concentration range of 0.01-0.0006 IU/ml. Samples were diluted at least 1+1 and five further 1+1 dilutions were analyzed in duplicates. The assay blank was also run in duplicates. For the data evaluation, a linear regression curve was calculated between the logarithms of both blank-corrected optical densities (ODs) measured and the known VWF:Ag concentrations of the six calibrators. Sample ODs were extrapolated on this curve only when they were within the range defined by the calibration curve and results were reported in IU/ml.

Sandwich ELISA for in vitro release experiments and for analysis of ex vivo plasma samples from the pharmacokinetic studies was also used. VWF:Ag was determined with a sandwich ELISA. Wells of microplates (Nunc-immuno 96-microwell plates, Maxisorp, Nunc, Roskilde, Denmark) were coated overnight with 1 µg/well polyclonal anti-VWF antibody (A-082, Dako, Glostrup, Denmark) in 50 mM sodium bicarbonate buffer, pH 9.6. Plates were then washed with washing buffer (20 mM Tris, 140 mM NaCl, 0.1% Tween-20, pH 7.4), and diluted samples in the range from 0.02 to 0.001 IU/ml VWF:Ag [in washing buffer+0.3% bovine serum albumin (BSA)] were incubated in the wells for 2 hours at 25-32° C., followed by washing and incubation with polyclonal anti-human VWF conjugated with horseradish peroxidase (P-0226, Dako, Glostrup, Denmark) in washing buffer+0.3% BSA. After a washing step, 0.4 mg/ml of ortho-phenylenediamine (P1063, Sigma, St. Louis, Mo., USA) in phosphate-citric acid buffer was added. Color development was stopped with 3 M sulfuric acid. Absorbance of wells was read in a microplate reader at 492 nm. Absorbance is directly proportional to VWF content in the sample. The VWF:Ag concentration in the samples was calculated relative to a human plasma reference preparation (SSC/ISTH secondary coagulation standard, #2).

Determination of VWF:RCo Activity:

VWF:RCo activities were measured with the BCS (Behring Coagulation System) analyzer (Dade Behring, Marburg, Germany) according to the instructions of the manufacturer by use of a lyophilized von Willebrand reagent containing stabilized platelets and ristocetin A (Dade Behring). The VWF (ristocetin cofactor) from the sample causes agglutination of the stabilized platelets in the presence of ristocetin. The resulting agglutination decreases the turbidity of the reaction suspension. The change in absorbance measured by the BCS analyzer at 570 nm is proportional to the sample's ristocetin cofactor activity. The ristocetin cofactor activity of the sample is quantified by means of a reference curve generated with Standard Human Plasma (Dade Behring) and reported in IU VWF:RCo/ml.

Determination of the Collagen-Binding Activity:

The VWF:CB activity was determined with a commercially available ELISA (Technozym VWF:CBA, Technoclone, Vienna, Austria) according to the instructions of the manufacturer. The precoated ELISA test strips with the immobilized human collagen type III were incubated with the sample solution. Collagen-bound VWF was detected by adding a peroxidase-conjugated polyclonal anti-VWF antibody. The VWF:CB activity of the sample was quantified by means of a reference curve generated with normal human plasma provided with the test-kit and expressed in U/ml VWF:CB.

Determination of VWF-FVIII-Binding Capacity by an ELISA Chromogenic Assay (ECA):

The VWF-FVIII interaction was determined by an ECA based on the assay described by Bendetowicz et al. See Bendetowicz et al. (1998) *Blood* 92(2):529-538. A commercially available polyclonal rabbit anti-human VWF antibody A082 (Dako, Glostrup, Denmark) was immobilized to the microtiter wells. Phosphate-buffered saline (PBS; 6.5 mM disodium hydrogenphosphate dihydrate, 1.5 mM potassium dihydrogen phosphate, 140 mM NaCl, pH 7.2) containing 0.05% Tween-20 was used as washing buffer. For sample dilution and as blocking solution, 0.1% non-fat dry milk (Bio-Rad, Hercules, Calif., USA) was added to the PBS-Tween buffer. A constant amount of rFVIII [0.2 IU/ml FVIII chromogenic activity (FVIII:C)] was mixed with the diluted VWF-containing sample (VWF:Ag concentration range 0.156 to 10 mIU/ml) in separate tubes and incubated at 37° C. for 25 minutes. The rFVIII source was a frozen bulk derived from the ADVATE brand of Factor VIII (Baxter Healthcare). The rFVIII bulk had a chromogenic FVIII activity of 4046 IU/ml, and contained less then 5 µg (~0.5 units) VWF:Ag/1000 IU of rFVIII. The rFVIII product was stored frozen in aliquots below −60° C. and thawed immediately before the assay.

This VWF-FVIII complex was transferred to the blocked microtiter plate and incubated for 60 minutes at room temperature. Unbound FVIII was removed by a subsequent washing step with washing buffer. Bound FVIII was quantified by a commercially available FVIII chromogenic assay (Technochrom FVIII:C reagent kit, Technoclone, Vienna, Austria), in which the reagent contains minute amounts of thrombin, FIXa, phospholipids and FX. The principle of this assay is that FVIII is activated by thrombin and thus released from VWF and subsequently forms a complex with phospholipid, FIXa and calcium ions. This complex activates FX to FXa, which in turn cleaves the chromogenic substrate, resulting in a color reaction measured in an ELISA reader (Benchmark, Bio-Rad, Hercules, Calif., USA) at 405 nm using the kinetic mode at 37° C. All samples were serially diluted and analyzed in duplicates. The blank corrected optical densities received (in mOD/min) were plotted against the VWF:Ag concentrations in logarithmic scale. The FVIII-binding activity of the sample was calculated from a fitted reference curve constructed from a normal reference plasma assuming that 1 IU of VWF:Ag has 1 U of VWF:FVIIIB activity.

For the applied concentration range from 0.156 to 10 mIU/ml VWF:Ag, the endogenous FVIII, which is bound to VWF of the normal plasma, had no influence on the measurement. The VWF:FVIIIB activity of the samples was expressed in U/ml, as read from the reference curve and the FVIII-binding capacity was calculated as a percent of the VWF:Ag measured in the sample.

Measurement of VWF-FVIII Affinity by Surface Plasmon Resonance Technology:

Unmodified and PEGylated VWF were immobilized on the flow cells of a CM5 sensor chip of a Biacore 3000 (Biacore AG, Uppsala, Sweden) apparatus to a constant level according to the instructions of the manufacturer. A series of dilutions of FVIII samples were then applied to the chip using the "kinject" mode, allowing 3 minutes for the association and 10 minutes for the dissociation of FVIII. After each of these cycles, FVIII was removed from the chip ("regeneration") and the experiment was repeated with a new FVIII sample.

Determination of the FVIII-Binding Capacity of PEG-rVWF in the Presence of Native rVWF Under Flow Conditions:

A constant amount of rVWF was immobilized on the flow cells of a CM5 sensor chip of a Biacore 3000 (Biacore AG, Uppsala, Sweden). Different amounts of rVWF were incubated with 5 IU/ml rFVIII at 37° C. for 5 minutes to form a complex and then injected into the flow cells with the immobilized rVWF. The amount of free FVIII bound to the immobilized rVWF was calculated from a reference curve, established by injecting rFVIII in the absence of rVWF in the range of 0.1 to 5 IU/ml. The rFVIII remaining in the complex was calculated and expressed as a percent of the added rFVIII bound in the absence of rVWF.

Measurement of Susceptibility for VWF Cleaving Protease (ADAMTS13):

Susceptibility of rVWF to ADAMTS13 was investigated by incubating the conjugates with increasing concentrations of preactivated ADAMTS13 under denaturing conditions to unfold the VWF. The degradation of VWF was measured by collagen-binding (VWF:CB) activity, which depends on the multimeric size of VWF, before and 4 hours after the incubation. The degradation of the multimer numbers and formation of the specific satellite bands were visualized by multimer analysis.

For the degradation of rVWF, normal human plasma (George King Bio-Medical, Overland Parks, Kans., USA) was used, as the ADAMTS13 source. ADAMTS13 in the dilutions of the plasma were activated with $BaCl_2$ for 30 minutes at 37° C. in the presence of 5 mM Tris, 1.5 M urea, pH 8.0 and mixed with constant amounts of rVWF (prediluted with 5 mM Tris, 1.5 M urea, pH 8.0) and further incubated at 37° C. for 4 hours. The incubation mixtures contained 6 µg/ml of native or PEGylated rVWF conjugates and 1 to 33 mU/ml of ADAMTS13. The reaction was stopped by the addition of $Na_2SO_4$ and the incubation mixtures were subsequently centrifuged for 5 minutes at 2500 g and the supernatant was used for further analysis.

Collagen-binding activity (VWF:CB) was determined. High-binding 96-well ELISA plates (Costar 3590, Corning Incorporated, NY, USA) were precoated with 100 µl of 1.5 µg/ml human collagen type 111 (Southern Biotechnology Associates, Inc., Birmingham, USA) in 6.5 mM di-sodium hydrogen phosphate dihydrate, 1.5 mM kalium dihydrogen phosphate, 140 mM NaCl, pH 7.2 (PBS) overnight at 4° C. and subsequently blocked with 200 µl of "Super Block Blocking Buffer in PBS" (Pierce, Rockford, Ill., USA) for 30 minutes at room temperature. The centrifuged digestion mixtures were diluted 1/5 with PBS containing 0.05% Tween-20 and 10% of the blocking solution and 100 µl of these dilutions were added to the blocked wells. After incubation for 2 hours at room temperature, the plates were further incubated for one hour with 100 µl of a solution of polyclonal horse-radish peroxidase-conjugated anti-human VWF antibody (P-0226, Dako, Glostrup, Denmark) diluted 1/10000 in PBS buffer, pH 7.2 containing 0.05% Tween-20 and 10% of the blocking solution. Between each step, the microtiter wells were washed three times with 250 µl PBS containing 0.05% Tween-20. The color reaction was achieved by addition of 100 µl of "ImmunoPure TMB Substrate" (Pierce, Rockford, Ill., USA), and after 5 minutes incubation the reaction was terminated by the addition of 100 µl 1 $NH_2SO_4$. The absorbance was read at 450 nm using an ELISA reader 680 (Bio-Rad Laboratories, Hercules. Calif., USA). As a negative control, physiological saline was used instead of normal plasma with the same procedure. Samples with 0.017 U/ml ADAMTS13 were subjected to low- and high-resolution multimer analysis as described below under "VWF multimer analysis."

SDS-PAGE and Silver Staining:

VWF samples (20 mIU, equal to 0.2 µg protein per lane) were applied to gradient (3-8%) Tris-acetate gels and electrophoresis was done under reducing conditions, followed by silver staining, as described by the manufacturer (Bio-Rad). As molecular weight standard the Precision Plus Protein All Blue standard was used (250-10 kDa, Bio-Rad, Hercules, Calif., USA).

SDS-PAGE and Coomassie Staining:

VWF samples (100 mIU, equal to 1 µg protein per lane) were applied to gradient (3-8%) Tris-acetate gels and electrophoresis was done under reducing conditions, followed by Coomassie staining, as described by the manufacturer (Bio-Rad, Hercules, Calif., USA). The Precision Plus Protein All Blue standard was used (250-10 kDa/Bio-Rad, Hercules, Calif., USA) as the molecular weight standard.

SDS-PAGE and Immunoblot for VWF

VWF samples (0.55 mIU equal to 5.5 ng protein per lane) were applied to gradient (3-8%) Trisacetate gels and electrophoresis was done under reducing conditions, followed by standard blotting procedures onto a polyvinylidene difluoride (PVDF) membrane. To visualize the VWF bands, a polyclonal rabbit anti-human VWF antibody (A-082, Dako, Glostrup, Denmark) was used as primary antibody. An alkaline phosphatase (ALP)-labeled goat anti-rabbit IgG was applied as a secondary antibody (Bethyl Laboratories Inc., Montgomery, Tex., USA). The blots were developed with the ALP Conjugate Substrate Kit (Bio-Rad, Hercules, Calif., USA). A full range rainbow marker (250-10 kDa, GE-Healthcare, Little Chalfont, Buckinghamshire, UK) was used as the molecular weight standard.

SDS-PAGE and Immunoblot for PEG

VWF samples (5.5 mIU equal to 55 ng protein per lane) were applied to gradient (3-8%) Tris-acetate gels and electrophoresis was done under reducing conditions, followed by standard blotting procedures onto a PVDF membrane. To visualize the PEG, polyclonal rabbit anti-human PEG antibody was used as primary antibody. The anti-PEG antibody was raised in rabbits by immunization with a PEGylated protein. The IgG fraction of the rabbit serum was purified by affinity chromatography on Protein G Sepharose 4B (GE-Healthcare, Uppsala, Sweden) followed by specific negative immunabsorption. An ALP-labeled goat anti-rabbit IgG (Bethyl Laboratories Inc., Montgomery, Tex., USA) was applied as a secondary antibody. The blots were developed with the ALP Conjugate Substrate Kit (Bio-Rad, Hercules, Calif., USA). A full range rainbow marker (250-10 kDa, GE-Healthcare, Little Chalfont, Buckinghamshire, UK) was used as the molecular weight standard.

VWF Multimer Analysis

The size distribution of the rVWF preparations were analyzed by high-density horizontal SDS agarose gel electrophoresis using high-resolution (2.5-2.7% agarose) conditions. Samples were diluted to the same concentration in the range of 0.3-1.0 IU/ml VWF:Ag and incubated with Tris-EDTA-SDS buffer. The multimers were separated under non-reducing conditions on an agarose gel.

VWF multimers and the distribution of PEG on the VWF multimers were either visualized in the gel by immunostaining with a polyclonal rabbit anti-human VWF antibody (A-082, Dako, Glostrup, Denmark) or with a polyclonal rabbit anti-PEG antibody after electroblotting to a PVDF-membrane, followed by ALP-conjugated goat anti-rabbit IgG H+L (Jackson Immuno Research, Soham, Cambridgeshire, UK) using the ALP Conjugate Substrate Kit (Bio-Rad, Hercules, Calif., USA).

As a hemophilia model, FVIII-knockout mice [Lawler et al. (1995) Nat. Genet. 10(1):119-121] were used. The mice suffered from severe hemophilia A (FVIII<0.01 IU/ml) but had normal levels of VWF (approximately 0.15 IU/ml relative to human VWF reference), mimicking human hemophilia A.

Application of VWF and FVIII:

Recombinant FVIII (214 IU FVIII/ml) from Baxter was used in all experiments in this example and co-injected with rVWF. The freeze-dried final containers were stored at 2-8° C. and reconstituted before use. The dissolved rFVIII and non-PEGylated or PEGylated rVWF were mixed with 20 mM Hepes, 150 mM NaCl, 3.2% mannitol, 0.8% trehalose, 2.5 mM $CaCl_2$, 1% human albumin, pH 7.4 buffer to achieve appropriate concentrations for infusion. The mixtures were aliquoted, frozen at −20° C. and thawed just before the applications. Target dose was 200 IU/ml FVIII:C and 1.6 to 2.1 mg/kg VWF. The concentrations were measured again from the thawed samples and the applied doses were calculated. Doses are given in the Figure legends. 10 ml/kg bodyweight were injected via the tail vein and groups of 5-6 mice were bled by heart puncture after 5 minutes, 3 hours, 6, 9, 16 and 24 hours, and if necessary, after 32 and 42 hours. Nine volumes of blood were mixed with 1 volume of 3.8% sodium citrate, and immediately centrifuged at 3000 g for 10 minutes. The supernatant was again centrifuged at 3000 g for 5 minutes, plasma was separated, frozen in aliquots and stored below −60° C. for analysis.

Determination of FVIII Activity in Mouse Plasma:

FVIII activity was determined with a chromogenic method following the assay principle as set forth above with respect to the determination of VWF-FVIII binding capacity by an ELISA chromogenic assay. The time course of the para-nitroaniline (pNA) released from the substrate was measured with a microplate reader at 405 nm using the kinetic mode. The slope of the reaction is proportional to the FVIII concentration in the sample. The FVIII concentration in the samples was calculated relative to a human plasma reference preparation, calibrated against the WHO plasma reference ($5^{th}$ IS for FVIII and VWF in human plasma, NIBSC #02/150) and expressed in IU/ml.

Determination of VWF Antigen in Mouse Plasma:

VWF:Ag was determined with the sandwich ELISA described above with respect to Sandwich ELISA for in vitro release experiments and for analysis fo ex vivo plasma samples from the pharmacokinetic studies. The VWF:Ag concentration of the samples was calculated relative to a human plasma reference preparation (SSC/ISTH secondary coagulation standard, #2). The baseline-level of mouse VWF was subtracted. The quantification limit of the assay in mouse plasma was 0.03 IU/ml of VWF:Ag.

Calculation of the Circulating Half-Life Parameters of Human VWF and FVIII:

For analyzing FVIII levels, the concentrations for $t_0=0$ hours was set to zero as FVIII deficient mice were studied. For analyzing VWF:Ag levels, the concentration for $t_0=0$ was set to zero and the arithmetic mean concentration of untreated mice was subtracted from mean concentrations at subsequent time points. FVIII levels over time were summarized using pharmacokinetic parameters AUC from zero to 24 hours, terminal elimination rate and mean residence time. VWF:Ag levels over time were summarized by the pharmacokinetic parameter AUC from zero to 24 hours.

Area Under the Concentration vs. Time Curve (AUC) from 0 to 24 Hours:

The area under the concentration vs. time curve (AUC) from 0 to 24 hours was calculated by the linear trapezoidal rule using the arithmetic means of the concentrations observed at individual time points. It was assumed that there exists a linear relationship between dose and AUC. Under this assumption, the AUCs for different items were adjusted for dose in case of different doses administered. Dose adjustment was performed by dividing the calculated AUC by the dose per kg body mass administered.

Terminal Elimination Rate:

The terminal elimination rate (k) was estimated using the arithmetic mean of the natural logarithms of individual concentrations at the last three time points modified with a bias correction. See Wolfsegger et al. (2005) J. Pharmacokinetic. Pharmacodyn. 32(5-6):757-766.

Mean Residence Time:

Mean residence time (MRT) was calculated as $AUMC_{0-infinity}$ divided by $AUC_{0-infinitiy}$. $AUMC_{0-infinity}$ and $AUC_{0-infinity}$ were calculated by the linear trapezoidal rule using the arithmetic means of the concentrations observed for different time points plus a three-point tail area correction. The tail area correction was calculated by log-linear fitting on the arithmetic means observed at the last three time points per item.

Results
Functional Parameters of PEG-rVWF:

The different biological functions of VWF were characterized by different parameters. VWF:CB, VWF:RCo and VWF:FVIIIB were measured to characterize the integrity of the collagen and platelet-binding site, required for the VWF-mediated platelet adhesion, one of the first steps of hemostasis. The VWF:FVIIIB capacity and affinity describes the availability of the FVIII-binding sites, needed for the chaperon function of VWF. Table 3 summarizes the measured values, while the calculated ratios and specific activities are summarized in Table 4.

To investigate the possible effect of the conjugation with the releasable PEG reagents, a mock preparation (control) was also manufactured which ran through the whole process but was not PEGylated. This preparation had similar activities to the controls, which confirmed that the process had no negative effect on rVWF.

Because all parameters were similarly affected, the VWF:FVIIIB capacity, which was expressed as a percent of the VWF:Ag level, only marginally decreased.

PEGylation with the 60K reagent had a substantial decreasing effect on the specific activities, even at low degrees of PEGylation. Increasing the PEGylation degree (Lys 20K br medium and Lys 20K br high conjugates) resulted in a substantial decrease in all activities, especially in the VWF:CB and VWF:FVIIIB, where only a few percent of the initial activities could be detected for the Lys 20K br high conjugate.

PEGylation with the releasable PEG reagents resulted in a substantial decrease in the specific activities, even at low degrees of PEGylation. The higher the MWs of the reagents were, the greater was the decrease in activities observed. No substantial differences were found between the "short" and "long" derivatives of the same MW.

The FVIII affinity was determined assuming homogeneous 1:1 interaction between the immobilized rVWF and FVIII, the association and dissociation constants were determined using the Langmuir model of the "Bioevaluation" program of the Biacore 3000 apparatus. The affinity constant (KD) for the PEGylated rVWF-FVIII interaction remained in the same order of magnitude as measured with non-PEGylated VWF, independently of the type or MW of the applied PEG reagent.

TABLE 3

Quantitative parameters of rVWF conjugates

| Samples | Protein (mg/ml) #1 | Protein (mg/ml) #2 | VWF:Ag (IU/ml) | VWF:RCo (IU/ml) | VWF:CB (U/ml) | VWF:FVIIIB (U/ml) | VWF:FVIII binding affinity KD (M) |
|---|---|---|---|---|---|---|---|
| native rVWF | n.a. | 0.344 | 54.6 | 24.3 | 63.5 | 46.0 | 5.5E−10 |
| 133P1-1 | n.d. | n.d. | 48.3 | 17.8 | n.d | 37.8 | 4.8E−10 |
| 133P1-2 | n.d. | 0.373 | 49.1 | 22.1 | n.d | 47.9 | 2.9E−10 |
| 133P1-3 | n.d. | 0.396 | 42.4 | 17.7 | n.d | 37.9 | n.d. |
| mean | n.a | 0.385 | 46.6 | 19.2 | n.a. | 41.2 | 3.9E−10 |
| Lys 20K br short low | 0.304 | 0.259 | 21.1 | 11.8 | 19.5 | 13.6 | 7.5E−10 |
| Lys 20K br long low | 0.450 | 0.529 | 25.3 | 18.7 | 21.7 | 16.8 | 3.9E−09 |
| Lys 40K br short low | 0.228 | 0.234 | 9.1 | 5.5 | 10.4 | 8.8 | 2.3E−09 |
| Lys 40K br long low | 0.315 | 0.212 | 14.3 | 8.1 | 15.8 | 15.8 | 2.6E−09 |
| Lys 60K br short low | 0.216 | 0.235 | 2.9 | 1.0 | 1.3 | 2.7 | 5.5E−09 |
| Lys 60K br long low | 0.410 | 0.459 | 10.3 | 3.5 | 9.9 | 10.9 | 5.4E−09 |
| control | 0.163 | 0.145 | 18.4 | 8.0 | n.d. | 15.5 | n.d. |

All results were obtained from a freshly thawed sample and are the mean of at least 2 measurements.

TABLE 4

Specific activities of rVWF conjugates

| Samples | Activity related to VWF:Ag VWF:RCo (IU/IUAg) | Activity related to VWF:Ag VWF:CB (U/IUAg) | Activity related to VWF:Ag VWF:FVIIIB capacity (%) | Specific activity related to the rVWF protein VWF:Ag (IU/mg) | Specific activity related to the rVWF protein VWF:RCo (IU/mg) | Specific activity related to the rVWF protein VWF:CB (U/mg) | Specific activity related to the rVWF protein VWF:FVIIIB (U/mg) |
|---|---|---|---|---|---|---|---|
| native rVWF | 0.45 | 1.16 | 84 | 159 | 71 | 185 | 134 |
| Control #1 | 0.41 | n.d. | 88 | 121 | 50 | n.d. | 107 |
| Lys 20K br short low | 0.56 | 0.92 | 64 | 69 | 39 | 64 | 45 |
| Lys 20K br long low | 0.74 | 0.86 | 66 | 56 | 42 | 48 | 37 |
| Lys 40K br short low | 0.60 | 1.14 | 97 | 40 | 24 | 46 | 39 |
| Lys 40K br long low | 0.57 | 1.10 | 110 | 45 | 26 | 50 | 50 |
| Lys 60K br short low | 0.34 | 0.45 | 93 | 13 | 5 | 6 | 13 |
| Lys 60K br long low | 0.34 | 0.96 | 106 | 25 | 9 | 24 | 27 |
| Control #2 | 0.43 | n.d. | 84 | 113 | 49 | n.d. | 95 |

Values were calculated from the measured data, shown in Table 4.

Releasable rVWF Conjugates:

Similar to the SDS-PAGE results of the stable conjugates, mature rVWF appeared as a prominent single band (monomer) with a MW of ~260 kDa with some minor bands down to 150 kDa. Remaining amounts of non-PEGylated rVWF monomers were still present in the PEG-rVWF preparations, especially in the 40K derivatives.

The PEGylation led to a band shift to higher MW which correlated with the MW of the applied PEG reagents. No structural changes were shown for the control preparations.

Figure 9B:
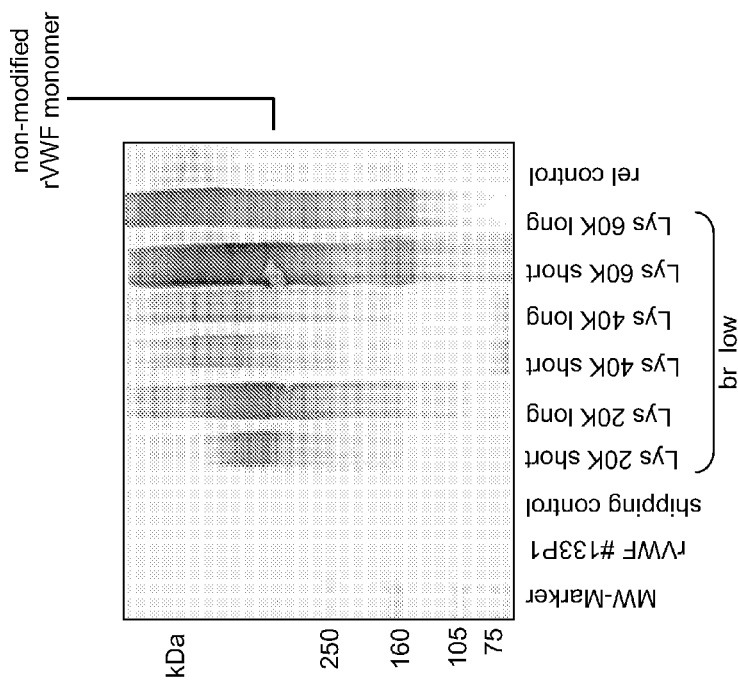
FIGS. 9A and 9B show the domain structure of releasable PEGylated rVWF visualized by immunoblots of reducing SDS-PAGE specific for VWF and PEG.
Figure 9A:
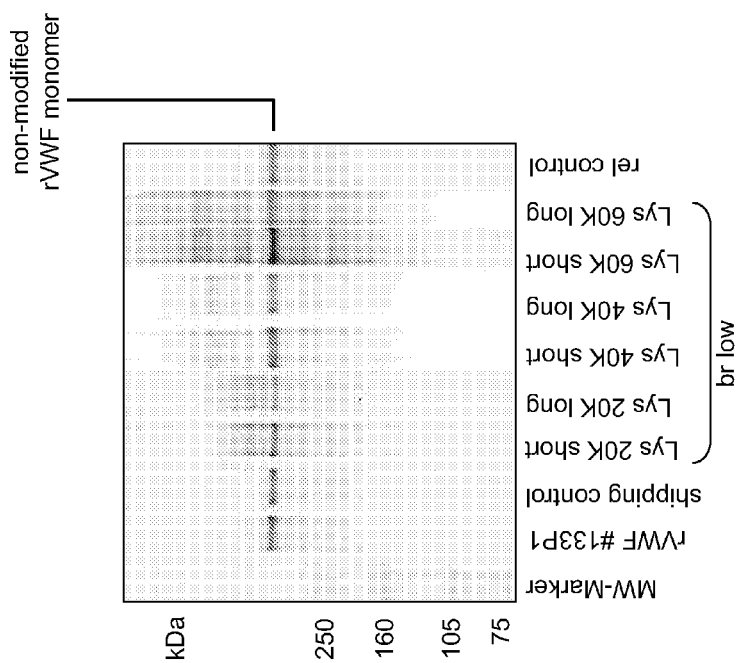

To verify the results of the protein-stained SDS-PAGE, the gels were immunoblotted with a polyclonal anti-human VWF antibody, as demonstrated in FIG. 9A. The unmodified native rVWF 133P1 appeared as a single VWF monomer in the anti-VWF immunoblot with some minor, non-relevant degradation bands. No structural changes were detected in the mock preparation (control).

All releasable conjugates showed a non-PEGylated band and some distinct bands in the higher MW range. The number of the increased bands might represent mono-, di-, tri- and higher PEGylated monomers. The MW of these bands correlated with the MW of the applied PEG reagents.

FIG. 9B shows the immunoblot for PEG when the blots were stained with a polyclonal anti-PEG antibody and confirmed that the higher MW bands contained PEG. No reaction was observed for the non-PEGylated materials rVWF 133P1 and rVWF control. Lower MW bands appeared in all samples, most likely representing some free PEG in the sample, released during sample preparation.

Structural Integrity of PEGylated rVWF Shown by VWF Multimer Analysis:

Multimer composition and the effect of PEGylation on this parameter was investigated by non-reducing agarose gel electrophoresis using a low-resolution (1%) gel to determine the number of the multimers and a high-resolution (2.5%) gel to investigate the fine structure of the multimers.

Figure 10B:
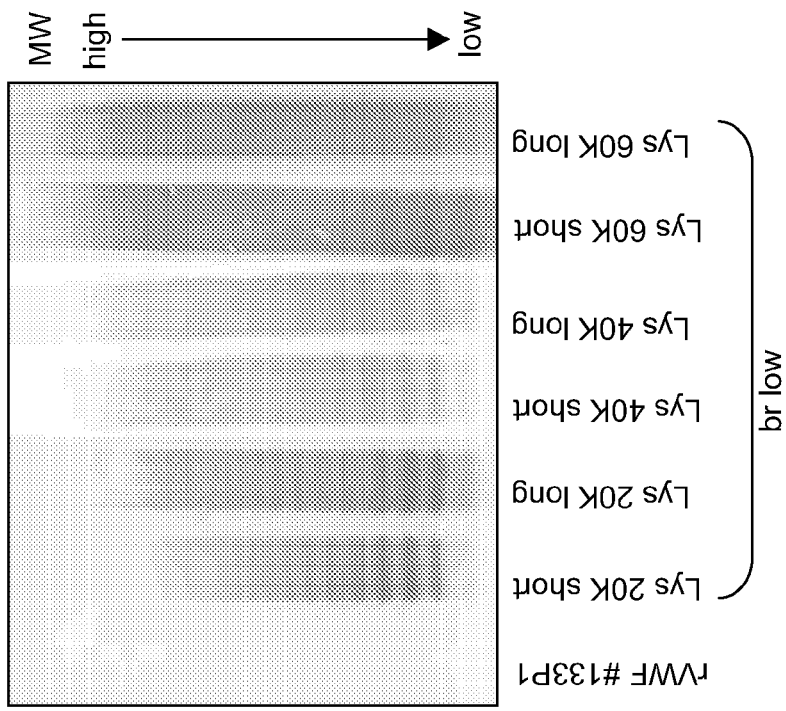
FIGS. 10A and 10B show the VWF multimer distribution of releasable rVWF conjugates visualized by low resolution agarose gel electrophoresis.
Figure 10A:
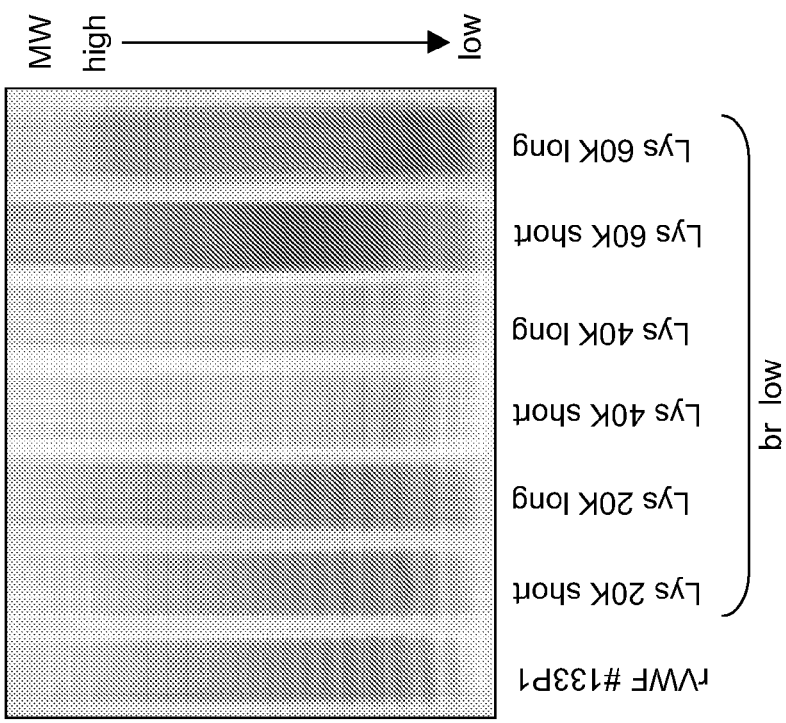

Similar to the stable conjugates, the increase in PEG size resulted in a loss of resolution in the high MW multimer range in the low-resolution agarose gel electrophoresis (blurred area in FIG. 10A), which made the exact number of the multimers difficult to determine. The immunoblot for PEG (FIG. 10B) demonstrated that apparently all multimers were PEGylated, which means that each multimer contained at least one PEGylated VWF monomer.

Figure 11A:
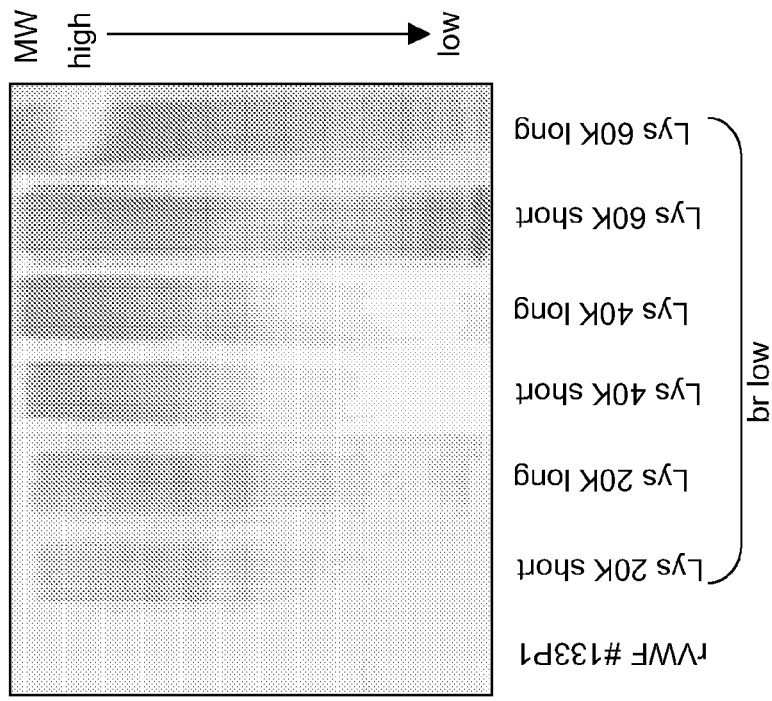
FIGS. 11A and 11B show the fine structure of VWF multimers of the releasable rVWF conjugates visualized by high-resolution agarose gel electrophoresis.

The high-resolution agarose gel (FIGS. 11A, 11B) showed a broadening and clear shift of the VWF multimers to higher molecular weights with a minor MW increase for the Lys 20K br short low and a medium increase for the Lys 20K br long low conjugates (FIG. 11A). These data correlated with the PEGylation degree described in Table 3. Multimer analysis of the 40K and particularly of the 60K conjugates resulted in a blurred area instead of distinct bands.

Figure 11B:
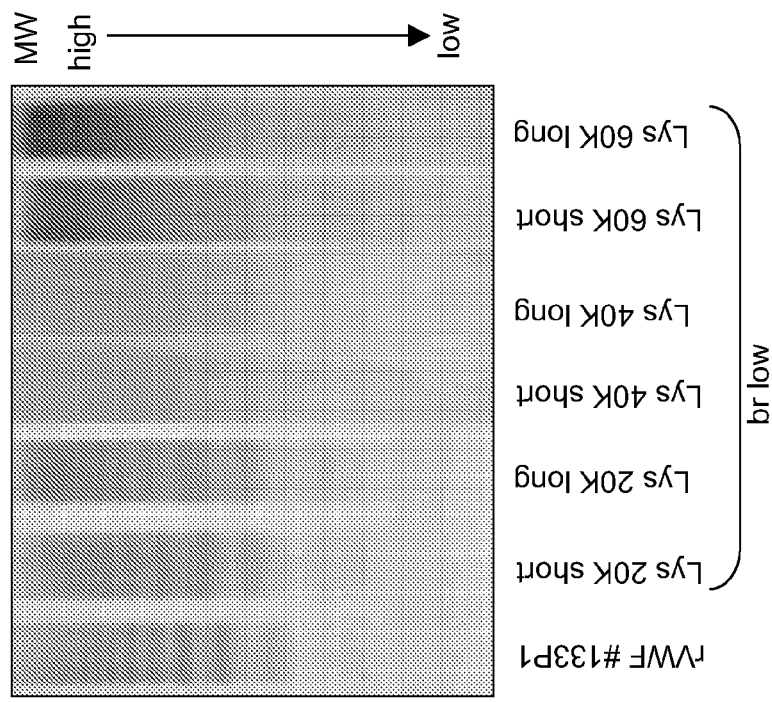

FIG. 11B confirmed that apparently all multimers were PEGylated, which means that each multimer contained at least one PEGylated VWF monomer. For the 60K conjugates some lower MW bands were stained with the anti-PEG antibody, which might represent some free PEG, probably released under the electrophoretic conditions.

Determination of the FVIII-Binding Capacity of the PEGylated-rVWF in the Presence of Unmodified rVWF Under Flow Conditions:

Hemophilia A patients to be treated with rFVIII complexed non-covalently with the PEGylated rVWF have normal levels of endogenous VWF, therefore the question arose, whether this VWF might compete with the PEGylated rVWF for the injected rFVIII. To address this question, competition of FVIII complexed with PEGylated rVWF with native rVWF was measured in a Biacore system, as described above with respect to determination of the FVIII-binding capacity of PEG-rVWF in the presence of native rVWF under flow conditions. Constant amounts of unmodified rVWF were immobilized to the sensor chip of the Biacore equipment and native or PEGylated rVWF-FVIII complex, containing 5 IU/ml rFVIII, and increasing amounts of VWF:Ag were injected. The rFVIII complexed with the injected VWF was expressed as a percent of the added FVIII.

Figure 12:
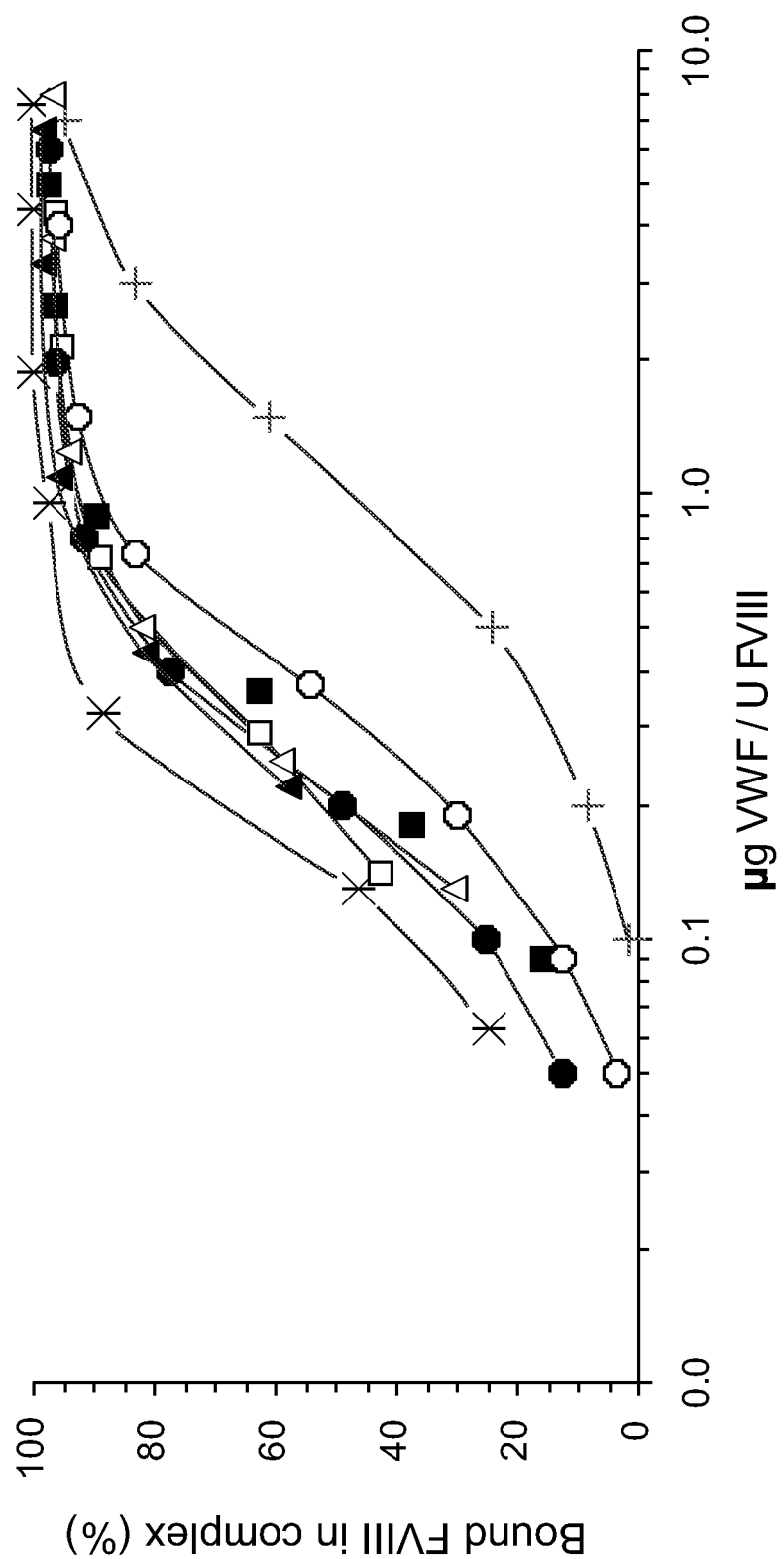
FIG. 12 shows the FVIII-binding capacity of the releasable PEG-rVWF conjugates in the presence of unmodified rVWF under flow conditions. Squares, open: PEGylated rVWF Lys 20K br rel short and rFVIII; squares: PEGylated rVWF Lys 20K br rel long and rFVIII; triangles, open: PEGylated rVWF Lys 40K br rel short and rFVIII; triangles: PEGylated rVWF Lys 40K br rel long and rFVIII; circles, open: PEGylated rVWF Lys 60K br rel short and rFVIII; circles: PEGylated rVWF Lys 60K br rel long and rFVIII; star: native rVWF (133 pool1) and rFVIII; cross: rproVWF198 and rFVIII. Further information concerning this figure is provided in Example 5.

FIG. 12 shows the percent of rFVIII that remained in complex with the releasable PEGylated rVWF conjugates as a function of the µg rVWF/IU FVIII. The star symbol (*) line shows the native rVWF, requiring the lowest VWF to FVIII ratio (approximately 1 µg/IU) to keep all FVIII in a complex. The cross (+) line with represents an inhouse rVWF preparation (rproVWF 198) containing about 50% of proVWF and mature VWF. This preparation can bind less FVIII because the propeptide shades the FVIII-binding site of VWF. Bendetowicz et al. (1998) *Blood* 92(2):529-538.

The ELISA-based VWF:FVIII-binding assay (ECA) revealed no substantial differences between the binding capacity of the releasable conjugates (Table 5). All showed a diminished capacity compared with the native rVWF. All conjugates showed a 100% binding of FVIII above a ratio of 1 µg VWF/U FVIII. These results correlate well with the animal models.

Susceptibility to ADAMTS13:

Under physiological conditions, ultra-large multimers of VWF are degraded by the VWF-cleaving protease (ADAMTS13), which thus plays a role in the prevention of platelet aggregation which could be induced by these ultra-large multimers of VWF. Because the expressed rVWF has never been exposed to ADAMTS13, its susceptibility to ADAMTS13 is an important measure of the structural integrity of an rVWF product. The ADAMTS13-induced physiological degradation can be simulated in vitro by incubating rVWF and ADAMTS13 under denaturing conditions.

Figure 13:
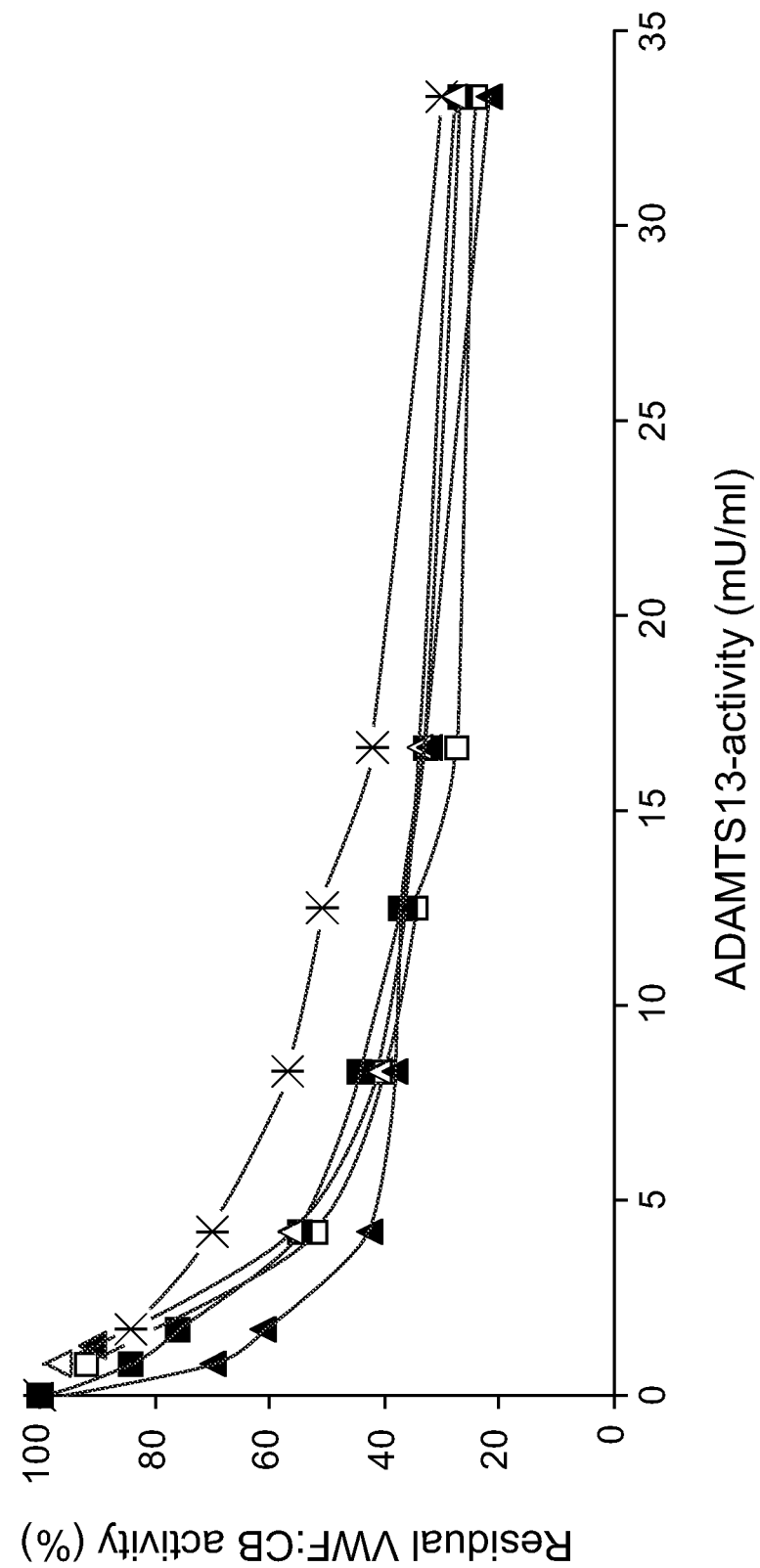
FIG. 13 shows the changes in VWF:CB activity of VWF in the ADAMTS13 digested samples. Squares, open: PEGylated rVWF Lys 20K br rel short; squares: PEGylated rVWF Lys 20K br rel long; triangles, open: PEGylated rVWF Lys 40K br rel short; triangles: PEGylated rVWF Lys 40K br rel long; star: native rVWF (133 P1). Further information concerning this figure is provided in Example 5.
Figure 14:
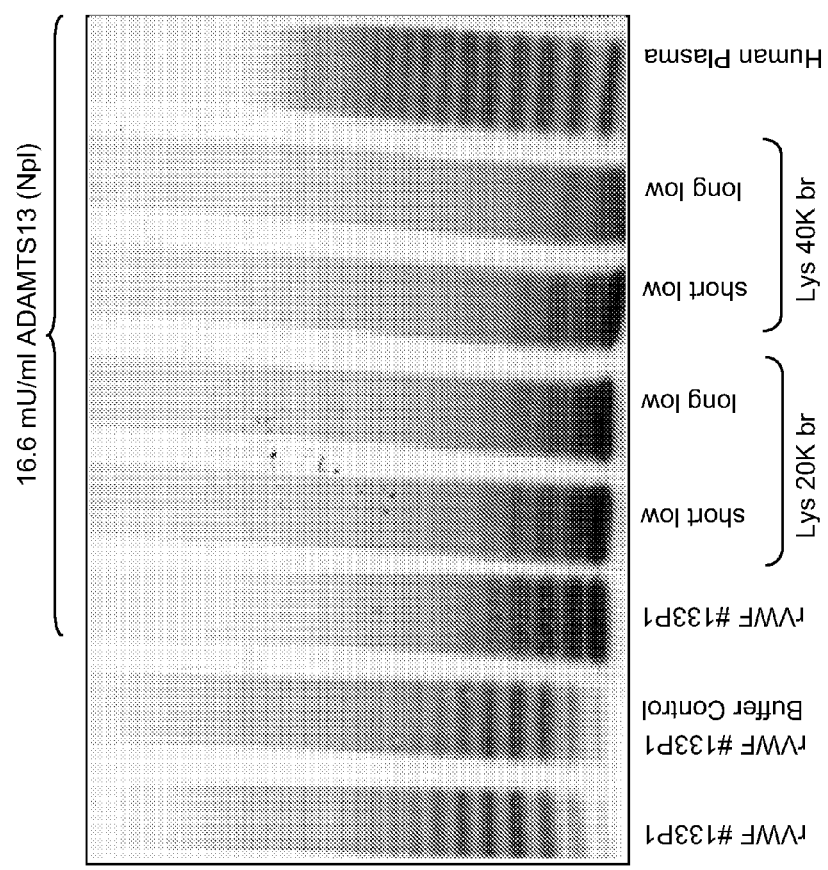
FIG. 14 shows the ADAMTS13-mediated satellite band formation in rVWF visualized by SDS-agarose gel. Further information concerning this figure is provided in Example 5.

FIG. 13 shows the relative changes of VWF:CB activity (% of the VWF:CB activity measured in the absence of ADAMTS13) of the conjugates as a function of ADAMTS13 concentration. The Lys 60 K br conjugate had a very low VWF:CB activity (Table 4). Therefore it could not be tested. All conjugates showed a similar gradual loss of VWF:CB activity incubated with increasing amounts of ADAMTS13. The PEGylated conjugates showed a slightly higher susceptibility to ADAMTS13 than their parent native rVWF. Multimer analysis demonstrated the disappearance of the higher molecular weight multimers (FIG. 14). All preparations showed similar sensitivity to ADAMTS13.

In Vitro Release of Releasable PEG-rVWF:

To investigate the kinetics of in vitro release of the PEG moieties from rVWF, the PEGylated rVWF samples were diluted to approximately 100 µg/ml with Hepes buffer (20 mM Hepes, 150 mM NaCl, 0.5% sucrose, adjusted to pH ~7.5 with 100 mM Tris). As a control, a native rVWF was treated the same way. All samples were kept at ambient temperature for 8 days. A sub-sample was taken every day at the same time, aliquoted, frozen and stored at −80° C. until analysis.

Table 5 shows the calculated VWF:Ag/protein ratio (IU/mg). The native rVWF 133P1 was stable over the whole time period. The VWF:Ag value differs at the start point (0 hours) because of the variation of the VWF:Ag to protein ratios between the different PEG-rVWF conjugates. Nevertheless all six derivatives showed an increase in VWF:Ag level during the incubation, albeit to different extents. With the exception of the Lys 60K br short low conjugate, the VWF:Ag to protein ratio reached the range of the native rVWF.

TABLE 5

Changes of VWF:Ag to protein ratio of releasable PEG-rVWF during in vitro incubation

| Incubation time (days) | Lys 20K short | Lys 20K long | Lys 40K short br low | Lys 40K long | Lys 60K short | Lys 60K long | rVWF native |
|---|---|---|---|---|---|---|---|
| 0 | 92 | 74 | 75 | 63 | 51 | 56 | 98 |
| 1 | 119 | 91 | 77 | 58 | 59 | 62 | 103 |
| 2 | 84 | 86 | 70 | 61 | 66 | 65 | 80 |
| 3 | 108 | 81 | 93 | 81 | 64 | 71 | 108 |
| 4 | 103 | 98 | 83 | 66 | 72 | 83 | 95 |
| 5 | 114 | 88 | 106 | 87 | 71 | 94 | 112 |
| 6 | 99 | 113 | 92 | 87 | 64 | n.d. | 81 |
| 7 | 124 | 94 | 83 | 102 | 69 | 93 | 113 |
| 8 | 116 | 83 | 87 | 102 | 63 | 103 | 97 |

TABLE 6

Changes in VWF:FVIIIB specific activity of releasable PEG-rVWF during in vitro incubation

| Incubation time (days) | Lys 20K short | Lys 20K long | Lys 40K short br low | Lys 40K long | Lys 60K short | Lys 60K long* | rVWF native |
|---|---|---|---|---|---|---|---|
| 0 | 46 | 34 | 37 | 35 | 17 | n.a. | 81 |
| 2 | 60 | 45 | 40 | 35 | 32 | n.a. | 66 |
| 5 | 102 | 54 | 82 | 63 | 57 | n.a. | 93 |
| 8 | 128 | 73 | 92 | 101 | 69 | n.a. | 84 |

*VWF:FVIIIB of the 60K long conjugate after release reaction in buffer could not be measured due to non-parallel dilution curves Table 6 shows the changes in the specific VWF:FVIIIB capacity calculated as U/mg protein. During the incubation period a full recovery of VWF:FVIIIB was observed for all batches evaluated.

Figure 15:
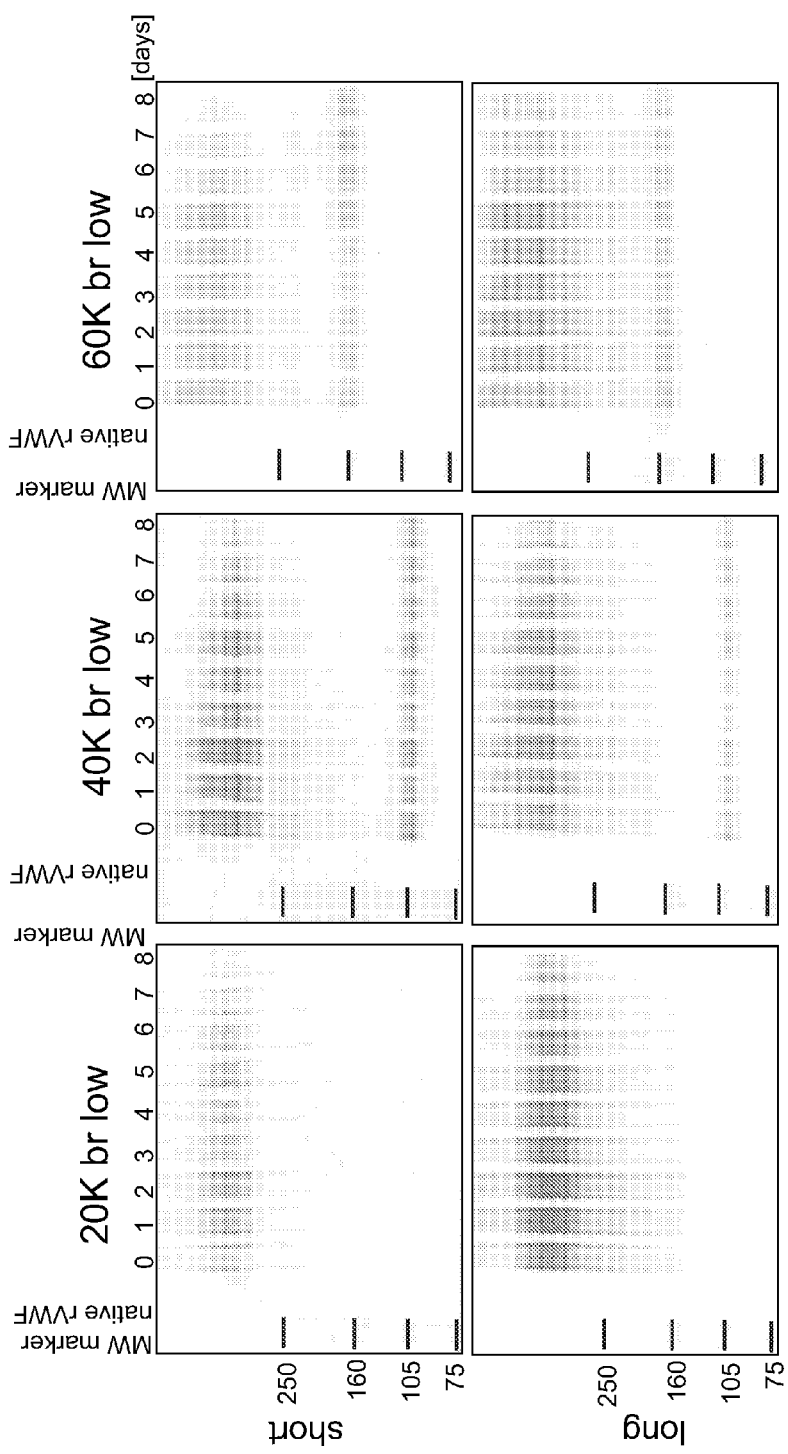
FIG. 15 shows the time course of changes in PEGylation degree demonstrated by anti-PEG immunoblot. Further information concerning this figure is provided in Example 5.

To assess the possible degradation of rVWF and the changes in PEGylation grade, the samples were subjected to SDS-PAGE under reducing conditions followed by immunoblots with a polyclonal anti-VWF antibody and a polyclonal anti-PEG antibody (FIG. 15). As shown in FIG. 15, all PEG-rVWF derivatives showed a gradual release of PEG after in vitro release in buffer with a moderately increased pH (7.5-7.7). Corresponding to the release behavior of the conjugates of "short" and "long," some differences in the PEGylation degree could be observed after longer incubation periods. In contrast, there was no substantial increase in the free PEG during the incubation, possibly because of the presence of free PEG already shown in the first sample after dilution with the incubation buffer. No free PEG was visualized for the 20K conjugates because the immunoblot showed only MW ranges above 75 kDa.

Pharmacokinetics of PEGylated rVWF and Co-Injected rFVIII in the Hemophilia Mouse Model:

FVIII-deficient knockout mice were infused with either a mixture of rVWF/rFVIII or PEGylated rVWF/rFVIII in a target ratio of 1.6-2.1 mg rVWF to 200 IU rFVIII/kg (based on Bradford protein determination). In the experiments, 6 mice per time group were used for each conjugate.

Figure 16A:
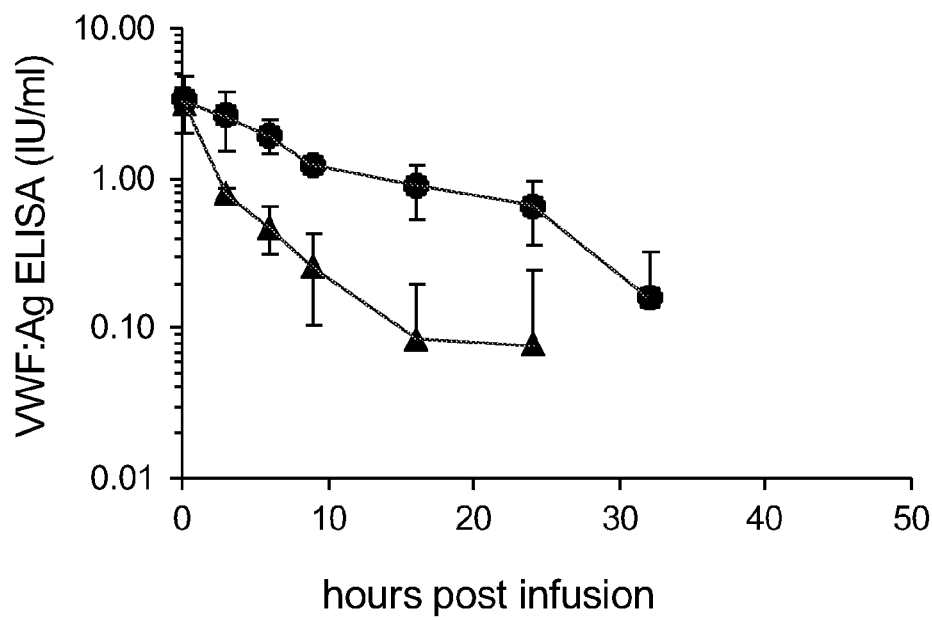
FIGS. 16A and 16B show the comparison of the native rVWF and PEGylated rVWF Lys 20K br short low (both with co-injected rFVIII) in FVIII-deficient knockout mice.
Figure 16B:
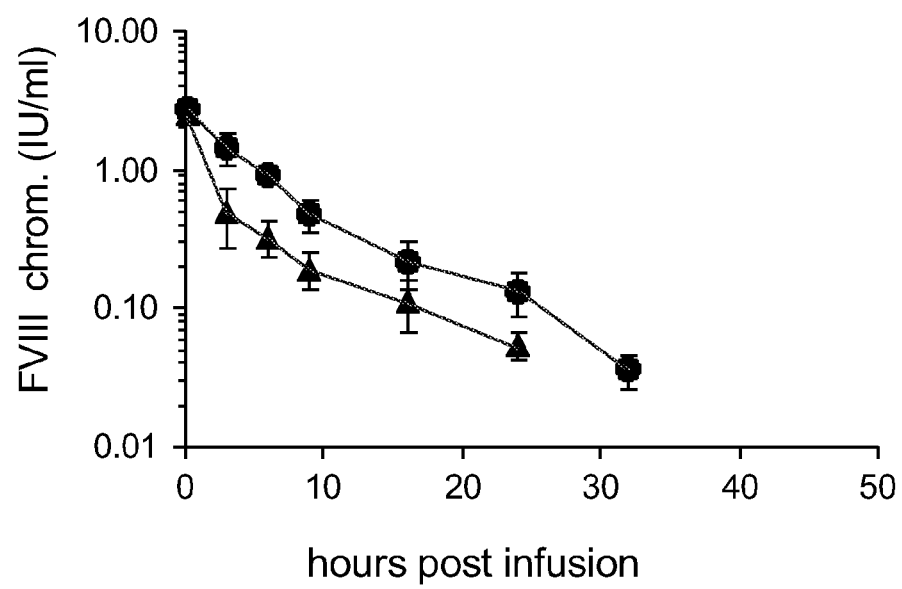
Figure 17A:
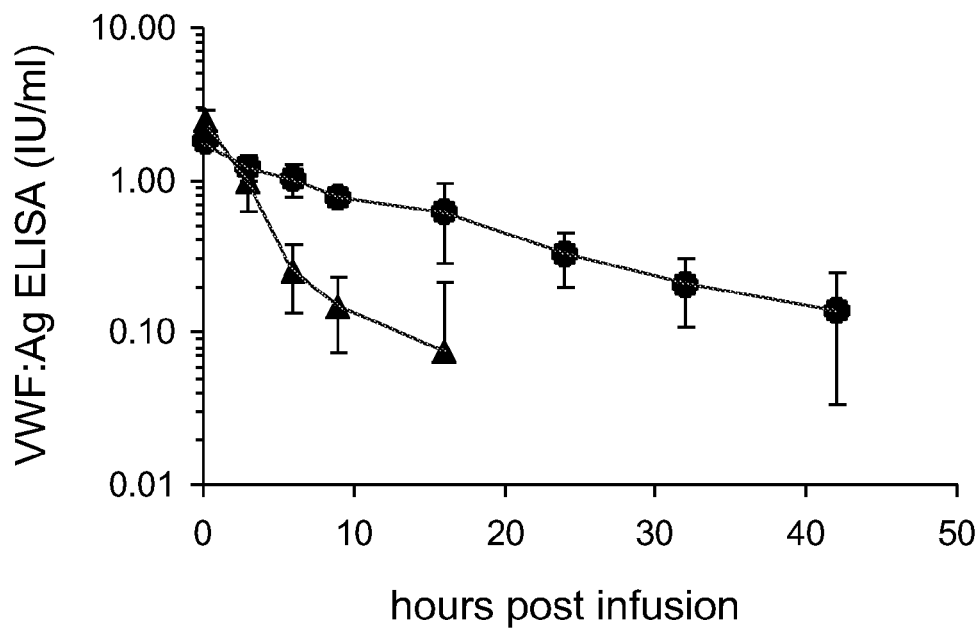
FIGS. 17A and 17B show the comparison of the native rVWF and PEGylated rVWF Lys 20K br long low (both with co-injected rFVIII) in FVIII-deficient knockout mice.
Figure 17B:
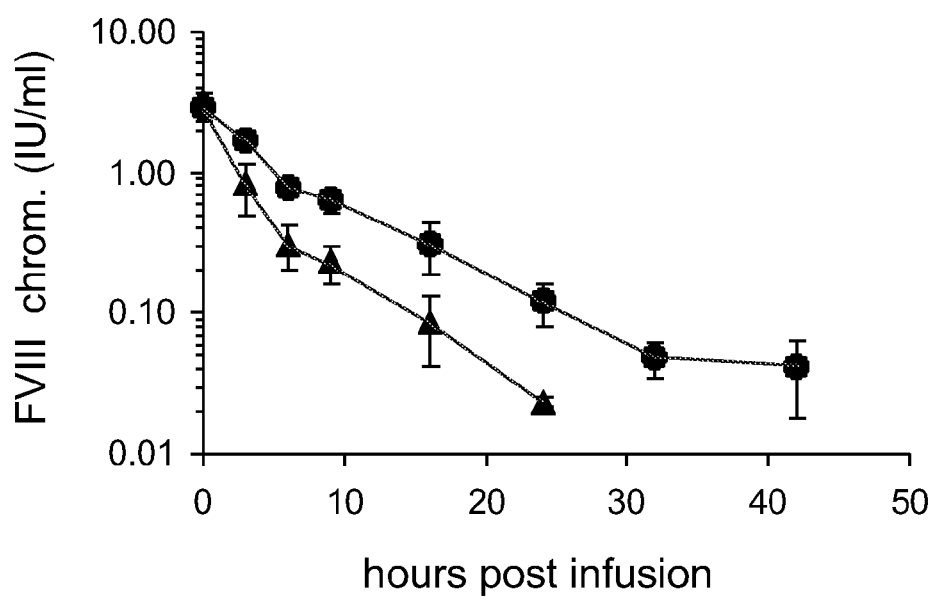
Figure 18A:
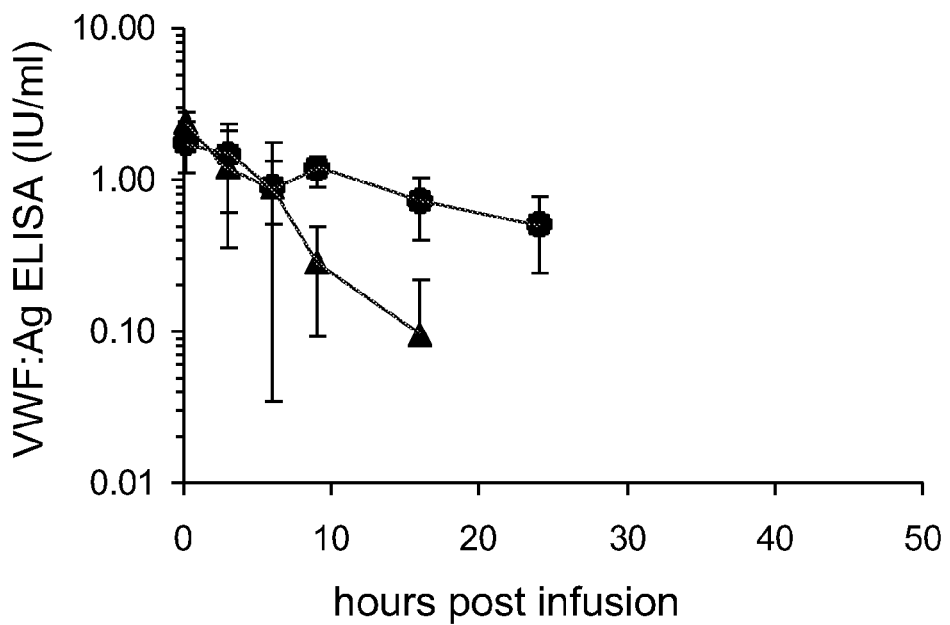
FIGS. 18A and 18B show the comparison of the native rVWF and PEGylated rVWF Lys 40K br short low (both with coinjected rFVIII) in FVIII-deficient knockout mice.
Figure 18B:
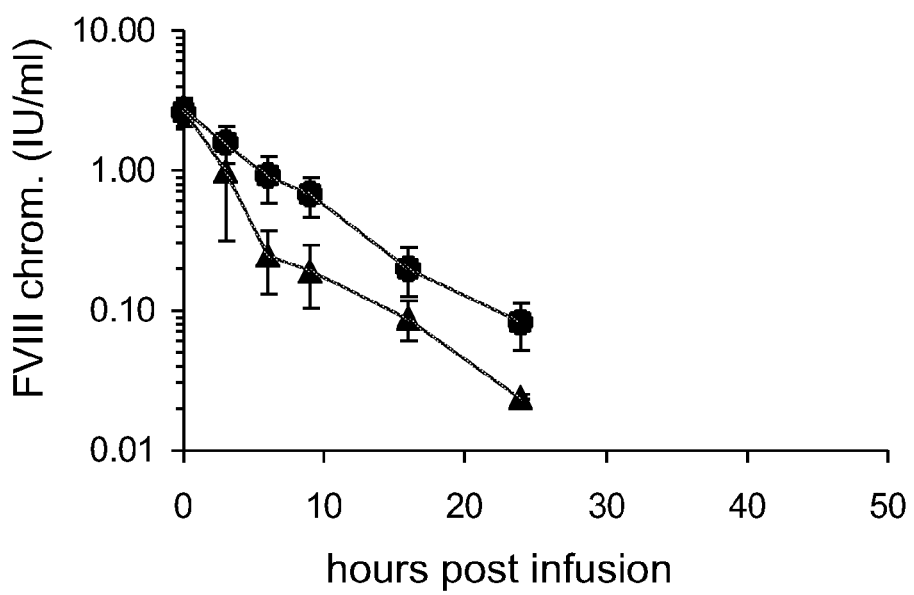
Figure 19A:
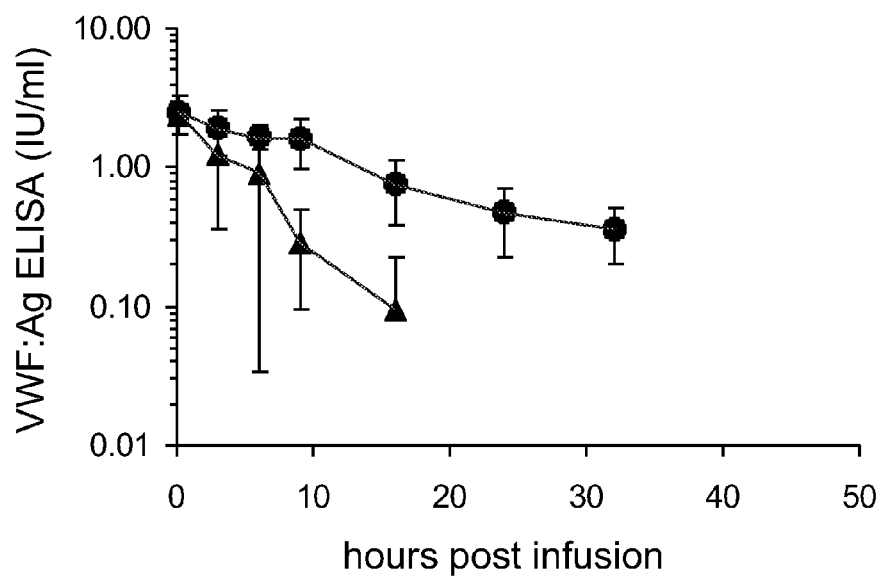
FIGS. 19A and 19B show the comparison of the native rVWF and PEGylated rVWF Lys 40K br long low (both with co-injected rFVIII) in FVIII-deficient knockout mice.
Figure 19B:
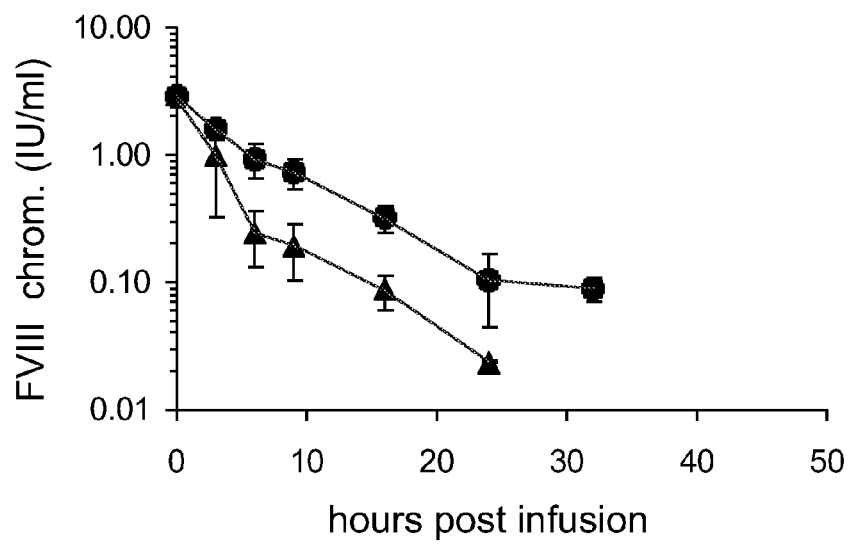
Figure 20A:
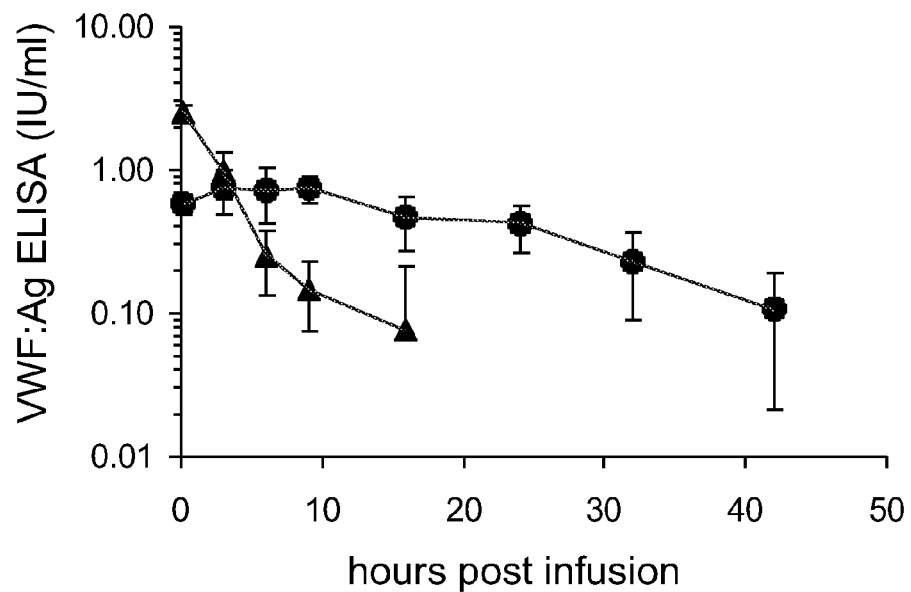
FIGS. 20A and 20B show the comparison of the native rVWF and PEGylated rVWF Lys 60K br short low (both with co-injected rFVIII) in FVIII-deficient knockout mice.
Figure 20B:
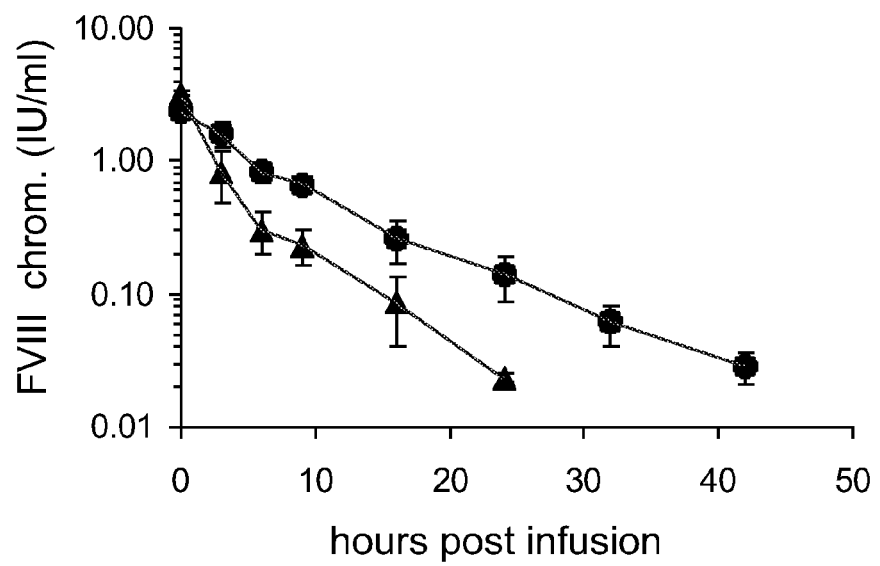
Figure 21A:
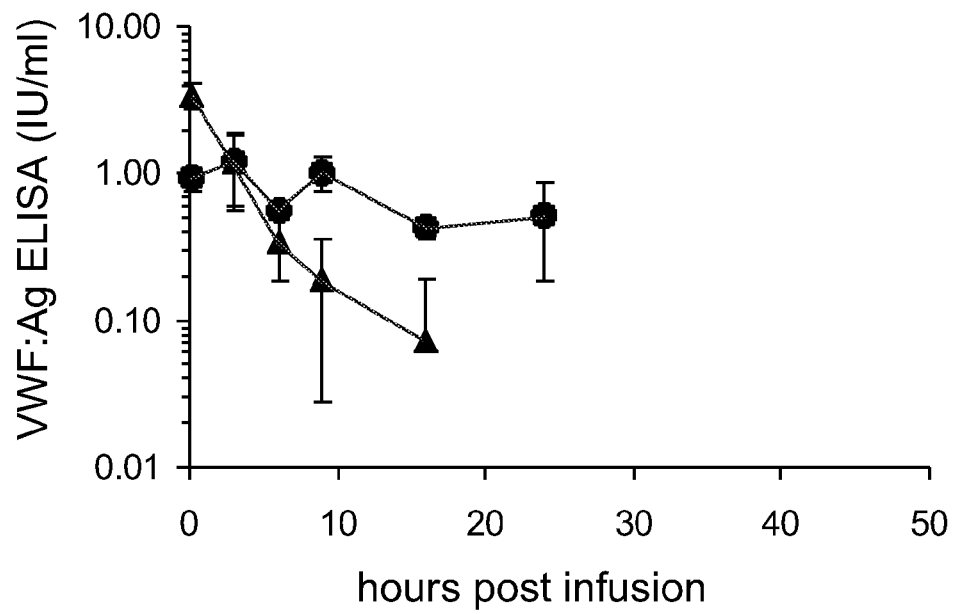
FIGS. 21A and 21B show the comparison of the native rVWF and PEGylated rVWF Lys 60K br long low (both with co-injected rFVIII) in FVIII-deficient knockout mice.
Figure 21B:
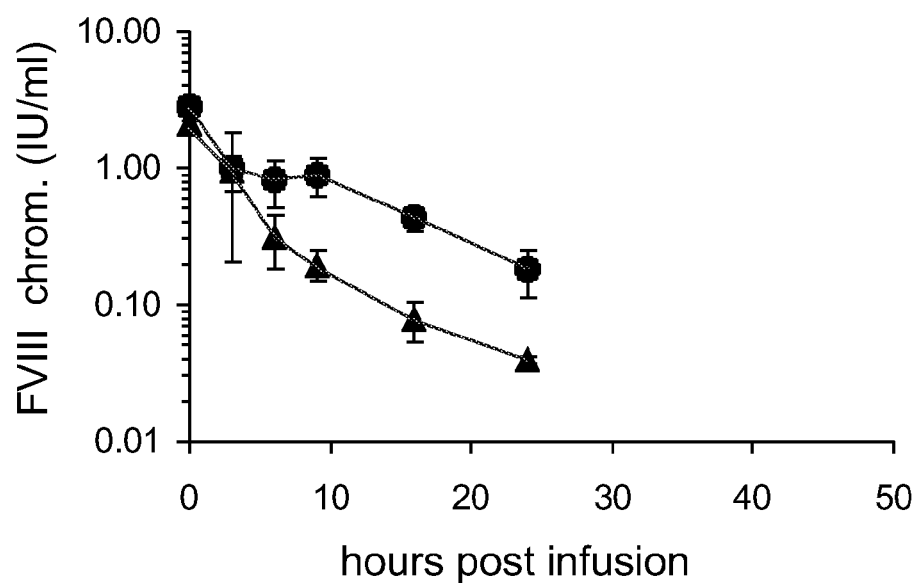

FIGS. 16A,B-21A,B show the changes in plasma levels of VWF:Ag (Panel A) and FVIII activity (Panel B) after substance injection. The exact amount of the injected material is shown in the appropriate figure legends.

In general, all PEGylated rVWF showed improved pharmacokinetics versus the native control (Panels A). The 60K PEG conjugates gave an increase in detectable VWF:Ag after injection, which might be an effect from the release of PEG chains, thus making masked epitopes accessible for the detection antibody. rFVIII, injected together with PEG-rVWF, was eliminated to a lower extent than rFVIII co-injected with native rVWF (Panels B). The degree of improvement of pharmacokinetic parameters was calculated with statistical methods (see Tables 7 and 8).

Figure 22A:
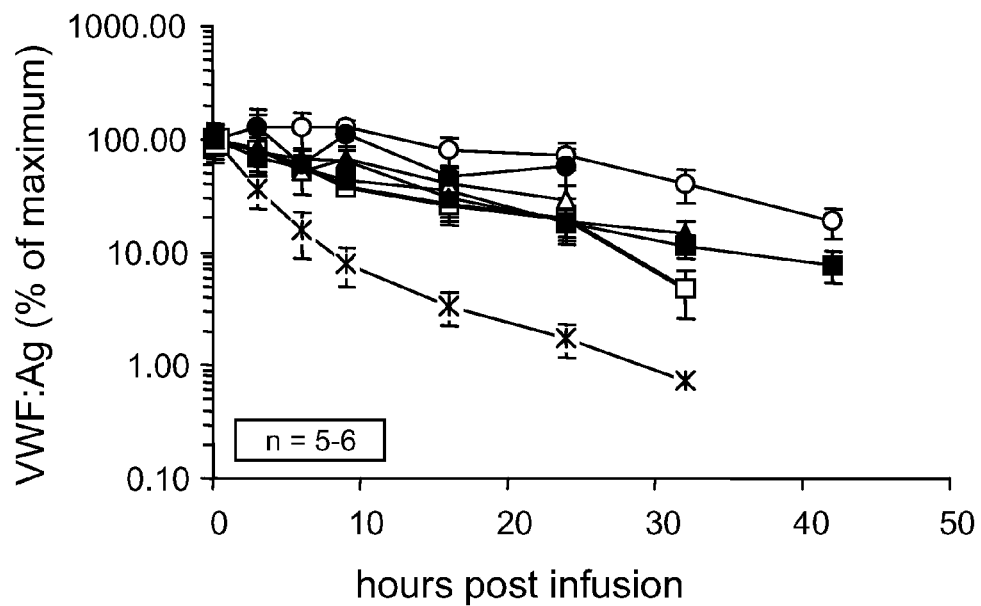
FIGS. 22A and 22B show the PEGylated rVWF candidates summary.
Figure 22B:
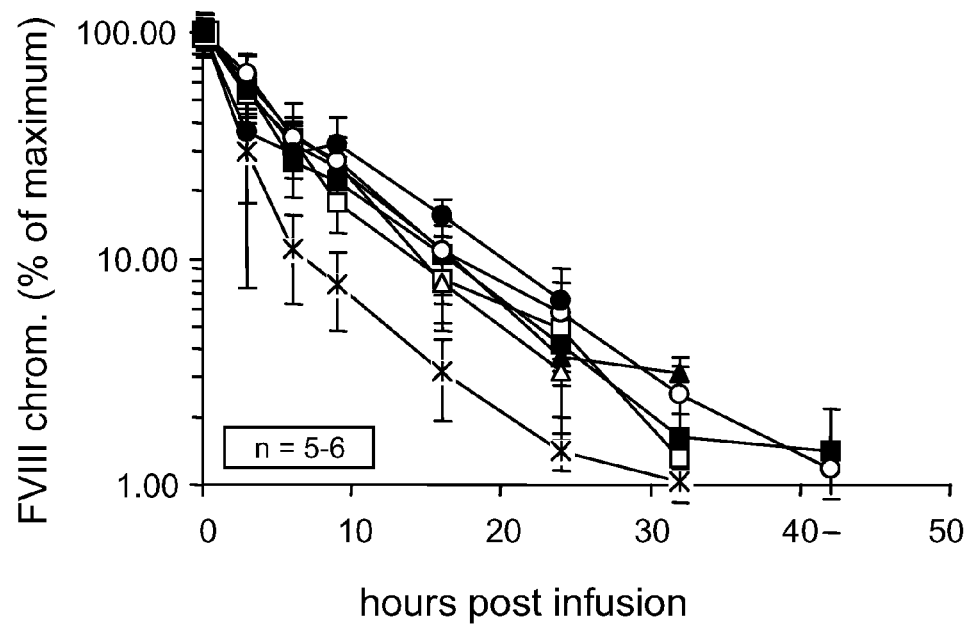

For in vivo experiments, a control mixture (native rVWF and rFVIII) was compared in one experimental set with one or two candidate mixtures (PEG-rVWF and rFVIII) and elimination curves were constructed (FIGS. 16A,B-21A,B). To allow comparative analysis of releasable PEG-rVWF candidates, the elimination curves were normalized. The plasma level obtained 5 minutes after application was set to 100% and all subsequent levels were calculated relative thereto. The mean of all control groups performed throughout the investigation (n=48 mice at each time group) is shown for comparison in FIGS. 22A,B together with all candidates.

The comparative analysis confirmed that all PEGylated rVWF circulated longer in FVIII-deficient mice, compared to native rVWF. rFVIII injected together with PEG-rVWF had superior elimination characteristics over the control mixture (rFVIII and native rVWF).

Area under the curve for VWF:Ag was calculated relative to the VWF:Ag units applied and also in relation to the amount of protein applied. Relative increase factors for the PEG-rVWF candidates versus control are given in Table 7.

TABLE 7

Increase in dose-adjusted AUC for VWF:Ag

| rVWF Sample | VWF:Ag AUC adjusted to protein dose increase versus control | VWF:Ag AUC adjusted to VWF antigen dose increase versus control |
|---|---|---|
| Lys 20K br short low | 3.2 | 4.3 |
| Lys 20K br long low | 2.2 | 3.8 |
| Lys 40K br short low | 1.9 | 3.9 |
| Lys 40K br long low | 2.5 | 2.9 |
| Lys 60K br short low | 1.6 | 5.1 |
| Lys 60K br long low | 1.5 | 3.4 |

The area under the curve for PEG-rVWF antigen was increased for all candidates in a range from 2.9 to 5.1 when dose-adjusted to VWF antigen units injected. The increase was statistically significant for all candidates. When calculated relative to the protein dose, AUC was increased between 1.5 and 3.2 fold, statistical significance was not calculated.

Figure 23B:
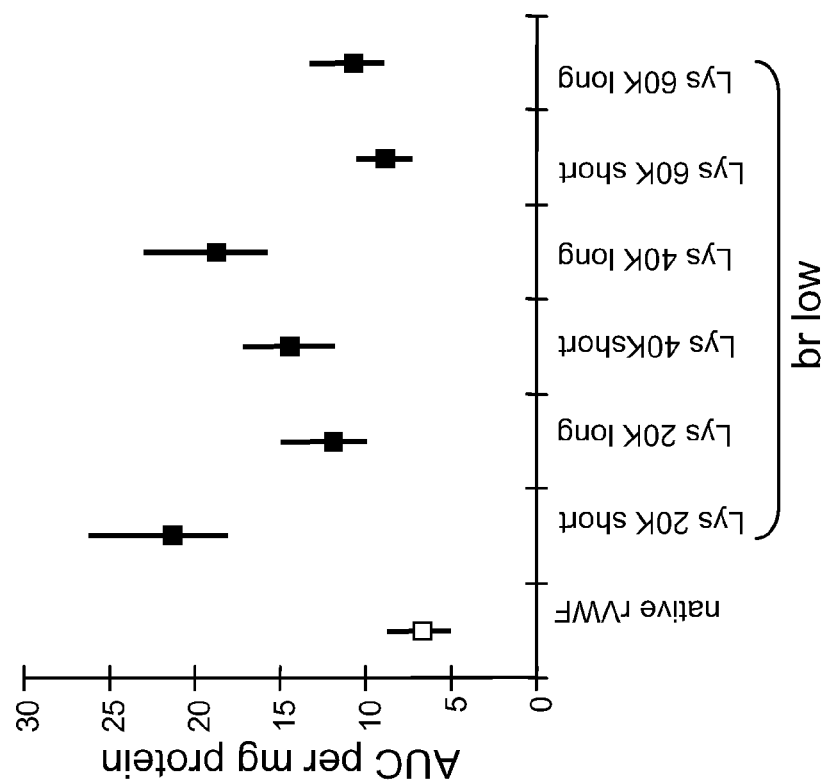
FIGS. 23A and 23B show the dose-adjusted AUC for VWF:Ag. Further information concerning this figure is provided in Example 5.
Figure 23A:
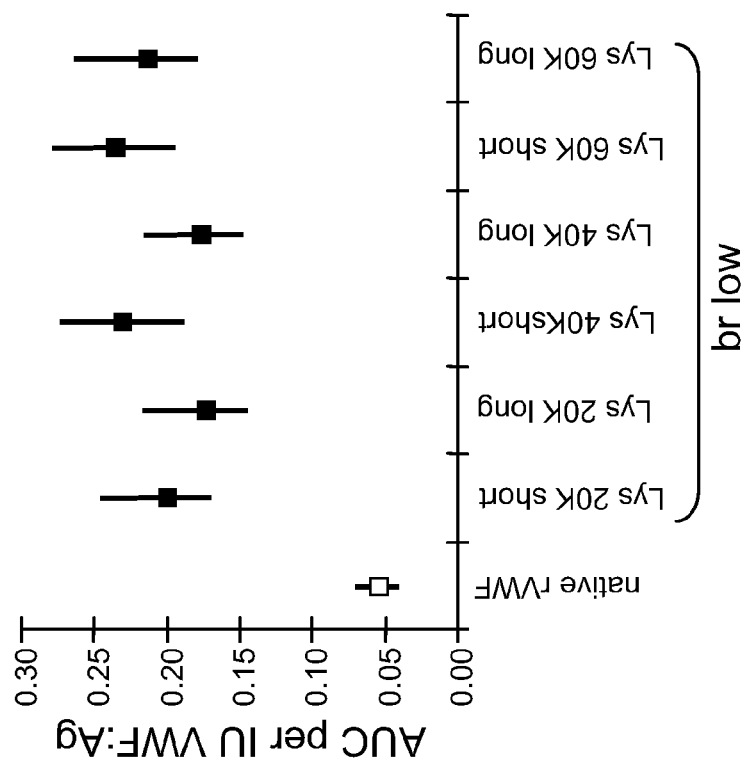

FIGS. 23A,B show the dose-adjusted AUC values together with 95% confidence intervals.

Table 8 summarizes the half-life parameters calculated for rFVIII, co-injected with PEG-rVWF candidates.

TABLE 8

Increase in pharmacokinetic parameters for co-injected rFVIII

| rVWF Sample | FVIII AUC | FVIII half life | FVIII MRT |
|---|---|---|---|
| | | increase versus control | |
| Lys 20K br short low | 2.0 s | 0.9 ns | 1.3 |
| Lys 20K br long low | 1.8 s | 1.0 ns | 1.7 |
| Lys 40K br short low | 1.8 s | 1.2 ns | 1.5 |
| Lys 40K br long low | 1.9 s | 1.3 ns | 1.7 |
| Lys 60K br short low | 1.6 s | 1.5 ns | 2.0 |
| Lys 60K br long low | 2.1 s | 0.9 ns | 1.8 | s: significant;
ns: not significant

As shown in Table 8, all PEGylated rVWF candidates caused a statistically significant increase in dose-adjusted AUC for co-injected rFVIII. FVIII half-life was not significantly changed by all candidates. Mean residence time was elevated by a factor between 1.2 and 2.0, however significance could not be calculated with the statistical model used.

FIGS. 24A,B show the dose adjusted AUC values and the terminal half life for FVIII together with the 95% confidence intervals.

Dose adjusted AUC for co-injected FVIII was higher with all PEGylated rVWF candidates, compared to the native rVWF control. In contrast, FVIII terminal half life in the presence of PEGylated rVWF was very similar to half life obtained with rFVIII and native rVWF control, which reflects the parallel run of the FVIII activity curves at later time points in FIGS. 22A,B Mean residence time for FVIII (FIG. 31A-C) was always increased when co-injected with PEGylated rVWF candidates In summary, all PEGylated rVWF conjugates preserved the multimeric structure without any degradation. In contrast all functional activities were decreased. The low VWF:RCo and VWF:CB activity has no effect on the chaperon function of VWF. It might even have the advantage of avoiding platelet adhesion. The diminished VWF:FVIIIB capacities measured in a static assay was improved under shear conditions, suggesting that PEG-rVWF is capable of carrying an appropriate amount of FVIII in the circulation. In conclusion, taking all in vivo data together, all PEGylated rVWF candidates show an improved pharmacokinetic profile for VWF:Ag in FVIII-deficient mice, which is paralleled by an improvement of pharmacokinetic profile for co-injected rFVIII.

Example 6

In Vitro and In Vivo Experiments of PEGylated FVIII

Figure 26:
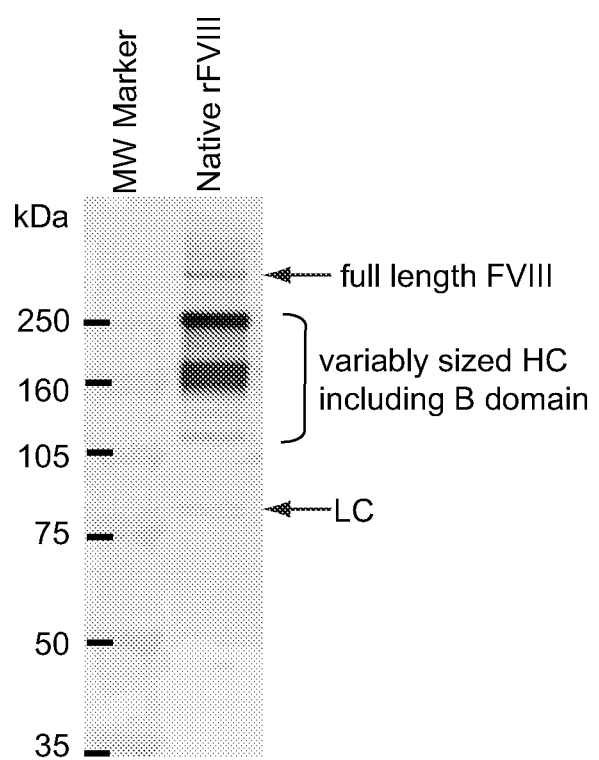
FIG. 26 shows the domain structure of the native rFVIII (MOQ HEPES01-E) visualized by reducing SDS-PAGE followed by immunoblot with a polyclonal anti-human FVIII antibody. Further information concerning this figure is provided in Example 6.

The native recombinant FVIII, was an Advate rAHF—PFM [Antihemophilic Factor (Recombinant) Plasma/Albumin Free Method bulk drug substance], a licensed lyophilized drug product of Baxter AG. This rFVIII bulk substance was formulated in a buffer of 50 mM HEPES, 5 mM $CaCl_2$, 350 mM NaCl and 0.1% Polysorbate 80 adjusted to pH 6.9. The analytical data of this rFVIII are given in Table 9. Protein content was determined using the BCA assay (Pierce, Rockford, Ill., USA) and specific activity is expressed as the ratio of FVIII chromogenic activity (IU)/protein (mg). The rFVIII bulk contained less than 2.3 µg VWF:Ag/1000 IU of rFVIII. SDS-PAGE performed under reducing conditions followed by immunoblot with a polyclonal antihuman FVIII antibody showed the intact domain structure of FVIII (FIG. 26).

TABLE 9

Analytical data of the native rFVIII MOQ HEPES 01-E

Native rFVIII
MOQ_HEPES_01-E

| | |
|---|---|
| Protein BCA (mg/ml) | 3.020 |
| FVIII:Chrom activity (IU/ml) | 19167 |
| Specific activity (IU/mg) | 6347 |
| FVIII:Ag (IU/ml) | 19698 |
| VWF:Ag (IU/ml) | 4.5 |

PEG-rFVIII conjugates with releasable bonds via the amino groups of the lysine residues of rFVIII were prepared in accordance with Examples 2A, 2A1, 2B, 2B1, 2C. 4A, 4B, 4B1, and 4C. The branched PEG derivatives had molecular weights of 20K, 40K and 60K, each of them with two different release characteristics (short and long release time). To investigate the possible effect of the conjugation conditions with the releasable PEG reagents, a mock preparation (control) was also manufactured which ran through the whole process but was not PEGylated.

TABLE 10

PEGylation degree of the PEG-rFVIII preparations

| Material Name | Protein (mg/ml) | PEG/FVIII* colorimetric (mol/mol) | PEG/FVIII** HPLC (mol/mol) | Free PEG |
|---|---|---|---|---|
| Lys 20K br short | 0.290 | 12.7 | 12.8 | <0.01% |
| Lys 20K br long | 0.265 | 5.9 | 11.1 | not detectable |
| resynthesized | 0.320 | — | 8 | <0.01% |
| Lys 40K br short | 0.400 | 107 | — | <0.01% |
| resynthesized | 0.100 | — | 11 | <0.01% |
| Lys 40K br long | 0.120 | 14.6 | — | <0.01% |
| resynthesized | 0.220 | — | 10.1 | <0.01% |
| Lys 60K br short | 0.500 | 9.8 | — | <0.01% |
| Lys 60K br long | 0.120 | 12.3 | 11.3 | <0.01% |

The protein content of the PEG-rFVIII was determined using the "DC Protein assay" of Bio-Rad (Hercules, CA, USA) with the unmodified rFVIII as standard.
*The number of PEGs per molecule was determined using a colorimetric determination
**The number of PEGs per molecule was determined by an HPLC method
— : no data avilbale
The remaining free PEG was determined by barium-iodide staining of the non-reduced SDS-PAGE.

Due to the extended in vitro and in vivo analytical testing, three conjugates had to be resynthesized to complete the investigations. Some differences in the PEG to FVIII ratio were observed between the resynthesized conjugates and the first batches for the 20K br long and Lys 40K br long PEG-rFVIII derivatives, which might be explained by the different analytical methods used. As investigated by barium-iodine staining, no free PEG remained in any sample solution.

Determination of FVIII Activity:

FVIII activity was determined with a chromogenic method. In the assay, the FVIII-containing sample was mixed with thrombin, activated factor IX (FIXa), phospholipids and factor X (FX), in a buffer containing calcium. FVIII is activated by thrombin and subsequently forms a complex with phospholipids, FIXa and calcium ions. This complex activates FX to FXa, which in turn cleaves a specific chromogenic substrate releasing para-nitroaniline (pNA) resulting in a color reaction.

For analysis of PEG-rFVIII conjugates, samples and the reference were pre-diluted to approximately 1 IU/ml FVIII:

Chrom activity in a human FVIII-deficient plasma and further diluted with the dilution buffer to a range from 0.5 to 0.008 IU/ml FVIII:Chrom. The time course of the pNA released from the substrate was measured with a microplate reader at 405 nm using the kinetic mode. The slope of the reaction is proportional to the FVIII concentration in the sample. The FVIII concentration in the samples was calculated relative to a recombinant FVIII concentrate standard, calibrated against the World Health Organization (WHO) concentrate reference (WHO 6) and expressed in IU/ml. The quantification limit of the assay was 0.03 IU/ml of FVIII.

Determination of FVIII antigen by enzyme-linked immunosorbent assay (ELISA):

The FVIII antigen level was determined according to the manufacturer's instructions with some minor modifications using the assay kit obtained from Cedarlane (Cedarlane Laboratories, Hornby, Ontario, Canada). High-binding 96-well ELISA plates (Costar 3590, Corning Incorporated, NY, USA) were coated with 100 µl/well of a polyclonal anti-human FVIII antibody and incubated for two hours at room temperature. Samples were diluted from 0.0078 to 0.5 IU/ml FVIII:Ag with the dilution buffer from the kit. Plates were then washed with phosphate-buffered saline (PBS; 6.5 mM disodium hydrogenphosphate dihydrate, 1.5 mM potassium dihydrogen phosphate, 140 mM NaCl, pH 7.2) containing 0.05% Tween-20 (PBST). 100 µl of the diluted samples were added to the plates and incubated for two hours at room temperature. After a washing step with PBST, 100 µl/well of peroxidase conjugated polyclonal anti-human FVIII antibody (#EIA8-0015R1, Cedarlane Laboratories, Hornby, Ontario, Canada) were added to the plates. Peroxidase activity was detected by using tetramethyl-benzidine (TMB) as substrate (Bio-Rad, Hercules, Calif., USA). The developed color intensity was measured with an ELISA reader at 450 nm. As a standard, a human normal plasma pool (coagulation reference, lot 1 R920031, Baxter) and as control a recombinant rFVIII bulk (Advate #B0206000-05/01) was used. The FVIII:Ag concentration was calculated relative to the standard preparation and expressed as FVIII:Ag IU/ml.

Measurement of VWF-FVIII Affinity by Surface Plasmon Resonance Technology:

Native rVWF was immobilized on the flow cells of a CM5 sensor chip of a Biacore 3000 (Biacore AG, Uppsala, Sweden) apparatus to a constant level according to the instructions of the manufacturer. A series of dilutions of native and PEG-rFVIII samples were then applied to the chip using the "kinject" mode, allowing three minutes for the association and ten minutes for the dissociation of FVIII. After each of these cycles FVIII was removed from the chip ("regeneration") and the experiment was repeated with a new FVIII sample.

SDS-PAGE and Immunoblot for FVIII:

FVIII samples (100 mIU equal to 10 ng protein per lane) were applied to gradient (4-12%) Bis-Tris gels and electrophoresis was done under mild reducing conditions, followed by standard blotting procedures onto a polyvinylidene difluoride (PVDF) membrane. To visualize the FVIII bands, a polyclonal anti-human FVIII antibody (CL20035A; Cedarlane Laboratories, Hornby, Ontario, Canada), a monoclonal anti-human heavy chain-A2 domain antibody (OBT0037, Oxford Biotechnology, Oxford, U.K.) or a monoclonal anti-human light chain-A3 domain antibody (10104; QED Bioscience Inc, San Diego, Calif., USA) was used as the primary antibody. As a secondary antibody, an alkaline phosphatase (ALP)-labeled rabbit anti-sheep IgG (H+L) (A130-101AP, Bethyl Laboratories, Inc, Montgomery, Tex., USA) was applied for the polyclonal antibody and an alkaline phosphatase (ALP)-labeled goat anti-mouse IgG (H+L) (A90-216AP, Bethyl Laboratories, Inc, Montgomery, Tex., USA.) for the monoclonal antibodies. The blots were developed with the ALP color development kit of Bio-Rad (Hercules, Calif. USA). A full range rainbow marker (250-10 kDa, GE-Healthcare, Little Chalfont, Buckinghamshire, UK) was used as the molecular weight standard.

SDS-PAGE and Immunoblot for PEG:

FVIII samples (300 mIU equal to 30 ng protein per lane) were applied to gradient (4-12%) Bis-Tris gels and electrophoresis was done under reducing conditions, followed by standard blotting procedures onto a PVDF membrane. To visualize the PEG, a polyclonal rabbit anti-human PEG antibody was used as the primary antibody. The anti-PEG antibody was raised in rabbits by immunization with a PEGylated protein. The IgG fraction of the rabbit serum was purified by affinity chromatography on Protein G Sepharose 4B (GE-Healthcare, Uppsala, Sweden) followed by specific negative immunoabsorption. An alkaline phosphatase (ALP)-labeled goat anti-rabbit IgG (A120-201AP, Bethyl Laboratories Inc., Montgomery, Tex., USA) was applied as a secondary antibody. The blots were developed with the ALP color development kit of Bio-Rad (Hercules, Calif. USA). A full range rainbow marker (250-10 kDa, GE-Healthcare, Little Chalfont, Buckinghamshire, UK) was used as molecular weight standard.

FIXa-Cofactor Activity Assay:

Untreated or thrombin-activated native rFVIIIa and PEG-rFVIII samples diluted to 1 IU/ml (according to their chromogenic activities) in the presence of a thrombin-specific inhibitor (Pefabloc TH, Penthapharm, Basel, Switzerland) were added to a prepared mixture of FIXa, FX, phospholipid (PL)-vesicles [composed of 60% phosphatidylcholine (PC) and 40% phosphatidylserine (PS), both from Avanti Polar Lipids Inc (Alabasta, Al, USA)] and $CaCl_2$. This reaction mix was incubated at 37° C. to allow complex formation and subsequent FXa generation. Subsamples were withdrawn at defined intervals up to 30 minutes and added to a chromogenic substrate, which is selectively cleaved by FXa. The substrate buffer contained ethylenediaminetetraacetic acid (EDTA) to stop any further FXa generation. After 15 minutes of incubation, the reaction was terminated by the addition of acetic acid. The absorbance at 405 nm (A405) which is proportional to the FXa concentrations, was measured in an ELISA reader. A reference curve was constructed by using a purified FXa (HFXa 1011, Enzyme Research Laboratories, Swansea, UK) and the absorbance values were converted to FXa concentration.

Thrombin-activated rFVIII (rFVIIIa) was prepared freshly for each test by incubating 1 IU/ml native or PEG-rFVIII with 1 nM thrombin for one minute at 37° C. and the reaction was stopped by adding 10 µM of a thrombin-specific inhibitor (Pefabloc TH, Penthapharm, Basel, Switzerland).

Figure 27:
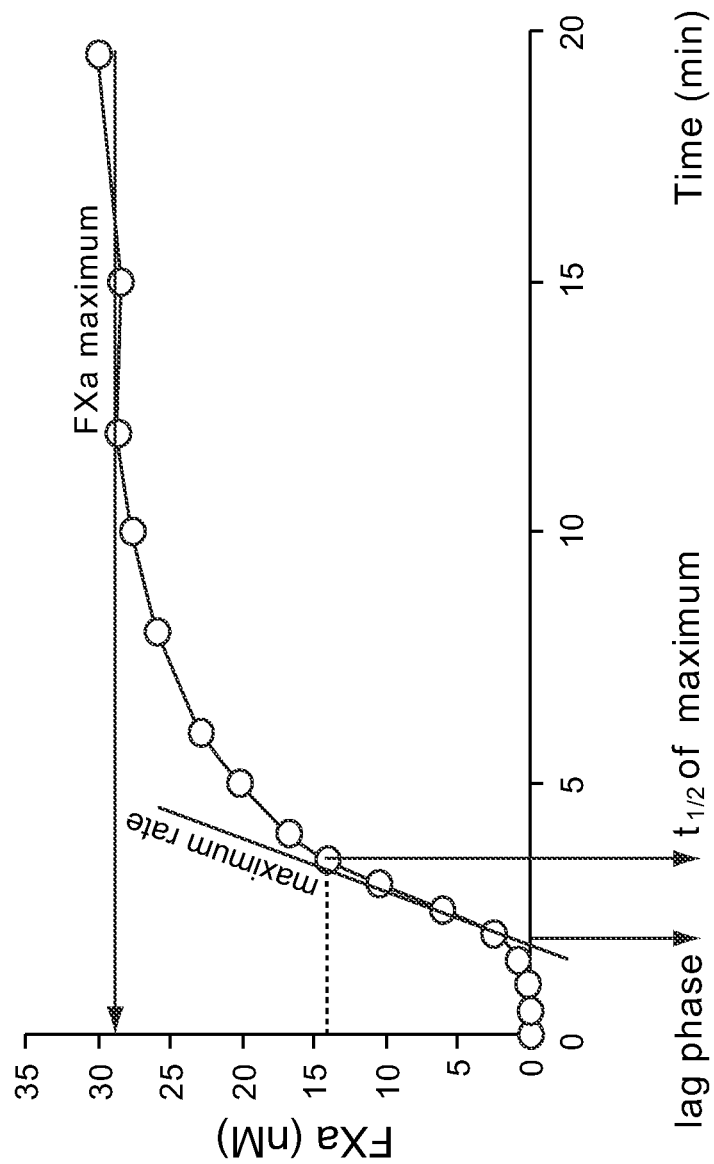
FIG. 27 shows the quantitative parameters of the FXa-generation curve. Further information concerning this figure is provided in Example 6.

The time course of FX activation (FIG. 27) was drawn and analysed as follows: The maximum rate of FX activation was calculated by determining the slope of the linear part of the curve and was expressed as nM FXa/min. The lag phase was determined by calculating the X-axis intercept of the linear part of the curve. The maximum activity was determined as the mean FXa concentration measured between 20 and 30 minutes and the half maximum time ($t_{1/2}$) was calculated using the following formula: $t_{1/2}$=(maximum AFXa/2+lag phase time*slope)/slope. All parameters were calculated by using the internal functions of Microsoft Excel.

Kinetics of Thrombin-Mediated Activation and Inactivation of FVIII Measured by the FIXa Cofactor Activity Assay:

Native rFVIII and PEG-rFVIII were diluted to 1 IU/ml FVIII activity (according to their chromogenic activities) with 25 nM HEPES; 175 mM NaCl, 5 mg/ml bovine serum albumin (BSA) pH7.35 buffer and incubated with 0.5 nM thrombin at 37° C. Subsamples taken at various time points up to 40 minutes were added to aliquots of prepared mixtures of FIXa, FX, phospholipid (PL)-vesicles (composed of 60% PC and 40% PS), $CaCl_2$ and a thrombin inhibitor to stop further activation of FVIII. These reaction mixes were incubated for three minutes at 37° C. to allow FXa to generate. A subsample of this mixture was added to a chromogenic substrate, which is selectively cleaved by FXa. The FXa concentration was determined as described above with respect to FIXa-cofactor activity assay and plotted against the incubation time of FVIII with thrombin. The rate of inactivation had been quantitatively evaluated from the ascending part of the curves by fitting them with a single exponential using the internal functions of Microsoft Excel.

Thrombin Generation Assay (TGA):

A severe hemophilia A plasma (FVIII activity<1%) obtained from George King Bio-Medical (Overland Parks, Kans., USA) was spiked with 0.0025 to 1 µg/ml native or PEG-rFVIII and thrombin generation was measured with the Technothrombin® TGA kit (Technoclone, Vienna, Austria) as described by the manufacturer. The reaction was triggered by a relipidated tissue factor (TF) preparation (TFPL RB reagent) containing low TF and low PL concentrations. An amount of 10 µl of this TFPL solution was pipetted to 40 µl FVIII-deficient plasma, without FVIII or supplemented with FVIII and 50 µl of TGA fluorescence substrate, into the wells of an ELISA plate. The plate was placed into a Microplate Fluorescence Reader FL800 (Bio-TEK Instruments, Winooski, Vt., USA). The increase in the fluorescence intensity, which is proportional to the concentration of the generated thrombin, was monitored continuously at 37° C. by automatic reading every minute up to 120 minutes using an excitation wavelength of 360 nm and an emission wavelength of 460 nm.

Because thrombin substrate was present in the assay mixture, curves were seen that represent the accumulated effect of all the thrombin that was generated and split the fluorogenic substrate during the reaction. Therefore, the rate of increase in the fluorescence intensity (the first derivative of the curve), which reflects the actual effective thrombin concentration, was calculated for each reading (FU/min) and converted to thrombin-equivalent concentrations (nM) using a reference curve prepared by measuring the rate of substrate conversion by a purified human thrombin. The thrombin generation curves were drawn as the thrombin concentration versus time, and the quantitative parameters (peak thrombin, onset time, and peak time) were calculated by the built-in KC4 software (Bio-TEK Instruments, Winooski, Vt., USA) of the reader.

APC-Mediated FVIII and FVIIIa Inactivation:

Untreated or thrombin-activated native and PEG-rFVIII samples were diluted to 1 IU/ml (according to their chromogenic activities) and incubated with 0.05 U/ml activated protein C (APC) in the presence of 10 µM PL vesicles (composed of 60% PC and 40% PS; both from Avanti Polar Lipids Inc, Alabasta, Al, USA) and 5 mM $CaCl_2$. In the control experiments the rFVIII samples were incubated in the absence of APC. Sub-samples were taken at defined time points to determine the residual active FVIII or FVIIIa by measuring its FIXa cofactor activity as described above with respect to FIX-cofactor activity assay.

The thrombin-activated FVIII (FVIIIa) was prepared freshly for each test by incubation of the 2 IU/ml native or PEG-rFVIIII samples with 1 nM thrombin (#2311 PL, Enzyme Research Laboratories, Swansea, UK) for 1 minute at 37° C. The reaction was stopped by adding 10 µM of a thrombin-specific inhibitor (Pefabloc TH, Penthapharm, Basel, Switzerland).

Mouse Model:

As a hemophilia model, FVIII-knockout mice were used. The mice suffer from severe hemophilia A (FVIII<0.01 IU/ml) but have normal levels of VWF (approximately 0.15 IU/ml relative to human VWF reference), mimicking human hemophilia A.

Application of FVIII:

The same recombinant FVIII bulk used for conjugation was used as a control substance (rFVIII MOQ_HEPES_01E). The bulk was stored in aliquots frozen below −60° C. and thawed before use. PEG-rFVIII candidates or the native rFVIII control were thawed and mixed with 20 mM HEPES, 150 mM NaCl, 3.2% mannitol, 0.8% trehalose, 2.5 mM $CaCl_2$, 1% human albumin, pH 7.4 buffer to achieve appropriate concentrations for infusion. The FVIII solutions were aliquoted, frozen at −20° C. and thawed just before the application. The target dose was 200 IU/kg FVIII:Chrom. The concentrations were measured again from the thawed samples and the applied doses were calculated. Doses are given in the figure legends in the results section. Seven to ten ml/kg bodyweight were injected via the tail vein and groups of 6 mice were bled by heart puncture after six minutes, 3, 6, 9, 16 and 24 hours, and if necessary, after 32 hours. Nine volumes of blood were mixed with 1 volume of 3.8% sodium citrate, and immediately centrifuged at 3000 g for ten minutes. The supernatant was again centrifuged at 3000 g for five minutes, plasma was separated, frozen in aliquots and stored below −60° C. for analysis.

Determination of FVIII Activity in Mouse Plasma:

FVIII activity was determined following the assay principle described above. The time course of the pNA released from the substrate was measured with a microplate reader at 405 nm using the kinetic mode. The slope of the reaction is proportional to the FVIII concentration in the sample. The FVIII concentration in the samples was calculated relative to a human plasma reference preparation, calibrated against the WHO plasma reference ($5^{th}$ IS for FVIII and VWF in human plasma, NIBSC #02/150) and expressed in IU/ml. The quantification limit of the assay was 0.03 IU/ml of FVIII.

Calculation of the circulating half-life parameters of human VWF and FVIII: For analyzing FVIII levels, the concentrations for $t_0$=0 hours was set to zero as FVIII-deficient mice were studied. FVIII levels over time were summarized using pharmacokinetic parameters AUC from 0 to 24 hours, terminal elimination rate and mean residence time.

Area Under the Concentration vs. Time Curve (AUC) from 0 to 24 Hours:

The area under the concentration vs. time curve (AUC) from 0 to 24 hours was calculated by the linear trapezoidal rule using the arithmetic means of the concentrations observed at individual time points. A linear relation was assumed to exist between dose and AUC. On this assumption, the AUCs for different items were adjusted for different doses administered. Dose adjustment was performed by dividing the calculated AUC by the dose per kg body mass administered.

Terminal Elimination Rate:

The terminal elimination rate (X) was estimated using the arithmetic mean of the natural logarithms of individual concentrations at the last three time points modified with a bias correction as suggested in Wolfsegger. See Wolfsegger et al. (2005) *J. Pharmacokinet. Pharmacodyn.* 32(5-6):757-766.

Mean Residence Time:

Mean residence time (MRT) was calculated as $AUMC_{0\text{-}infinity}$ divided by $AUC_{0\text{-}infinity}$. $AUMC_{0\text{-}infinity}$ and $AUC_{0\text{-}infinity}$ were calculated by the linear trapezoidal rule using the arithmetic means of the concentrations observed for different time points plus a three-point tail area correction. The tail area correction was calculated by log-linear fitting on the arithmetic means observed at the last three time points per item.

Functional Parameters of PEGylated rFVIII:

The potency of modified FVIII was measured by its chromogenic activity. Under the assay conditions, FVIII is activated by thrombin and thus the assay reflects its maximum potency to enhance the FIXa-mediated FX activation. To distinguish between biological active and inactive FVIII, the FVIII:Ag was determined by ELISA, as described in the experimental section. To compare the specific activities of the different conjugates both parameters were related to the protein content of the products. Table 11 summarizes the measured values.

TABLE 11

Quantitative parameters of PEGylated rFVIII conjugates

| Samples | Protein (mg/ml) | Measured values FVIII:Ag (IU/ml) | FVIII:chrom (IU/ml) | VWF:FVIII binding affinity KD (M) |
|---|---|---|---|---|
| native rFVIII | 3.02 | 19698 | 19167 | 1.5E−09 |
| FVIII control | 0.170 | 1120 | 820 | 5.5E−10 |
| Lys 20K br short | 0.290 | 82 | 277 | 2.4E−10 |
| Lys 20K br long | 0.265 | 116 | 231 | 2.9E−10 |
|  | 0.320 | 114 | 281 | n.d. |
| Lys 40K br short | 0.400 | 122 | 512 | 3.4E−10 |
|  | 0.100 | 33 | 111 | n.d. |
| Lys 40K br long | 0.120 | 25 | 130 | 1.2E−10 |
|  | 0.220 | 32 | 183 | n.d. |
| Lys 60K br short | 0.500 | 142 | 526 | 1.2E−09 |
| Lys 60K br long | 0.120 | 65 | 272 | 2.1E−10 |

(All results were obtained from a freshly thawed aliquot and are the mean of at least 2 measurements.)

The FVIII affinity for VWF was determined using the Biacore 3000 system as described above with respect to measurement of VWF-FVIII affinity by surface plasmon resonance technology with an immobilized native rVWF (rVWF 133P1) and the sample (native rFVIII or PEG-rFVIII conjugates) in the fluid phase. Assuming a homogenous 1:1 interaction between VWF and FVIII, the association and dissociation constants were determined using the Langmuir model of the "Bioevaluation" program of Biacore. No relevant differences for the affinity constant (KD) with VWF between the native and the PEG-rFVIII were found. Only an approximate evaluation could be performed because the PEG-rFVIII conjugates did not give an optimal fitting, either with this or any other interaction-models, possibly because of some conformational changes of rFVIII due to the PEGylation. The ratios of the measured values and the specific activities are summarized in Table 12.

TABLE 12

Specific activities of PEG-rFVIII conjugates

| Samples | Ratio FVIII:Chrom to FVIII:Ag (IU/IU) | Specific Activity related to the rFVIII protein | |
|---|---|---|---|
| | | FVIII:Chrom (IU/mg) | FVIII:Ag (IU/mg) |
| native rFVIII | 0.97 | 6347 | 6523 |
| FVIII control | 0.73 | 4824 | 6588 |
| Lys 20K br short | 3.38 | 955 | 283 |
| Lys 20K br long | 1.99 | 872 | 438 |
| Resynthesized | 2.46 | 878 | 356 |
| Lys 40K br short | 4.20 | 1280 | 305 |
| Resynthesized | 3.36 | 1110 | 330 |
| Lys 40K br long | 5.20 | 1083 | 208 |
| Resynthesized | 5.71 | 832 | 145 |
| Lys 60K br short | 3.70 | 1052 | 284 |
| Lys 60K br long | 4.18 | 2267 | 542 |

Values were calculated from the measured data, shown in Table 3.

All PEG-rFVIII conjugates had a markedly reduced FVIII activity compared with the native rFVIII. However, the FVIII specific activity was also slightly reduced for the FVIII control, which was not PEGylated but ran through the whole process.

The decrease in activity was not related either to the MW or to the characteristics of the PEG reagents. For example, the Lys 60K br long conjugate had an approximately 65% reduced FVIII specific activity, while the specific activity of the Lys 20K br long conjugates was reduced to approximately 14% compared with the native rFVIII. The correlation between PEGylation degree and specific activities cannot be assessed, because two different methods for determination of the degree of PEGylation were used throughout the analytical characterization, except for the Lys 20K br long conjugate, where data obtained with the HPLC-method are available for both the original conjugate and the resynthesized material. Although the resynthesized Lys 20K br long had a lower PEGylation degree than the original conjugate, both had similar specific activities.

The FVIII antigen to protein ratio was below 10% in all conjugates. Because two polyclonal antibodies were applied in the assay described above with respect to determination of FVIII antigen by enzyme-linked immunosorbent assay (ELISA), this decrease indicates a strong shading effect of the PEG moieties throughout the molecule. The FVIII chromogenic activity (FVIII:Chrom) to FVIII:Ag ratio was elevated, which might suggest that despite of the strong coverage of some epitopes PEG-rFVIII can be activated or a partial release of the PEG moieties occurred immediately under the activity determination conditions, possibly due to the effect of thrombin in the reagents.

The detailed biochemical characterization was carried out on the first batches of each PEGrFVIII conjugate. Due to the lack of the original material, the resynthesized conjugates were used for the investigation of APC-mediated inactivation of rFVIII (described below under "APC-mediated inactivation of FVIII and FVIIIa") and for the investigation of the in vitro hydrolysis in a human FVIII-deficient plasma (described below under "in vitro release of releasable PEG-rFVIII in a human FVIII-deficient plasma").

Figure 28B:
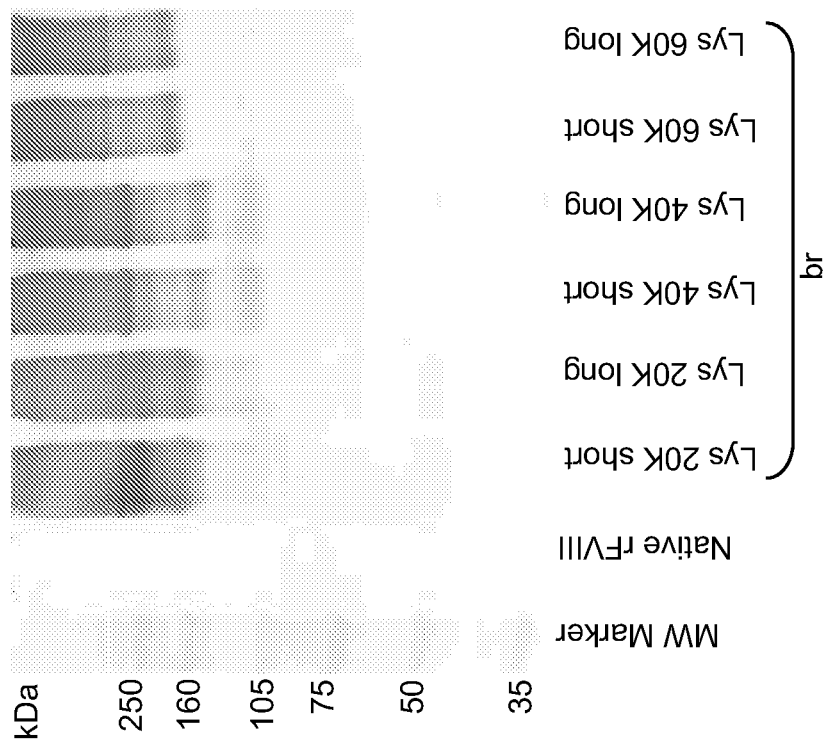
FIGS. 28A and 28B show the domain structure of releasable PEG-rFVIII conjugates visualized by reducing SDSPAGE followed by immunoblot.
Figure 28A:
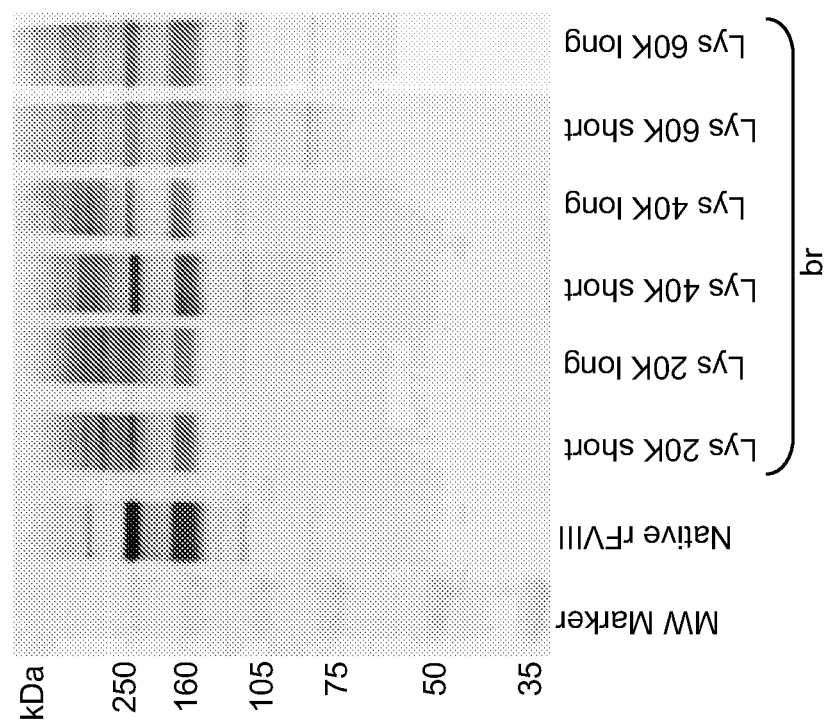

The domain structure of the PEG-rFVIII conjugates was visualized by non-reducing SDS-PAGE followed by immunoblot with a polyclonal anti-human FVIII antibody (FIG. 28A). For the assessment of successful PEGylation, the gels were immunoblotted with a polyclonal anti-PEG antibody, as demonstrated in FIG. 28B. All samples were applied to the gel according to the measured protein value.

The characteristic domain structure of FVIII was not affected by PEGylation in any of the PEGrFVIII conjugates. As a result of PEGylation, new, high MW bands appeared with a concomitant decrease in the intensity of some heavy chain (HC)-B domain bands. Staining with the anti-PEG antibody confirmed successful PEGylation. No degradation products were seen on the gels.

Figure 29B:
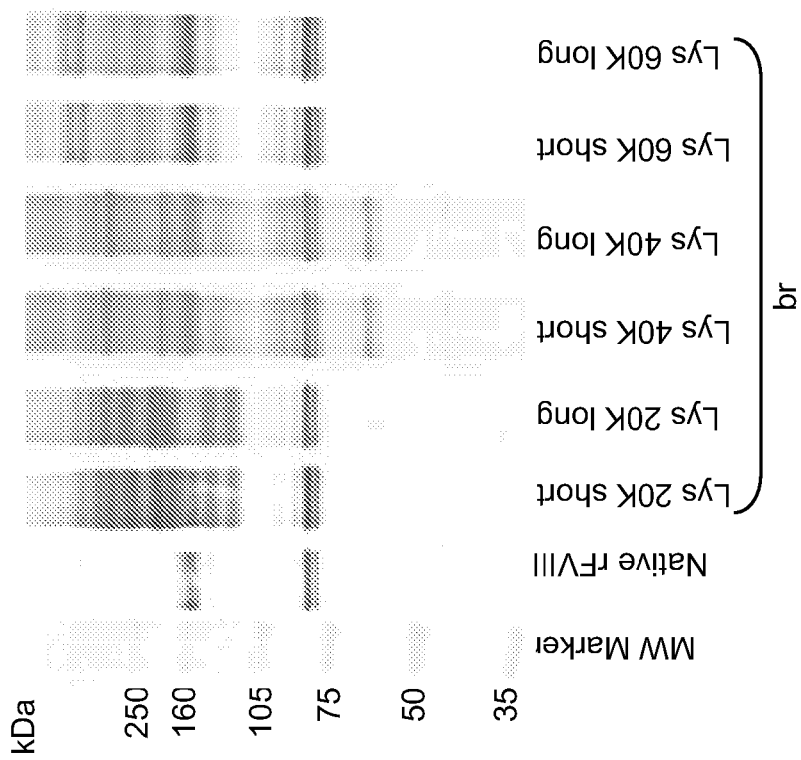
FIGS. 29A and 29B show the structure of HC and LC of releasable PEG-rFVIII conjugates visualized by reducing SDS-PAGE followed by immunoblots.
Figure 29A:
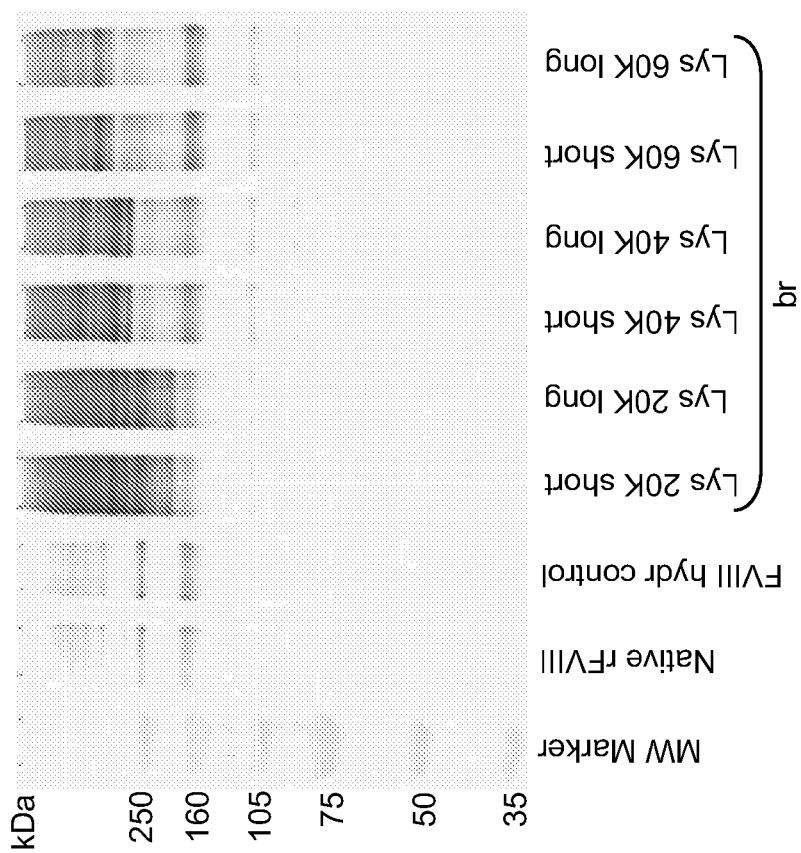

Because the polyclonal antibody did not have the same affinity for the different domains, the gels were also immunoblotted with antibodies specific against the HC-A2 fragment and the light chain(LC)-A3 domain (FIG. 29A,B).

FIG. 29A shows the PEG MW-dependent increase of the HC-containing bands. The antibody also shows some 90-kDa intact HC bands, without any further degradation bands. The rFVIII used as the starting material contained an "extended" light chain, which was also detected by the anti-LC antibody (FIG. 29B). A MW increase is observed for both the 80-kDa and the 160-kDa bands in the immunoblot, suggesting that the light chain has also been PEGylated, albeit possibly to a lower extent. Some lower MW degradation products appeared in the 40K PEG-rFVIII conjugates.

Figure 30A:
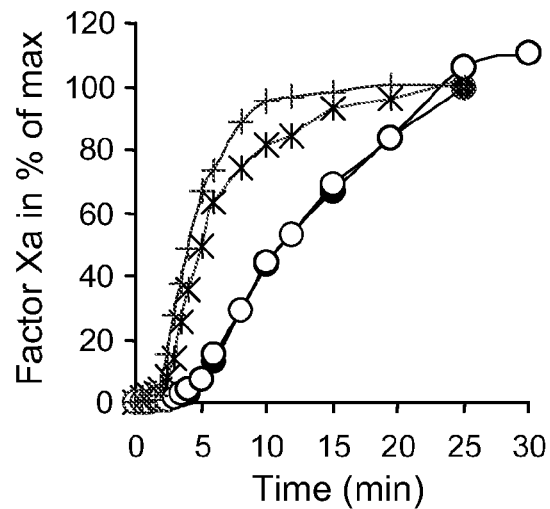
FIGS. 30A-30C show the Factor Xa ("FXa") generation curves in presence of non-activated PEG-rFVIII. Stars: native rFVIII MOQ HEPES01-E; circles: PEG-rFVIII Lys 20K br short; triangles: PEG-rFVIII Lys 40K br short; squares: PEG-rFVIII Lys 60K br short; cross: FVIII control; circles, open: PEG-rFVIII Lys 20K br long; triangles, open: PEG-rFVIII Lys 40K br long; squares, open: PEG-rFVIII Lys 60K br long. Further information concerning this figure is provided in Example 6.
Figure 30B:
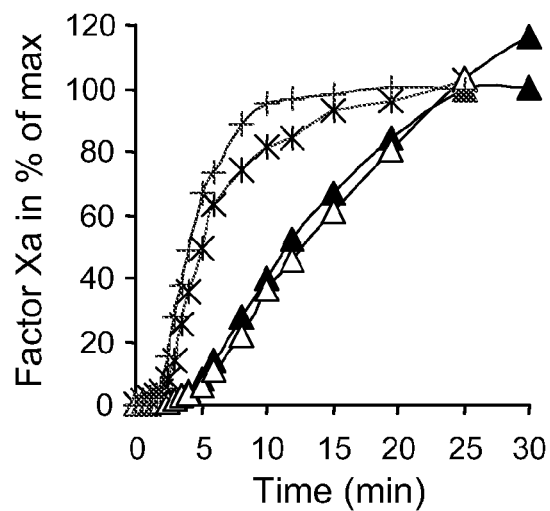
Figure 30C:
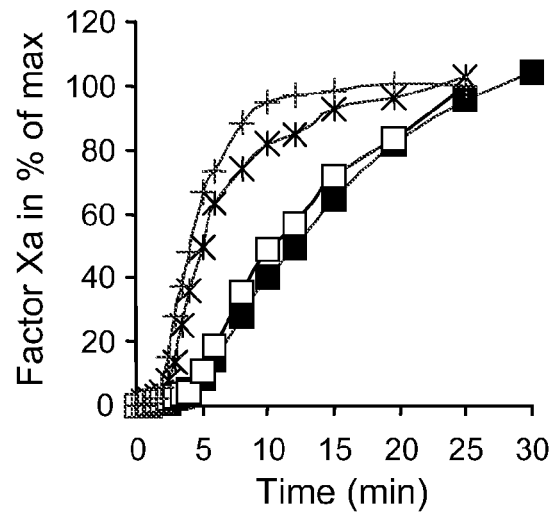

Effect of PEGylation of rFVIII on FIXa-Cofactor Activity:

The FXa-generation assay, also known as the FIXa-cofactor assay, is based on the fact that both FVIII and thrombin-activated FVIII (FVIIIa) form a complex with FIXa on an appropriate phospholipid (PL) surface in the presence of $Ca^{++}$ ions, which rapidly activates FX. See Elodi et al. (1981) *Thrombosis Research* 21:695. The kinetics of the assembly and activity of the complex is regulated by FVIII and is a sensitive measure of the functional integrity of the FVIII molecule. The PEG-rFVIII conjugates as well as the FVIII control and a native rFVIII were diluted to 1 IU/ml according to the measured FVIII chromogenic activities and added to the prepared mixture of FIXa, FX, PL-vesicles and calcium chloride. At defined intervals up to 30 minutes subsamples were withdrawn and the generated FXa determined as described above with respect to FIXa-cofactor activity assay. However, even if all rFVIII conjugates were diluted to 1 IU/ml, there were slight differences in the maximum FXa achieved (Table 13). Therefore, for a better visual comparison of the time course of FX activation, FXa activity was expressed as a percent of the maximum FXa activity (FIGS. 30A-C).

Without thrombin activation, all PEG-rFVIII conjugates showed a delayed complex formation and a slower rate of FX activation than that of both native rFVIII and the FVIII control. No relevant differences in the rate of FX activation were observed between the conjugates, except that the Lys 40K br long showed a slightly more reduced FX activation rate. The control seemed to be slightly more active than the native rFVIII.

TABLE 13

Quantitative parameters of the FIXa-cofactor activity without thrombin activation

| | | without thrombin activation | | | | | |
|---|---|---|---|---|---|---|---|
| | Native rFVIII | rFVIII control | Lys 20K br short | Lys 20K br long | Lys 40K br short | Lys 40K br long | Lys 60K br short | Lys 60K br long |
| lag phase (min) | 2.4 | 1.8 | 4.2 | 4.0 | 3.9 | 4.3 | 3.8 | 3.7 |
| maximum rate (nM FXa/min) | 6.7 | 8.8 | 2.6 | 2.1 | 2.0 | 1.3 | 2.0 | 2.3 |
| $t_{1/2}$ of maximum (min) | 4.6 | 4.0 | 10.8 | 10.8 | 11.4 | 12.3 | 11.3 | 9.8 |
| maximum FXa (nM) | 30.1 | 39.6 | 33.6 | 28.7 | 30.6 | 21.6 | 30.2 | 28.8 |

Thrombin-activated rFVIII (rFVIIIa) was prepared from all products by incubating 1 IU/ml native or PEG-rFVIII with 1 nM thrombin for one minute at 37° C. The reaction was stopped by adding 10 µM of a thrombin-specific inhibitor (Pefabloc TH, Penthapharm, Basel, Switzerland) and the cofactor activity of rFVIIIa was measured as for the non-activated rFVIII.

Figure 31A:
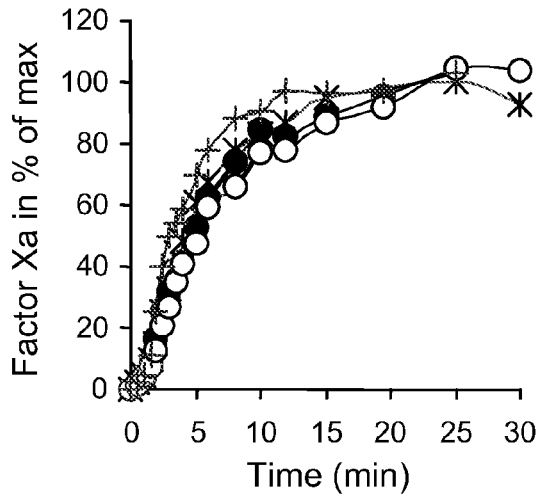
FIGS. 31A-31C show the FXa generation curves in presence of thrombin-activated PEG-rFVIII. Stars: native rFVIII MOQ HEPES01-E; circles: PEG-rFVIII Lys 20K br short; triangles: PEG-rFVIII Lys 40K br short; squares: PEG-rFVIII Lys 60K br short; cross: FVIII control; circles, open: PEG-rFVIII Lys 20K br long; triangles, open: PEG-rFVIII Lys 40K br long; squares, open: PEG-rFVIII Lys 60K br long. Further information concerning this figure is provided in Example 6.
Figure 31B:
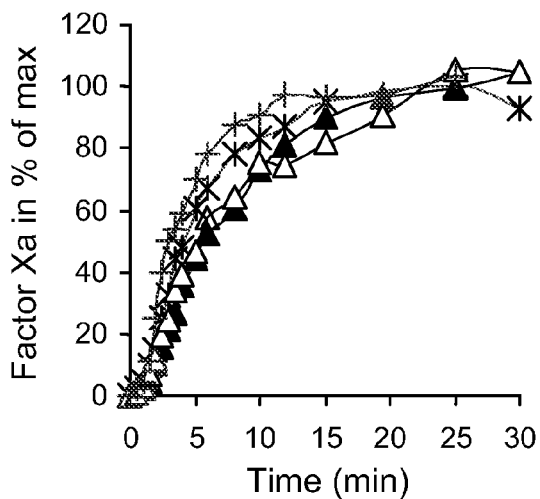
Figure 31C:
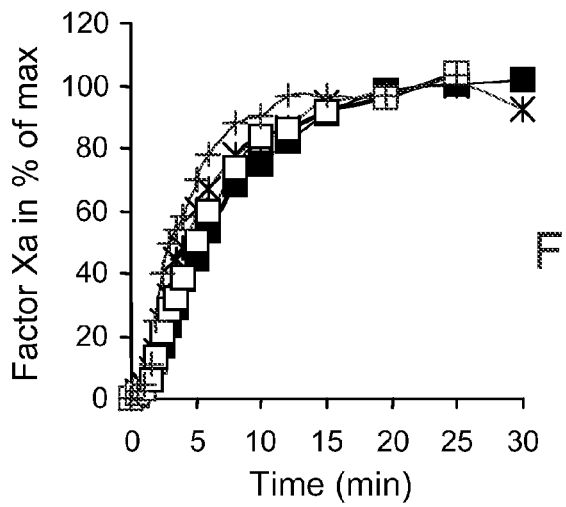

For showing the time course of FX activation obtained with the different PEG-rFVIII conjugates, FXa activity was expressed as a percent of the maximum FXa activity (FIGS. 31A-C). The quantitative kinetic parameters are summarized in Table 14.

TABLE 14

Quantitative parameters of the FIXa-cofactor activity after thrombin activation

| | | after thrombin activation | | | | | |
|---|---|---|---|---|---|---|---|
| | Native rFVIII | rFVIII control | Lys 20K br short | Lys 20K br long | Lys 40K br short | Lys 40K br long | Lys 60K br short | Lys 60K br long |
| lag phase (min) | 1.15 | 1.13 | 0.98 | 1.10 | 1.55 | 1.36 | 1.37 | 1.16 |
| maximum rate (nM FXa/min) | 4.24 | 9.79 | 6.22 | 5.07 | 5.08 | 5.18 | 4.94 | 5.09 |
| $t_{1/2}$ of maximum (min) | 4.24 | 2.85 | 4.06 | 4.60 | 5.13 | 4.61 | 4.94 | 4.40 |
| maximum FXa (nM) | 25.1 | 33.7 | 38.3 | 35.5 | 36.3 | 33.6 | 35.3 | 32.9 |

After activation with thrombin, all PEG-rFVIII conjugates showed a rate of FX activation similar to that of the native rFVIII or the control, which still had an enhanced activity. Also a slight increase had been observed in the maximum FXa-generating capacity.

Kinetics of Thrombin-Mediated Activation and Inactivation of FVIII Measured by the FIXa Cofactor Activity Assay:

The time course of thrombin activation and inactivation was measured with the FIXa-cofactor activity assay. Samples containing 1 IU/ml native or PEG-rFVIII were incubated with 0.5 nM thrombin. Subsamples were withdrawn before the addition of thrombin and at intervals afterwards up to 40 minutes and added to a prepared mixture of FIXa, FX, PL-vesicles, calcium chloride and a thrombin inhibitor to stop further reaction on FVIII. This reaction mix was incubated for three minutes because at this time point there was only a minimum FXa formation without thrombin and about 40% of maximum activity was already reached after full activation by thrombin.

Figure 32:
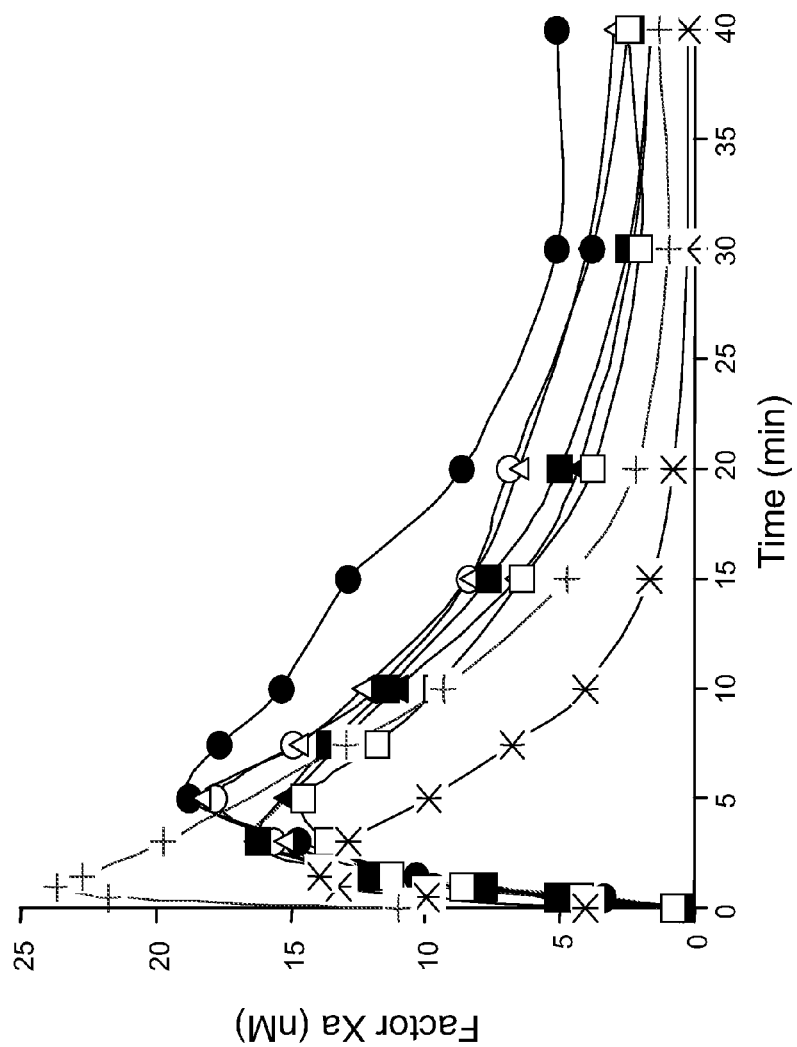
FIG. 32 shows the activation and inactivation of PEG-rFVIII by thrombin. Stars: native rFVIII MOQ HEPES01-E; circles: PEG-rFVIII Lys 20K br short; triangles: PEG-rFVIII Lys 40K br short; squares: PEG-rFVIII Lys 60K br short; cross: FVIII control; circles, open: PEG-rFVIII Lys 20K br long; triangles, open: PEG-rFVIII Lys 40K br long; squares, open: PEG-rFVIII Lys 60K br long. Further information concerning this figure is provided in Example 6.

FIG. 32 shows the time course of thrombin activation and inactivation for the native and PEG-rFVIII conjugates. Table 15 shows the relative first order inactivation rates compared with that of the native rFVIII.

TABLE 15

Rate Constants of thrombin activation

| Sample | Relative k' |
|---|---|
| FVIII control| | 0.72 |
| Lys 20K br short | 0.35 |
| Lys 20K br long | 0.39 |
| Lys 40K br short | 0.48 |
| Lys 40K br long | 0.44 |
| Lys 60K br short | 0.46 |
| Lys 60K br long | 0.51 |

In the presence of 0.5 nM thrombin, both the native rFVIII and the control showed a rapid activation with a maximum activity within 2 minutes followed by a fast inactivation that was almost completed within 20 and 30 minutes, respectively. In accordance with the FXa generation characteristics, the control could be more activated by thrombin and showed a slightly slower inactivation rate. The PEG-rFVIII candidates showed a slightly slower activation rate reaching a maximum between 3 to 5 minutes and a substantially decreased inactivation rate with residual FIXa-cofactor activities.

Figure 33:
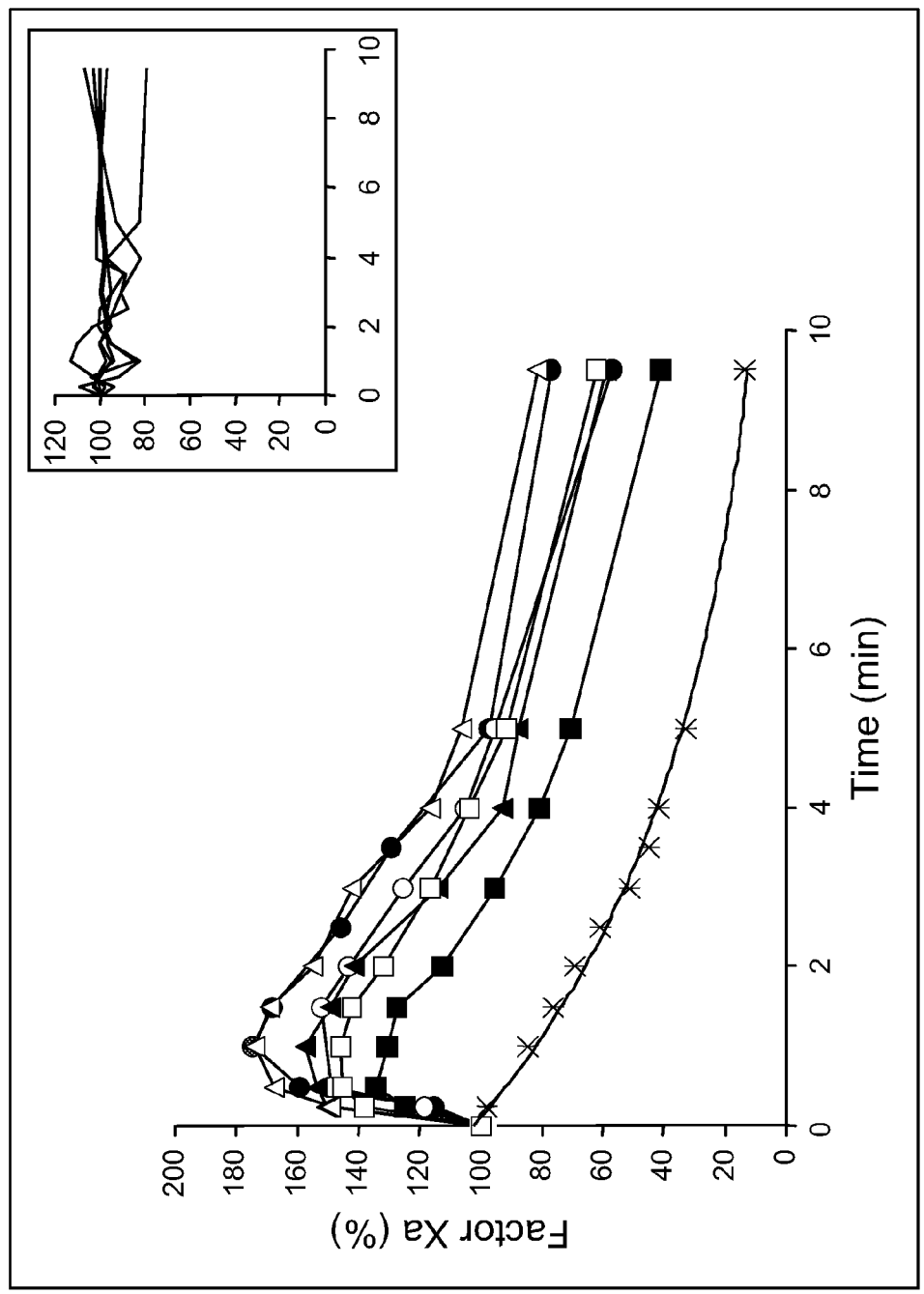
FIG. 33 shows the APC-mediated inactivation of PEGylated FVIII conjugates. Stars: native rFVIII MOQ HEPES01-E; circles: PEG-rFVIII Lys 20K br short; triangles: PEG-rFVIII Lys 40K br short; squares: PEG-rFVIII Lys 60K br short; cross: FVIII control; circles, open: PEG-rFVIII Lys 20K br long; triangles, open: PEG-rFVIII Lys 40K br long; squares, open: PEG-rFVIII Lys 60K br long. Further information concerning this figure is provided in Example 6.
Figure 34:
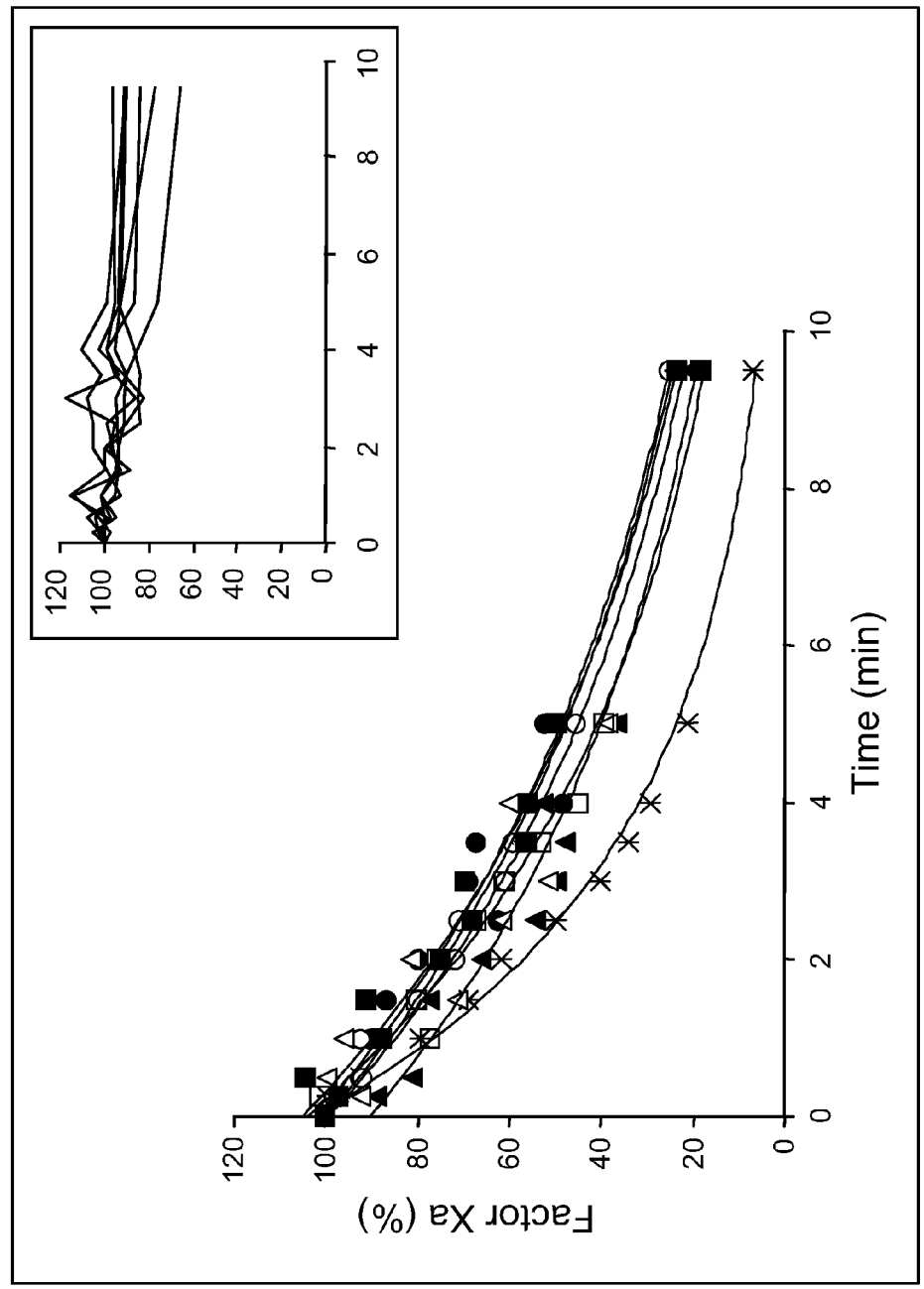
FIG. 34 shows the APC-mediated inactivation of thrombin activated PEGylated FVIII conjugates. Stars: native rFVIII MOQ HEPES01-E; circles: PEG-rFVIII Lys 20K br short; triangles: PEG-rFVIII Lys 40K br short; squares: PEG-rFVIII Lys 60K br short; cross: FVIII control; circles, open: PEG-rFVIII Lys 20K br long; triangles, open: PEG-rFVIII Lys 40K br long; squares, open: PEG-rFVIII Lys 60K br long. Further information concerning this figure is provided in Example 6.

APC-Mediated Inactivation of FVIII and FVIIIa:

Native and PEGylated FVIII (1 IU/ml diluted according to FVIII:Chrom activity) were incubated with 0.05 U/ml activated protein C (APC) either with or without pre-activation by thrombin in the presence of PL-vesicles and $CaCl_2$ (as described above). The residual FVIII activity after APC inactivation was determined by measuring the FIXa cofactor activity, similar as described for investigating the thrombin-mediated activation and inactivation kinetics. Subsamples of the APC-rFVIII mixes were withdrawn at intervals up to ten minutes and added to a prepared mixture of FIXa, FX, PL-vesicles, and calcium chloride. The mixtures were incubated for ten minutes when non-activated and for five minutes, when thrombin-activated PEG-rFVIII was investigated. These incubation times were based on the time courses of FXa generation measured in the presence of non-activated and activated PEG-rFVIII conjugates (FIGS. 30A-C and 31A-C); at the chosen time points about 70% of the full activity has been already reached with the PEG-conjugates. In the appropriate control experiments native and PEG-rFVIII were incubated in the absence of APC. FIGS. 33 and 34 show the time course of inactivation, where FXa activity was expressed as a percent of the FXa measured during the first minute in the appropriate control mixtures incubated without APC. Table 16 and 17 show the calculated relative first order rate constants compared with that measured for the native rFVIII.

TABLE 16

Rate Constants of APC-mediated inactivation

| Sample | Relative k' |
|---|---|
| Lys 20K br short | 0.46 |
| Lys 20K br long | 0.56 |
| Lys 40K br short | 0.44 |
| Lys 40K br long | 0.35 |
| Lys 60K br short | 0.52 |
| Lys 60K br long | 0.38 |

When non-activated native rFVIII was incubated with 0.05 U/ml APC, a first order rate inactivation was observed, with a k' of $0.220*min^{-1}$. In contrast, the PEG-rFVIII conjugates first showed a transient increase in their FIXa-cofactor activities followed by a first order inactivation, albeit at an approximately 50% slower rate. There were no such changes in the samples incubated in the absence of APC. Both native and PEG-rFVIII conjugates remained stable (insert in FIG. 33). No data are available for the control due to the lack of test material at the test time point.

TABLE 17

Inactivation Rate Constants

| Sample | Relative k' |
|---|---|
| Lys 20K br short | 0.50 |
| Lys 20K br long | 0.50 |
| Lys 40K br short | 0.55 |
| Lys 40K br long | 0.54 |
| Lys 60K br short | 0.54 |
| Lys 60K br long | 0.64 |

Incubation of thrombin-activated native or PEG-rFVIII showed first order inactivations (FIG. 34) with approximately 50% slower rates for the PEG-rFVIII conjugates (Table 9). Thrombin-activated native rFVIIIa and PEG-rFVIIIa conjugates remained stable or showed only a negligible decrease in FIXa-cofactor activity in the absence of APC.

Figure 35A:
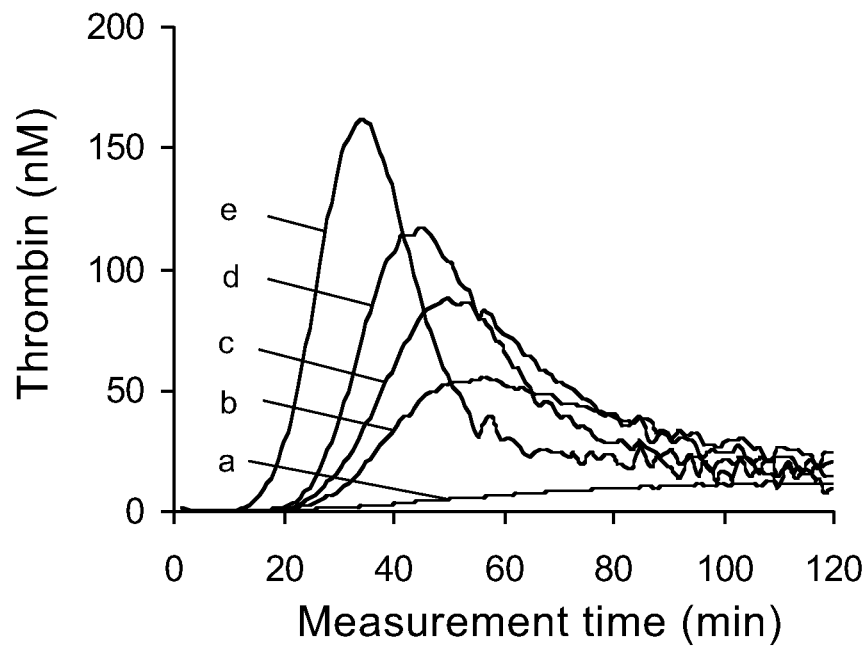
FIGS. 35A and 35B show the improvement of thrombin generation of a FVIII-deficient plasma by in vitro addition of native rFVIII.
Figure 35B:
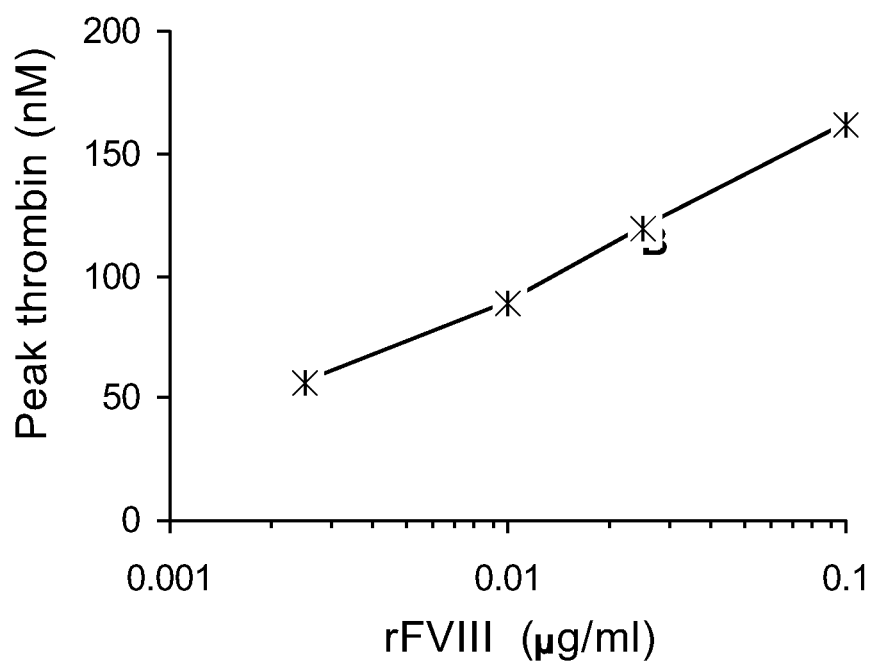
Figure 36A:
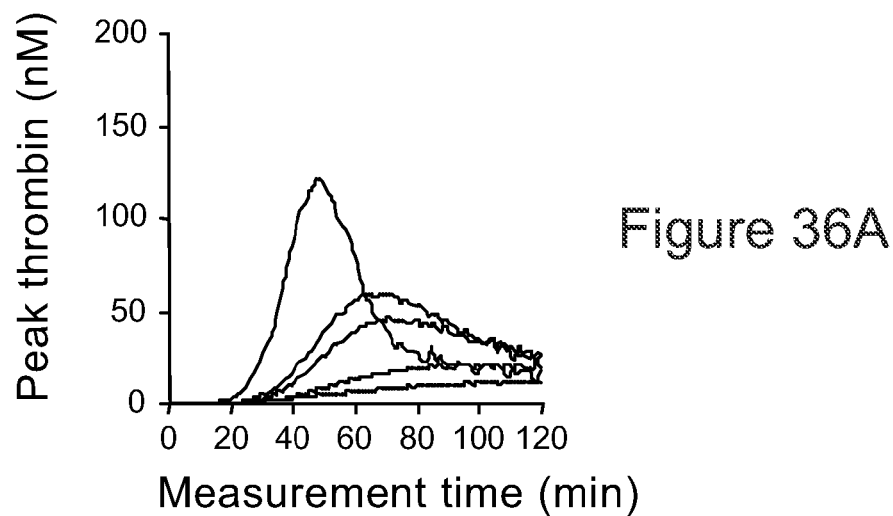
FIGS. 36A-36G show the thrombin generation curves (FIGS. 36A-36F) obtained with the PEG-rFVIII samples in the FVIII-deficient plasma and the dose-response curves (FIG. 36G) of the peak thrombin values. Stars: native rFVIII MOQ HEPES01-E; circles: PEG-rFVIII Lys 20K br short; triangles: PEG-rFVIII Lys 40K br short; squares: PEG-rFVIII Lys 60K br short; cross: FVIII control; circles, open: PEG-rFVIII Lys 20K br long; triangles, open: PEG-rFVIII Lys 40K br long; squares, open: PEG-rFVIII Lys 60K br long. Further information concerning this figure is provided in Example 6.
Figure 36B:
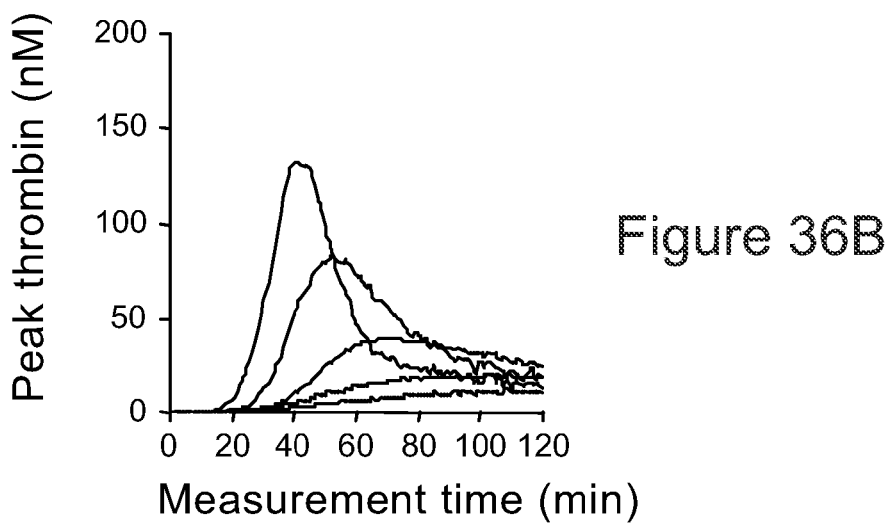
Figure 36C:
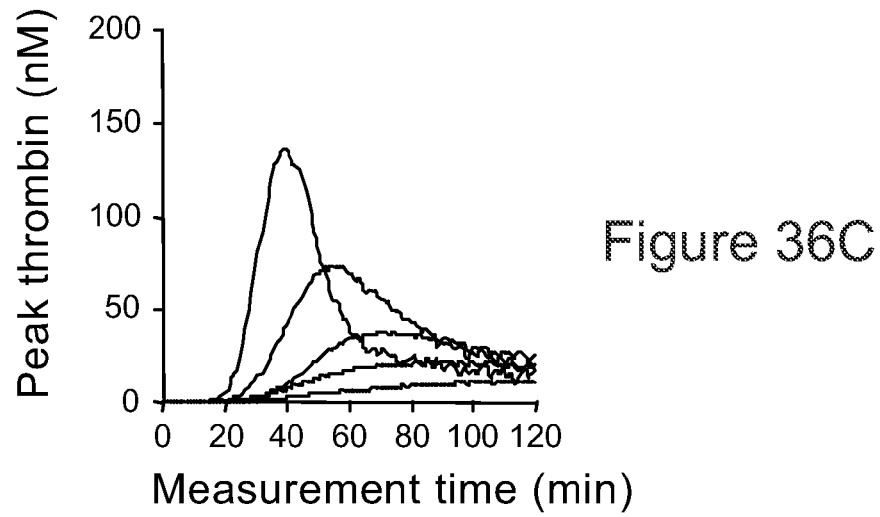
Figure 36D:
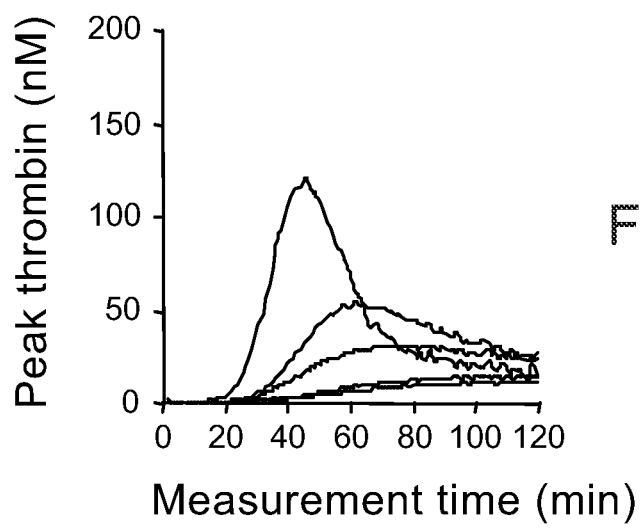
Figure 36E:
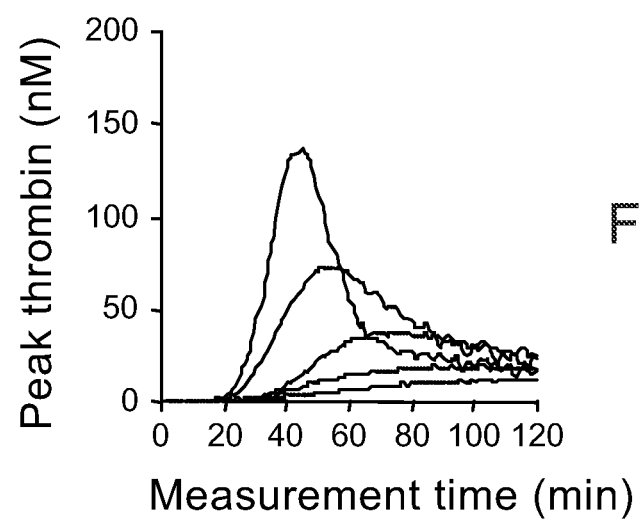
Figure 36F:
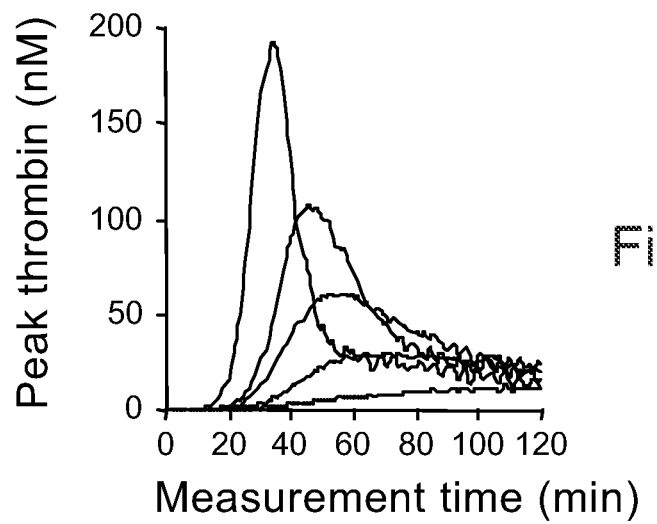
Figure 36G:
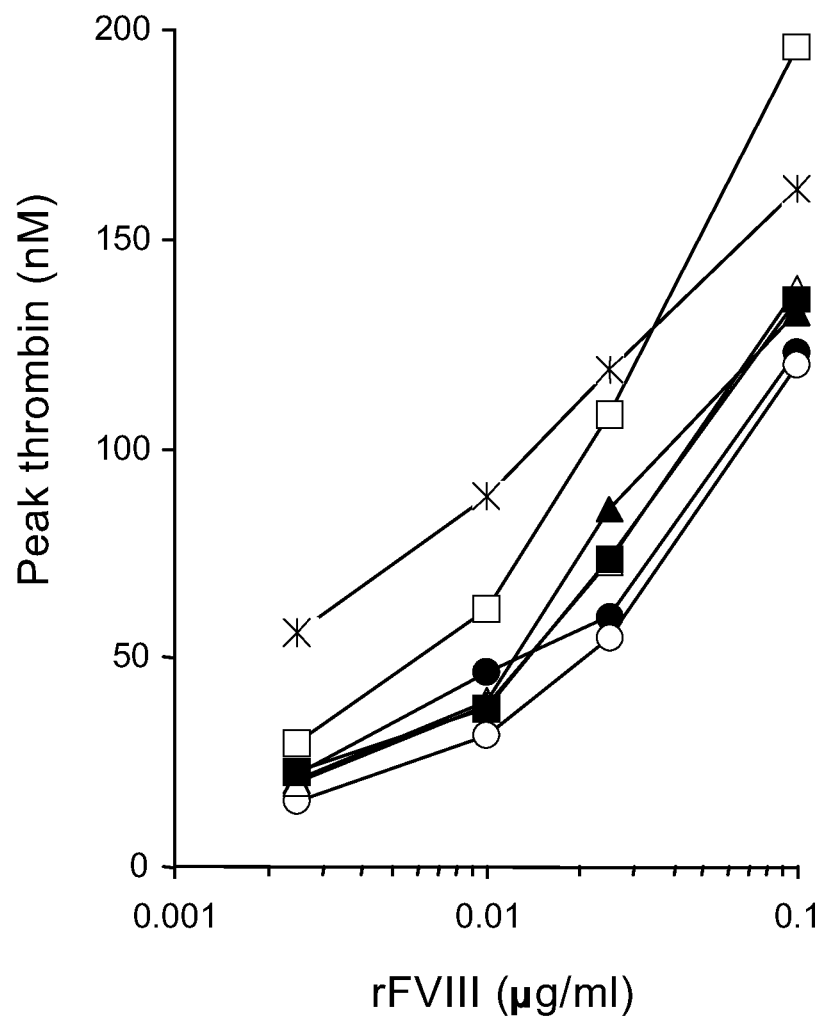
Figure 37A:
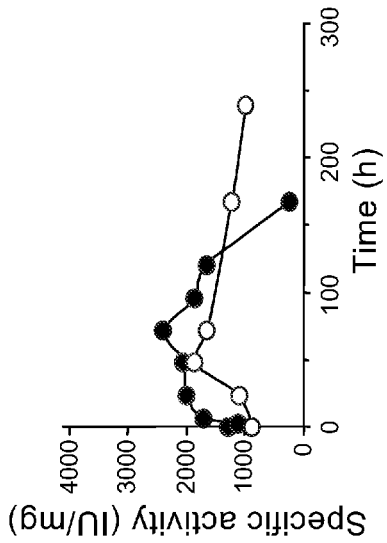
FIGS. 37A-37D show the recovery of in FVIII-specific activity upon incubation in buffer at pH 8.1.
Figure 37B:
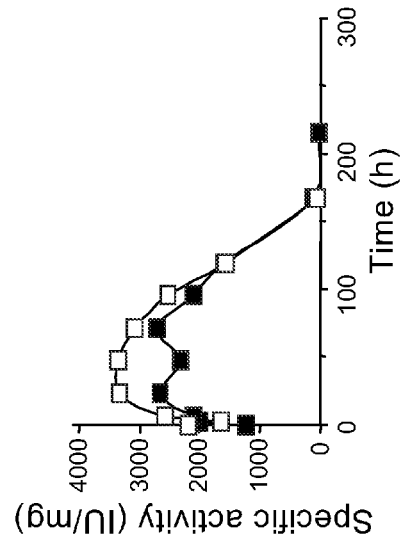
Figure 37C:
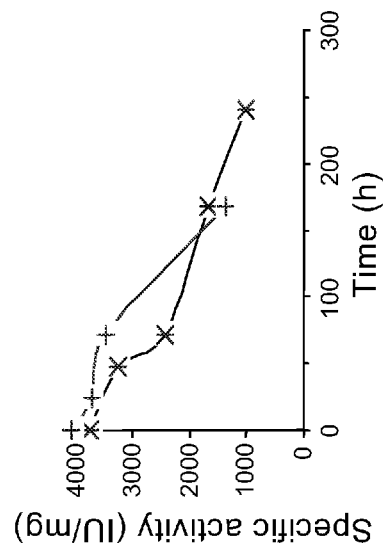
Figure 37D:
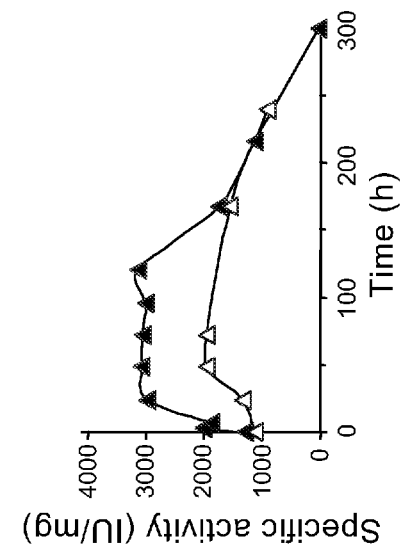

Effect of PEGylation on the Thrombin-Generating Capacity of FVIII in FVIII-Deficient Plasma:

A plasma sample of a severe hemophilia A patient with FVIII activity below 0.01 U/ml (<1%) was spiked in vitro with increasing amounts of native and PEG-rFVIII in the range of 0.0025 and 0.1 µg/ml, corresponding to an activity range of the intact FVIII of 0.025 to 1 IU/ml. Thrombin generation triggered with low concentrations of TF and PL complex was measured as described in the experimental procedures. As shown in FIG. 35A, the addition of native rFVIII dose-dependently improved the impaired thrombin generation of FVIII-deficient plasma. The improvement resulted in a shortening of the onset time and peak time and an increase in the peak thrombin, which showed a linear dose-response with the logarithmic of FVIII concentrations, as drawn in FIG. 35B. This correlation implies that the most effect occurs in the low concentration range.

FIGS. 36A-G show the thrombin generation curves (Panels A-F) obtained with the PEG-rFVIII samples in the FVIII-deficient plasma and the dose-response curves (Panel G) of the peak thrombin values.

All PEG-rFVIII conjugates corrected the impaired thrombin generation of FVIII-deficient plasma in a dose-dependent manner, however with minimal effect below 0.01 μg/ml plasma. Above this concentration parallel dose-response curves with the native rFVIII were measured, which indicates that more FVIII is needed to achieve the same peak level as the native rFVIII. The Lys 60K br long conjugate seemed to have a higher activity in this assay, especially in the higher concentration range.

In vitro release of releasable PEG-rFVIII at increased pH: To investigate the kinetics of in vitro release of the PEG moieties from rFVIII, the PEGylated rFVIII samples were incubated in the original rFVIII buffer (50 mM HEPES, 5 mM $CaCl_2$, 0.1% Polysorbate 80. 350 mM NaCl, pH ~6.9) adjusted to pH 8.1 with a 1/10 volume of 0.1M NaOH. As a control, a native rFVIII and the un-PEG-rFVIII control was treated the same way. All samples were kept at ambient temperature. A sub-sample was taken at different time points and changes in FVIII:Ag, FVIII chromogenic activity were measured. The structural changes were investigated by SDS-PAGE followed by immunoblotting with FVIII and PEG-specific antibodies.

Changes in FVIII:Ag and Chromogenic Activity During In Vitro Release of the PEG Moiety:

FIGS. 37A-D show the changes in FVIII-specific activity and FIG. 38 in FVIII:Ag, both expressed as IU/mg protein.

The native rFVIII and the shipping control showed a continuous decrease of activity and antigen levels. In contrast, both the activity and antigen levels of the PEGylated rFVIII conjugates gradually increased in the first 48 hours and after a plateau decreased again. The highest relative activity increase (2.4 fold) was achieved for the Lys 40K br short conjugates. The fastest increase with the shortest plateau was observed for the two 60K conjugates.

Figure 40:
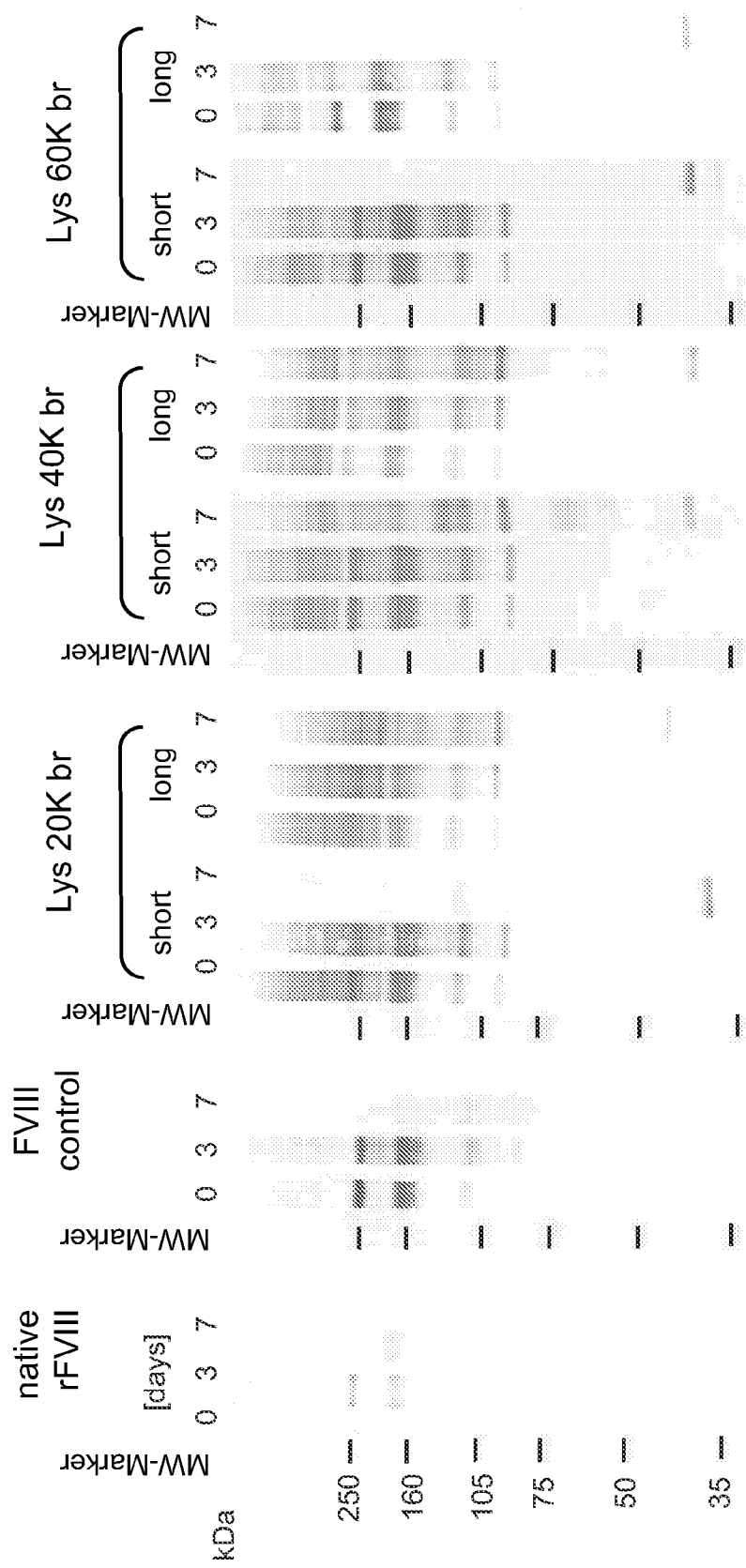
FIG. 40 shows the structural changes of FVIII upon incubation at increased pH demonstrated by anti-FVIII HC-A2 domain immunoblot. Further information concerning this figure is provided in Example 6.
Figure 41:
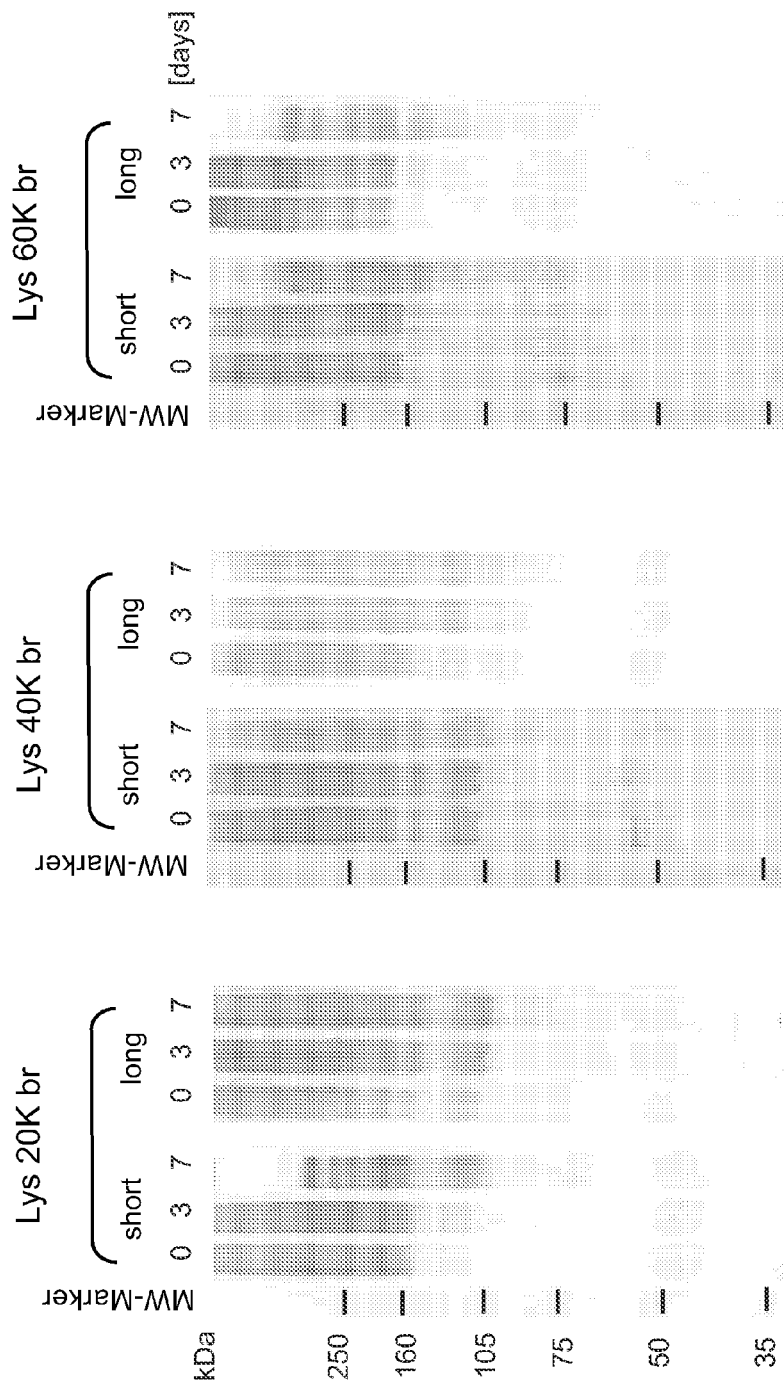
FIG. 41 shows the structural changes of FVIII upon incubation at increased pH demonstrated by anti-PEG immunoblot. Further information concerning this figure is provided in Example 6.

Structural Changes in PEG-rFVIII During In Vitro Release of the Peg Moiety:

To visualize structural changes upon incubation at higher pH of pH 8.1, the samples were subjected to SDS-PAGE under reducing conditions followed by immunoblots with polyclonal anti-human FVIII antibody (FIG. 39), monoclonal anti-human heavy chain A2 domain antibody (FIG. 40) and polyclonal anti-PEG antibody (FIG. 41). Native rFVIII and the FVIII control showed a continuous decrease in FVIII activity and FVIII:Ag level, which corresponds to the degradation of FVIII during the incubation.

Because both the FVIII:Ag level and the FVIII:Chrom activity increases upon incubation at buffer pH 8.1, suggesting a demasking effect of PEG release, the amount of FVIII applied to the gel accorded with the measured FVIII:Chrom activity of the material without performing a release reaction (100 mIU FVIII:Chrom for the anti-FVIII antibodies and 300 mIU FVIII:Chrom for anti-PEG antibody)

Figure 39:
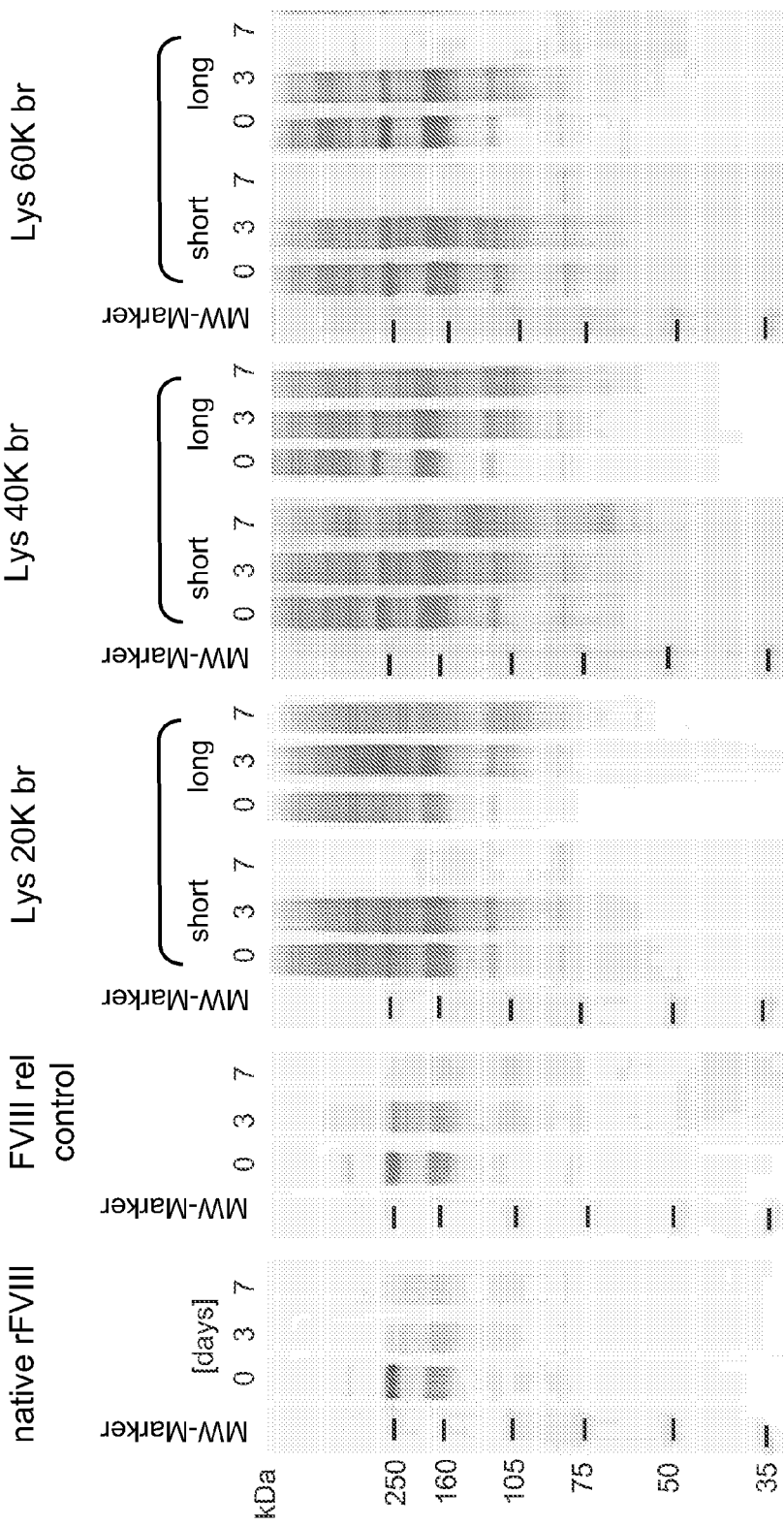
FIG. 39 shows the structural changes of FVIII upon incubation at increased pH demonstrated by anti-FVIII immunoblot. Further information concerning this figure is provided in Example 6.

As shown in FIG. 39, after 3 days incubation in buffer pH 8.1 no substantial changes could be found for the PEG-rFVIII conjugates but a slight blurring effect for both native rFVIII and the FVIII control with the anti-FVIII immuoblots was observed. Longer incubation up to 7 days resulted in degradation with non-detectable epitopes. By comparison of the different candidates, the Lys 40K br long and Lys 20K br long conjugates, showed the longest structural integrities. Some MW decrease in the heavy chain of the PEG-rFVIII conjugates occurred after 3 days incubation as demonstrated by FIG. 40. After 7 days incubation in all conjugates the HC-A2 fragment appeared. A time-dependent decrease of the molecular weight of all domains was also observed with the anti-PEG immunoblot (FIG. 41), which reflects some release of the bound PEG. No substantial amounts of free PEG were detected. After 7 days incubation time, all conjugates were degraded to such an extent that they cannot be visualized by the FVIII-specific immunoblots (data not shown).

In Vitro Release of Releasable PEG-rFVIII in a Human FVIII-Deficient Plasma:

To simulate the physiological conditions, in the second release experiment the PEG-rFVIII conjugates with 20K and 40K PEG were incubated in a human FVIII-deficient plasma at +37° C. The dissociation of the PEG was investigated under these conditions by measuring the changes in FVIII chromogenic activity and FVIII antigen level. The PEG-rFVIII conjugates together with a native rFVIII and the FVIII control were diluted to 0.1 μg/ml protein concentration and added to a FVIII-deficient plasma with an FVIII activity below 1% (George King Bio-Medical Overland Parks, Kans., USA) with 0.005% sodium-azide to prevent microbiological contamination during the incubation time. Samples were withdrawn at defined time points and tested immediately in the case of FVIII chromogenic activity determination or aliquoted and frozen at −80° C. for FVIII: Ag determination.

Because of a lack of material, PEG-rFVIII conjugates were resynthesized for this experiment, only the Lys 20K br short was from the first production. The resynthesized Lys 20K br long had a lower PEGylation degree. The resynthetized Lys 40K br long had also a lower PEgylation degree, however due to different analytical methods, no direct comparison was feasible (Table 9). There were also some differences in the specific activities, however they did not seem to correlate with the PEGylation degree (Table 11).

Figure 42A:
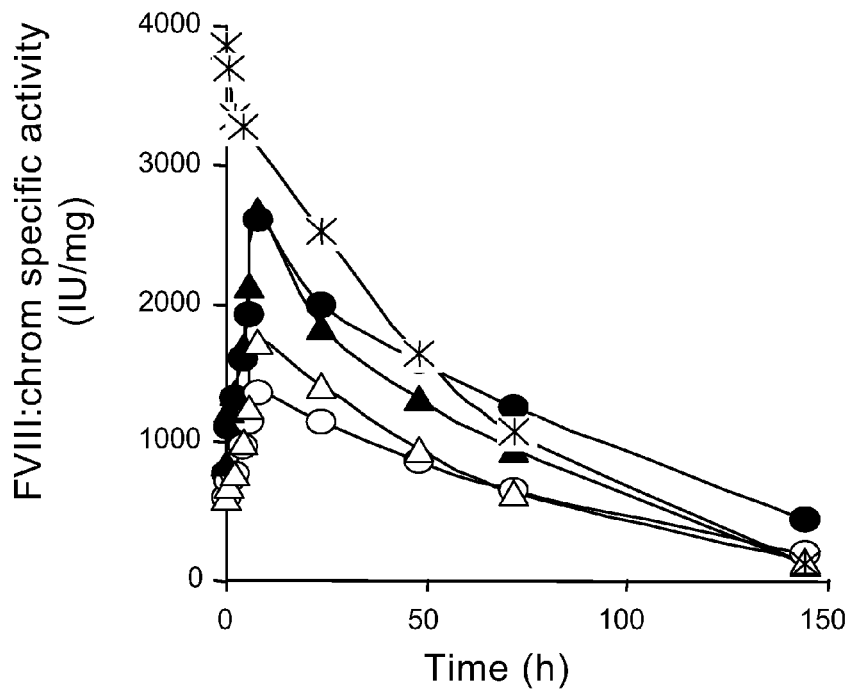
FIGS. 42A and 42B show the changes in FVIII-specific activities of the PEG-rFVIII upon incubation in FVIII-deficient plasma at +37° C.
Figure 42B:
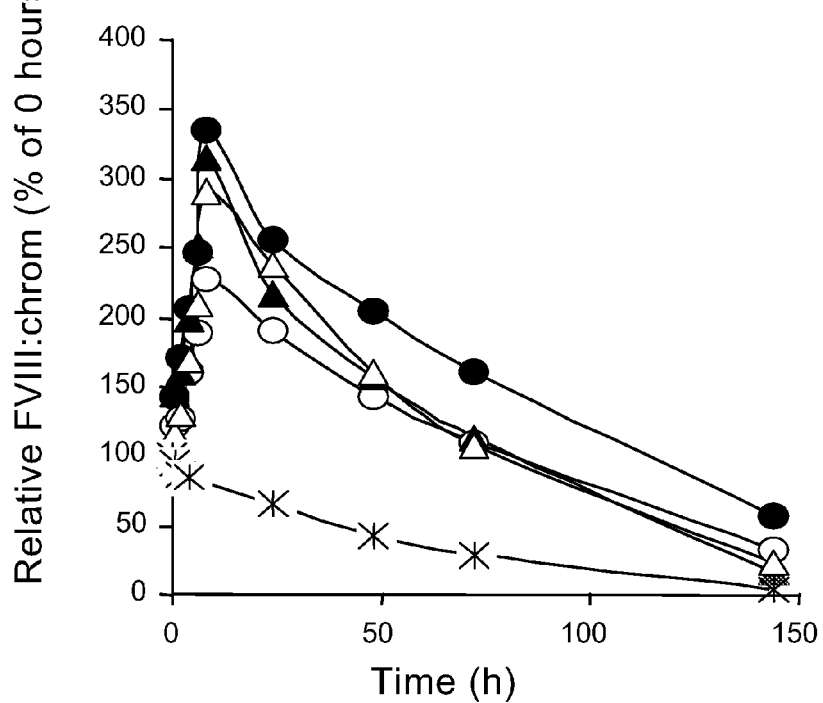
Figure 43A:
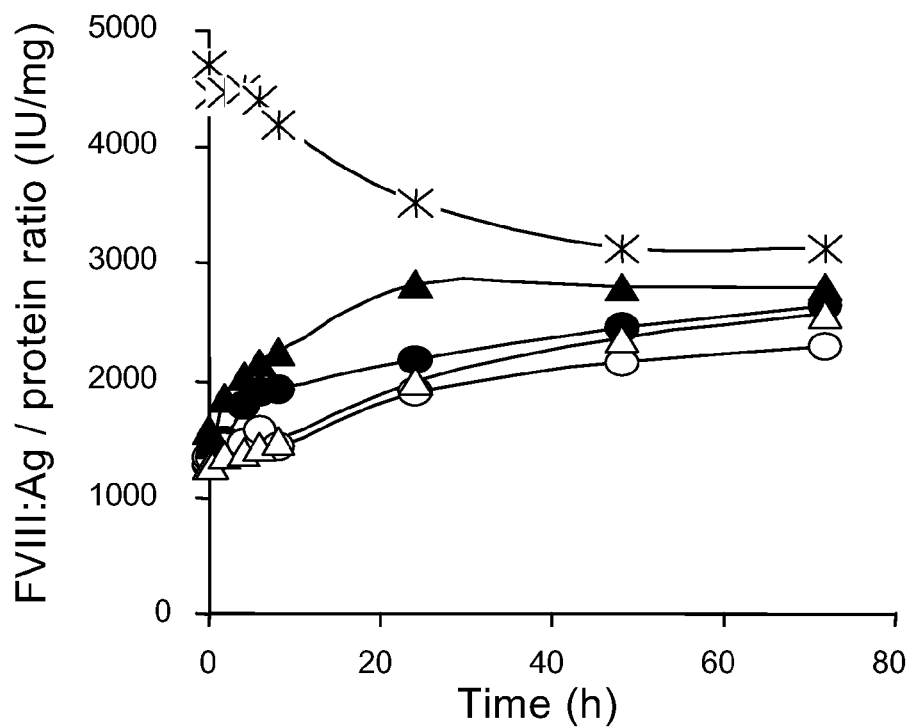
FIGS. 43A and 43B show the changes in the FVIII antigen to protein ratio of the PEG-rFVIII upon incubation in FVIII-deficient plasma at +37° C.
Figure 43B:
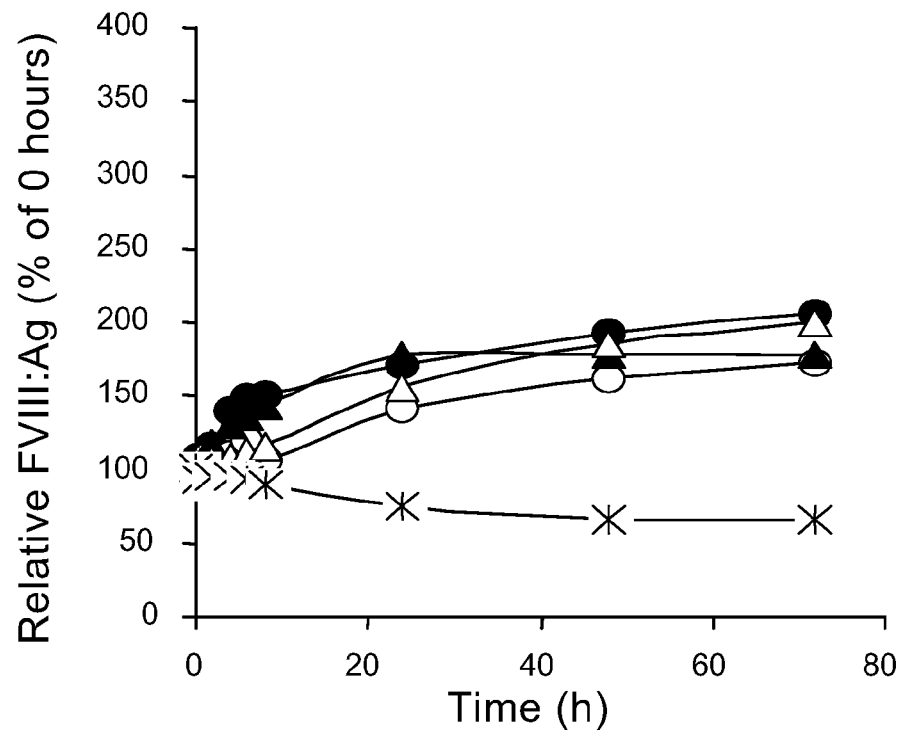

The specific activity of the native rFVIII decreased upon incubation in the plasma system (FIG. 42A,B). In contrast to this, the specific activity of the conjugates increased transiently upon incubation reaching a maximum level after approximately 10 hours. None of the conjugates achieved the initial specific activity of the native rFVIII. There were no substantial differences between the inactivation rates, determined from the ascending part of the curves, between the different conjugates and the native rFVIII (data not shown). The FVIII antigen level also increased during the incubation (FIG. 43A,B), which hint at a demasking effect. Similar to the FVIII activity results, none of the conjugates achieved the initial level of the native rFVIII.

FVIII-deficient knockout mice were infused with either rFVIII or PEG-rFVIII in a target dose of 200 IU FVIII/kg bodyweight. Groups of 6 mice per time point were used for each conjugate. To allow direct comparison of elimination curves independent of the FVIII dose applied, FVIII plasma levels were normalized relative to the FVIII concentration found in plasma 5 minutes after substance application (normalized %).

Figure 44A:
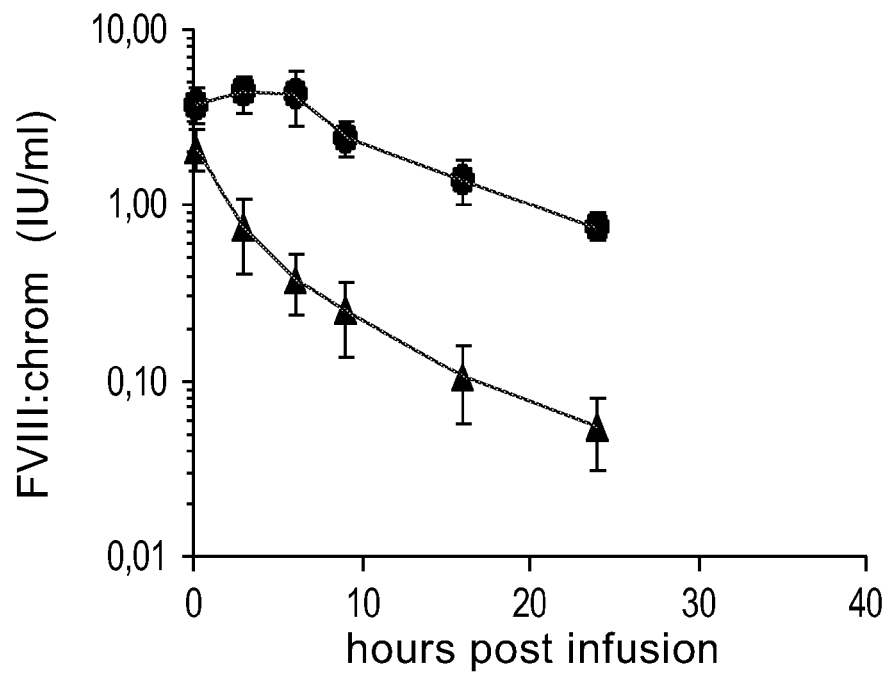
FIGS. 44A and 44B show the comparison of native rFVIII and PEG-rFVIII Lys 20K br short in FVIII-deficient knock-out mice.
Figure 44B:
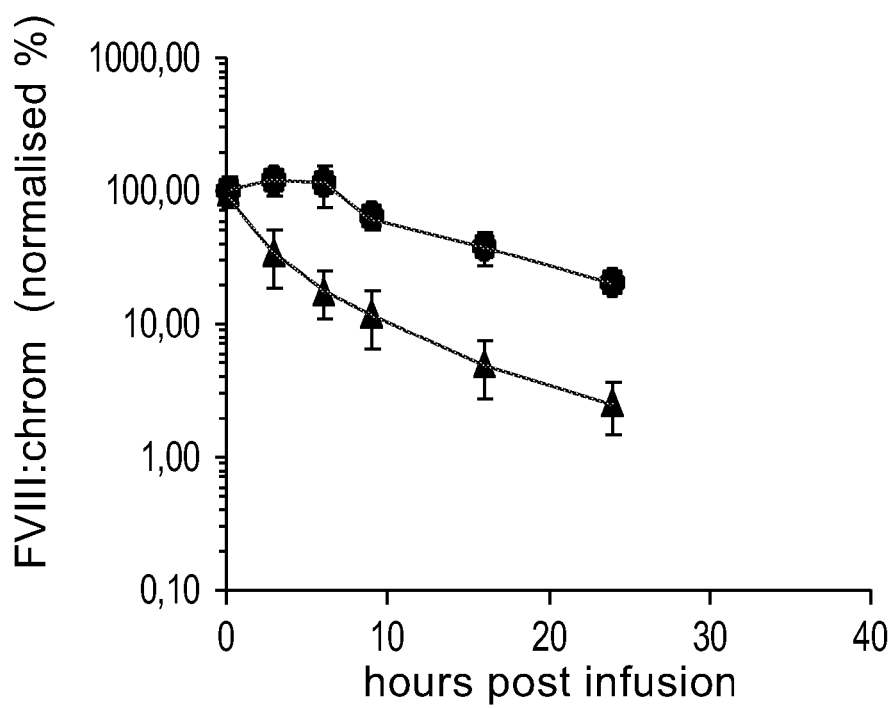
Figure 45A:
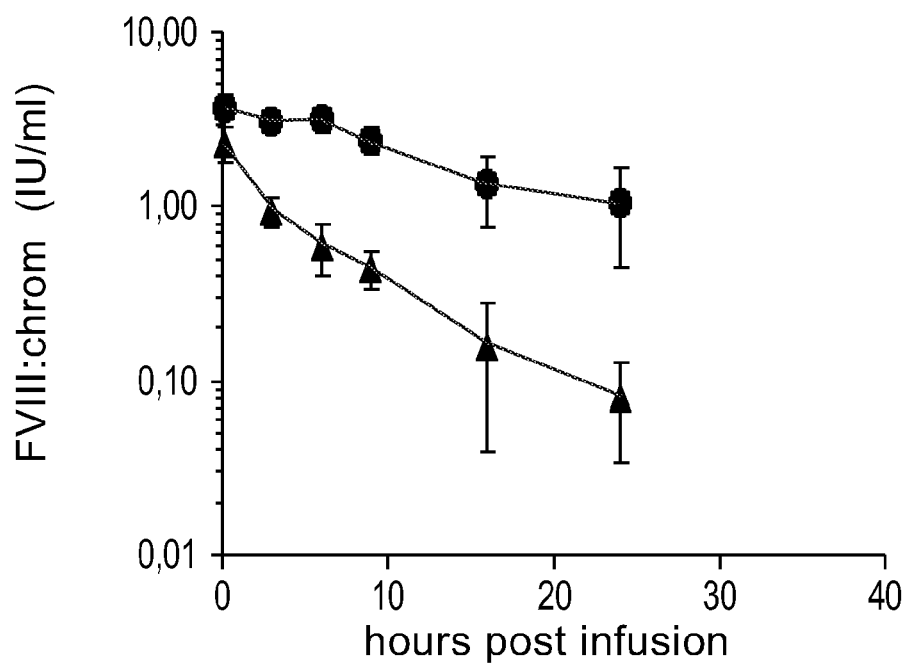
FIGS. 45A and 45B show the comparison of native rFVIII and PEG-rFVIII Lys 20K br long in FVIII-deficient knock-out mice.
Figure 45B:
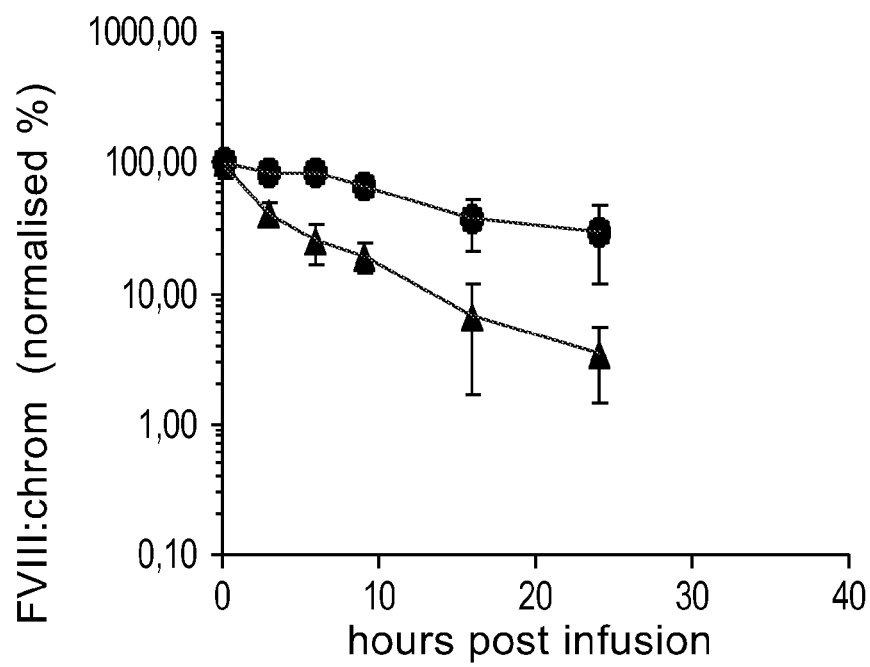
Figure 46A:
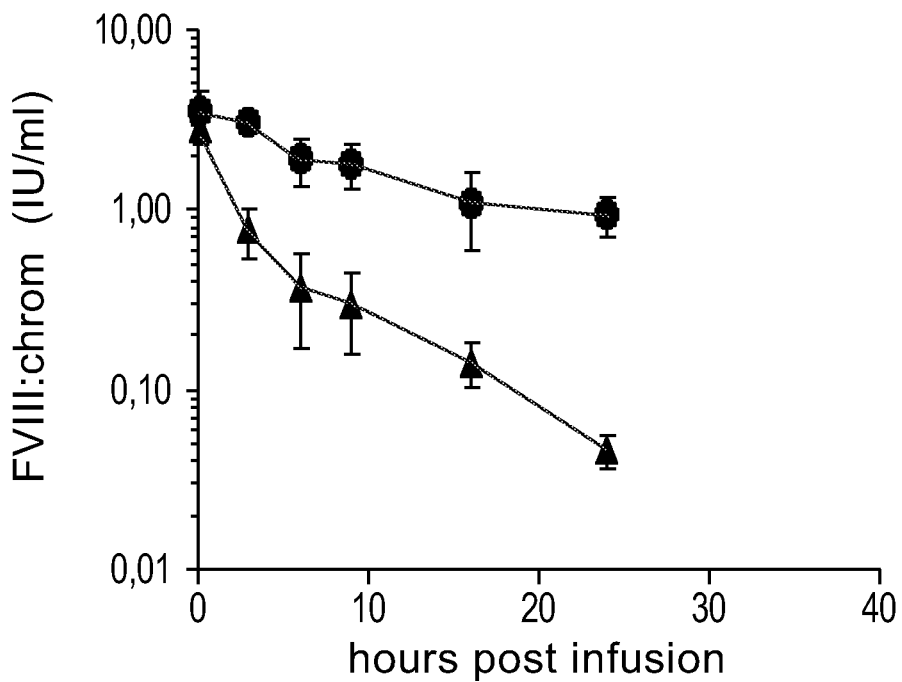
FIGS. 46A and 46B show the comparison of native rFVIII and PEG-rFVIII Lys 40K br short in FVIII-deficient knockout mice.
Figure 46B:
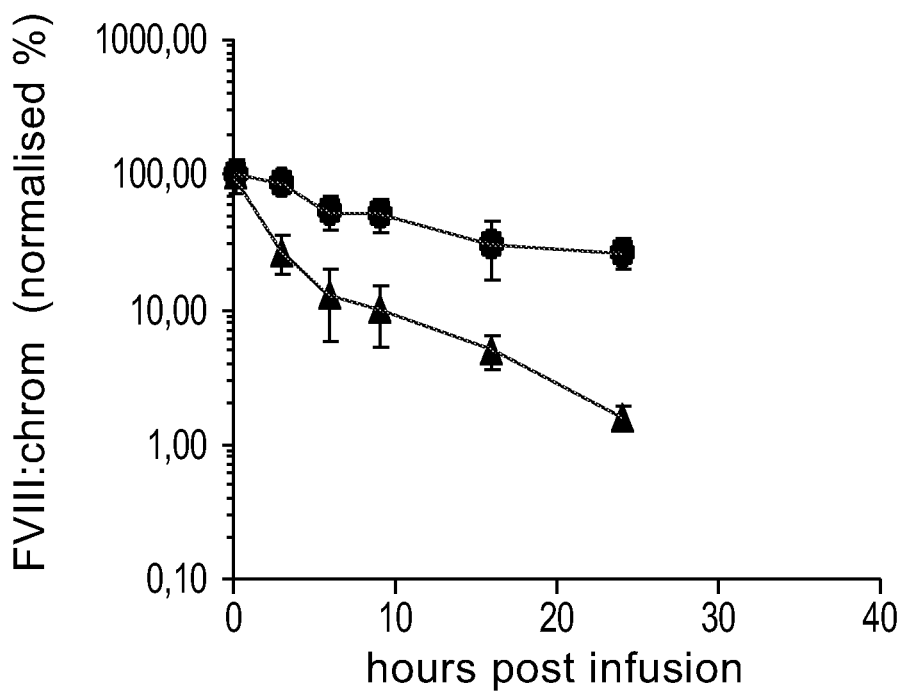
Figure 47A:
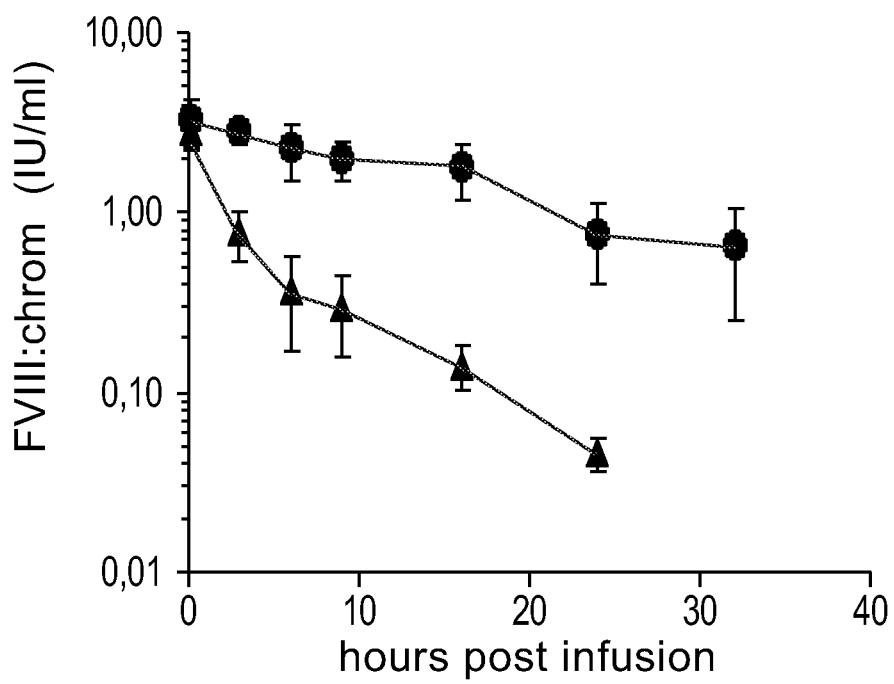
FIGS. 47A and 47B show the comparison of native rFVIII and PEG-rFVIII Lys 40K br long in FVIII-deficient knockout mice.
Figure 47B:
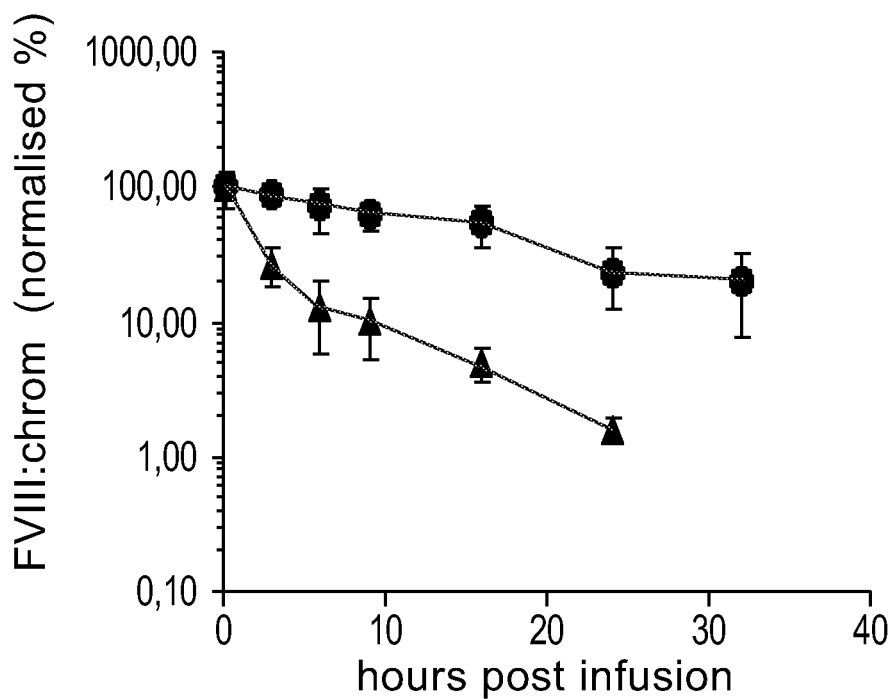
Figure 48A:
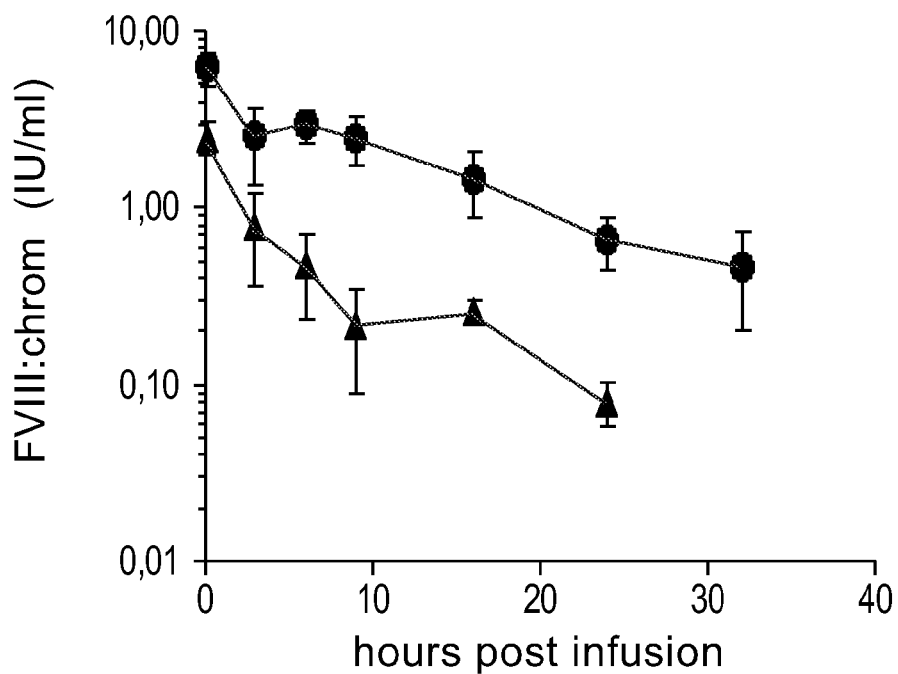
FIGS. 48A and 48B show the comparison of native rFVIII and PEG-rFVIII Lys 60K br short in FVIII-deficient knockout mice.
Figure 48B:
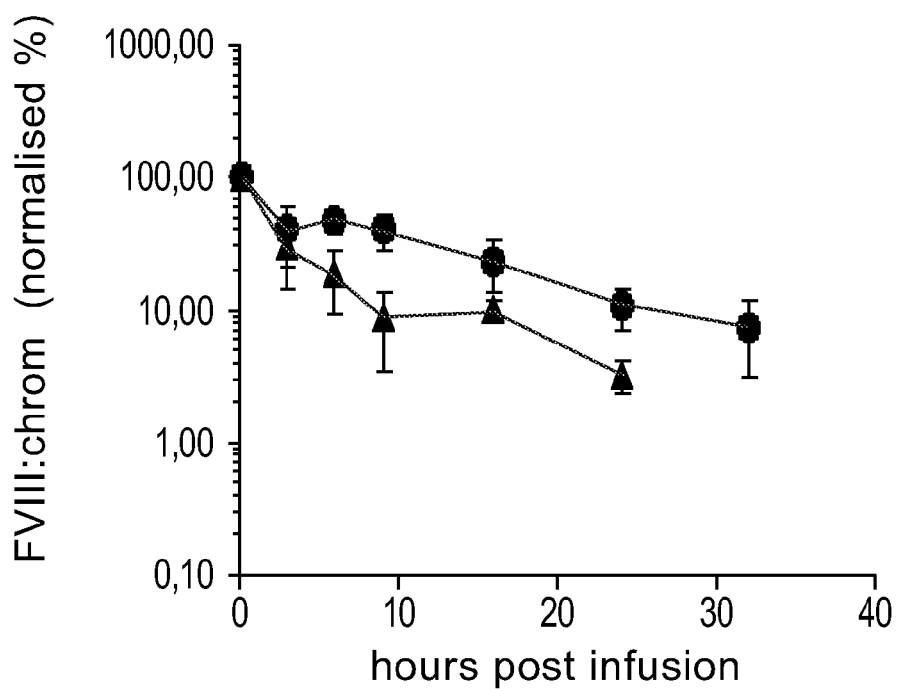
Figure 49A:
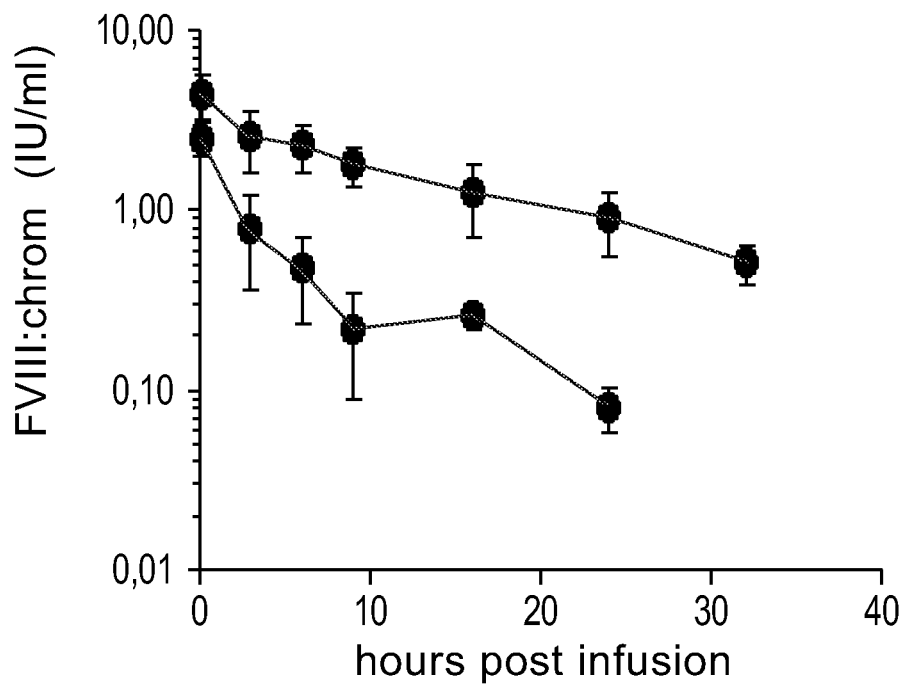
FIGS. 49A and 49B show the comparison of native rFVIII and PEG-rFVIII Lys 60K br long in FVIII-deficient knockout mice.
Figure 49B:
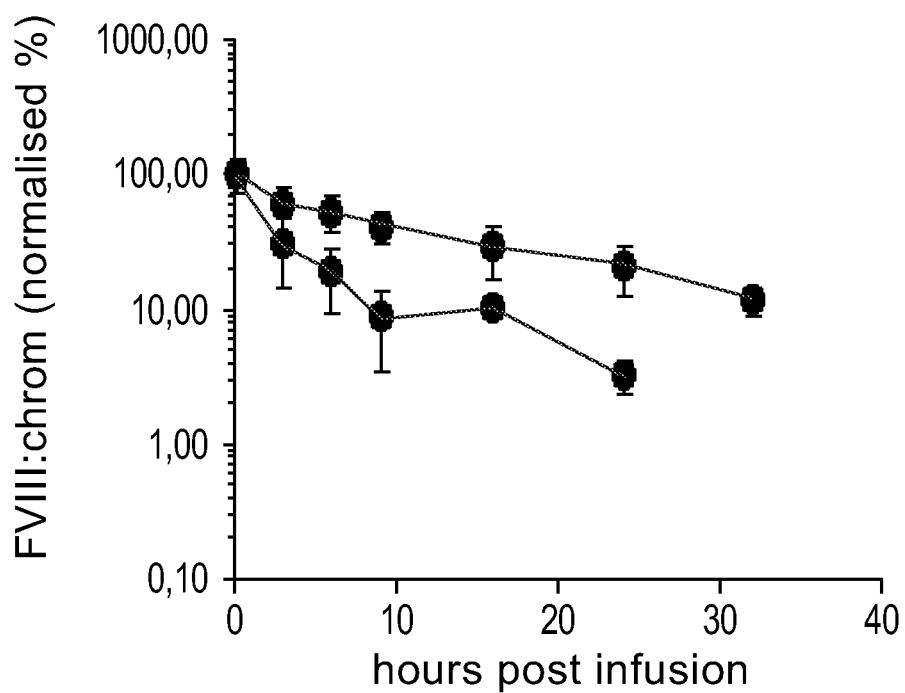
Figure 50:
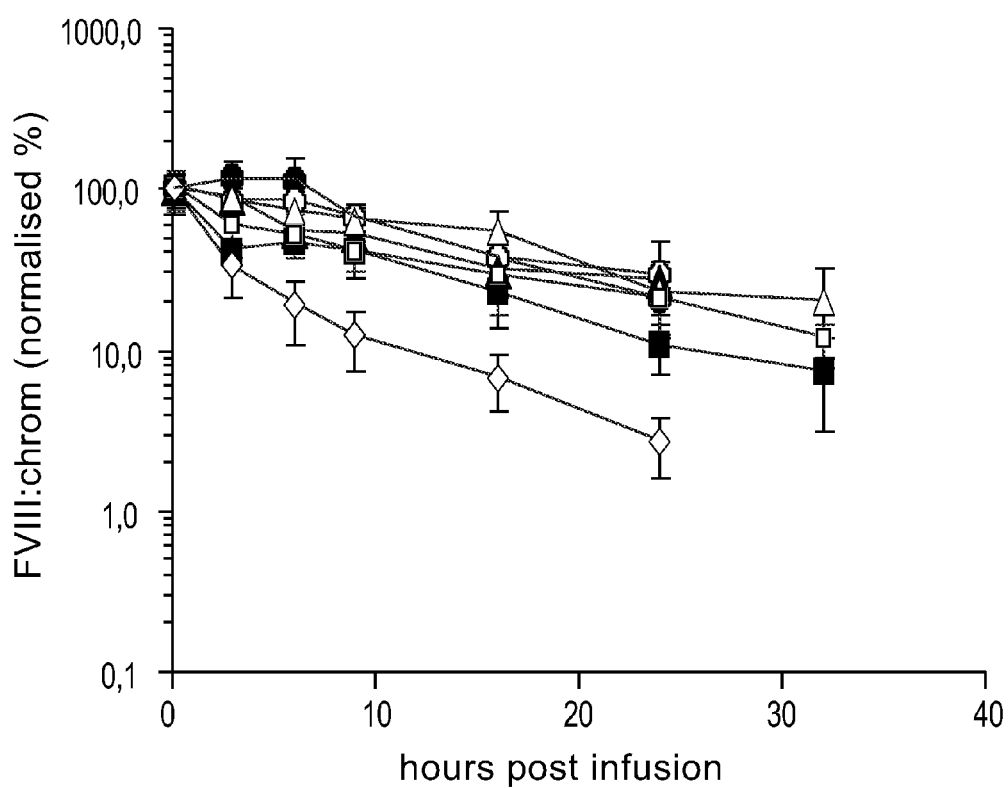
FIG. 50 shows the comparison of native rFVIII and PEGylated rFVIII conjugates in FVIII deficient mice. Closed circles, PEG rFVIII Lys 20K br short; open circles, PEG rFVIII Lys 20K br long; closed triangles, PEG rFVIII Lys 40K br short; open triangles, PEG rFVIII Lys 40K br long; closed squares, PEG rFVIII Lys 60K br short; open squares, PEG rFVIII Lys 60K br long; open diamonds, native rFVIII. The symbols show the "normalized %" mean values±SD of the 6 plasma samples obtained at each time point (for PEG-rFVIII) or the mean values±SD of the 24 plasma samples obtained at each time point (native rFVIII). Further information concerning this figure is provided in Example 6.

FIGS. 44A,B-49A,B show plasma levels of FVIII after substance injection, either in IU FVIII/ml ("A" figures) or normalized as a percent ("B" figures). The exact amount of the injected material is shown in the appropriate figure legends.

In general, all PEG-rFVIII showed improved pharmacokinetics over the native control. The degrees of improvement of pharmacokinetic parameters were calculated with statistical methods and are summarized in Table 10.

Immediately after infusion of PEG-rFVIII, the plasma FVIII activity increased, reached a plateau between 3 hours and 6 hours with a subsequent decline. 24 hours after infusion, approximately 10 times more PEG-rFVIII activity was measured in the mouse plasma than after injection of native rFVIII.

Similar to the Lys 20K br short candidate, PEG-rFVIII 20K br long circulated much longer than native rFVIII.

Recombinant FVIII, PEGylated with 40K br short PEG, circulated longer than native rFVIII.

24 hours after injection, native rFVIII was close to the limit of quantification, while PEG-rFVIII Lys 40K br long was still detectable 32 hours after infusion.

The 60K conjugate with short releasable characteristics was eliminated much slower than native rFVIII from mouse plasma.

Figure 25:
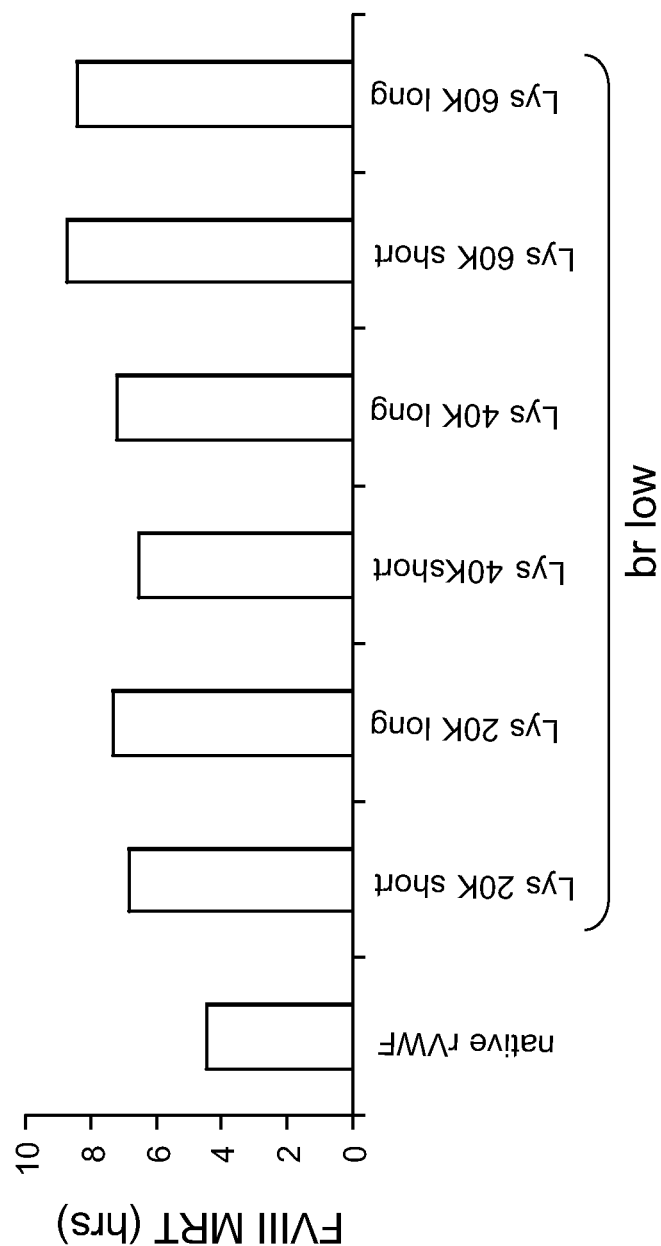
FIG. 25 shows the MRT for FVIII, co-injected with PEGylated rVWF candidates. Further information concerning this figure is provided in Example 5.

The PEG-rFVIII Lys 60K br long conjugate circulated much longer in hemophilic mice than the native control rFVIII did. For direct comparison, the normalized elimination curves for all PEG-rFVIII candidates are summarized in FIG. 25. The control group is the mean of all experiments, performed throughout the investigation (24 animals per time point).

The results from the statistical evaluation are given in Table 18. Data are given as increase in pharmacokinetic parameters versus the dedicated controls, run together with each rFVIII conjugate. FVIII area under the curve (AUC) was significantly increased for all candidates, but none of the candidates appears superior to the others. Increase in FVIII half-life varied between the candidates. PEG-rFVIII Lys 20K br long resulted in a significant increase in FVIII half-life. For the 40K candidates, a statistical trend towards significantly increased FVIII half-lives was observed, but a study extension with plasma sampling points up to 60 hours would be necessary to confirm significances. The 60K variants gave no significant increase in half-lives. Mean residence time was always higher for the PEG-rFVIII conjugates than the native control. The highest increase in MRT was observed for the Lys 40K br short candidate, whereas the Lys 60K conjugates gave the lowest increase.

TABLE 18

Pharmacokinetic parameters for PEG-rFVIII (increase versus control)

| rVWF Sample | FVIII AUC | FVIII half life | FVIII MRT |
|---|---|---|---|
| | | increase versus control | |
| Lys 20K br short | 3.6$^s$ | 1.4$^{ns}$ | 2.1 |
| Lys 20K br long | 4.1$^s$ | 2.0$^s$ | 2.6 |
| Lys 40K br short | 3.9$^s$ | 2.8$^{s\S}$ | 3.9 |
| Lys 40K br long | 4.8$^s$ | 2.0$^{s\S}$ | 3.1 |
| Lys 60K br short | 4.7$^s$ | 0.9$^{ns}$ | 1.5 |
| Lys 60K br long | 4.6$^s$ | 1.2$^{ns}$ | 1.9 |

$^s$significant,
$^{s\S}$statistical trend,
$^{ns}$not significant
data show the increase in pharmacokinetic parameters versus the respective control group with native rFVIII, run together with each PEG-rFVIII conjugate.

Figure 51A:
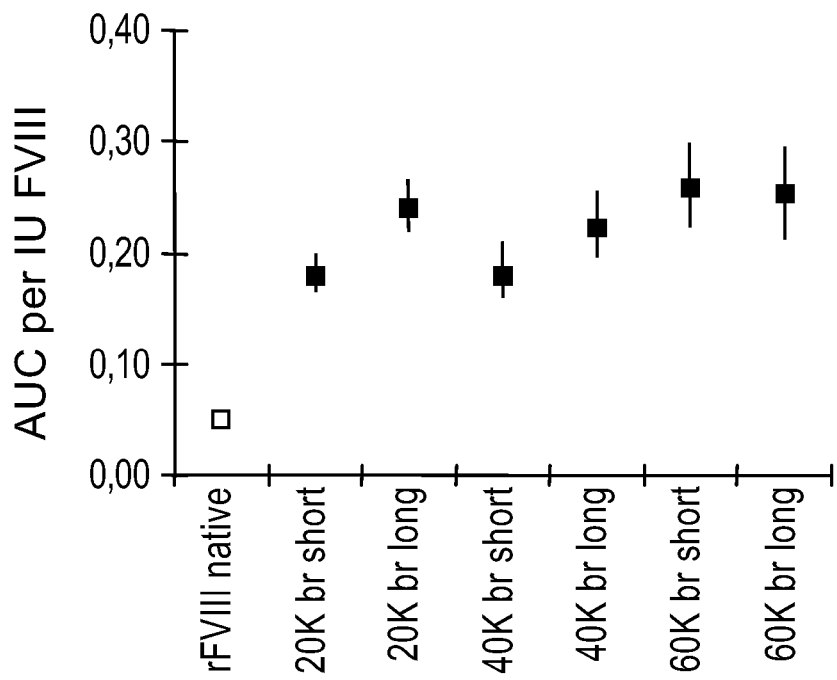
FIGS. 51A and 51B show the dose-adjusted AUC and half-life for native rFVIII and PEG-rFVIII conjugates.
Figure 51B:
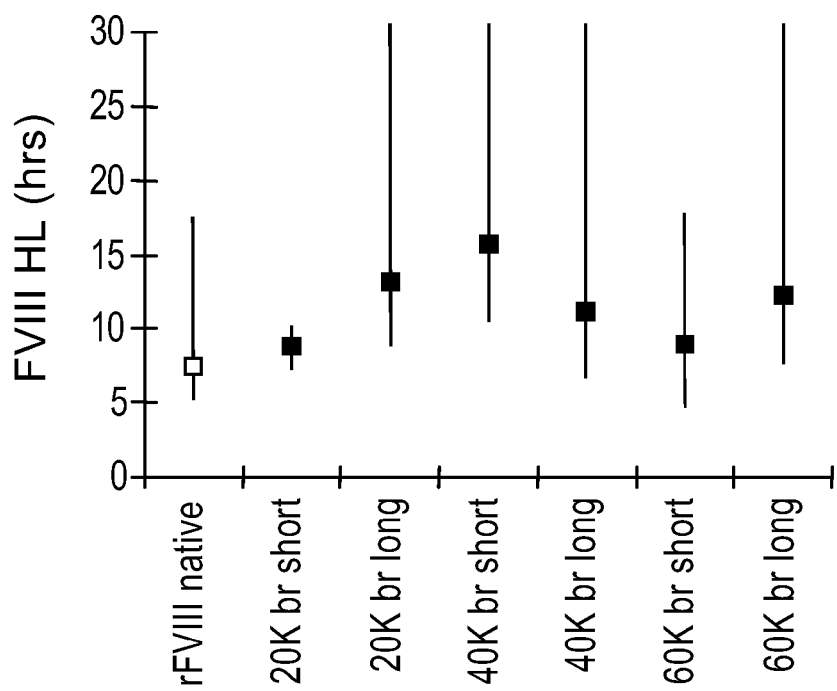
Figure 52:
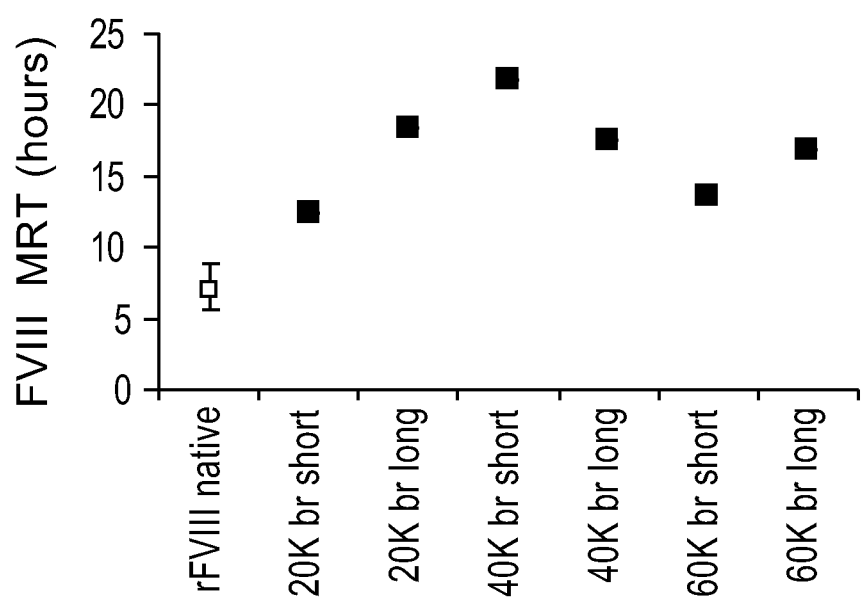
FIG. 52 shows the mean residence time ("MRT") for native rFVIII and PEG-rFVIII conjugates. Mean residence time and range for rFVIII control (open square, mean of all control groups, 24 animal per sampling point) and for PEG-rFVIII candidates (closed squares). Further information concerning this figure is provided in Example 6.

Whereas in Table 18 results are given as relative increase versus the individual control experiment, FIGS. 51A,B show the absolute data for AUC and half life from statistical evaluation together with the 95% confidence intervals to allow direct comparison between candidates.

The AUC for all PEG-rFVIII conjugates was clearly higher than for the mean native rFVIII control. The 95% confidence intervals for the PEG-rFVIII did not overlap with those from the control. Within the PEG-rFVIII candidates the Lys 60K conjugates and the Lys 20K br long candidate seemed to have the most pronounced effect. FVIII half-life was also increased with all PEG-rFVIII candidates.

Mean residence time was elevated for all PEG-rFVIII candidates versus the native rFVIII control (range for native control was from 5.6 to 8.9 hours). The highest MRT was found for the Lys 20K br long and the Lys 40K br short and long candidates.

In summary, all PEG-rFVIII conjugates preserved the domain structure without any degradation. In contrast, all functional activities were decreased, which could only be partially recovered upon in vitro incubation. However, it should be taken into account that the measured values were influenced by the rate of three simultaneous reactions, i.e. the release of PEG moieties, the inactivation of PEG-rFVIII and the inactivation of liberated native rFVIII. The Lys 60K br long conjugate had a higher specific activity and as a consequence an elevated thrombin generation capacity. However, it did not show any other functional or structural beneficial properties properties over the 20K or 40 K PEG-rFVIII conjugates in the tests performed.

FVIII-deficient mice were injected with rFVIII or PEG-rFVIII and FVIII activity in plasma was followed up to 32 hours. All PEG-rFVIII conjugates showed slower elimination than that of the native rFVIII control. Whereas native rFVIII was eliminated in the mouse model in a biphasic manner with a faster initial phase and a slower terminal phase, the PEG-rFVIII candidates followed a more linear elimination characteristic. The Lys 20K br short candidate resulted in an increase in the FVIII plasma levels up to 6 hours after injection into hemophilic mice, followed by a FVIII activity decline. The initial increase in FVIII activity might be explained by the release of releasable PEG from the PEG-rFVIII, thus recovering FVIII activity.

The slower elimination of FVIII activity with the PEG-rFVIII conjugates might also be a result of two overlapping effects, a longer circulating PEG-rFVIII that continuously liberates native rFVIII, which is then cleared with the normal elimination rate.

The FVIII dose applied in the animal model was based on the detectable FVIII activity. Because specific activity of FVIII was lower for the PEG-rFVIII candidates, this resulted in 1.9- to 6.7-fold higher protein doses for PEG-rFVIII conjugates than for the native rFVIII control. Slower elimination of PEG-rFVIII seems not to be dependent on the higher protein dose applied, but further experiments are needed to assess the effect of higher protein doses of native rFVIII on the FVIII plasma levels, in comparison to similar protein doses of PEG-rFVIII.

The invention claimed is:

1. A method of treating a bleeding disorder in a subject, said method comprising administering a therapeutically effective amount of a modified protein having an extended in-vivo half life over the unmodified parent protein, wherein the unmodified parent protein is either a von Willebrand Factor moiety or a Factor VIII moiety and the modified protein is a conjugate having a formula:

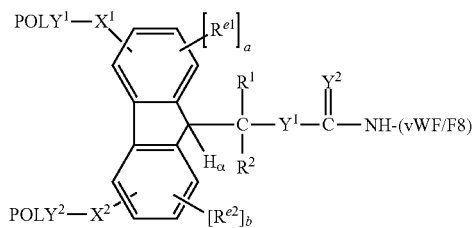

wherein:
POLY$^1$ is a first water-soluble polymer;
POLY$^2$ is a second water-soluble polymer;
X$^1$ is a first spacer moiety;
X$^2$ is a second spacer moiety;
H$_\alpha$ is an ionizable hydrogen atom;

$R^1$ is H or an organic radical;

$R^2$ is H or an organic radical;

(a) is either zero or one;

(b) is either zero or one;

$R^{e1}$, when present, is a first electron altering group;

$R^{e2}$, when present, is a second electron altering group;

$Y^1$ is O or S; and $Y^2$ is O or S, such that

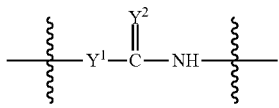

from the formula is a releasable linkage that is selected from a carbamate linkage, a thiocarbamate linkage, and a dithiocarbamate linkage; and (vWF/F8) is a residue of an amine-containing biologically active agent that is either a von Willebrand Factor moiety or a Factor VIII moiety.

2. The method of claim 1, wherein

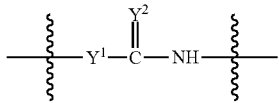

from the formula is a releasable linkage that is either a carbamate linkage or a thiocarbamate linkage.

3. The method of claim 2, wherein the releasable linkage is a carbamate linkage, and the compound possesses the structure:

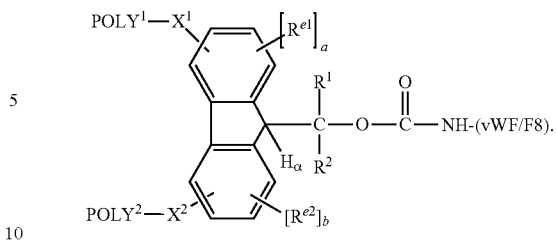

4. The method of claim 1, wherein the first water-soluble polymer is a poly(alkylene oxide) and the second water-soluble polymer is a poly(alkylene oxide).

5. The method of claim 4, wherein the first water-soluble polymer has a weight-average molecular weight of between 10,000 Daltons to 85,000 Daltons and the second water-soluble polymer has a weight-average molecular weight of between 10,000 Daltons to 85,000 Daltons.

6. The method of claim 1, wherein the amine-containing biologically active agent is a von Willebrand Factor moiety.

7. The method of claim 6, wherein the von Willebrand Factor moiety is human recombinant von Willebrand Factor.

8. The method of claim 1, wherein the amine-containing biologically active agent is a Factor VIII moiety.

9. The method of claim 8, wherein the Factor VIII moiety is human recombinant B-domain deleted Factor VIII.

10. The method of claim 8, wherein the Factor VIII moiety is human recombinant full length Factor VIII.

11. The method of claim 1, wherein the conjugate is comprised in a composition together with one or more pharmaceutically acceptable excipients.

12. The method of claim 11, wherein said administering is by injection.

13. The method of claim 12, wherein the composition is in a form selected from the group consisting of a powder that can be reconstituted, a suspension, and a solution.

14. The method of claim 12, wherein the composition is in a unit dosage form.

15. The method of claim 1, wherein the modified protein has a structure selected from the group consisting of:

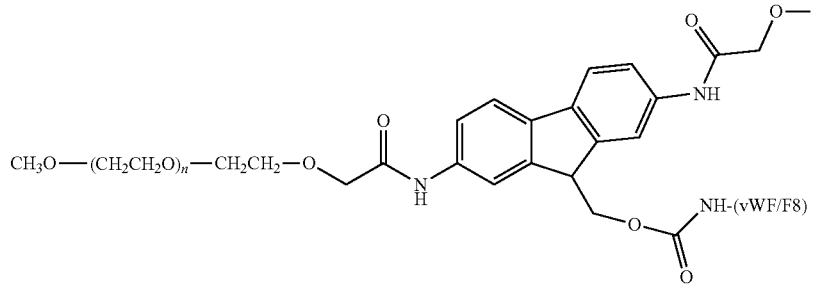

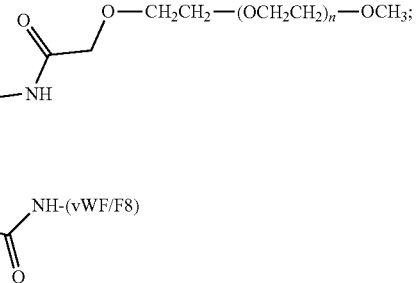

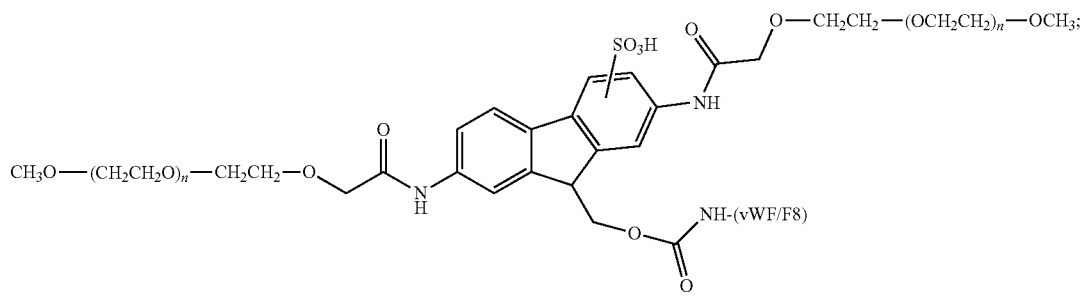

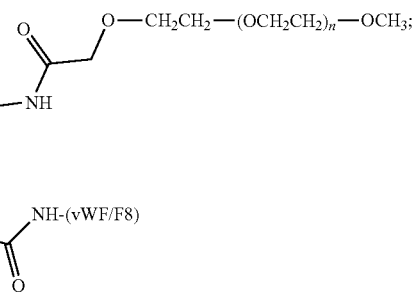

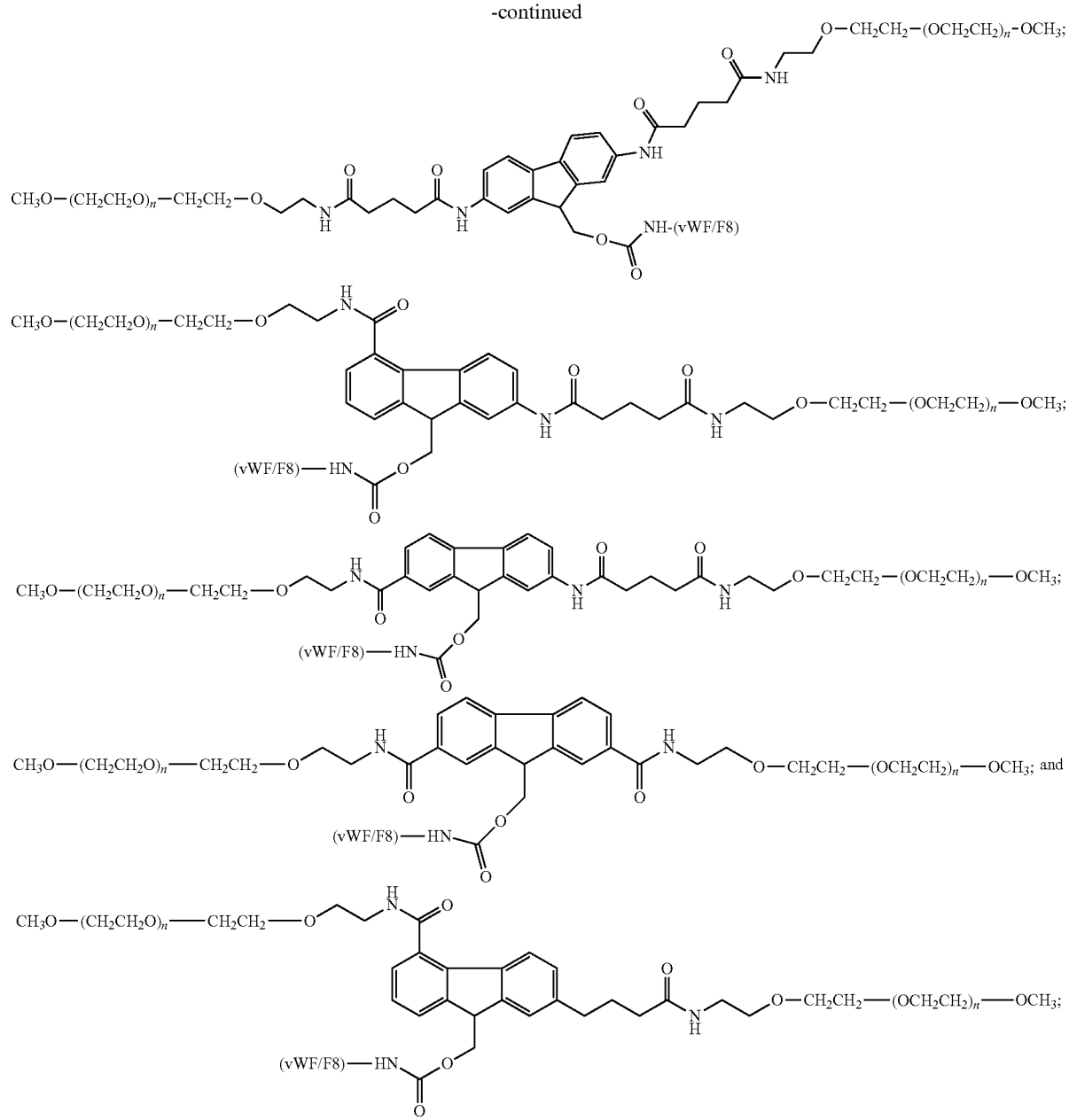

wherein, for each structure and in each instance, (n) is independently an integer from 4 to 1500.

16. The method of claim 15, wherein the amine-containing biologically active agent is a von Willebrand Factor moiety.

17. The method of claim 16, wherein the von Willebrand Factor moiety is human recombinant von Willebrand Factor.

18. The method of claim 15, wherein the amine-containing biologically active agent is a Factor VIII moiety.

19. The method of claim 17, wherein the Factor VIII moiety is human recombinant B-domain deleted Factor VIII.

20. The method of claim 15, wherein the Factor VIII moiety is human recombinant full length Factor VIII.

* * * * *